(12) United States Patent
Murray et al.

(10) Patent No.: US 7,582,769 B2
(45) Date of Patent: Sep. 1, 2009

(54) DICYCLOALKYL UREA GLUCOKINASE ACTIVATORS

(75) Inventors: Anthony Murray, Hellerup (DK); Jesper Lau, Farum (DK); Per Vedso, Vaerlose (DK); Marit Kristiansen, Soborg (DK); Lone Jeppesen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/994,728

(22) PCT Filed: Jul. 7, 2006

(86) PCT No.: PCT/EP2006/064026

§ 371 (c)(1),
(2), (4) Date: Jul. 9, 2008

(87) PCT Pub. No.: WO2007/006760

PCT Pub. Date: Jan. 18, 2007

(65) Prior Publication Data

US 2009/0118501 A1    May 7, 2009

Related U.S. Application Data

(60) Provisional application No. 60/737,143, filed on Nov. 16, 2005, provisional application No. 60/700,264, filed on Jul. 18, 2005, provisional application No. 60/698,515, filed on Jul. 12, 2005.

(30) Foreign Application Priority Data

Jul. 8, 2005  (EP) .................................. 05106284
Jul. 15, 2005 (EP) .................................. 05106519
Nov. 16, 2005 (EP) .................................. 05110779

(51) Int. Cl.
C07D 277/22 (2006.01)

(52) U.S. Cl. .................. 548/185; 548/190; 548/193; 548/195; 548/199

(58) Field of Classification Search ................. 548/185, 548/190, 193, 195, 199
See application file for complete search history.

(56) References Cited

U.S. PATENT DOCUMENTS

| | | | |
|---|---|---|---|
| 3,551,442 A | 12/1970 | Guilor et al. |
| 3,734,923 A | 5/1973 | Dowding et al. |
| 3,862,163 A | 1/1975 | Boroschewski et al. |
| 3,874,873 A | 4/1975 | Volpp et al. |
| 3,887,709 A | 6/1975 | Brzozowski et al. |
| 3,967,950 A | 7/1976 | Kano et al. |
| 4,153,710 A | 5/1979 | Brzozowski et al. |
| 4,175,081 A | 11/1979 | Driscoll |
| 4,183,856 A | 1/1980 | Makisumi et al. |
| 4,241,072 A | 12/1980 | Bolhofer |
| 4,243,404 A | 1/1981 | Krüger et al. |
| 4,808,722 A | 2/1989 | Henrie, II |
| 5,262,415 A | 11/1993 | Takemoto et al. |
| 5,371,086 A | 12/1994 | Takemoto et al. |
| 5,846,985 A | 12/1998 | Murugesan |
| 5,846,990 A | 12/1998 | Murugesan et al. |
| 5,891,917 A | 4/1999 | Tang et al. |
| 5,935,993 A | 8/1999 | Tang et al. |
| 6,001,860 A | 12/1999 | Hamanaka |
| 6,140,343 A | 10/2000 | DeNinno et al. |
| 6,180,635 B1 | 1/2001 | Cheshire et al. |
| 6,225,346 B1 | 5/2001 | Tang et al. |
| 6,268,384 B1 | 7/2001 | Novak et al. |
| 6,271,248 B1 | 8/2001 | Murugesan et al. |
| 6,384,220 B2 | 5/2002 | Corbett et al. |
| 6,448,290 B1 | 9/2002 | Ohuchida et al. |
| 6,486,184 B2 | 11/2002 | Kester et al. |
| 6,489,478 B1 | 12/2002 | DeNinno et al. |
| 6,500,817 B1 | 12/2002 | Fischer et al. |
| 6,608,218 B2 | 8/2003 | Kester et al. |
| 6,863,647 B2 | 3/2005 | Pevarello et al. |
| 6,875,760 B2 | 4/2005 | Lau et al. |
| 6,903,125 B2 | 6/2005 | Kontani et al. |
| 2002/0198200 A1 | 12/2002 | Kester et al. |
| 2003/0171411 A1 | 9/2003 | Kodra et al. |
| 2003/0220350 A1 | 11/2003 | Lau et al. |
| 2004/0014789 A1 | 1/2004 | Lau et al. |
| 2004/0014968 A1 | 1/2004 | Bizzarro et al. |

FOREIGN PATENT DOCUMENTS

| | | |
|---|---|---|
| EP | 885890 | 12/1998 |
| EP | 1169312 | 10/2004 |
| EP | 979823 | 3/2006 |
| GB | 771147 | 3/1957 |
| GB | 1282308 | 7/1972 |
| WO | WO 9104027 | 4/1991 |
| WO | WO 9414801 | 7/1994 |

(Continued)

OTHER PUBLICATIONS

Colowick, S. P., "The Hexokinases", The Enzymes, 1973, vol. 9, pp. 1-48.

(Continued)

*Primary Examiner*—Rebecca L Anderson
*Assistant Examiner*—Robert Havlin
(74) *Attorney, Agent, or Firm*—Rosemarie R. Wilk-Orescan

(57) ABSTRACT

Dicycloalkyl urea glucokinase activators compounds are glucokinase inhibitors useful for the treatment of diabetes. (I)

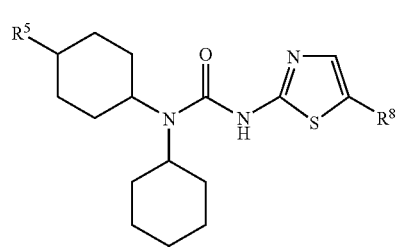

11 Claims, No Drawings

FOREIGN PATENT DOCUMENTS

| | | |
|---|---|---|
| WO | WO 9962890 | 12/1999 |
| WO | WO 0017165 | 3/2000 |
| WO | WO 0026203 | 5/2000 |
| WO | WO 0058293 | 10/2000 |
| WO | WO 0144216 | 6/2001 |
| WO | WO 0144217 | 6/2001 |
| WO | WO 0183465 | 11/2001 |
| WO | WO 0183478 | 11/2001 |
| WO | WO 0185706 | 11/2001 |
| WO | WO 0185707 | 11/2001 |
| WO | WO 02082090 | 1/2002 |
| WO | WO 03/055482 A1 | 7/2003 |
| WO | WO 2004/002481 A1 | 1/2004 |
| WO | WO 2004/085388 | 10/2004 |
| WO | WO 2005/066145 * | 7/2005 |
| WO | WO 2005/066145 A1 | 7/2005 |
| WO | WO 2005/103050 | 11/2005 |

OTHER PUBLICATIONS

Chipkin, S. R. et al., "Hormone-Fuel Interrelationships: Fed State, Starvation, and Diabetes Mellitus", Joslin's Diabetes, 1994, pp. 97-115.

Printz, R. L. et al., "Mammalian Glucokinase", Annual Review of Nutrition, 1993, vol. 13, pp. 463-496.

Meglasson, M. D. et al., "New Perspectives on Pancreatic Islet Glucokinase", American Journal of Physiology, 1984, vol. 246, pp. E1-E13.

Grupe, A. et al., "Transgenic Knockouts Reveal a Critical Requirement for Pancreatic β Cell Glucokinase in Maintaining Glucose Homeostasis", Cell, 1995, vol. 83, pp. 69-78.

Ferre, T. et al., "Evidence From Transgenic Mice that Glucokinase is Rate Limiting for Glucose Utilization in the Liver", The Faseb Journal, 1996, vol. 10, pp. 1213-1218.

Liang, Y. et al., "Variable Effects of Maturity-Onset-Diabetes-of-Youth (MODY)-associated Glucokinase Mutations on Substrate Interactions and Stability of the Enzyme", Biochem. J., 1995, vol. 309, pp. 167-173.

Glaser, B. et al., "Familial Hyperinsulinism Caused by an Activating Glucokinase Mutation", The New England Journal of Medicine, 1998, vol. 338, pp. 226-230.

Mann, G. V., "The Influence of Obesity on Health", The New England Journal of Medicine, 1974, vol. 291, pp. 226-232.

"Health Implications of Obesity", National Institutes of Health Consensus Development Conference Statement, Annals of Internal Medicine, 1985, vol. 103, pp. 147-151.

U.S. Appl. No. 12/188,402, filed Aug. 8, 2008, inventor Murray et al.
U.S. Appl. No. 60/879,683, filed Jan. 10, 2007, inventor Murray et al.
U.S. Appl. No. 60/879,961, filed Jan. 11, 2007, inventor Murray et al.
Office Action from the European Patent Office dated Oct. 17, 2006.
Wolff. Burger's Medical Chemistry and Drug Discovery, vol. 1, Principles and Practice, pp. 172-178 (1995).

* cited by examiner

DICYCLOALKYL UREA GLUCOKINASE ACTIVATORS

CROSS-REFERENCE TO RELATED APPLICATIONS

This application is a 35 U.S.C. § 371 national stage application of International Patent Application PCT/EP2006/064026 (published as WO 2007/006760 A1), filed Jul. 7, 2006, which claimed priority of European Patent Application 05106284.2, filed Jul. 8, 2005 and European Patent Application 05106519.1, filed Jul. 15, 2005 and European Patent Application 05110779.5, filed Nov. 16, 2005; this application further claims priority under 35 U.S.C. § 119 of U.S. Provisional Application 60/698,515, filed Jul. 12, 2005 and U.S. Provisional Application 60/700,264, filed Jul. 18, 2005 and U.S. Provisional Application 60/737,143, filed Nov. 16, 2005.

FIELD OF THE INVENTION

This application relates to novel dicycloalkyl urea glucokinase activators and their use in treatment in assorted diseases.

BACKGROUND OF THE INVENTION

Glucokinase (GK) is one of four hexokinases that are found in mammals [Colowick, S. P., in The Enzymes, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. Amer. J. Physiol. 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). While mutations of the GK gene are not found in the majority of patients with type 2 diabetes, compounds that activate GK and, thereby, increase the sensitivity of the GK sensor system will still be useful in the treatment of the hyperglycemia characteristic of all type 2 diabetes. Glucokinase activators will increase the flux of glucose metabolism in β-cells and hepatocytes, which will be coupled to increased insulin secretion. Such agents would be useful for treating type II diabetes. Several GK activators are known, see, for example, US 2004/0014968 (Hofmann-La Roche Inc.), WO 2003/055482 (Novo Nordisk A/S) and WO 2004/002481 (Novo Nordisk A/S). Diabetes is characterised by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin metformin is a representative example.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment. Since existing forms of therapy of diabetes does not lead to sufficient glycaemic control and therefore are unsatisfactory, there is a great demand for novel therapeutic approaches.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis. Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain haemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain haemorrhaging. However, the development of atherosclerosis or heart disease due to hypertension over a long period of time remains a problem. This implies that although high blood pressure is being reduced, the underlying cause of essential hypertension is not responding to this treatment. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary bypass surgery annually, perioperative myocardial infarction is estimated to occur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients. Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exists. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity. The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal induced gastric distension is another possible inhibitory factor. Additionally the hypothalamic centres are sensitive to catecholamines, and beta adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

SUMMARY OF THE INVENTION

The invention provides a compound of general formula (I)

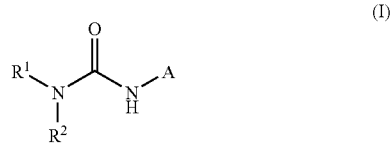

(I)

wherein the substituents are defined below, as well as further embodiments hereof described in the attached embodiments.

The present invention also provides use of the compounds of the invention for preparation of a medicament for the treatment of various diseases, e.g. for the treatment of type 2 diabetes.

DEFINITION

In the structural formulas given herein and throughout the present specification, the following terms have the indicated meaning:

The term "optionally substituted" as used herein means that the moiety which is optionally substituted is either unsubstituted or substituted with one or more of the substituents specified. When the moiety in question is substituted with more than one substituent, the substituent may be the same or different.

The term "adjacent" as used herein regards the relative positions of two atoms or variables, these two atoms or variables sharing a bond or one variable preceding or succeeding the other in a variable specification. By way of example, "atom A adjacent to atom B" means that the two atoms A and B share a bond.

The term "halogen" or "halo" means fluorine, chlorine, bromine or iodine.

The term "perhalomethyl" means trifluoromethyl, trichloromethyl, tribromomethyl, or triiodomethyl.

The use of prefixes of this structure: $C_{x-y}$-alkyl, $C_{x-y}$-alkenyl, $C_{x-y}$-alkynyl, $C_{x-y}$-cycloalyl or $C_{x-y}$-cycloalkyl-$C_{x-y}$-alkenyl- and the like designates radical of the designated type having from x to y carbon atoms.

The term "alkyl" as used herein, alone or in combination, refers to a straight or branched chain saturated monovalent hydrocarbon radical having from one to ten carbon atoms, for example $C_{1-8}$-alkyl or $C_{1-6}$-alkyl. Typical $C_{1-8}$-alkyl groups and $C_{1-6}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl. The term "$C_{1-6}$-alkyl" as used herein also includes secondary $C_{3-6}$-alkyl and tertiary $C_{4-6}$-alkyl.

The term "alkenyl" as used herein, alone or in combination, refers to a straight or branched chain monovalent hydrocarbon radical containing from two to ten carbon atoms and at least one carbon-carbon double bond, for example $C_{2-8}$-alkenyl or $C_{2-6}$-alkenyl. Typical $C_{2-8}$-alkenyl groups and $C_{2-6}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "alkynyl" as used herein alone or in combination, refers to a straight or branched monovalent hydrocarbon radical containing from two to ten carbon atoms and at least one triple carbon-carbon bond, for example $C_{2-8}$-alkynyl or $C_{2-6}$-alkynyl. Typical $C_{2-8}$-alkynyl groups and $C_{2-6}$-alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "cycloalkyl" as used herein, alone or in combination, refers to a saturated mono-, bi-, or tricarbocyclic radical having from three to twelve carbon atoms, for example $C_{3-8}$-cycloalkyl. Typical $C_{3-8}$-cycloalkyl groups include, but are not limited to, cyclopropyl, cyclobutyl, cyclopentyl, cyclohexyl, cycloheptyl, cyclooctyl, bicyclo[3.2.1]octyl, bicyclo[2.2.1]heptyl, norpinyl, norbonyl, norcaryl, adamantyl and the like.

The term "cycloalkenyl" as used herein, alone or in combination, refers to an non-aromatic unsaturated mono-, bi-, or tricarbocyclic radical having from three to twelve carbon atoms, for example $C_{3-8}$-cycloalkenyl. Typical $C_{3-8}$-cycloalkyl groups include, but are not limited to cyclohexene, cycloheptene and cyclopentene, and the like.

The term "heterocyclic" or the term "heterocyclyl" as used herein, alone or in combination, refers to a saturated mono-, bi-, or tricarbocyclic group having three to twelve carbon atoms and one or two additional heteroatoms or groups selected from nitrogen, oxygen, sulphur, SO or $SO_2$, for example $C_{3-8}$-heterocyclyl. Typical $C_{3-8}$-heterocyclyl groups include, but are not limited to, tetrahydrofuryl, tetrahydrothienyl, tetrahydropyranyl, tetrahydrothiopyranyl, 1,4-dioxanyl, 1,3-dioxanyl, piperidyl, pyrrolidinyl, morpholinyl, piperazinyl, and the like.

The term "heterocycloalkenyl" as used herein, alone or in combination, refers to a non-aromatic unsaturated mono-, bi-, or tricyclic radical having from three to twelve carbon atoms, and one or two additional heteroatoms or groups selected from nitrogen, oxygen, sulphur, SO or $SO_2$, for example $C_{3-8}$-heteroecycloalkenyl. Typical $C_{3-8}$-hetereocycloalkenyl groups include, but are not limited to tetrahydropyridine, azacycloheptene, 2-pyrroline, 3-pyrroline, 2-pyrazoline, imidazoline, 4H-pyran, and the like.

The terms "alkoxy" or "alkyloxy", which are interchangeable terms herein, as used herein, alone or in combination, refers to the monovalent radical $R^aO$—, where $R^a$ is alkyl as defined above, for example $C_{1-8}$-alkyl giving $C_{1-8}$-alkoxy. Typical $C_{1-8}$-alkoxy groups include, but are not limited to, methoxy, ethoxy, n-propoxy, isopropoxy, butoxy, sec-butoxy, tert-butoxy, pentoxy, isopentoxy, hexoxy, isohexoxy and the like.

The term "alkenyloxy", as used herein, alone or in combination, refers to the monovalent radical $R^aO$—, where $R^a$ is alkenyl as defined above, for example $C_{2-8}$-alkyl giving $C_{2-8}$-alkenyloxy. Typical $C_{2-8}$-alkenyloxy groups include, but are not limited to, vinyloxy, propenyloxy, 2-methyl-propenyloxy, butenyloxy, and the like.

The term "alkylthio" as used herein, alone or in combination, refers to a straight or branched monovalent radical comprising an alkyl group as described above linked through a divalent sulphur atom having its free valence bond from the sulphur atom, for example $C_{1-6}$-alkylthio. Typical $C_{1-6}$-alkylthio groups include, but are not limited to, methylthio, ethylthio, propylthio, butylthio, pentylthio, hexylthio and the like.

The term "alkoxycarbonyl" as used herein refers to the monovalent radical $R^aOC(O)$—, where $R^a$ is alkyl as described above, for example $C_{1-8}$-alkoxycarbonyl. Typical $C_{1-8}$-alkoxycarbonyl groups include, but are not limited to, methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "aryl" as used herein refers to a carbocyclic aromatic ring radical or to a aromatic ring system radical. Aryl is also intended to include the partially hydrogenated derivatives of the carbocyclic systems.

The term "heteroaryl", as used herein, alone or in combination, refers to an aromatic ring radical with for instance 5 to 7 member atoms, or to a aromatic ring system radical with for instance from 7 to 18 member atoms, containing one or more heteroatoms selected from nitrogen, oxygen, or sulphur heteroatoms, wherein N-oxides and sulphur monoxides and sulphur dioxides are permissible heteroaromatic substitutions; such as e.g. furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like. Heteroaryl is also intended to include the partially hydrogenated derivatives of the heterocyclic systems enumerated below.

Examples of "aryl" and "heteroaryl" includes, but are not limited to phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxaz-5-yl), isothiazolyl (isothiazo-3-yl, isothiazo-4-yl, isothiaz-5-yl) thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydrobenzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydrobenzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), purinyl, and tetrazolyl (5-tetrazolyl, N-tetrazolyl).

The present invention also relates to partly or fully saturated analogues of the ring systems mentioned above.

When two or more of the above defined terms are used in combination, such as in aryl-alkyl, heteroaryl-alkyl, cycloalkyl-$C_{1-6}$-alkyl and the like, it is to be understood that the first mentioned radical is a substituent on the latter mentioned radical, where the point of substitution, i.e. the point of attachment to another part of the molecule, is on the latter of the radicals, for example aryl-alkyl-:

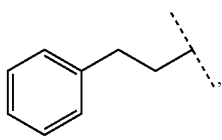

cycloalkyl-alkyl-:

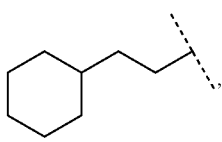

and aryl-alkoxy-:

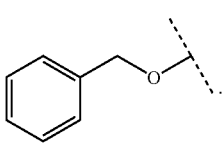

The term "fused arylcycloalkyl", as used herein, refers to an aryl group, as defined above, fused to a cycloalkyl group, as defined above and having the indicated number of carbon atoms, the aryl and cycloalkyl groups having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

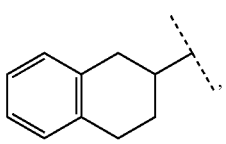

and the like.

The term "fused heteroarylcycloalkyl", as used herein, refers to a heteroaryl group, as defined above, fused to a cycloalkyl group, as defined above and having the indicated number of carbon atoms, the aryl and cycloalkyl groups having two atoms in common, and wherein the cycloalkyl group is the point of substitution. Examples of fused heteroarylcycloalkyl used herein include 6,7-dihydro-5H-cyclopenta[b]pyridine, 5,6,7,8-tetrahydroquinoline, 5,6,7,8-tetrahydrisoquinoline, 5,6,7,8-tetrahydroquinazoline and the like The term "alkylsulfanyl", as used herein, refers to the group $R^aS$—, where $R^a$ is alkyl as described above.

The term "alkylsulfenyl", as used herein, refers to the group $R^aS(O)$—, where $R^a$ is alkyl as described above.

The term "alkylsulfonyl", as used herein, refers to the group $R^aSO_2$—, where $R^a$ is alkyl as described above.

The term "alkylsulfamoyl", as used herein, refers to the group $R^aNHSO_2$—, where $R^a$ is alkyl as described above.

The term "dialkylsulfamoyl", as used herein, refers to the group $R^aR^bNSO_2$—, where $R^a$ and $R^b$ are alkyl as described above.

The term "alkylsulfinamoyl", as used herein, refers to the group $R^aNHSO$—, where $R^a$ is alkyl as described above.

The term "dialkylsulfinamoyl", as used herein, refers to the group $R^aR^bNSO$—, where $R^a$ and $R^b$ are alkyl as described above.

The term "alkylamino", as used herein, refers to the group $R^aNH$—, where $R^a$ is alkyl as described above.

The term "acyl", as used herein, refers to the group $R^aC(O)$—, where $R^a$ is alkyl, alkenyl, alkynyl, cycloalkyl, cycloalkenyl, or heterocyclyl as described above.

The term "heteroaryloxy" as used herein, alone or in combination, refers to the monovalent radical $R^aO$—, where $R^a$ is heteroaryl as defined above.

The term "aryloxycarbonyl", as used herein, refers to the group $R^a$—O—C(O)—, where $R^a$ is aryl as described above.

The term "acyloxy", as used herein, refers to the group $R^aC(O)O$—, where $R^a$ is alkyl, alkenyl, alkynyl, cycloalkyl, cycloalkenyl, or heterocyclyl as described above.

The term "aryloxy", as used herein refers to the group $R^a$—O—, where $R^a$ is aryl as described above.

The term "aroyloxy", as used herein, refers to the group $R^aC(O)O$—, where $R^a$ is aryl as described above.

The term "heteroaroyloxy", as used herein, refers to the group $R^aC(O)O$—, where $R^a$ is heteroaryl as described above.

Whenever the terms "alkyl", "cycloalkyl", "aryl", "heteroaryl" or the like or either of their prefix roots appear in a name of a substituent (e.g. arylalkoxyaryloxy) they shall be interpreted as including those limitations given above for "alkyl" and "aryl".

As used herein, the term "oxo" shall refer to the substituent =O.

As used herein, the term "mercapto" shall refer to the substituent —SH.

As used herein, the term "carboxy" shall refer to the substituent —C(O)OH.

As used herein, the term "cyano" shall refer to the substituent —CN.

As used herein, the term "nitro" shall refer to the substituent —$NO_2$.

As used herein, the term "aminosulfonyl" shall refer to the substituent —$SO_2NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

As used herein, the term "direct bond", where part of a structural variable specification, refers to the direct joining of the substituents flanking (preceding and succeeding) the variable taken as a "direct bond".

The term "lower", as used herein, refers to an group having between one and six carbons, and may be indicated with the prefix $C_{x-6}$-. Lower alkyl may thus be indicated as $C_{1-6}$-alkyl, while lower alkylene may be indicated as $C_{2-6}$-alkylene.

A radical such as $C_{x-y}$-cycloalkyl-$C_{a-b}$-alkenyl shall designate that the radical's point of attachment is in part of the radical mentioned last.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "attached" or "—" (e.g. —C(O)R$^{11}$ which indicates the carbonyl attachment point to the scaffold) signifies a stable covalent bond.

As used herein, the terms "contain" or "containing" can refer to in-line substitutions at any position along the above defined alkyl, alkenyl, alkynyl or cycloalkyl substituents with one or more of any of O, S, SO, SO$_2$, N, or N-alkyl, including, for example, —CH$_2$—O—CH$_2$—, —CH$_2$—SO$_2$—CH$_2$—, —CH$_2$—NH—CH$_3$ and so forth.

Certain of the above defined terms may occur more than once in the structural formulae, and upon such occurrence each term shall be defined independently of the other.

As used herein, the term "solvate" is a complex of variable stoichiometry formed by a solute (in this invention, a compound of formula (I)) and a solvent. Such solvents for the purpose of the present invention may not interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is trans-formed to (I) in plasma. Many examples of such are known in the art and include by way of example lower alkyl esters (e.g., C$_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" and "treating" as used herein means the management and care of a patient for the purpose of combating a disease, disorder or condition. The term is intended to include the full spectrum of treatments for a given disorder from which the patient is suffering, such as the delaying of the progression of the disease, disorder or condition, the alleviation or relief of symptoms and complications, the prevention of the disease and/or the cure or elimination of the disease, disorder or condition. The patient to be treated is preferably a mammal, in particular a human being.

The term "pharmaceutically acceptable salt" as used herein includes pharmaceutically acceptable acid addition salts, pharmaceutically acceptable base addition salts, pharmaceutically acceptable metal salts, ammonium salts, and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, and magnesium hydroxide, in solvents such as ether, THF, methanol, t-butanol, dioxane, isopropanol, ethanol etc. Mixture of solvents may be used. Organic bases such as lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, dioxane etc. Mixture of solvents may also be used. The term "combination therapy", "combined", "in combination with", and the like, as used herein refers to the administration of a single pharmaceutical dosage formulation which comprises the glucokinase activator compound of the present invention and another active agent(s), as well as administration of each active agent(s) in its own separate pharmaceutical dosage formulation. Where separate dosage formulations are used, the compound of the present invention and another active agent(s) can be administered to the patient at essentially the same time, i.e. concurrently, or at separate staggered times, i.e. sequentially. When given by different dosage formulations, the route of administration may be the same or

DESCRIPTION OF THE INVENTION

In embodiment 1 the invention provides a compound of general formula (I)

$$R^1\text{-}N(R^2)\text{-}C(=O)\text{-}N(H)\text{-}A \quad (I)$$

wherein $R^1$ is $C_{3-8}$-cycloalkyl, $C_{3-8}$-cycloalkenyl, $C_{3-8}$-heterocyclyl, $C_{3-8}$-heterocycloalkenyl, fused aryl-$C_{3-8}$-cycloalkyl, or fused heteroaryl-$C_{3-8}$-cycloalkyl, each of which is optionally substituted with one or more substituents $R^3$, $R^4$, $R^5$ and $R^6$;

$R^2$ is $C_{3-8}$-cycloalkyl, $C_{3-8}$-cycloalkenyl, $C_{3-8}$-heterocyclyl, $C_{3-8}$-heterocycloalkenyl, fused aryl-$C_{3-8}$-cycloalkyl or fused heteroaryl-$C_{3-8}$-cycloalkyl, each of which is optionally substituted with one or more substituents $R^{30}$, $R^{31}$, $R^{32}$ and $R^{33}$ A is heteroaryl which is optionally substituted with one or more substituents independently selected from $R^7$, $R^8$ and $R^9$; and At least one of $R^1$ and $R^2$ must have one substituent selected from $R^3$, $R^4$, $R^5$, $R^6$, $R^{30}$, $R^{31}$, $R^{32}$ and $R^{33}$; and At least one of $R^3$, $R^4$, $R^5$, $R^6$, $R^{30}$, $R^{31}$, $R^{32}$ and $R^{33}$ is independently selected from the group consisting of $C_{3-8}$-cycloalkyl-$C_{3-6}$-alkenyl, aryl-$C_{2-6}$-alkenyl, heteroaryl-$C_{2-6}$-alkenyl, $C_{3-6}$-alkenyloxy, $C_{3-8}$-cycloalkyl-$C_{3-6}$-alkenyloxy, aryl-$C_{3-6}$-alkenyloxy, heteroaryl-$C_{3-6}$-alkenyloxy, $C_{3-8}$-cycloalkenyl-$C_{1-6}$-alkoxy, $C_{3-8}$-heterocyclyl-$C_{1-6}$-alkoxy, fused aryl-$C_{3-8}$-cycloalkenyl-$C_{1-6}$-alkoxy, $C_{3-8}$-heterocyclyl-$C_{3-6}$-alkenyloxy, fused aryl-$C_{3-8}$-cycloalkenyl-$C_{3-6}$-alkenyloxy, $C_{1-6}$-alkoxy-$C_{3-6}$-alkenyloxy, $C_{3-8}$-alkenyloxy-$C_{1-6}$-alkoxy, aryloxy-$C_{1-6}$-alkyl, aryloxy-$C_{3-6}$-alkenyl, heteroaryloxy-$C_{1-6}$-alkyl, heteroaryloxy-$C_{3-6}$-alkenyl, aryl-$C_{1-6}$-alkyloxy-$C_{1-6}$-alkyl, aryl-$C_{3-6}$-alkenyloxy-$C_{1-6}$-alkyl, aryl-$C_{1-6}$-alkyloxy-$C_{3-6}$-alkenyl, heteroaryl-$C_{1-6}$-alkyloxy-$C_{1-6}$-alkyl, heteroaryl-$C_{3-6}$-alkenyloxy-$C_{1-6}$-alkyl, heteroaryl-$C_{1-6}$-alkyloxy-$C_{3-6}$-alkenyl, $C_{3-8}$-cycloalkyl-$C_{1-6}$-alkyloxy-$C_{1-6}$-alkyl, $C_{3-8}$-cycloalkyl-$C_{3-6}$-alkenyloxy-$C_{1-6}$-alkyl, $C_{3-8}$-cycloalkyl-$C_{1-6}$-alkyloxy-$C_{3-6}$-alkenyl, $C_{3-8}$-heterocyclyl-$C_{1-6}$-alkyloxy-$C_{1-6}$-alkyl, $C_{3-8}$-heterocyclyl-$C_{3-6}$-alkenyloxy-$C_{1-6}$-alkyl, $C_{3-8}$-heterocyclyl-$C_{1-6}$-alkyloxy-$C_{3-6}$-alkenyl, fused aryl-$C_{3-8}$-cycloalkenyl-$C_{1-6}$-alkyloxy-$C_{1-6}$-alkyl, fused aryl-$C_{3-8}$-cycloalkenyl-$C_{3-6}$-alkenyloxy-$C_{1-6}$-alkyl, fused aryl-$C_{3-8}$-cycloalkenyl-$C_{1-6}$-alkyloxy-$C_{3-6}$-alkenyl, $C_{3-6}$-alkenylthio, $C_{3-8}$-cycloalkyl-$C_{3-6}$-alkenylthio, aryl-$C_{3-6}$-alkenylthio, heteroaryl-$C_{3-6}$-alkenylthio, $C_{3-8}$-cycloalkyl-$C_{1-6}$-alkthio, $C_{3-8}$-heterocyclyl-$C_{1-6}$-alkthio, fused aryl-$C_{3-8}$-cycloalkenyl-$C_{1-6}$-alkthio, $C_{1-6}$-alkylthio-$C_{3-6}$-alkenyloxy, $C_{1-6}$-alkoxy-$C_{3-6}$-alkenylthio, $C_{3-8}$-alkenylthio-$C_{1-6}$-alkoxy, $C_{3-8}$-alkenyloxy-$C_{1-6}$-alkylthio, arylthio-$C_{1-6}$-alkyl, arylthio-$C_{3-6}$-alkenyl, heteroarylthio-$C_{1-6}$-alkyl, heteroarylthio-$C_{3-6}$-alkenyl, aryl-$C_{1-6}$-alkylthio-$C_{1-6}$-alkyl, aryl-$C_{3-6}$-alkenylthio-$C_{1-6}$-alkyl, aryl-$C_{1-6}$-alkylthio-$C_{3-6}$-alkenyl, heteroaryl-$C_{1-6}$-alkylthio-$C_{1-6}$-alkyl, heteroaryl-$C_{3-6}$-alkenylthio-$C_{1-6}$-alkyl, heteroaryl-$C_{1-6}$-alkylthio-$C_{3-6}$-alkenyl, $C_{3-8}$-cycloalkyl-$C_{1-6}$-alkylthio-$C_{1-6}$-alkyl, $C_{3-8}$-cycloalkyl-$C_{3-6}$-alkenylthio-$C_{1-6}$-alkyl, $C_{3-8}$-cycloalkyl-$C_{1-6}$-alkylthio-$C_{3-6}$-alkenyl, $C_{3-8}$-heterocyclyl-$C_{1-6}$-alkylthio-$C_{1-6}$-alkyl, $C_{3-8}$-heterocyclyl-$C_{3-6}$-alkenylthio-$C_{1-6}$-alkyl, $C_{3-8}$-heterocyclyl-$C_{1-6}$-alkylthio-$C_{3-6}$-alkenyl, fused aryl-$C_{3-8}$-cycloalkenyl-$C_{1-6}$-alkylthio-$C_{1-6}$-alkyl, fused aryl-$C_{3-8}$-cycloalkenyl-$C_{3-6}$-alkenylthio-$C_{1-6}$-alkyl, fused aryl-$C_{3-8}$-cycloalkenyl-$C_{1-6}$-alkylthio-$C_{3-6}$-alkenyl each of which is optionally substituted with one or more substituents independently selected from $R^{12}$; and If more than one of $R^3$, $R^4$, $R^5$, $R^6$, or more than one of $R^{30}$, $R^{31}$, $R^{32}$ and $R^{33}$ is present, that additional $R^3$, $R^4$, $R^5$, $R^6$, or $R^{30}$, $R^{31}$, $R^{32}$ or $R^{33}$ may be independently selected from halogen, nitro, cyano, hydroxy, oxo, carboxy, —$CF_3$; or —$NR^{10}R^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, arylthio, heteroarylthio, $C_{3-8}$-cycloalkylthio, aryl-$C_{1-6}$-alkylthio, heteroaryl-$C_{1-6}$-alkylthio, $C_{1-6}$-alkylsulfenyl, $C_{3-6}$-cycloalkyl-$C_{1-6}$-alkylthio, $C_{1-6}$-alkyl-C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or —C(O)—$R^{27}$, —S(O)$_2$—$R^{27}$, —C(O)—$NR^{13}R^{14}$, —S(O)$_2$—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—(CH$_2$)$_{1-3}$—O—; and $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{2-6}$-alkenyl, aryl, aryl-$C_{1-6}$-alkyl, aryloxy-$C_{1-6}$-alkyl, aryl-$C_{2-6}$-alkenyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—$C_{2-6}$-alkenyl, $R^{10}R^{11}$—N—S(O)$_2$—$C_{1-6}$-alkyl, $R^{10}R^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-S(O)$_2$—NH—$C_{1-6}$-alkyl, aryl-S(O)$_2$—NH—$C_{1-6}$-alkyl, heteroaryl-S(O)$_2$—NH—$C_{1-6}$-alkyl, or $C_{3-8}$-cycloalkyl-S(O)$_2$—NH—$C_{1-6}$-alkyl, each of which is optionally substituted with one or more substituents independently selected from $R^{12}$; and $R^{12}$ is halogen, cyano, hydroxy, —C(O)—O—$C_{1-6}$-alkyl, carboxy, —$CF_3$, $C_{1-6}$-alkyl, $C_{1-6}$-alkoxy, $C_{2-6}$-alkenyloxy, $C_{3-8}$-cycloalkyloxy, cycloalkenyloxy, heterocyclyloxy, aryloxy, heteroaryloxy, aryl-$C_{1-6}$-alkoxy, aryl-$C_{1-6}$-alkenyloxy, heteroaryl-$C_{1-6}$-alkoxy, heteroaryl-$C_{1-6}$-alkenyloxy, $C_{3-8}$-cycloalkyl-$C_{1-6}$-alkoxy, $C_{3-8}$-cycloalkyl-$C_{1-6}$-alkenyloxy, heterocyclyl-$C_{1-6}$-alkoxy, heterocyclyl-$C_{1-6}$-alkenyloxy, fused aryl-cycloalkyl- $C_{1-6}$-alkoxy, fused aryl-cycloalkyl-$C_{1-6}$-alkenyloxy, $C_{1-6}$-alkylthio, $C_{2-6}$-alkenylthio, $C_{3-8}$-cycloalkylthio, cycloalkenylthio, heterocyclylthio, arylthio, heteroarylthio, aryl-$C_{1-6}$-alkylthio, aryl-$C_{1-6}$-alkenylthio, heteroaryl-$C_{1-6}$-alkyltio, heteroaryl-$C_{1-6}$-alkenylthio, $C_{3-8}$-cycloalkyl-$C_{1-6}$-alkylthio, $C_{3-8}$-cycloalkyl-$C_{1-6}$-alkenylthio, heterocyclyl-$C_{1-6}$-alkylthio, heterocyclyl-$C_{1-6}$-alkenylthio, fused aryl-cycloalkyl-$C_{1-6}$-alkylthio, fused arylcycloalkyl-$C_{1-6}$-alkenylthio, —$NR^{10}R^{11}$, —$S(O)_2CH_3$, —$S(O)_2CF_3$, —$S(O)_2CH_2CF_3$ or —$S(O)_2NH_2$; and $R^{10}$ and $R^{11}$ independently represent hydrogen, $C_{1-6}$-alkyl, —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —$S(O)_2$—$C_{1-6}$-alkyl, or aryl; and $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur; and $R^{15}$ is halogen, cyano, hydroxy, carboxy, —$CF_3$, $C_{1-6}$-alkyl, —$S(O)_2CH_3$, or —$S(O)_2NH_2$; and $R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{2-6}$-alkynyl, $C_{1-6}$-alkoxy, $C_{1-6}$-alkylthio, $C_{2-6}$-alkenylthio, $C_{1-6}$-alkylamino, $C_{1-6}$-alkylsulfenyl, —C(O)—O—$C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, carboxy-$C_{1-6}$-alkyl, or hydroxy-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, heteroaryl-oxy-$C_{1-6}$-alkyl, aryloxy, heteroaryloxy, arylthio, heteroarylthio, aryl-$C_{1-6}$-alkylamino, —C(O)-aryl, or —C(O)-heteroraryl, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkylthio, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, $C_{3-8}$-heterocyclyl-$C_{1-6}$-alkylthio, $C_{3-8}$-heterocyclylthio, $C_{3-8}$-heterocyclyl-amino-$C_{1-6}$-alkyl, or —C(O)—$C_{3-8}$-heterocyclyl, each of which is optionally substituted with one or more substituents independently selected from $R^{16}$; or —$NR^{19}R^{20}$, —$C_{1-6}$-alkyl-$NR^{19}R^{20}$, —$C_{2-6}$-alkenyl-$NR^{19}R^{20}$, —$C_{1-6}$-alkyl-S—$R^{21}$, —$C_{1-6}$-alkyl-S(O)—$R^{21}$, —$C_{1-6}$-alkyl-$S(O)_2$—$R^{21}$, —$S(O)_2$—$R^{21}$, —$S(O)_2$—$N(R^{19})(C_{1-6}$-alkyl-$C(O)NR^{22}R^{23})$ or —$S(O)_2$—$NR^{19}R^{20}$, wherein each alkyl part may be substituted with one or more substituents independently selected from $R^{25}$; or —$C(O)NR^{22}R^{23}$, —$C_{1-6}$-alkyl-$C(O)NR^{22}R^{23}$—$C_{1-6}$-alkyl-NH—$NR^{22}R^{23}$—$C_{1-6}$-alkyl-NH—C(O)—$C_{1-6}$-alkyl-$NR^{22}R^{23}$, each optionally substituted with one or more substituents independently selected from $R^{26}$; or two of $R^7$, $R^8$ and $R^9$ can be taken together to form a $C_{2-5}$-alkylene bridge; the $C_{2-5}$-alkylene bridge is optionally substituted with one or more substituents independently selected from $R^{16}$; and $R^{16}$, $R^{17}$, and $R^{18}$ are independently $C_{1-6}$-alkyl, halogen, nitro, cyano, hydroxy, carboxy, oxo, —$CF_3$, carboxy-$C_{1-6}$-alkyl, hydroxy-$C_{1-6}$-alkyl, —$C_{1-6}$-alkyl-C(O)—O—$C_{1-6}$-alkyl, —$C_{1-6}$-alkyl-C(O)—$NR^{19}R^{20}$, —C(O)—O—$C_{1-6}$-alkyl, —C(O)—$C_{1-6}$-alkyl-C(O)—$C_{1-6}$-alkyl, —$NR^{19}R^{20}$, —$NHS(O)_2C_{1-6}$-alkyl, —$NHS(O)_2CF_3$, —$NHS(O)_2CH_2CF_3$, —$C(O)NR^{19}R^{20}$—$S(O)_2$ $C_{1-6}$-alkyl, —$S(O)_2CF_3$, —$S(O)_2CH_2CF_3$ or —$S(O)_2NR^{19}R^{20}$; and $R^{19}$ and $R^{20}$ independently represent hydrogen, $C_{1-6}$-alkyl, $C_{2-6}$-alkenyl, $C_{3-8}$-cycloalkyl, $C_{3-8}$-cycloalkyl-$C_{1-6}$-alkyl, hydroxy-$C_{1-6}$-alkyl, carboxy-$C_{1-6}$-alkyl, aryl, heteroaryl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, or —$S(O)_2$—$C_{1-6}$-alkyl, each of which is optionally substituted with one or more substituents independently selected from $R^{24}$, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$; and $R^{21}$ is selected from $C_{1-6}$-alkyl, $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-$NR^{22}R^{23}$; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{24}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl; and $R^{22}$ and $R^{23}$ are independently selected from hydrogen, $C_{1-6}$-alkyl, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-$S(O)_2$—$C_{1-6}$-alkyl, $C_{3-8}$-cycloalkyl, aryl, or heteroaryl; or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$; and $R^{24}$ is halogen, nitro, cyano, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, —C(O)-heteroaryl, —C(O)—$C_{3-8}$-heterocyclyl-C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —$C_{1-6}$-alkyl-C(O)—$C_{3-8}$-heterocyclyl, —C(O)—O—$C_{1-6}$-alkyl-aryl, —NH—S(O)$_2$R$^{28}$, or —S(O)$_2$R$^{28}$, wherein each cyclic moiety is optionally substituted with one or more substituents independently selected from R$^{29}$; and R$^{25}$ and R$^{26}$ are independently $C_{1-6}$-alkyl, halogen, nitro, cyano, hydroxy, —C(O)—O—$C_{1-6}$-alkyl, carboxy, —$C_{1-6}$-alkyl-C(O)—O—$C_{1-6}$-alkyl, carboxy-$C_{1-6}$-alkyl, —CF$_3$, —S(O)$_2$CH$_3$, or —S(O)$_2$NH$_2$; and R$^{28}$ is $C_{1-6}$-alkyl, carboxy-$C_{1-6}$-alkyl, —$C_{1-6}$-alkyl-C(O)—O—$C_{1-6}$-alkyl, $C_{3-8}$-cycloalkyl, aryl, aryl-$C_{1-6}$-alkyl, heteroaryl optionally substituted with $C_{1-6}$-alkyl, —NH$_2$, or —N(CH$_3$)$_2$; and R$^{29}$ is halogen, nitro, cyano, hydroxy, carboxy, oxo, —CF$_3$, $C_{1-6}$-alkyl, or $C_{1-6}$-alkoxy; or R$^3$, R$^4$, R$^5$, R$^6$, R$^{30}$, R$^{31}$, R$^{32}$ and R$^{33}$ are independently selected from the group consisting of halogen, nitro, cyano, hydroxy, oxo, carboxy, —CF$_3$; or —NR$^{10}$R$^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, arylthio, heteroarylthio, $C_{3-8}$-cycloalkylthio, aryl-$C_{1-6}$-alkylthio, heteroaryl-$C_{1-6}$-alkylthio, $C_{1-6}$-alkylsulfenyl, $C_{3-6}$-cycloalkyl-$C_{1-6}$-alkylthio, $C_{1-6}$-alkyl-C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from R$^{12}$; or —C(O)—R$^{27}$, —S(O)$_2$—R$^{27}$, —C(O)—NR$^{13}$R$^{14}$, —S(O)$_2$—NR$^{13}$R$^{14}$, —$C_{1-6}$-alkyl-C(O)—NR$^{13}$R$^{14}$; or two substituents selected from R$^3$, R$^4$, R$^5$ and R$^6$ or R$^{30}$, R$^{31}$, R$^{32}$ and R$^{33}$ attached to the same or adjacent atoms together form a radical —O—(CH$_2$)$_{1-3}$—O—; and R$^{10}$ and R$^{11}$ independently represent hydrogen, $C_{1-6}$-alkyl, —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —S(O)$_2$—$C_{1-6}$-alkyl, or aryl; and R$^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{2-6}$-alkenyl, aryl, aryl-$C_{1-6}$-alkyl, aryloxy-$C_{1-6}$-alkyl, aryl-$C_{2-6}$-alkenyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $C_{1-6}$-alkylthio-$C_{1-6}$-alkyl, R$^{10}$HN—$C_{1-6}$-alkyl, R$^{10}$R$^{11}$—N—$C_{1-6}$-alkyl, R$^{10}$R$^{11}$—N—$C_{2-6}$-alkenyl, R$^{10}$R$^{11}$—N—S(O)$_2$—$C_{1-6}$-alkyl, R$^{10}$R$^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-S(O)$_2$—NH—$C_{1-6}$-alkyl, aryl-S(O)$_2$—NH—$C_{1-6}$-alkyl, heteroaryl-S(O)$_2$—NH—$C_{1-6}$-alkyl, or $C_{3-8}$-cycloalkyl-S(O)$_2$—NH—$C_{1-6}$-alkyl, each of which is optionally substituted with one or more substituents independently selected from R$^{12}$; and R$^{12}$ is halogen, cyano, hydroxy, —C(O)—O—$C_{1-6}$-alkyl, carboxy, —CF$_3$, $C_{1-6}$-alkyl, $C_{1-6}$-alkoxy, —NR$^{10}$R$^{11}$, —S(O)$_2$CH$_3$, or —S(O)$_2$NH$_2$; and R$^{13}$ and R$^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from R$^{15}$; or R$^{13}$ and R$^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur; and R$^{15}$ is halogen, cyano, hydroxy, carboxy, —CF$_3$, $C_{1-6}$-alkyl, —S(O)$_2$CH$_3$, or —S(O)$_2$NH$_2$; and A must have at least one substituent selected from R$^7$, R$^8$ and R$^9$; and At least one of R$^7$, R$^8$ and R$^9$ is independently selected from $C_{1-6}$-alkoxy, $C_{1-6}$-alkylthio, $C_{2-6}$-alkenylthio each of which is substituted with one or more substituents independently selected from R$^{16}$; or —NR$^{19}$R$^{20}$, —$C_{1-6}$-alkyl-NR$^{19}$R$^{20}$, —$C_{2-6}$-alkenyl-NR$^{19}$R$^{20}$, —$C_{1-6}$-alkyl-S—R$^{21}$, —$C_{1-6}$-alkyl-S(O)—R$^{21}$, —$C_{1-6}$-alkyl-S(O)$_2$—R$^{21}$, —S(O)$_2$—R$^{21}$—S(O)$_2$—NR$^{19}$R$^{20}$ or —S(O)$_2$NR$^{19}$($C_{1-6}$-alkyl-C(O)NR$^{22}$R$^{23}$), wherein each alkyl part may be substituted with one or more substituents independently selected from R$^{25}$;

If more than one R$^7$, R$^8$ and R$^9$ is present, that additional one or more of R$^7$, R$^8$ and R$^9$ may be independently selected from halogen, carboxy, cyano, nitro, hydroxy, —CF$_3$, —SCN; or $C_{1-6}$-alkyl, $C_{2-6}$-alkenyl, $C_{2-6}$-alkynyl, $C_{1-6}$-alkoxy, $C_{1-6}$-alkylthio, $C_{2-6}$-alkenylthio, $C_{1-6}$-alkylamino, $C_{1-6}$-alkylsulfenyl, —C(O)—O—$C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, carboxy-$C_{1-6}$-alkyl, or hydroxy-$C_{1-6}$-alkyl, each of which is optionally substituted with one or more substituents independently selected from R$^{40}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, heteroaryl-oxy-$C_{1-6}$-alkyl, aryloxy, heteroaryloxy, arylthio, heteroarylthio, aryl-$C_{1-6}$-alkylamino, —C(O)-aryl, or —C(O)-heteroraryl, each of which is optionally substituted on the aryl or heteroaryl part with one or more substituents independently selected from R$^{41}$; or $C_{3-8}$-cycloalkyl, $C_{3-8}$-cycloalkenyl, $C_{3-8}$-cycloalkylthio, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from R$^{42}$; or $C_{3-8}$-heterocyclyl, $C_{3-8}$-heterocyclyl-$C_{1-6}$-alkyl, $C_{3-8}$-heterocyclyl-$C_{1-6}$-alkylthio, $C_{3-8}$-heterocyclylthio, $C_{3-8}$-heterocyclyl-amino-$C_{1-6}$-alkyl, or —C(O)—$C_{3-8}$-heterocyclyl, each of which is optionally substituted with one or more substituents independently selected from R$^{40}$; or —NR$^{43}$R$^{44}$, —$C_{1-6}$-alkyl-NR$^{43}$R$^{44}$, —$C_{2-6}$-alkenyl-NR$^{43}$R$^{44}$, —$C_{1-6}$-alkyl-S—R$^{45}$—$C_{1-6}$-alkyl-S(O)—R$^{45}$, —$C_{1-6}$-alkyl-S(O)$_2$—R$^{45}$, —S(O)$_2$—R$^{45}$, —S(O)$_2$—N(R$^{43}$)($C_{1-6}$-alkyl-C(O)NR$^{46}$R$^{47}$) or —S(O)$_2$—NR$^{43}$R$^{44}$, wherein each alkyl part may be substituted with one or more substituents independently selected from R$^{49}$; or —C(O)NR$^{46}$R$^{47}$, —$C_{1-6}$-alkyl-C(O)NR$^{46}$R$^{47}$—$C_{1-6}$-alkyl-NH—NR$^{46}$R$^{47}$—$C_{1-6}$-alkyl-NH—C(O)—

$C_{1-6}$-alkyl-NNR$^{46}$R$^{47}$, each optionally substituted with one or more substituents independently selected from R$^{50}$; and R$^{16}$ is —NR$^{19}$R$^{20}$, —NHS(O)$_2$CF$_3$, —NHS(O)$_2$CH$_2$CF$_3$, —C(O)NR$^{19}$R$^{20}$, —S(O)$_2$C$_{1-6}$-alkyl, —S(O)$_2$CF$_3$, —S(O)$_2$CH$_2$CF$_3$, or —S(O)$_2$NR$^{19}$R$^{20}$; and R$^{19}$ represents hydrogen, $C_{1-6}$-alkyl, $C_{2-6}$-alkenyl, $C_{3-8}$-cycloalkyl, $C_{3-8}$-cycloalkyl-$C_{1-6}$-alkyl, hydroxy-$C_{1-6}$-alkyl, hydroxy-$C_{2-6}$-alkenyl, carboxy-$C_{1-6}$-alkyl, aryl, heteroaryl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-NR$^{22}$R$^{23}$, or —S(O)$_2$—$C_{1-6}$-alkyl, each of which is optionally substituted with one or more substituents independently selected from R$^{24}$; and R$^{20}$ represents $C_{2-6}$-alkenyl, $C_{3-8}$-cycloalkyl, $C_{3-8}$-cycloalkyl-$C_{1-6}$-alkyl each of which is optionally substituted with one or more substituents independently selected from R$^{24}$; and R$^{21}$ is selected from
$C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-NR$^{22}$R$^{23}$ which is substituted with one or more substituents independently selected from R$^{24}$; and R$^{22}$ and R$^{23}$ are independently selected from hydrogen, $C_{1-6}$-alkyl, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-S(O)$_2$—$C_{1-6}$-alkyl, $C_{3-8}$-cycloalkyl, aryl, or heteroaryl; or R$^{22}$ and R$^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from R$^{24}$; and R$^{24}$ is halogen, nitro, cyano, hydroxy, carboxy, oxo, —CF$_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, —C(O)-heteroaryl, —C(O)—$C_{3-8}$-heterocyclyl-C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —$C_{1-6}$-alkyl-C(O)—$C_{3-8}$-heterocyclyl, —C(O)—O—$C_{1-6}$-alkyl-aryl, —NH—S(O)$_2$R$^2$, or —S(O)$_2$R$^{28}$, wherein each cyclic moiety is optionally substituted with one or more substituents independently selected from R$^{29}$; and R$^{25}$ is $C_{1-6}$-alkyl, halogen, nitro, cyano, hydroxy, —C(O)—O—$C_{1-6}$-alkyl, carboxy, —$C_{1-6}$-alkyl-C(O)—O—$C_{1-6}$-alkyl, carboxy-$C_{1-6}$-alkyl, —CF$_3$, —S(O)$_2$CH$_3$, or —S(O)$_2$NH$_2$; and R$^{28}$ is $C_{1-6}$-alkyl, carboxy-$C_{1-6}$-alkyl, —$C_{1-6}$-alkyl-C(O)—O—$C_{1-6}$-alkyl, $C_{3-8}$-cycloalkyl, aryl, aryl-$C_{1-6}$-alkyl, heteroaryl optionally substituted with $C_{1-6}$-alkyl, —NH$_2$, or —N(CH$_3$)$_2$; and R$^{29}$ is halogen, nitro, cyano, hydroxy, carboxy, oxo, —CF$_3$, $C_{1-6}$-alkyl, or $C_{1-6}$-alkoxy; and R$^{40}$, R$^{41}$, and R$^{42}$ are independently $C_{1-6}$-alkyl, halogen, nitro, cyano, hydroxy, carboxy, oxo, —CF$_3$, carboxy-$C_{1-6}$-alkyl, hydroxy-$C_{1-6}$-alkyl, —$C_{1-6}$-alkyl-C(O)—O—$C_{1-6}$-alkyl, —$C_{1-6}$-alkyl-C(O)—NR$^{43}$R$^{44}$, —C(O)—O—$C_{1-6}$-alkyl, —C(O)—$C_{1-6}$-alkyl-C(O)—$C_{1-6}$-alkyl, —NR$^{43}$R$^{44}$, —NHS(O)$_2$$C_{1-6}$-alkyl, —NHS(O)$_2$CF$_3$, —NHS(O)$_2$CH$_2$CF$_3$, —C(O)NR$^{43}$R$^{44}$, —S(O)$_2$$C_{1-6}$-alkyl, —S(O)$_2$CF$_3$, —S(O)$_2$CH$_2$CF$_3$ or —S(O)$_2$NR$^{43}$R$^{44}$; and R$^{43}$ and R$^{44}$ independently represent hydrogen, $C_{1-6}$-alkyl, $C_{2-6}$-alkenyl, $C_{3-8}$-cycloalkyl, $C_{3-8}$-cycloalkyl-$C_{1-6}$-alkyl, hydroxy-$C_{1-6}$-alkyl, carboxy-$C_{1-6}$-alkyl, aryl, heteroaryl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-NR$^{46}$R$^{47}$, or —S(O)$_2$—$C_{1-6}$-alkyl, each of which is optionally substituted with one or more substituents independently selected from R$^{48}$, or R$^{43}$ and R$^{44}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from R$^{43}$; and R$^{45}$ is selected from
$C_{1-6}$-alkyl, $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-NR$^{46}$R$^{47}$; or
aryl, heteroaryl, aryl-$C_{1-6}$-alkyl, or heteroaryl-$C_{1-6}$-alkyl, wherein the aryl or heteroaryl part is optionally substituted with one or more substituents independently selected from R$^{48}$; or
$C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl; and R$^{46}$ and R$^{47}$ are independently selected from hydrogen, $C_{1-6}$-alkyl, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-S(O)$_2$—$C_{1-6}$-alkyl, $C_{3-8}$-cycloalkyl, aryl, or heteroaryl; or R$^{46}$ and R$^{47}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from R$^{48}$; and R$^{48}$ is halogen, nitro, cyano, hydroxy, carboxy, oxo, —CF$_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, —C(O)-heteroaryl, —C(O)—$C_{3-8}$-heterocyclyl-C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —$C_{1-6}$-alkyl-C(O)—$C_{3-8}$-heterocyclyl, —C(O)—O—$C_{1-6}$-alkyl-aryl, —NH—S(O)$_2$R$^{52}$, or —S(O)$_2$R$^{52}$, wherein each cyclic moiety is optionally substituted with one or more substituents independently selected from R$^{53}$; and R$^{49}$ and R$^{50}$ are independently $C_{1-6}$-alkyl, halogen, nitro, cyano, hydroxy, —C(O)—O—$C_{1-6}$-alkyl, carboxy, —$C_{1-6}$-alkyl-C(O)—O—$C_{1-6}$-alkyl, carboxy-$C_{1-6}$-alkyl, —CF$_3$, —S(O)$_2$CH$_3$, or —S(O)$_2$NH$_2$; and R$^{52}$ is $C_{1-6}$-alkyl, carboxy-$C_{1-6}$-alkyl, —$C_{1-6}$-alkyl-C(O)—O—$C_{1-6}$-alkyl, $C_{3-8}$-cycloalkyl, aryl, aryl-$C_{1-6}$-alkyl, heteroaryl optionally substituted with $C_{1-6}$-alkyl, —NH$_2$, or —N(CH$_3$)$_2$; and R$^{53}$ is halogen, nitro, cyano, hydroxy, carboxy, oxo, —CF$_3$, $C_{1-6}$-alkyl, or $C_{1-6}$-alkoxy;

as well as any salt hereof with a pharmaceutically acceptable acid or base, or any optical isomer or mixture of optical isomers, including a racemic mixture, or any tautomeric forms

EMBODIMENT 2

A compound according to embodiment 1 wherein $R^1$ is $C_{3-8}$-cycloalkyl, $C_{3-8}$-cycloalkenyl, indanyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

EMBODIMENT 3

A compound according to any one of the embodiments 1 to 2 wherein $R^1$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norbonyl, norcaryl, adamantyl, indanyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

EMBODIMENT 4

A compound according to embodiment 3 wherein $R^1$ is cyclopropyl, cyclobutyl, cyclopentyl, cyclohexyl, cyclohexenyl, cycloheptyl, bicyclo[3.2.1]octyl, bicyclo[2.2.1]heptyl, adamantyl, indanyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

EMBODIMENT 5

A compound according to embodiment 4 wherein $R^1$ is cyclopentyl, cyclohexyl, cyclohexenyl, cycloheptyl, bicyclo[2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

EMBODIMENT 6

A compound according to embodiment 5 wherein $R^1$ is selected from

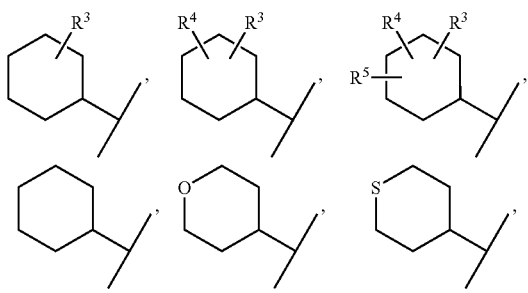

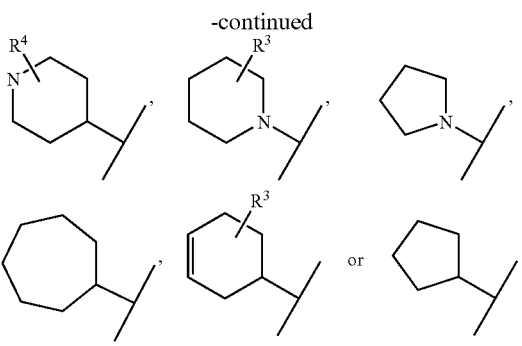

EMBODIMENT 7

A compound according to embodiment 6 wherein $R^1$ is selected from

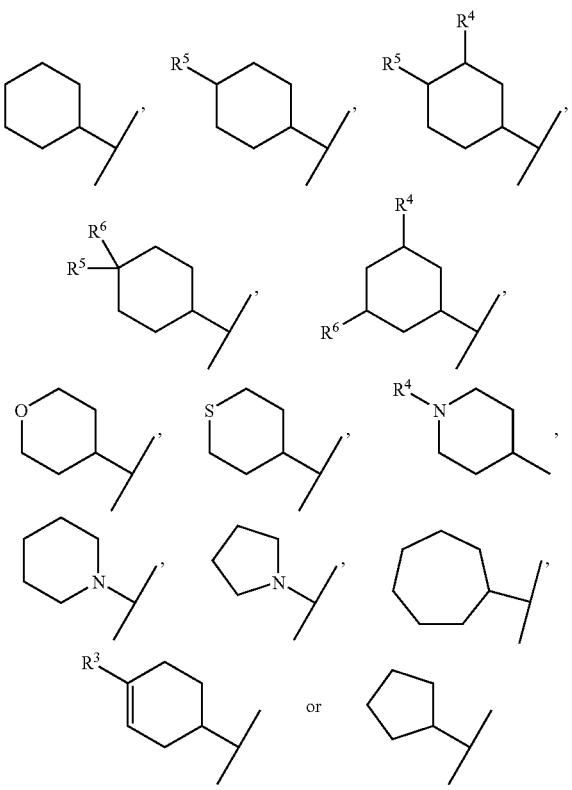

EMBODIMENT 8

A compound according to embodiment 7 wherein $R^1$ is selected from

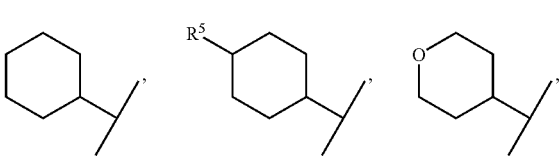

-continued

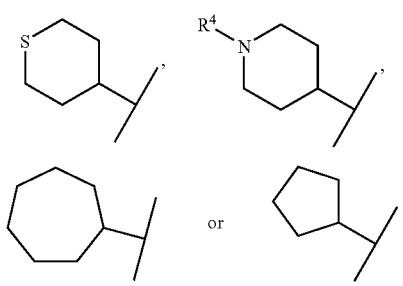

EMBODIMENT 9

A compound according to embodiment 8 wherein $R^1$ is selected from

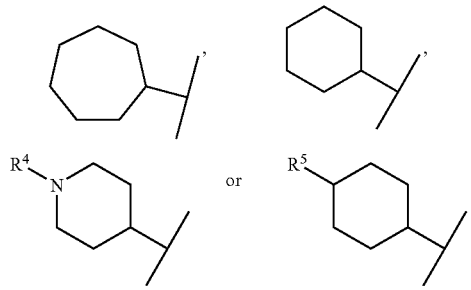

EMBODIMENT 10

A compound according to embodiment 9 wherein $R^1$ is selected from

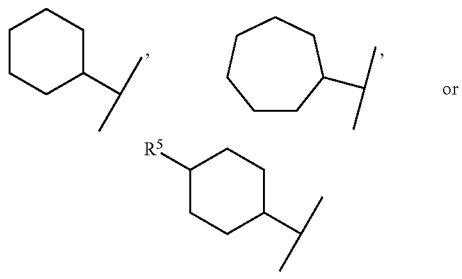

EMBODIMENT 11

A compound according to embodiment 10 wherein $R^1$ is

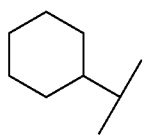

EMBODIMENT 12

A compound according to embodiment 10 wherein $R^1$ is

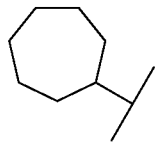

EMBODIMENT 13

A compound according to embodiment 10 wherein $R^1$ is

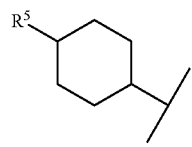

EMBODIMENT 14

A compound according to any one of the embodiments 1 to 13 wherein $R^2$ is $C_{3-8}$-cycloalkyl, $C_{3-8}$-cycloalkenyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

EMBODIMENT 15

A compound according to embodiment 14 wherein $R^2$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norbonyl, norcaryl, adamantyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

EMBODIMENT 16

A compound according to embodiment 15 wherein $R^2$ is cyclopropyl, cyclobutyl, cyclopentyl, cyclohexyl, cyclohexenyl, bicyclo[3.2.1]octyl, bicyclo[2.2.1]heptyl, adamantyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

EMBODIMENT 17

A compound according to embodiment 16 wherein $R^2$ is cyclopentyl, cyclohexyl, cyclohexenyl, bicyclo[2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

EMBODIMENT 18
A compound according to embodiment 17 wherein $R^2$ is selected from
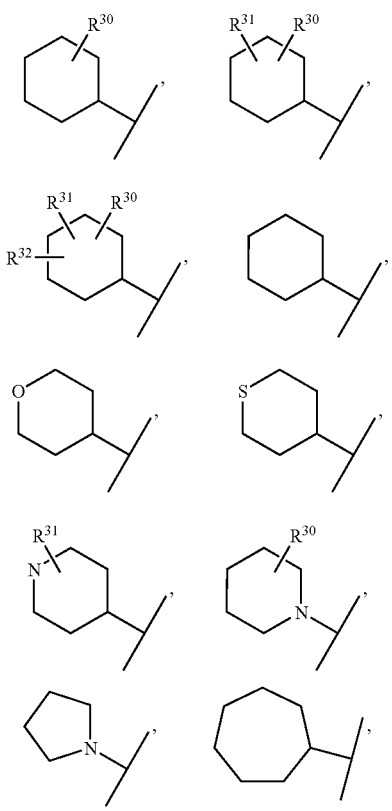
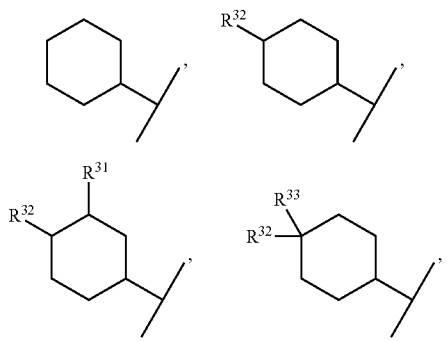
EMBODIMENT 19
A compound according to embodiment 17 wherein $R^2$ is selected from
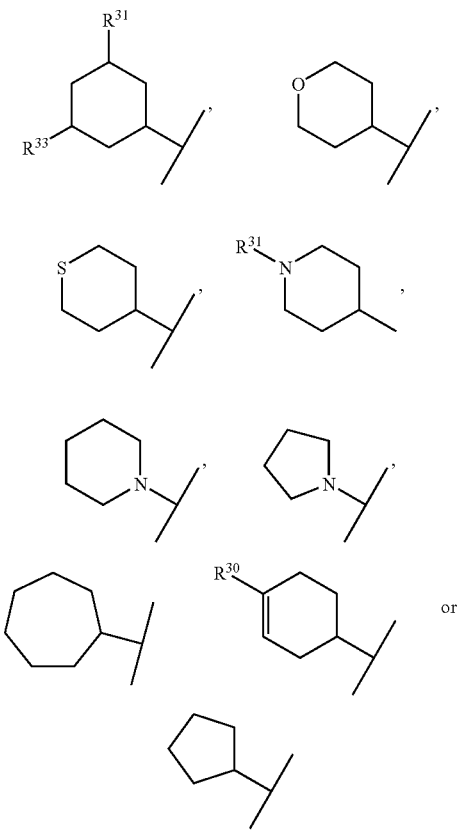
EMBODIMENT 20
A compound according to embodiment 19 wherein $R^2$ is selected from
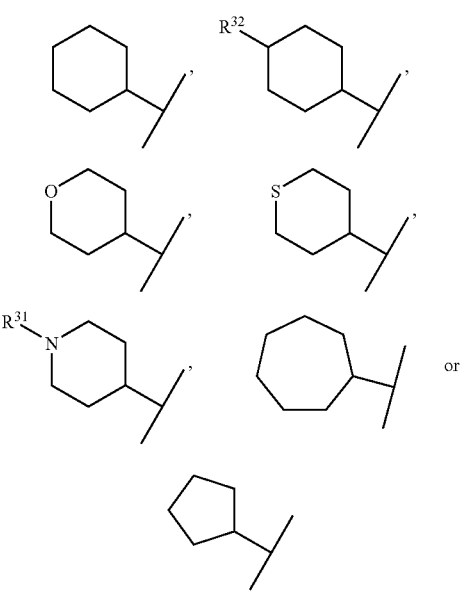

EMBODIMENT 21

A compound according to embodiment 20 wherein $R^2$ is selected from

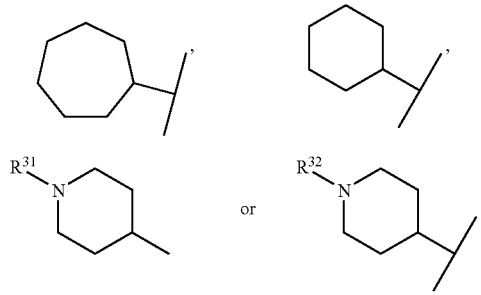

EMBODIMENT 22

A compound according to embodiment 21 wherein $R^2$ is selected from

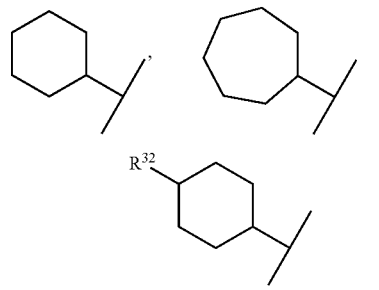

EMBODIMENT 23

A compound according to embodiment 22 wherein $R^2$ is

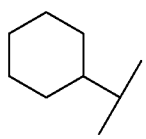

EMBODIMENT 24

A compound according to embodiment 22 wherein $R^2$ is

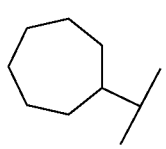

EMBODIMENT 25

A compound according to embodiment 22 wherein $R^2$ is

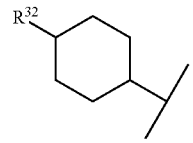

EMBODIMENT 26

A compound according to any one of the embodiments 1 to 25 wherein $R^1$ is

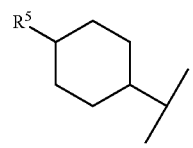

and $R^2$ is cycloheptyl.

EMBODIMENT 27

A compound according to any one of the embodiments 1 to 25 wherein $R^1$ is

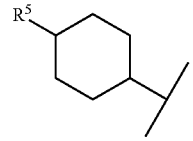

and $R^2$ is cyclohexyl.

EMBODIMENT 28

A compound according to any one of the embodiments 1 to 27 wherein A is thiazolyl, thiadiazolyl, pyrazinyl, pyridyl, benzothiazolyl, 5,6-dihydro-4H-cyclopentathiazolyl, 4,5,6,7-tetrahydro-benzothiazolo-pyridyl, 6,7-dihydro-pyranothiazolyl, or 4,5,6,7-tetrahydrobenzothiazolyl optionally substituted with one or more substituents independently selected from $R^7$, $R^8$ and $R^9$.

EMBODIMENT 29

A compound according to embodiment 28 wherein A is

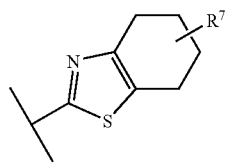

EMBODIMENT 30

A compound according to embodiment 28 wherein A is thiazolyl or thiadiazolyl optionally substituted with one or more substituents independently selected from $R^7$, $R^8$ and $R^9$.

EMBODIMENT 31

A compound according to embodiment 30 wherein A is thiazolyl, 1,2,4-thiadiazolyl, or 1,3,4-thiadiazolyl, optionally substituted with one or more substituents independently selected from $R^7$, $R^8$ and $R^9$.

EMBODIMENT 32

A compound according to embodiment 31 wherein A is

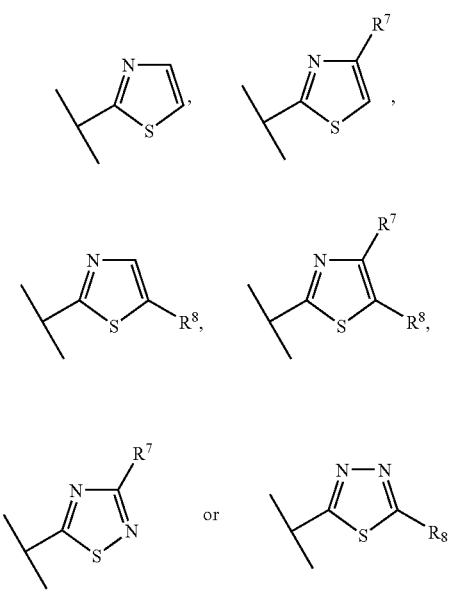

EMBODIMENT 33

A compound according to embodiment 32 wherein A is

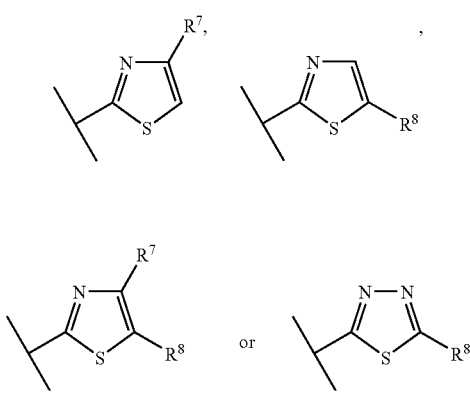

EMBODIMENT 34

A compound according to embodiment 33 wherein A is

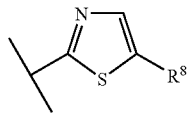

EMBODIMENT 35

A compound according to any one of the embodiments 1 to 34 wherein at least one of $R^3$, $R^4$, $R^5$, $R^6$, $R^{30}$, $R^{31}$, $R^{32}$ and $R^{33}$ is independently selected from the group consisting of $C_{3-8}$-cycloalkyl-$C_{3-6}$-alkenyl, aryl-$C_{2-6}$-alkenyl, $C_{3-6}$-alkenyloxy, $C_{3-8}$-cycloalkyl-$C_{3-6}$-alkenyloxy, aryl-$C_{3-6}$-alkenyloxy, $C_{3-8}$-cycloalkenyl-$C_{1-6}$-alkoxy, $C_{3-8}$-heterocyclyl-$C_{1-6}$-alkoxy, $C_{3-8}$-heterocyclyl-$C_{3-6}$-alkenyloxy, $C_{1-6}$-alkoxy-$C_{3-6}$-alkenyloxy, $C_{3-8}$-alkenyloxy-$C_{1-6}$-alkoxy, aryloxy-$C_{1-6}$-alkyl, aryloxy-$C_{3-6}$-alkenyl, aryl-$C_{1-6}$-alkyloxy-$C_{1-6}$-alkyl, aryl-$C_{3-6}$-alkenyloxy-$C_{1-6}$-alkyl, heteroaryl-$C_{1-6}$-alkyloxy-$C_{1-6}$-alkyl, aryl-$C_{3-6}$-alkenyloxy-$C_{1-6}$-alkyl, aryl-$C_{1-6}$-alkyloxy-$C_{3-6}$-alkenyl, $C_{3-8}$-cycloalkyl-$C_{1-6}$-alkyloxy-$C_{1-6}$-alkyl, $C_{3-8}$-cycloalkyl-$C_{3-6}$-alkenyloxy-$C_{1-6}$-alkyl, $C_{3-8}$-cycloalkyl-$C_{1-6}$-alkyloxy-$C_{3-6}$-alkenyl, $C_{3-8}$-heterocyclyl-$C_{1-6}$-alkyloxy-$C_{1-6}$-alkyl, $C_{3-8}$-heterocyclyl-$C_{3-6}$-alkenyloxy-$C_{1-6}$-alkyl, $C_{3-8}$-heterocyclyl-$C_{1-6}$-alkyloxy-$C_{3-6}$-alkenyl, $C_{3-6}$-alkenylthio, $C_{3-8}$-cycloalkyl-$C_{3-6}$-alkenylthio, aryl-$C_{3-6}$-alkenylthio, heteroaryl-$C_{3-6}$-alkenylthio, $C_{3-8}$-cycloalkenyl-$C_{1-6}$-alkylthio, $C_{3-8}$-heterocyclyl-$C_{1-6}$-alkylthio, $C_{1-6}$-alkylthio-$C_{3-6}$-alkenyloxy, $C_{1-6}$-alkoxy-$C_{3-6}$-alkenylthio, $C_{3-8}$-alkenylthio-$C_{1-6}$-alkoxy, $C_{3-8}$-alkenyloxy-$C_{1-6}$-alkylthio, arylthio-$C_{1-6}$-alkyl, arylthio-$C_{3-6}$-alkenyl, heteroaryloxy-$C_{1-6}$-alkyl, heteroarylthio-$C_{1-6}$-alkyl, heteroarylthio-$C_{3-6}$-alkenyl, aryl-$C_{1-6}$-alkylthio-$C_{1-6}$-alkyl, aryl-$C_{3-6}$-alkenylthio-$C_{1-6}$-alkyl, aryl-$C_{1-6}$-alkylthio-$C_{3-6}$-alkenyl, heteroaryl-$C_{1-6}$-alkylthio-$C_{1-6}$-alkyl, heteroaryl-$C_{3-6}$-alkenylthio-$C_{1-6}$-alkyl, heteroaryl-$C_{1-6}$-alkylthio-$C_{3-6}$-alkenyl, $C_{3-8}$-cycloalkyl-$C_{1-6}$-alkylthio-$C_{1-6}$-alkyl, $C_{3-8}$-cycloalkyl-$C_{3-6}$-alkenylthio-$C_{1-6}$-alkyl, $C_{3-8}$-cycloalkyl-$C_{1-6}$-alkylthio-$C_{3-6}$-alkenyl, $C_{3-8}$-heterocyclyl-$C_{1-6}$-alkylthio-$C_{1-6}$-alkyl, $C_{3-8}$-heterocyclyl-$C_{3-6}$-alkenylthio-$C_{1-6}$-alkyl, $C_{3-8}$-heterocyclyl-$C_{1-6}$-alkylthio-$C_{3-6}$-alkenyl, each of which is optionally substituted with one or more substituents independently selected from $R^{12}$.

EMBODIMENT 36

A compound according to embodiment 35 wherein at least one of $R^3$, $R^4$, $R^5$, $R^6$, $R^{30}$, $R^{31}$, $R^{32}$ and $R^{33}$ is independently selected from the group consisting of $C_{3-8}$-cycloalkyl-$C_{3-6}$-alkenyl, aryl-$C_{2-6}$-alkenyl, $C_{3-6}$-alkenyloxy, $C_{3-8}$-cycloalkyl-$C_{3-6}$-alkenyloxy, aryl-$C_{3-6}$-alkenyloxy, $C_{3-8}$-cycloalkenyl-$C_{1-6}$-alkoxy, $C_{3-8}$-heterocyclyl-$C_{1-6}$-alkoxy, $C_{3-8}$-heterocyclyl-$C_{3-6}$-alkenyloxy, $C_{1-6}$-alkoxy-$C_{3-6}$-alkenyloxy, $C_{3-8}$-alkenyloxy-$C_{1-6}$-alkoxy, aryloxy-$C_{1-6}$-alkyl, aryloxy-$C_{3-6}$-alkenyl, aryl-$C_{1-6}$-alkyloxy-$C_{1-6}$-alkyl, heteroaryl-$C_{1-6}$-alkyloxy-$C_{1-6}$-alkyl, aryl-$C_{3-6}$-alkenyloxy-$C_{1-6}$-alkyl, aryl-$C_{1-6}$-alkyloxy-$C_{3-6}$-alkenyl, $C_{3-8}$-cycloalkyl-$C_{1-6}$-alkyloxy-$C_{1-6}$-alkyl, $C_{3-8}$-cycloalkyl-$C_{3-6}$-alkenyloxy-$C_{1-6}$-alkyl, $C_{3-8}$-cycloalkyl-$C_{1-6}$-alkyloxy-$C_{3-6}$-alkenyl, $C_{3-8}$-heterocyclyl-$C_{1-6}$-alkyloxy-$C_{1-6}$-alkyl, $C_{3-8}$-heterocyclyl-$C_{3-6}$-alkenyloxy-$C_{1-6}$-alkyl, $C_{3-8}$-heterocyclyl-$C_{1-6}$-alkyloxy-$C_{3-6}$-alkenyl, heteroaryloxy-$C_{1-6}$-alkyl, $C_{3-6}$-alkenylthio, $C_{3-8}$- cycloalkyl-$C_{3-6}$-alkenylthio, aryl-$C_{3-6}$-alkenylthio, $C_{3-8}$-cycloalkenyl-$C_{1-6}$-alkylthio, $C_{3-8}$-heterocyclyl-$C_{1-6}$-alkylthio, $C_{1-6}$-alkylthio-$C_{3-6}$-alkenyloxy, $C_{1-6}$-alkoxy-$C_{3-6}$-alkenylthio, $C_{3-8}$-alkenylthio-$C_{1-6}$-alkoxy, $C_{3-8}$-alkenyloxy-$C_{1-6}$-alkylthio, arylthio-$C_{1-6}$-alkyl, arylthio-$C_{3-6}$-alkenyl, aryl-$C_{1-6}$-alkylthio-$C_{1-6}$-alkyl, aryl-$C_{3-6}$-alkenylthio-$C_{1-6}$-alkyl, aryl-$C_{1-6}$-alkylthio-$C_{3-6}$-alkenyl, $C_{3-8}$-cycloalkyl-$C_{1-6}$-alkylthio-$C_{1-6}$-alkyl, $C_{3-8}$-cycloalkyl-$C_{3-6}$-alkenylthio-$C_{1-6}$-alkyl, $C_{3-8}$-cycloalkyl-$C_{1-6}$-alkylthio-$C_{3-6}$-alkenyl, $C_{3-8}$-heterocyclyl-$C_{1-6}$-alkylthio-$C_{1-6}$-alkyl, $C_{3-8}$-heterocyclyl-$C_{3-6}$-alkenylthio-$C_{1-6}$-alkyl, $C_{3-8}$-heterocyclyl-$C_{1-6}$-alkylthio-$C_{3-6}$-alkenyl, each of which is optionally substituted with one or more substituents independently selected from $R^{12}$.

EMBODIMENT 37

A compound according to embodiment 36 wherein at least one of $R^3$, $R^4$, $R^5$, $R^6$, $R^{30}$, $R^{31}$, $R^{32}$ and $R^{33}$ is independently selected from the group consisting of $C_{3-8}$-cycloalkyl-$C_{3-6}$-alkenyl, aryl-$C_{2-6}$-alkenyl, $C_{3-6}$-alkenyloxy, $C_{3-8}$-cycloalkyl-$C_{3-6}$-alkenyloxy, aryl-$C_{3-6}$-alkenyloxy, $C_{3-8}$-cycloalkenyl-$C_{1-6}$-alkoxy, $C_{3-8}$-heterocyclyl-$C_{1-6}$-alkoxy, $C_{3-8}$-heterocyclyl-$C_{3-6}$-alkenyloxy, $C_{1-6}$-alkoxy-$C_{3-6}$-alkenyloxy, $C_{3-8}$-alkenyloxy-$C_{1-6}$-alkoxy, aryloxy-$C_{1-6}$-alkyl, aryloxy-$C_{3-6}$-alkenyl, aryl-$C_{1-6}$-alkyloxy-$C_{1-6}$-alkyl, heteroaryl-$C_{1-6}$-alkyloxy-$C_{1-6}$-alkyl, aryl-$C_{3-6}$-alkenyloxy-$C_{1-6}$-alkyl, aryl-$C_{1-6}$-alkyloxy-$C_{3-6}$-alkenyl, $C_{3-8}$-cycloalkyl-$C_{1-6}$-alkyloxy-$C_{1-6}$-alkyl, $C_{3-8}$-cycloalkyl-$C_{3-6}$-alkenyloxy-$C_{1-6}$-alkyl, $C_{3-8}$-cycloalkyl-$C_{1-6}$-alkyloxy-$C_{3-6}$-alkenyl, $C_{3-8}$-heterocyclyl-$C_{1-6}$-alkyloxy-$C_{1-6}$-alkyl, $C_{3-8}$-heterocyclyl-$C_{3-6}$-alkenyloxy-$C_{1-6}$-alkyl, $C_{3-8}$-heterocyclyl-$C_{1-6}$-alkyloxy-$C_{3-6}$-alkenyl, $C_{3-6}$-alkenylthio, $C_{3-8}$-cycloalkyl-$C_{3-6}$-alkenylthio, aryl-$C_{3-6}$-alkenylthio, $C_{3-8}$-cycloalkenyl-$C_{1-6}$-alkylthio, $C_{3-8}$-heterocyclyl-$C_{1-6}$-alkylthio, $C_{1-6}$-alkylthio-$C_{3-6}$-alkenyloxy, $C_{1-6}$-alkoxy-$C_{3-6}$-alkenylthio, $C_{3-8}$-alkenylthio-$C_{1-6}$-alkoxy, $C_{3-8}$-alkenyloxy-$C_{1-6}$-alkylthio, arylthio-$C_{1-6}$-alkyl, arylthio-$C_{3-6}$-alkenyl, aryl-$C_{1-6}$-alkylthio-$C_{1-6}$-alkyl, aryl-$C_{3-6}$-alkenylthio-$C_{1-6}$-alkyl, aryl-$C_{1-6}$-alkylthio-$C_{3-6}$-alkenyl, $C_{3-8}$-cycloalkyl-$C_{1-6}$-alkylthio-$C_{1-6}$-alkyl, $C_{3-8}$-cycloalkyl-$C_{3-6}$-alkenylthio-$C_{1-6}$-alkyl, $C_{3-8}$-cycloalkyl-$C_{1-6}$-alkylthio-$C_{3-6}$-alkenyl, $C_{3-8}$-heterocyclyl-$C_{1-6}$-alkylthio-$C_{1-6}$-alkyl, $C_{3-8}$-heterocyclyl-$C_{3-6}$-alkenylthio-$C_{1-6}$-alkyl, $C_{3-8}$-heterocyclyl-$C_{1-6}$-alkylthio-$C_{3-6}$-alkenyl, or heteroaryloxy-$C_{1-6}$-alkyl, each of which is optionally substituted with one or more substituents independently selected from $R^{12}$.

EMBODIMENT 38

A compound according to embodiment 37 wherein at least one of $R^3$, $R^4$, $R^5$, $R^6$, $R^{30}$, $R^{31}$, $R^{32}$ and $R^{33}$ is independently selected from the group consisting of $C_{3-6}$-alkenyloxy, aryloxy-$C_{1-6}$-alkyl, $C_{3-8}$-cycloalkyl-$C_{1-6}$-alkyloxy-$C_{1-6}$-alkyl, aryl-$C_{1-6}$-alkyloxy-$C_{1-6}$-alkyl, heteroaryl-$C_{1-6}$-alkyloxy-$C_{1-6}$-alkyl, $C_{3-6}$-alkenylthio, arylthio-$C_{1-6}$-alkyl, $C_{3-8}$-cycloalkyl-$C_{3-6}$-alkylthio-$C_{1-6}$-alkyl, or heteroaryloxy-$C_{1-6}$-alkyl, each of which is optionally substituted with one or more substituents independently selected from $R^{12}$, and wherein each aryl is phenyl and heteroaryl is pyridyl.

EMBODIMENT 39

A compound according to embodiment 38 wherein at least one of $R^3$, $R^4$, $R^5$, $R^6$, $R^{30}$, $R^{31}$, $R^{32}$ and $R^{33}$ is independently selected from the group consisting of $C_{3-6}$-alkenyloxy, phenyloxy-$C_{1-6}$-alkyl, benzyloxy-$C_{1-6}$-alkyl, $C_{3-8}$-cycloalkyl-$C_{1-6}$-alkyloxy-$C_{1-6}$-alkyl.

EMBODIMENT 40

A compound according to embodiment 39 wherein at least one of $R^3$, $R^4$, $R^5$, $R^6$, $R^{30}$, $R^{31}$, $R^{32}$ and $R^{33}$ is independently selected from the group consisting of $C_{3-6}$-alkenyloxy, phenyloxy-methyl, benzyloxy-methyl, or cyclopropyl-methoxymethyl.

EMBODIMENT 41

A compound according to any one of the embodiments 35 to 40 wherein, if more than one of $R^3$, $R^4$, $R^5$, $R^6$, $R^{30}$, $R^{31}$, $R^{32}$ and $R^{33}$ is present, that additional $R^3$, $R^4$, $R^5$, $R^6$, $R^{30}$, $R^{31}$, $R^{32}$ or $R^{33}$ is independently selected from the group consisting of
  halogen, oxo, cyano, hydroxy, carboxy, —$CF_3$; or
    —$NR^{10}R^{11}$; or
  $C_{1-6}$-alkyl, $C_{2-6}$-alkenyl, $C_{3-8}$-cycloalkyl, $C_{3-8}$-cycloalkyl-$C_{1-6}$-alkyl, aryl, aryl-$C_{1-6}$-alkyl, $C_{1-6}$-alkoxy, $C_{3-6}$-cycloalkyl-$C_{1-6}$-alkoxy, aryl-$C_{1-6}$-alkoxy, $C_{1-6}$-alkylthio, arylthio,
    —$C(O)$—$O$—$C_{1-6}$-alkyl, or $C_{1-6}$-alkyl-$C(O)$—$O$—$C_{1-6}$-alkyl, each of which is optionally substituted with one or more substituents independently selected from $R^{12}$; or
    —$C(O)$—$R^{27}$, —$S(O)_2$—$R^{27}$, —$C(O)$—$NR^{13}R^{14}$, —$S(O)_2$—$NR^{13}R^{14}$, —$C_{1-6}$-alkyl-$C(O)$—$NR^{13}R^{14}$; or
  two substituents selected from $R^3$, $R^4$, $R^5$ and $R^6$ or $R^{30}$, $R^{31}$, $R^{32}$ and $R^{33}$ attached to the same or adjacent atoms together form a radical —$O$—$(CH_2)_{1-3}$—$O$—.

EMBODIMENT 42

A compound according to embodiment 41 wherein the additional $R^3$, $R^4$, $R^5$, $R^6$, $R^{30}$, $R^{31}$, $R^{32}$ and $R^{33}$ are independently selected from the group consisting of
  halogen, oxo, —$CF_3$; or
    —$NR^{10}R^{11}$; or
  $C_{1-6}$-alkyl, $C_{3-8}$-cycloalkyl, $C_{1-6}$-alkoxy, $C_{3-6}$-cycloalkyl-$C_{1-6}$-alkoxy, aryl-$C_{1-6}$-alkoxy, $C_{1-6}$-alkylthio, aryl, aryl-$C_{1-6}$-alkyl, arylthio, —$C(O)$—$O$—$C_{1-6}$-alkyl, or $C_{1-6}$-alkyl-$C(O)$—$O$—$C_{1-6}$-alkyl, each of which is optionally substituted with one or more substituents independently selected from $R^{12}$; or
    —$C(O)$—$R^{27}$, —$S(O)_2$—$NR^{13}R^{14}$ or —$S(O)_2$—$R^{27}$; or
  two substituents selected from $R^3$, $R^4$, $R^5$ and $R^6$ or $R^{30}$, $R^{31}$, $R^{32}$ and $R^{33}$ attached to the same or adjacent atoms together form a radical —$O$—$(CH_2)_{1-3}$—$O$—.

EMBODIMENT 43

A compound according to embodiment 42 wherein the additional $R^3$, $R^4$, $R^5$, $R^6$, $R^{30}$, $R^{31}$, $R^{32}$ and $R^{33}$ are independently selected from the group consisting of
  halogen, —$CF_3$; or
  methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, cyclopropyl-methyloxy, benzyloxy, phenylthio, —$C(O)$—$O$—$CH_3$, or —$C(O)$—$O$—$CH_2CH_3$, each of which is optionally substituted with one or more substituents independently selected from $R^{12}$; or
    —$C(O)$—$R^{27}$, —$S(O)_2$—$NR^{13}R^{14}$ or —$S(O)_2$—$R^{27}$; or
  two substituents selected from $R^3$, $R^4$, $R^5$ and $R^6$ or $R^{30}$, $R^{31}$, $R^{32}$ and $R^{33}$ attached to the same or adjacent atoms together form a radical —$O$—$(CH_2)_{1-3}$—$O$—.

EMBODIMENT 44

A compound according to embodiment 43 wherein the additional $R^3$, $R^4$, $R^5$, $R^6$, $R^{30}$, $R^{31}$, $R^{32}$ and $R^{33}$ are independently selected from the group consisting of
halogen, —$CF_3$; or
methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, phenylthio, —C(O)—O—$CH_3$, or —C(O)—O—$CH_2CH_3$, each of which is optionally substituted with one or more substituents independently selected from $R^{12}$; or
—C(O)—$R^{27}$, —S(O)$_2$—$NR^{13}R^{14}$ or —S(O)$_2$—$R^{27}$.

EMBODIMENT 45

A compound according to embodiment 44 wherein the additional $R^3$, $R^4$, $R^5$, $R^6$, $R^{30}$, $R^{31}$, $R^{32}$ and $R^{33}$ are independently selected from the group consisting of F, Cl, —$CF_3$, methyl, ethyl, propyl, isopropyl, butyl, tert-butyl, methoxy, ethoxy, propoxy, —C(O)—$R^{27}$, S(O)$_2$—$NR^{13}R^{14}$ or —S(O)$_2$—$R^{27}$.

EMBODIMENT 46

A compound according to any one of the embodiments 35 to 45 wherein $R^{12}$ is halogen, cyano, hydroxy, carboxy, —$CF_3$, $C_{1-6}$-alkyloxy, $C_{3-8}$-cycloalkyloxy, aryloxy, aryl-$C_{1-6}$-alkyloxy or $C_{1-6}$-alkyl.

EMBODIMENT 47

A compound according to embodiment 46 wherein $R^{12}$ is halogen, cyano, hydroxy, carboxy, —$CF_3$, methoxy, ethoxy, propoxy, cyclopropyloxy, cyclobutyloxy, cyclopentyloxy, cyclohexyloxy, cycloheptyloxy, phenoxy, benzyloxy, phenyl-ethyloxy, phenyl-propoxy, methyl, ethyl or propyl.

EMBODIMENT 48

A compound according to embodiment 47 wherein $R^{12}$ is halogen, carboxy, ethoxy, propoxy, cyclopropyloxy, cyclobutyloxy, cyclopentyloxy, cyclohexyloxy, cycloheptyloxy, phenoxy, benzyloxy, phenyl-ethyloxy, phenyl-propoxy, methyl, ethyl or propyl.

EMBODIMENT 49

A compound according to any one of the embodiments 35 to 48 wherein $R^{10}$ and $R^{11}$ independently represent hydrogen, methyl, ethyl, propyl, —C(O)—$CH_3$, —C(O)—$CH_2CH_3$, —$CH_2C(O)OH$, —$CH_2CH_2C(O)OH$, —C(O)—$CH_2$—C(O)OH, —C(O)—$CH_2CH_2$—C(O)OH, —S(O)$_2CH_3$, or phenyl.

EMBODIMENT 50

A compound according to embodiment 49 wherein $R^{10}$ and $R^{11}$ independently represent hydrogen, methyl, ethyl, —C(O)—$CH_3$, —$CH_2C(O)OH$, —C(O)—$CH_2$—C(O)OH, —S(O)$_2CH_3$, or phenyl.

EMBODIMENT 51

A compound according to embodiment 50 wherein $R^{10}$ and $R^{11}$ independently represent hydrogen, methyl, ethyl, or phenyl.

EMBODIMENT 52

A compound according to any one of the embodiments 35 to 51 wherein $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryl-$C_{2-6}$-alkenyl, heteroaryl, heteroaryl-$C_{1-6}$-alkyl, carboxy-$C_{1-6}$-alkyl, $C_{1-6}$-alkoxy-$C_{1-6}$-alkyl, $C_{1-6}$-alkylthio-$C_{1-6}$-alkyl, $R^{10}HN$—$C_{1-6}$-alkyl, $R^{10}R^{11}N$—$C_{1-6}$-alkyl, $R^{10}R^{11}N$—S(O)$_2$—$C_{1-6}$-alkyl, or $R^{10}R^{11}N$—C(O)—$C_{1-6}$-alkyl, each of which is optionally substituted with one or more substituents independently selected from $R^{12}$.

EMBODIMENT 53

A compound according to embodiment 52 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl-$C_{2-6}$-alkenyl, aryl, heteroaryl, heteroaryl-$C_{1-6}$-alkyl, carboxy-$C_{1-6}$-alkyl, carboxy-$C_{1-6}$-alkyl, $C_{1-6}$-alkoxy-$C_{1-6}$-alkyl, $R^{11}HN$—$C_{1-6}$-alkyl, $R^{10}R^{11}N$—$C_{1-6}$-alkyl, $R^{10}R^{11}N$—S(O)$_2$—$C_{1-6}$-alkyl, or $R^{10}R^{11}N$—C(O)—$C_{1-6}$-alkyl, each of which is optionally substituted with one or more substituents independently selected from $R^{12}$.

EMBODIMENT 54

A compound according to embodiment 53 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl, heteroaryl-$C_{1-6}$-alkyl, aryl-$C_{1-6}$-alkyl, $C_{1-6}$-alkoxy-$C_{1-6}$-alkyl, carboxy-$C_{1-6}$-alkyl, or heteroaryl, each of which is optionally substituted with one or more substituents independently selected from $R^{12}$.

EMBODIMENT 55

A compound according to embodiment 54 wherein $R^{27}$ is methyl, ethyl, propyl, n-butyl, isobutyl, 1,1,1-trifluoroethyl, cyclopropyl, cyclopentyl, cyclopropylmethyl, phenyl, pyridyl, thiophene, imidazole, or thiazole, each of which is optionally substituted with one or more substituents independently selected from $R^{12}$.

EMBODIMENT 56

A compound according to embodiment 55 wherein $R^{27}$ is methyl, ethyl, propyl, n-butyl, isobutyl, 1,1,1-trifluoroethyl, cyclopropyl, cyclopentyl, cyclopropylmethyl, phenyl, or pyridyl, thiophene, imidazole, or thiazole.

EMBODIMENT 57

A compound according to embodiment 56 wherein $R^{27}$ is methyl, ethyl, or propyl

EMBODIMENT 58

A compound according to any one of the embodiments 35 to 57 wherein $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

EMBODIMENT 59

A compound according to embodiment 58 wherein $R^{13}$ and $R^{14}$ are independently selected from the group consisting of hydrogen, methyl, ethyl, propyl, hydroxymethyl, hydroxy-ethyl, carboxy-methyl, carboxy-ethyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

EMBODIMENT 60

A compound according to embodiment 59 wherein $R^{13}$ and $R^{14}$ are independently selected from the group consisting of hydrogen, methyl, ethyl, propyl, or phenyl, each of which is optionally substituted with one or more substituents independently selected from $R^{15}$.

EMBODIMENT 61

A compound according to any one of the embodiments 35 to 60 wherein $R^{15}$ is halogen, cyano, hydroxy, carboxy, —$CF_3$, methyl, ethyl, or propyl.

EMBODIMENT 62

A compound according to embodiment 61 wherein $R^{15}$ is halogen, hydroxy, carboxy, —$CF_3$, methyl, or ethyl.

EMBODIMENT 63

A compound according to any one of the embodiments 1 to 34 wherein $R^7$, $R^8$ and $R^9$ are independently selected from
halogen, carboxy, cyano, nitro, hydroxy, —$CF_3$, —SCN; or
$C_{1-6}$-alkyl, $C_{2-6}$-alkenyl, $C_{1-6}$-alkoxy, $C_{1-6}$-alkylthio, $C_{1-6}$-alkylamino, $C_{1-6}$-alkylsulfenyl, 5-C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, $C_{3-8}$-cycloalkyl-$C_{1-6}$-alkyl, $C_{3-6}$-cycloalkyl-$C_{1-6}$-alkoxy, $C_{3-6}$-cycloalkyl-$C_{1-6}$-alkylthio each of which is optionally substituted with one or more substituents independently selected from $R^{16}$; or
aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, heteroarylthio-$C_{1-6}$-alkyl, aryloxy, heteroaryloxy, heteroarylthio, each of which is optionally substituted on the aryl or heteroaryl part with one or more substituents independently selected from $R^{17}$; or
$C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{18}$; or
$C_{3-8}$-heterocyclyl, $C_{3-8}$-heterocyclyl-$C_{1-6}$-alkyl, $C_{3-8}$-heterocyclylthio, or —C(O)—$C_{3-8}$-heterocyclyl, each of which is optionally substituted with one or more substituents independently selected from $R^{16}$; or
—$NR^{19}R^{20}$, —$C_{1-6}$-alkyl-$NR^{19}R^{20}$, —$C_{1-6}$-alkyl-S—$R^{21}$, —$C_{1-6}$-alkyl-S(O)—$R^{21}$, —$C_{1-6}$-alkyl S(O)$_2$—$R^{21}$, —S(O)$_2$—$R^{21}$, —S(O)$_2$—N($R^{19}$)($C_{1-6}$-alkyl-C(O)$NR^{22}R^{23}$) or —S(O)$_2$—$NR^{19}R^{20}$, wherein each alkyl part may be substituted with one or more substituents independently selected from $R^{25}$; or
—C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

EMBODIMENT 64

A compound according to embodiment 63 wherein $R^7$, $R^8$ and $R^9$ are independently selected from
halogen, carboxy, cyano, or —$CF_3$; or
$C_{1-6}$-alkyl, $C_{2-6}$-alkenyl, $C_{1-6}$-alkoxy, $C_{1-6}$-alkylthio, —C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —$C_{1-6}$-alkoxy-$C_{1-6}$-alkyl, $C_{3-8}$-cycloalkyl-$C_{1-6}$-alkyl, each of which is optionally substituted with one or more substituents independently selected from $R^{16}$; or
aryl, heteroaryl, aryl-$C_{1-6}$-alkyl, heteroaryl-$C_{1-6}$-alkyl, each of which is optionally substituted on the aryl or heteroaryl part with one or more substituents independently selected from $R^{17}$; or
$C_{3-8}$-cycloalkyl, $C_{3-8}$-cycloalkyl-$C_{1-6}$-alkyl, each of which is optionally substituted on the cycloalkyl part with one or more substituents independently selected from $R^{18}$; or
$C_{3-8}$-heterocyclyl, $C_{3-8}$-heterocyclyl-$C_{1-6}$-alkyl, or —C(O)—$C_{3-8}$-heterocyclyl, each of which is optionally substituted with one or more substituents independently selected from $R^{16}$; or
—$NR^{19}R^{20}$, —$C_{1-6}$-alkyl-$NR^{19}R^{20}$, —S(O)$_2$—$R^{21}$, —S(O)$_2$—N($R^{19}$)($C_{1-6}$-alkyl-C(O)$NR^{22}R^{23}$) or
—S(O)$_2$—$NR^{19}R^{20}$, wherein each alkyl part may be substituted with one or more substituents independently selected from $R^{25}$; or
—C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

EMBODIMENT 65

A compound according to embodiment 64 wherein $R^7$, $R^8$ and $R^9$ are independently selected from
halogen, carboxy or —$CF_3$; or
$C_{1-6}$-alkyl, $C_{1-6}$-alkoxy, $C_{1-6}$-alkylthio, —$C_{1-6}$-alkyl-C(O)—O—$C_{1-6}$-alkyl, —$C_{1-6}$-alkyl-O—C(O)—$C_{1-6}$-alkyl or —C(O)—O—$C_{1-6}$-alkyl, each of which is optionally substituted with one or more substituents independently selected from $R^{16}$; or
phenyl, benzyl, or heteroarylthio, wherein heteroaryl is pyridyl or imidazolyl, and wherein each aryl or heteroaryl is optionally substituted on the aryl or heteroaryl part with one or more substituents independently selected from $R^{17}$; or
cyclopropyl, cyclobutyl, cyclopentyl, or cyclohexyl, each of which is optionally substituted on the cycloalkyl part with one or more substituents independently selected from $R^{18}$; or
pyrrolidinyl, piperidyl, piperazinyl, or morpholinyl, each of which is optionally substituted with one or more substituents independently selected from $R^{16}$; or —C(O)NR$^{22}$R$^{23}$, —S(O)$_2$—R$^{21}$, —S(O)$_2$—N(R$^{19}$)(C$_{1-6}$-alkyl-C(O)NR$^{22}$R$^{23}$) or —S(O)$_2$—NR$^{19}$R$^{20}$; or two of R$^7$, R$^8$ and R$^9$ can be taken together to form a C$_{2-5}$-alkylene bridge.

EMBODIMENT 66

A compound according to embodiment 65 wherein R$^7$, R$^8$ and R$^9$ are independently selected from halogen, carboxy, —CF$_3$, —S—CH$_3$, —S—CH$_2$CH$_3$, —S—CH$_2$CH$_2$CH$_3$, methyl, ethyl, propyl, isopropyl, butyl, isobutyl, tert-butyl, methoxy, ethoxy, —CH$_2$—C(O)—O—CH$_3$, —CH$_2$—C(O)—O—CH$_2$CH$_3$, —CH$_2$CH$_2$—C(O)—O—CH$_3$, —CH$_2$CH$_2$—C(O)—O—CH$_2$CH$_3$, —CH$_2$—O—C(O)—CH$_3$, —CH$_2$—O—C(O)—CH$_2$CH$_3$, —CH$_2$CH$_2$—O—C(O)—CH$_3$, —CH$_2$CH$_2$—O—C(O)—CH$_2$CH$_3$, —C(O)—O—CH$_3$, —C(O)—O—CH$_2$CH$_3$, each of which is optionally substituted with one or more substituents independently selected from R$^{16}$; or heteroarylthio, wherein heteroaryl is pyridyl or imidazolyl, each optionally substituted on the heteroaryl part with one or more substituents independently selected from R$^{17}$, or pyrrolidinyl, piperidyl, piperazinyl, or morpholinyl, each of which is optionally substituted with one or more substituents independently selected from R$^{16}$; or —S(O)$_2$—NR$^{19}$R$^{20}$ or —S(O)$_2$—R$^{21}$.

EMBODIMENT 67

A compound according to embodiment 66 wherein R$^7$, R$^8$ and R$^9$ are independently selected from Cl, —S—CH$_3$, —S—CH$_2$CH$_3$, —S—CH$_2$CH$_2$CH$_3$, —S—CH(CH$_3$)$_2$, —S—CH$_2$CH(CH$_3$)$_2$, methyl, or ethyl, each of which is optionally substituted with one or more substituents independently selected from R$^{16}$; —S(O)$_2$—NR$^{19}$R$^{20}$ or —S(O)$_2$—R$^{21}$.

EMBODIMENT 68

A compound according to embodiment 67 wherein R$^7$, R$^8$ and R$^9$ are independently selected from —S—CH$_3$, —S—CH$_2$CH$_3$—S—CH(CH$_3$)$_2$, or —S—CH$_2$CH(CH$_3$)$_2$, each of which is optionally substituted with one or more substituents independently selected from R$^{16}$.

EMBODIMENT 69

A compound according to any one of the embodiments 1 to 68 wherein R$^{16}$, R$^{17}$, and R$^{13}$ are independently C$_{1-6}$-alkyl, halogen, hydroxy, oxo, carboxy, —CF$_3$, carboxy-C$_{1-6}$-alkyl, hydroxy-C$_{1-6}$-alkyl, —C$_{1-6}$-alkyl-C(O)—O—C$_{1-6}$-alkyl, —C(O)—O—C$_{1-6}$-alkyl, —NR$^{19}$R$^{20}$—C(O)NR$^{19}$R$^{20}$ or —S(O)$_2$—C$_{1-6}$-alkyl.

EMBODIMENT 70

A compound according to embodiment 69 wherein R$^{16}$, R$^{17}$, and R$^{13}$ are independently methyl, ethyl, propyl, halogen, hydroxy, oxo, carboxy, —CF$_3$, carboxy-methyl, carboxy-ethyl, carboxy-propyl, hydroxy-methyl, hydroxy-ethyl, hydroxy-propyl, —CH$_2$—C(O)—O—CH$_3$, —CH$_2$—C(O)—O—CH$_2$CH$_3$, —CH$_2$CH$_2$—C(O)—O—CH$_3$, —CH$_2$CH$_2$—C(O)—O—CH$_2$CH$_3$, —C(O)—O—CH$_3$, —C(O)—O—CH$_2$CH$_3$, —C(O)—O—CH$_2$CH$_2$CH$_3$, or —S(O)$_2$CH$_3$.

EMBODIMENT 71

A compound according to embodiment 70 wherein R$^{16}$, R$^{17}$, and R$^{13}$ are independently methyl, ethyl, propyl, halogen, oxo, carboxy, carboxy-methyl, carboxy-ethyl, carboxy-propyl, hydroxy-methyl, hydroxy-ethyl, hydroxy-propyl, —CH$_2$—C(O)—O—CH$_3$, —CH$_2$—C(O)—O—CH$_2$CH$_3$, —CH$_2$CH$_2$—C(O)—O—CH$_3$, —CH$_2$CH$_2$—C(O)—O—CH$_2$CH$_3$, —C(O)—O—CH$_3$, —C(O)—O—CH$_2$CH$_3$, —C(O)—O—CH$_2$CH$_2$CH$_3$, or —S(O)$_2$CH$_3$.

EMBODIMENT 72

A compound according to embodiment 69 wherein R$^{16}$, R$^{17}$, and R$^{13}$ are independently methyl, ethyl, propyl, isopropyl, isobutyl, halogen, hydroxy, oxo, carboxy, —CF$_3$, carboxy-methyl, carboxy-ethyl, carboxy-propyl, hydroxy-methyl, hydroxy-ethyl, hydroxy-propyl, —CH$_2$—C(O)—O—CH$_3$, —CH$_2$—C(O)—O—CH$_2$CH$_3$, —CH$_2$CH$_2$—C(O)—O—CH$_3$, —CH$_2$CH$_2$—C(O)—O—CH$_2$CH$_3$, —C(O)—O—CH$_3$, —C(O)—O—CH$_2$CH$_3$, —C(O)—O—CH$_2$CH$_2$CH$_3$, or —S(O)$_2$CH$_3$.

EMBODIMENT 73

A compound according to embodiment 72 wherein R$^{16}$, R$^{17}$, and R$^{18}$ are independently methyl, ethyl, propyl, isopropyl, isobutyl, halogen, oxo, carboxy, carboxy-methyl, carboxy-ethyl, carboxy-propyl, hydroxy-methyl, hydroxy-ethyl, hydroxy-propyl, —CH$_2$—C(O)—O—CH$_3$, —CH$_2$—C(O)—O—CH$_2$CH$_3$, —CH$_2$CH$_2$—C(O)—O—CH$_3$, —CH$_2$CH$_2$—C(O)—O—CH$_2$CH$_3$, —C(O)—O—CH$_3$, —C(O)—O—CH$_2$CH$_3$, —C(O)—O—CH$_2$CH$_2$CH$_3$, or —S(O)$_2$CH$_3$.

EMBODIMENT 74

A compound according to embodiment 69 wherein R$^{16}$, R$^{17}$, and R$^{18}$ are independently C$_{1-6}$-alkyl, carboxy, —NR$^{19}$R$^{20}$, —C(O)—O—C$_{1-6}$-alkyl, —S(O)$_2$CH$_3$ or —C(O)NR$^{19}$R$^{20}$.

EMBODIMENT 75

A compound according to embodiment 74 wherein R$^{16}$, R$^{17}$, and R$^{18}$ are carboxy.

EMBODIMENT 76

A compound according to any one of the embodiments 1 to 75 wherein R$^{19}$ and R$^{20}$ independently represent hydrogen, C$_{1-6}$-alkyl, hydroxy-C$_{1-6}$-alkyl, carboxy-C$_{1-6}$-alkyl, phenyl, naphtyl, C$_{3-8}$-cycloalkyl, C$_{3-8}$-heterocyclyl, phenyl-C$_{1-6}$-alkyl, C$_{3-8}$-heterocyclyl-C$_{1-6}$-alkyl, —C(O)—O—C$_{1-6}$-alkyl, —C$_{1-6}$-alkyl-C(O)—O—C$_{1-6}$-alkyl, —C$_{1-6}$-alkyl-NR$^{22}$R$^{23}$ or —S(O)$_2$—C$_{1-6}$-alkyl, each of which is optionally substituted with one or more substituents independently selected from R$^{24}$; or R$^{19}$ and R$^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from R$^{24}$.

EMBODIMENT 77

A compound according to embodiment 76 wherein R$^{19}$ and R$^{20}$ independently represent hydrogen, methyl, ethyl, propyl, carboxy-methyl, carboxy-ethyl, carboxy-propyl, hydroxy-methyl, hydroxy-ethyl, hydroxy-propyl, phenyl, C$_{3-8}$-cycloalkyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, —$S(O)_2$—$C_{1-6}$-alkyl or naphtyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

EMBODIMENT 78

A compound according to embodiment 76 wherein $R^{19}$ and $R^{20}$ independently represent hydrogen, $C_{1-6}$-alkyl, —$S(O)_2$—$C_{1-6}$-alkyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

EMBODIMENT 79

A compound according to embodiment 78 wherein $R^{19}$ and $R^{20}$ independently represent hydrogen, methyl, ethyl, or propyl, —$S(O)_2$—$CH_3$, or $R^{19}$ and $R^{20}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

EMBODIMENT 80

A compound according to any one of the embodiments 1 to 79 wherein $R^{21}$ is selected from
$C_{1-6}$-alkyl, carboxy-$C_{1-6}$-alkyl, —$C_{1-6}$-alkyl-$NR^{22}R^{23}$ or hydroxy-$C_{1-6}$-alkyl; or
phenyl, naphtyl, or phenyl-$C_{1-6}$-alkyl, wherein the aryl part is optionally substituted with one or more substituents independently selected from $R^{24}$; or
$C_{3-8}$-cycloalkyl, or $C_{3-8}$-cycloalkyl-$C_{1-6}$-alkyl.

EMBODIMENT 81

A compound according to embodiment 80 wherein $R^{21}$ is selected from
methyl, ethyl, propyl, carboxy-methyl, carboxy-ethyl, carboxy-propyl, hy-droxy-methyl, hydroxy-ethyl, hydroxy-propyl; or
phenyl, naphtyl, or phenyl-$C_{1-6}$-alkyl, wherein the aryl part is optionally substituted with one or more substituents independently selected from $R^{24}$; or
$C_{3-8}$-cycloalkyl, or $C_{3-8}$-cycloalkyl-$C_{1-6}$-alkyl.

EMBODIMENT 82

A compound according to embodiment 81 wherein $R^{21}$ is selected from
methyl, ethyl, carboxy-methyl, carboxy-ethyl, carboxy-propyl; or
phenyl, naphtyl, or phenyl-$C_{1-6}$-alkyl, wherein the aryl part is optionally substituted with one or more substituents independently selected from $R^{24}$.

EMBODIMENT 83

A compound according to embodiment 82 wherein $R^{21}$ is selected from car-boxy-methyl, carboxy-ethyl, or carboxy-propyl.

EMBODIMENT 84

A compound according to any one of the embodiments 1 to 83 wherein $R^{22}$ and $R^{23}$ are independently selected from hydrogen, $C_{1-6}$-alkyl, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, $C_{3-8}$-cycloalkyl, phenyl, naphtyl, or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$

EMBODIMENT 85

A compound according to embodiment 84 wherein $R^{22}$ and $R^{23}$ are independently selected from hydrogen, methyl, ethyl, propyl, butyl, carboxymethyl, carboxyethyl, carboxypropyl, hydroxymethyl, hydroxyethyl, hydroxypropyl, cyclopropyl, cyclobutyl, cyclopentyl, cyclohexyl, cycloheptyl, phenyl, naphtyl, or $R^{22}$ and $R^{23}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

EMBODIMENT 86

A compound according to embodiment 85 wherein $R^{22}$ and $R^{23}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

EMBODIMENT 87

A compound according to embodiment 85 wherein $R^{22}$ and $R^{23}$ is selected from methyl, ethyl or propyl.

EMBODIMENT 88

A compound according to any one of the embodiments 1 to 87 wherein $R^{24}$ is halogen, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —C(O)—O—$C_{1-6}$-alkyl-aryl, or —$S(O)_2R^{28}$, wherein aryl is phenyl or naphtyl, and heteroaryl is pyridyl or pyrimidyl, and wherein each cyclic moiety is optionally substituted with one or more substituents independently selected from $R^{29}$.

EMBODIMENT 89

A compound according to embodiment 88 wherein $R^{24}$ is halogen, hydroxy, carboxy, oxo, —$CF_3$, $C_{1-6}$-alkyl, hydroxy- $C_{1-6}$-alkyl, carboxy-$C_{1-6}$-alkyl, —C(O)—$C_{1-6}$-alkyl, —C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, or —S(O)$_2$R$^{28}$, wherein aryl is phenyl or naphtyl, and heteroaryl is pyridyl or pyrimidyl, and wherein each cyclic moiety is optionally substituted with one or more substituents independently selected from R$^{29}$.

EMBODIMENT 90

A compound according to embodiment 89 wherein R$^{24}$ is halogen, carboxy, oxo, —CF$_3$, $C_{1-6}$-alkyl, carboxy-$C_{1-6}$-alkyl, —C(O)—$C_{1-6}$-alkyl, —C(O)—O—$C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —S(O)$_2$R$^{28}$, wherein aryl is phenyl or naphtyl, and wherein each cyclic moiety is optionally substituted with one or more substituents independently selected from R$^{29}$.

EMBODIMENT 91

A compound according to embodiment 88 wherein R$^{24}$ is halogen, carboxy, $C_{1-6}$-alkyl, carboxy-$C_{1-6}$-alkyl, or —C(O)—O—$C_{1-6}$-alkyl.

EMBODIMENT 92

A compound according to any one of the embodiments 1 to 91 wherein R$^{25}$ and R$^{26}$ are independently $C_{1-6}$-alkyl, halogen, hydroxy, carboxy, or —CF$_3$.

EMBODIMENT 93

A compound according to embodiment 92 wherein R$^{25}$ and R$^{26}$ are independently methyl, ethyl, propyl, halogen, hydroxy, carboxy, or —CF$_3$.

EMBODIMENT 94

A compound according to any one of the embodiments 1 to 93 wherein R$^{23}$ is $C_{1-6}$-alkyl, —$C_{1-6}$-alkyl-C(O)—O—$C_{1-6}$-alkyl, phenyl, phenyl-$C_{1-6}$-alkyl, heteroaryl optionally substituted with $C_{1-6}$-alkyl or —N(CH$_3$)$_2$, wherein heteroaryl is imidazolyl, pyridyl or pyrimidyl.

EMBODIMENT 95

A compound according to embodiment 94 wherein R$^{28}$ is $C_{1-6}$-alkyl, —$C_{1-6}$-alkyl-C(O)—O—$C_{1-6}$-alkyl, or —N(CH$_3$)$_2$.

EMBODIMENT 96

A compound according to any one of the embodiments 1 to 95 wherein R$^{29}$ is halogen, carboxy, —CF$_3$, $C_{1-6}$-alkyl, or $C_{1-6}$-alkoxy.

EMBODIMENT 97

A compound according to any one of the embodiments 1 to 34 wherein R$^3$, R$^4$, R$^5$, R$^6$, R$^{30}$, R$^{31}$, R$^{32}$ and R$^{33}$ are independently selected from the group consisting of
halogen, nitro, cyano, hydroxy, oxo, carboxy, —CF$_3$; or —NR$^{10}$R$^{11}$; or
$C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, aryl-thio, heteroarylthio, $C_{3-8}$-cycloalkylthio, aryl-$C_{1-6}$-alkylthio, heteroaryl-$C_{1-6}$-alkylthio, $C_{1-6}$-alkylsulfenyl, $C_{3-6}$-cycloalkyl-$C_{1-6}$-alkylthio, $C_{1-6}$-alkyl-C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from R$^{12}$; or
—C(O)—R$^{27}$, —S(O)$_2$—R$^{27}$, —C(O)—NR$^{13}$R$^{14}$, —S(O)$_2$—NR$^{13}$R$^{14}$, —$C_{1-6}$-alkyl-C(O)—NR$^{13}$R$^{14}$; or
two substituents selected from R$^3$, R$^4$, R$^5$ and R$^6$ or R$^{30}$R$^{31}$R$^{32}$ and R$^{33}$ attached to the same or adjacent atoms together form a radical —O—(CH$_2$)$_{1-3}$—O—; and R$^{10}$ and R$^{11}$ independently represent hydrogen, $C_{1-6}$-alkyl, —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —S(O)$_2$—$C_{1-6}$-alkyl, or aryl; and R$^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{2-6}$-alkenyl, aryl, aryl-$C_{1-6}$-alkyl, aryloxy-$C_{1-6}$-alkyl, aryl-$C_{2-6}$-alkenyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $C_{1-6}$-alkylthio-$C_{1-6}$-alkyl, R$^{10}$HN—$C_{1-6}$-alkyl, R$^{10}$R$^{11}$—N—$C_{1-6}$-alkyl, R$^{10}$R$^{11}$—N—$C_{2-6}$-alkenyl, R$^{10}$R$^{11}$—N—S(O)$_2$—$C_{1-6}$-alkyl, R$^{10}$R$^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-S(O)$_2$—NH—$C_{1-6}$-alkyl, aryl-S(O)$_2$—NH—$C_{1-6}$-alkyl, heteroaryl-S(O)$_2$—NH—$C_{1-6}$-alkyl, or $C_{3-8}$-cycloalkyl-S(O)$_2$NH—$C_{1-6}$-alkyl, each of which is optionally substituted with one or more substituents independently selected from R$^{12}$; and R$^{12}$ is halogen, cyano, hydroxy, —C(O)—O—$C_{1-6}$-alkyl, carboxy, —CF$_3$, $C_{1-6}$-alkyl, $C_{1-6}$-alkoxy, —NR$^{10}$R$^{11}$, —S(O)$_2$CH$_3$, or —S(O)$_2$NH$_2$; and R$^{13}$ and R$^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from R$^{15}$; or R$^{13}$ and R$^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur; and R$^{15}$ is halogen, cyano, hydroxy, carboxy, —CF$_3$, $C_{1-6}$-alkyl, —S(O)$_2$CH$_3$, or —S(O)$_2$NH$_2$; and At least one of R$^7$, R$^8$ and R$^9$ is independently selected from
$C_{1-6}$-alkoxy, $C_{1-6}$-alkylthio, $C_{2-6}$-alkenylthio each of which is substituted with one or more substituents independently selected from R$^{16}$; or
—NR$^{19}$R$^{20}$, —$C_{1-6}$-alkyl-NR$^{19}$R$^{20}$, —$C_{2-6}$-alkenyl-NR$^{19}$R$^{20}$, —$C_{1-6}$-alkyl-S—R$^{21}$, —$C_{1-6}$-alkyl-S(O)—R$^{21}$, —$C_{1-6}$-alkyl-S(O)$_2$—R$^{21}$, —S(O)—R$^{21}$, —S(O)$_2$—NR$^{19}$R$^{20}$ or —S(O)$_2$NR$^{19}$($C_{1-6}$-alkyl-C(O)

$NR^{22}R^{23}$), wherein each alkyl part may be substituted with one or more substituents independently selected from $R^{25}$;

If more than one $R^7$, $R^8$ and $R^9$ is present, that additional one or more of $R^7$, $R^8$ and $R^9$ may additionally be independently selected from halogen, carboxy, cyano, nitro, hydroxy, —$CF_3$, —SCN; or $C_{1-6}$-alkyl, $C_{2-6}$-alkenyl, $C_{2-6}$-alkynyl, $C_{1-6}$-alkoxy, $C_{1-6}$-alkylthio, $C_{2-6}$-alkenylthio, $C_{1-6}$-alkylamino, $C_{1-6}$-alkylsulfenyl, —C(O)—O—$C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, carboxy-$C_{1-6}$-alkyl, or hydroxy-$C_{1-6}$-alkyl, each of which is optionally substituted with one or more substituents independently selected from $R^{40}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, heteroaryl-oxy-$C_{1-6}$-alkyl, aryloxy, heteroaryloxy, arylthio, heteroarylthio, aryl-$C_{1-6}$-alkylamino, —C(O)-aryl, or —C(O)-heteroraryl, each of which is optionally substituted on the aryl or heteroaryl part with one or more substituents independently selected from $R^{41}$; or $C_{3-8}$-cycloalkyl, $C_{3-8}$-cycloalkenyl, $C_{3-8}$-cycloalkylthio, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{42}$; or $C_{3-8}$-heterocyclyl, $C_{3-8}$-heterocyclyl-$C_{1-6}$-alkyl, $C_{3-8}$-heterocyclyl-$C_{1-6}$-alkylthio, $C_{3-8}$-heterocyclylthio, $C_{3-8}$-heterocyclyl-amino-$C_{1-6}$-alkyl, or —C(O)—$C_{3-8}$-heterocyclyl, each of which is optionally substituted with one or more substituents independently selected from $R^{40}$; or —$NR^{43}R^{44}$, —$C_{1-6}$-alkyl-$NR^{43}R^{44}$, —$C_{2-6}$-alkenyl-$NR^{43}R^{44}$, —$C_{1-6}$-alkyl-S—$R^{45}$—$C_{1-6}$-alkyl-S(O)—$R^{45}$, —$C_{1-6}$-alkyl-S(O)$_2$—$R^{45}$, —S(O)$_2$—$R^{45}$, —S(O)$_2$—N($R^{43}$)($C_{1-6}$-alkyl-C(O)$NR^{46}R^{47}$) or —S(O)$_2$—$NR^{43}R^{44}$, wherein each alkyl part may be substituted with one or more substituents independently selected from $R^{49}$; or —C(O)$NR^{46}R^{47}$, —$C_{1-6}$-alkyl-C(O)$NR^{46}R^{47}$—$C_{1-6}$-alkyl-NH—$NR^{46}R^{47}$—$C_{1-6}$-alkyl-NH—C(O)—$C_{1-6}$-alkyl-$NNR^{46}R^{47}$, each optionally substituted with one or more substituents independently selected from $R^{50}$; and $R^{16}$ is —$NR^{19}R^{20}$, —NHS(O)$_2$CF$_3$, —NHS(O)$_2$CH$_2$CF$_3$, —C(O)$NR^{19}R^{20}$, —S(O)$_2$CF$_3$, —S(O)$_2$CH$_2$CF$_3$, or —S(O)$_2$$NR^{19}R^{20}$; and $R^{19}$ represents hydrogen, $C_{1-6}$-alkyl, $C_{2-6}$-alkenyl, $C_{3-8}$-cycloalkyl, $C_{3-8}$-cycloalkyl-$C_{1-6}$-alkyl, hydroxy-$C_{1-6}$-alkyl, hydroxy-$C_{2-6}$-alkenyl, carboxy-$C_{1-6}$-alkyl, aryl, heteroaryl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, or —S(O)$_2$—$C_{1-6}$-alkyl, each of which is optionally substituted with one or more substituents independently selected from $R^{24}$; and $R^{20}$ represents $C_{2-6}$-alkenyl, $C_{3-8}$-cycloalkyl, $C_{3-8}$-cycloalkyl-$C_{1-6}$-alkyl each of which is optionally substituted with one or more substituents independently selected from $R^{24}$; and $R^{21}$ is selected from
$C_{3-8}$-cycloalkyl, $C_{3-8}$-cycloalkyl-$C_{1-6}$-alkyl, $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-$NR^{22}R^{23}$ which is substituted with one or more substituents independently selected from $R^{24}$; or
$C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl which is substituted with one or more substituents independently selected from $R^{24}$; and $R^{22}$ and $R^{23}$ are independently selected from hydrogen, $C_{1-6}$-alkyl, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-S(O)$_2$—$C_{1-6}$-alkyl, $C_{3-8}$-cycloalkyl, aryl, or heteroaryl; or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$; and $R^{24}$ is halogen, nitro, cyano, hydroxy, carboxy, oxo, —CF$_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, —C(O)-heteroaryl, —C(O)—$C_{3-8}$-heterocyclyl-C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —$C_{1-6}$-alkyl-C(O)—$C_{3-8}$-heterocyclyl, —C(O)—O—$C_{1-6}$-alkyl-aryl, —NH—S(O)$_2$R$^2$, or —S(O)$_2$R$^{28}$, wherein each cyclic moiety is optionally substituted with one or more substituents independently selected from $R^{29}$; and $R^{25}$ is $C_{1-6}$-alkyl, halogen, nitro, cyano, hydroxy, —C(O)—O—$C_{1-6}$-alkyl, carboxy, —$C_{1-6}$-alkyl-C(O)—O—$C_{1-6}$-alkyl, carboxy-$C_{1-6}$-alkyl, —CF$_3$, —S(O)$_2$CH$_3$, or —S(O)$_2$NH$_2$; and $R^{28}$ is $C_{1-6}$-alkyl, carboxy-$C_{1-6}$-alkyl, —$C_{1-6}$-alkyl-C(O)—O—$C_{1-6}$-alkyl, $C_{3-8}$-cycloalkyl, aryl, aryl-$C_{1-6}$-alkyl, heteroaryl optionally substituted with $C_{1-6}$-alkyl, —NH$_2$, or —N(CH$_3$)$_2$; and $R^{29}$ is halogen, nitro, cyano, hydroxy, carboxy, oxo, —CF$_3$, $C_{1-6}$-alkyl, or $C_{1-6}$-alkoxy; and $R^{40}$, $R^{41}$, and $R^{42}$ are independently $C_{1-6}$-alkyl, halogen, nitro, cyano, hydroxy, carboxy, oxo, —CF$_3$, carboxy-$C_{1-6}$-alkyl, hydroxy-$C_{1-6}$-alkyl, —$C_{1-6}$-alkyl-C(O)—O—$C_{1-6}$-alkyl, —$C_{1-6}$-alkyl-C(O)—$NR^{43}R^{44}$, —C(O)—O—$C_{1-6}$-alkyl, —C(O)—$C_{1-6}$-alkyl-C(O)—$C_{1-6}$-alkyl, —$NR^{43}R^{44}$—NHS(O)$_2$$C_{1-6}$-alkyl, —NHS(O)$_2$CF$_3$, —NHS(O)$_2$CH$_2$CF$_3$, —C(O)$NR^{43}R^{44}$, —S(R)$C_{1-6}$-alkyl, —S(O)$_2$CF$_3$, —S(O)$_2$CH$_2$CF$_3$ or —S(O)$_2$$NR^{43}R^{44}$; and $R^{43}$ and $R^{44}$ independently represent hydrogen, $C_{1-6}$-alkyl, $C_{2-6}$-alkenyl, $C_{3-8}$-cycloalkyl, $C_{3-8}$-cycloalkyl-$C_{1-6}$-alkyl, hydroxy-$C_{1-6}$-alkyl, carboxy-$C_{1-6}$-alkyl, aryl, heteroaryl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{46}R^{47}$, or —S(O)$_2$—$C_{1-6}$-alkyl, each of which is optionally substituted with one or more substituents independently selected from $R^{48}$, or $R^{43}$ and $R^{44}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{48}$; and $R^{45}$ is selected from
  $C_{1-6}$-alkyl, $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-$NR^{46}R^{47}$; or
  aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{48}$; or
  $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl; and $R^{46}$ and $R^{47}$ are independently selected from hydrogen, $C_{1-6}$-alkyl, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-S(O)$_2$—$C_{1-6}$-alkyl, $C_{3-8}$-cycloalkyl, aryl, or heteroaryl; or $R^{46}$ and $R^{47}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{48}$; and $R^{48}$ is halogen, nitro, cyano, hydroxy, carboxy, oxo, —CF$_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, —C(O)-heteroaryl, —C(O)—$C_{3-8}$-heterocyclyl-C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —$C_{1-6}$-alkyl-C(O)—$C_{3-8}$-heterocyclyl, —C(O)—O—$C_{1-6}$-alkyl-aryl, —NH—S(O)$_2$R$^{52}$, or —S(O)$_2$R$^{52}$, wherein each cyclic moiety is optionally substituted with one or more substituents independently selected from $R^{53}$; and $R^{49}$ and $R^{50}$ are independently $C_{1-6}$-alkyl, halogen, nitro, cyano, hydroxy, —C(O)—O—$C_{1-6}$-alkyl, carboxy, —$C_{1-6}$-alkyl-C(O)—O—$C_{1-6}$-alkyl, carboxy-$C_{1-6}$-alkyl, —CF$_3$, —S(O)$_2$CH$_3$, or —S(O)$_2$NH$_2$; and $R^{52}$ is $C_{1-6}$-alkyl, carboxy-$C_{1-6}$-alkyl, —$C_{1-6}$-alkyl-C(O)—O—$C_{1-6}$-alkyl, $C_{3-8}$-cycloalkyl, aryl, aryl-$C_{1-6}$-alkyl, heteroaryl optionally substituted with $C_{1-6}$-alkyl, —NH$_2$, or —N(CH$_3$)$_2$; and $R^{53}$ is halogen, nitro, cyano, hydroxy, carboxy, oxo, —CF$_3$, $C_{1-6}$-alkyl, or $C_{1-6}$-alkoxy.

EMBODIMENT 98

A compound according to embodiment 97 wherein at least one of $R^7$, $R^8$ and $R^9$ is independently selected from
  $C_{1-6}$-alkoxy, $C_{1-6}$-alkylthio, each of which is substituted with one or more substituents independently selected from $R^{16}$; or
  —NR$^{19}$R$^{20}$—$C_{1-6}$-alkyl-NR$^{19}$R$^{20}$, —$C_{1-6}$-alkyl-S—R$^{21}$, —$C_{1-6}$-alkyl-S(O)$_2$—R$^{21}$, —S(O)$_2$—R$^{21}$, —S(O)$_2$—NR$^{19}$R$^{20}$ or —S(O)$_2$NR$^{19}$($C_{1-6}$-alkyl-C(O)NR$^{22}$R$^{23}$), wherein each alkyl part may be substituted with one or more substituents independently selected from $R^{25}$.

EMBODIMENT 99

A compound according to embodiment 98 wherein at least one of $R^7$, $R^8$ and $R^9$ is independently selected from
  $C_{1-6}$-alkoxy, $C_{1-6}$-alkylthio, each of which is substituted with one or more substituents independently selected from $R^{16}$; or
  —$C_{1-6}$-alkyl-S—R$^{21}$, —$C_{1-6}$-alkyl-S(O)$_2$—R$^{21}$, —S(O)$_2$—R$^{21}$, —S(O)$_2$—NR$^{19}$R$^{20}$ or —S(O)$_2$NR$^{19}$($C_{1-6}$-alkyl-C(O)NR$^{22}$R$^{23}$), wherein each alkyl part may be substituted with one or more substituents independently selected from $R^{25}$.

EMBODIMENT 100

A compound according to embodiment 99 wherein at least one of $R^7$, $R^8$ and $R^9$ is independently selected from
  $C_{1-6}$-alkoxy, $C_{1-6}$-alkylthio, each of which is substituted with one or more substituents independently selected from $R^{16}$; or
  —S(O)$_2$—R$^{21}$, —S(O)$_2$—NR$^{19}$R$^{20}$, or —S(O)$_2$NR$^{19}$($C_{1-6}$-alkyl-C(O)NR$^{22}$R$^{23}$), wherein each alkyl part may be substituted with one or more substituents independently selected from $R^{25}$.

EMBODIMENT 101

A compound according to embodiment 100 wherein at least one of $R^7$, $R^8$ and $R^9$ is independently selected from $C_{1-6}$-alkylthio substituted with one or more substituents independently selected from $R^{16}$, or —S(O)$_2$—R$^{21}$, —S(O)$_2$—NR$^{19}$R$^{20}$, or —S(O)$_2$NR$^{19}$($C_{1-6}$-alkyl-C(O)NR$^{22}$R$^{23}$), wherein each alkyl part may be substituted with one or more substituents independently selected from $R^{25}$.

EMBODIMENT 102

A compound according to embodiment 101 wherein at least one of $R^7$, $R^8$ and $R^9$ is independently selected from —S—CH$_3$, —S—CH$_2$CH$_3$, —S—CH$_2$CH$_2$CH$_3$ each of which is substituted with one or more substituents independently selected from $R^{16}$, or —S(O)$_2$—R$^{21}$, —S(O)$_2$—NR$^{19}$R$^{20}$, or —S(O)$_2$NR$^{19}$(CH$_3$)—C(O)NR$^{22}$R$^{23}$)

EMBODIMENT 103

A compound according to any one of the embodiments 97 to 102 wherein, if more than one of $R^7$, $R^8$, or $R^9$ is present, that additional one or more of $R^7$, $R^8$, and $R^9$ is independently selected from the group consisting of
  halogen, carboxy, cyano, nitro, hydroxy, —CF$_3$, —SCN; or
  $C_{1-6}$-alkyl, $C_{2-6}$-alkenyl, $C_{2-6}$-alkynyl, $C_{1-6}$-alkoxy, $C_{1-6}$-alkylthio, $C_{2-6}$-alkenylthio, $C_{1-6}$-alkylamino, $C_{1-6}$-alkylsulfenyl, —C(O)—O—$C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, carboxy-$C_{1-6}$-alkyl, or hydroxy-$C_{1-6}$-alkyl, each of which is optionally substituted with one or more substituents independently selected from $R^{40}$; or
  aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$- alkylthio, heteroaryl-$C_{1-6}$-alkylthio, heteroaryl-thio-$C_{1-6}$-alkyl, heteroaryl-oxy-$C_{1-6}$-alkyl, aryloxy, heteroaryloxy, arylthio, heteroarylthio, aryl-$C_{1-6}$-alkylamino, —C(O)-aryl, or —C(O)-heteroaryl, each of which is optionally substituted on the aryl or heteroaryl part with one or more substituents independently selected from $R^{41}$; or $C_{3-8}$-cycloalkyl, $C_{3-8}$-cycloalkenyl, $C_{3-8}$-cycloalkylthio, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{42}$; or $C_{3-8}$-heterocyclyl, $C_{3-8}$-heterocyclyl-$C_{1-6}$-alkyl, $C_{3-8}$-heterocyclyl-$C_{1-6}$-alkylthio, $C_{3-8}$-heterocyclylthio, $C_{3-8}$-heterocyclyl-amino-$C_{1-6}$-alkyl, or —C(O)—$C_{3-8}$-heterocyclyl, each of which is optionally substituted with one or more substituents independently selected from $R^{40}$; or —$NR^{43}R^{44}$, —$C_{1-6}$-alkyl-$NR^{43}R^{44}$, —$C_{2-6}$-alkenyl-$NR^{43}R^{44}$, —$C_{1-6}$-alkyl-S—$R^{45}$, —$C_{1-6}$-alkyl-S(O)—$R^{45}$, —$C_{1-6}$-alkyl-S(O)$_2$—$R^{45}$, —S(O)$_2$—$R^{45}$, —S(O)$_2$N($R^{43}$)($C_{1-6}$-alkyl-C(O)$NR^{46}R^{47}$) or —S(O)$_2$—$NR^{43}R^{44}$, wherein each alkyl part may be substituted with one or more substituents independently selected from $R^{49}$; or —C(O)$NR^{46}R^{47}$, —$C_{1-6}$-alkyl-C(O)$NR^{46}R^{47}$—$C_{1-6}$-alkyl-NH—$NR^{46}R^{47}$—$C_{1-6}$-alkyl-NH—C(O)—$C_{1-6}$-alkyl-$NR^{46}R^{47}$, each optionally substituted with one or more substituents independently selected from $R^{50}$.

EMBODIMENT 104

A compound according to embodiment 103 wherein the additional one or more of $R^7$, $R^8$, and $R^9$ is independently selected from halogen, carboxy, cyano, nitro, hydroxy, —$CF_3$, —SCN; or $C_{1-6}$-alkyl, $C_{2-6}$-alkenyl, $C_{1-6}$-alkoxy, $C_{1-6}$-alkylthio, $C_{1-6}$-alkylamino, $C_{1-6}$-alkylsulfenyl, —C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, $C_{3-8}$-cycloalkyl-$C_{1-6}$-alkyl, $C_{3-6}$-cycloalkyl-$C_{1-6}$-alkoxy, $C_{3-6}$-cycloalkyl-$C_{1-6}$-alkylthio each of which is optionally substituted with one or more substituents independently selected from $R^{40}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, heteroaryl-thio-$C_{1-6}$-alkyl, aryloxy, heteroaryloxy, heteroarylthio, each of which is optionally substituted on the aryl or heteroaryl part with one or more substituents independently selected from $R^{42}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{42}$; or $C_{3-8}$-heterocyclyl, $C_{3-8}$-heterocyclyl-$C_{1-6}$-alkyl, $C_{3-8}$-heterocyclylthio, or —C(O)—$C_{3-8}$-heterocyclyl, each of which is optionally substituted with one or more substituents independently selected from $R^{40}$; or —$NR^{43}R^{44}$, —$C_{1-6}$-alkyl-$NR^{43}R^{44}$, —$C_{1-6}$-alkyl-S—$R^{45}$, —$C_{1-6}$-alkyl-S(O)—$R^{45}$—C alkyl-S(O)$_2$—$R^{45}$, —S(O)$_2$—$R^{45}$ or —S(O)$_2$—$NR^{43}R^{44}$, wherein each alkyl part may be substituted with one or more substituents independently selected from $R^{49}$; or —C(O)$NR^{46}R^{47}$, —$C_{1-6}$-alkyl-C(O)$NNR^{46}R^{47}$ optionally substituted with one or more substituents independently selected from $R^{50}$; or two of $R^7$, $R^8$ and $R^9$ can be taken together to form a $C_{2-5}$-alkylene bridge.

EMBODIMENT 105

A compound according to embodiment 104 wherein the additional one or more of $R^7$, $R^8$, and $R^9$ is independently selected from halogen, carboxy, cyano, or —$CF_3$; or $C_{1-6}$-alkyl, $C_{2-6}$-alkenyl, $C_{1-6}$-alkoxy, $C_{1-6}$-alkylthio, —C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —$C_{1-6}$-alkoxy-$C_{1-6}$-alkyl, $C_{3-8}$-cycloalkyl-$C_{1-6}$-alkyl, each of which is optionally substituted with one or more substituents independently selected from $R^{40}$; or aryl, heteroaryl, aryl-$C_{1-6}$-alkyl, heteroaryl-$C_{1-6}$-alkyl, each of which is optionally substituted on the aryl or heteroaryl part with one or more substituents independently selected from $R^{41}$; or $C_{3-8}$-cycloalkyl, $C_{3-8}$-cycloalkyl-$C_{1-6}$-alkyl, each of which is optionally substituted on the cycloalkyl part with one or more substituents independently selected from $R^{42}$; or $C_{3-8}$-heterocyclyl, $C_{3-8}$-heterocyclyl-$C_{1-6}$-alkyl, or —C(O)—$C_{3-8}$-heterocyclyl, each of which is optionally substituted with one or more substituents independently selected from $R^{40}$; or —$NR^{43}R^{44}$—$C_{1-6}$-alkyl-$NR^{43}R^{44}$, —S(O)$_2$—$R^{45}$ or —S(O)$_2$—$NR^{43}R^{44}$, wherein each alkyl part may be substituted with one or more substituents independently selected from $R^{49}$; or —C(O)$NR^{46}R^{47}$, —$C_{1-6}$-alkyl-C(O)$NR^{46}R^{47}$ optionally substituted with one or more substituents independently selected from $R^{50}$; or two of $R^7$, $R^8$ and $R^9$ can be taken together to form a $C_{2-5}$-alkylene bridge.

EMBODIMENT 106

A compound according to embodiment 105 wherein the additional one or more of $R^7$, $R^8$, and $R^9$ is independently selected from halogen, carboxy or —$CF_3$; or $C_{1-6}$-alkyl, $C_{1-6}$-alkoxy, $C_{1-6}$-alkylthio, —$C_{1-6}$-alkyl-C(O)—O—$C_{1-6}$-alkyl, —$C_{1-6}$-alkyl-O—C(O)—$C_{1-6}$-alkyl or —C(O)—O—$C_{1-6}$-alkyl, each of which is optionally substituted with one or more substituents independently selected from $R^{40}$; or phenyl, benzyl, or heteroarylthio, wherein heteroaryl is pyridyl or imidazolyl, and wherein each aryl or heteroaryl is optionally substituted on the aryl or heteroaryl part with one or more substituents independently selected from $R^{41}$; or cyclopropyl, cyclobutyl, cyclopentyl, or cyclohexyl, each of which is optionally substituted on the cycloalkyl part with one or more substituents independently selected from $R^{42}$; or pyrrolidinyl, piperidyl, piperazinyl, or morpholinyl, each of which is optionally substituted with one or more substituents independently selected from $R^{40}$; or —C(O)$NR^{46}R^{47}$, —S(O)$_2$—$R^{45}$ or —S(O)$_2$—$NR^{43}R^{44}$; or two of $R^7$, $R^8$ and $R^9$ can be taken together to form a $C_{2-5}$-alkylene bridge.

EMBODIMENT 107

A compound according to embodiment 106 wherein the additional one or more of $R^7$, $R^8$, and $R^9$ is independently selected from halogen, carboxy, —$CF_3$, —S—$CH_3$, —S—$CH_2CH_3$, —S—$CH_2CH_2CH_3$, methyl, ethyl, propyl, isopropyl, butyl, tert-butyl, methoxy, ethoxy, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —$CH_2$—O—C(O)—$CH_3$, —$CH_2$—O—C(O)—$CH_2CH_3$, —$CH_2CH_2$—O—C(O)—$CH_3$, —$CH_2CH_2$—O—C(O)—$CH_2CH_3$, —C(O)—O—$CH_3$, —C(O)—O—$CH_2CH_3$, each of which is optionally substituted with one or more substituents independently selected from $R^{40}$; or heteroarylthio, wherein heteroaryl is pyridyl or imidazolyl, each optionally substituted on the heteroaryl part with one or more substituents independently selected from $R^{41}$, or pyrrolidinyl, piperidyl, piperazinyl, or morpholinyl, each of which is optionally substituted with one or more substituents independently selected from $R^{40}$, —$S(O)_2$—$R^{45}$, or —$S(O)_2$—$NR^{43}R^{44}$.

EMBODIMENT 108

A compound according to embodiment 107 wherein the additional one or more of $R^7$, $R^8$, and $R^9$ is independently selected from halogen, —S—$CH_3$, —S—$CH_2CH_3$, —S—$CH_2CH_2CH_3$, methyl, or ethyl, —$S(O)_2$—$R^{45}$, or —$S(O)_2$—$NR^{43}R^{44}$.

EMBODIMENT 109

A compound according to any one of the embodiments 97 to 108 wherein $R^{40}$, $R^{41}$, and $R^{42}$ are independently $C_{1-6}$-alkyl, halogen, hydroxy, oxo, carboxy, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$NR^{43}R^{44}$, —C(O)$NR^{43}R^{44}$ or —$S(O)_2$—$C_{1-6}$-alkyl.

EMBODIMENT 110

A compound according to embodiment 109 wherein $R^{40}$, $R^{41}$, and $R^{42}$ are independently methyl, ethyl, propyl, halogen, hydroxy, oxo, carboxy, —$CF_3$, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

EMBODIMENT 111

A compound according to embodiment 110 wherein $R^{40}$, $R^{41}$, and $R^{42}$ are independently methyl, ethyl, propyl, halogen, oxo, carboxy, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

EMBODIMENT 112

A compound according to embodiment 111 wherein $R^{40}$, $R^{41}$, and $R^{42}$ are independently $C_{1-6}$-alkyl, carboxy, —$NR^{43}R^{44}$, —C(O)—O—$C_{1-6}$-alkyl or —C(O)$NR^{43}R^{44}$.

EMBODIMENT 113

A compound according to any one of the embodiments 97 to 112 wherein $R^{19}$, $R^{43}$ and $R^{44}$ independently represent hydrogen, $C_{1-6}$-alkyl, hydroxy-$C_{1-6}$-alkyl, $C_{3-8}$-cycloalkyl, $C_{3-8}$-cycloalkyl-$C_{1-6}$-alkyl, carboxy-$C_{1-6}$-alkyl, phenyl, naphtyl, $C_{3-8}$-heterocyclyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{46}R^{47}$ or —$S(O)_2$—$C_{1-6}$-alkyl, each of which is optionally substituted with one or more substituents independently selected from $R^{48}$; or $R^{43}$ and $R^{44}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{48}$.

EMBODIMENT 114

A compound according to embodiment 113 wherein $R^{19}$, $R^{43}$ and $R^{44}$ independently represent hydrogen, methyl, ethyl, propyl, carboxy-methyl, carboxy-ethyl, carboxypropyl, hydroxy-methyl, hydroxy-ethyl, hydroxy-propyl, phenyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{46}R^{47}$—$S(O)_2$—$C_{1-6}$-alkyl or naphtyl, or $R^{43}$ and $R^{44}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{48}$.

EMBODIMENT 115

A compound according to embodiment 114 wherein $R^{19}$, $R^{43}$ and $R^{44}$ independently represent hydrogen, $C_{1-6}$-alkyl, —$S(O)_2$—$C_{1-6}$-alkyl or $R^{43}$ and $R^{44}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{48}$.

EMBODIMENT 116

A compound according to embodiment 115 wherein $R^{19}$, $R^{43}$ and $R^{44}$ independently represent hydrogen, methyl, ethyl, or propyl, —$S(O)_2$—$CH_3$ or $R^{43}$ and $R^{44}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{48}$.

EMBODIMENT 117

A compound according to any one of the embodiments 97 to 116 wherein $R^{45}$ is selected from $C_{1-6}$-alkyl, carboxy-$C_{1-6}$-alkyl, —$C_{1-6}$-alkyl-$NR^{46}R^{47}$ or hydroxy-$C_{1-6}$-alkyl; or phenyl, naphtyl, or phenyl-$C_{1-6}$-alkyl, wherein the aryl part is optionally substituted with one or more substituents independently selected from $R^{48}$; or $C_{3-8}$-cycloalkyl, or $C_{3-8}$-cycloalkyl-$C_{1-6}$-alkyl.

EMBODIMENT 118

A compound according to embodiment 117 wherein $R^{45}$ is selected from methyl, ethyl, propyl, carboxy-methyl, carboxy-ethyl, carboxy-propyl, hydroxy-methyl, hydroxy-ethyl, hydroxy-propyl; or phenyl, naphtyl, or phenyl-$C_{1-6}$-alkyl, wherein the aryl part is optionally substituted with one or more substituents independently selected from $R^{48}$; or $C_{3-8}$-cycloalkyl, or $C_{3-8}$-cycloalkyl-$C_{1-6}$-alkyl.

EMBODIMENT 119

A compound according to embodiment 118 wherein $R^{45}$ is selected from methyl, ethyl, carboxy-methyl, carboxy-ethyl, carboxy-propyl; or phenyl, naphtyl, or phenyl-$C_{1-6}$-alkyl, wherein the aryl part is optionally substituted with one or more substituents independently selected from $R^{48}$.

EMBODIMENT 120

A compound according to embodiment 119 wherein $R^{45}$ is selected from carboxy-methyl, carboxy-ethyl, carboxy-propyl.

EMBODIMENT 121

A compound according to any one of the embodiments 97 to 120 wherein $R^{46}$ and $R^{47}$ are independently selected from hydrogen, $C_{1-6}$-alkyl, hydroxy-$C_{1-6}$-alkyl, carboxy-$C_{1-6}$-alkyl, —$C_{1-6}$-alkyl-C(O)—O—$C_{1-6}$-alkyl, —C(O)—O—$C_{1-6}$-alkyl, $C_{3-8}$-cycloalkyl, phenyl, naphtyl, or $R^{46}$ and $R^{47}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{48}$.

EMBODIMENT 122

A compound according to embodiment 121 wherein $R^{46}$ and $R^{47}$ are independently selected from hydrogen, methyl, ethyl, propyl, butyl, carboxymethyl, carboxyethyl, carboxypropyl, hydroxymethyl, ethoxypropyl, hydroxypropyl, cyclopropyl, cyclobutyl, cyclopentyl, cyclohexyl, cycloheptyl, phenyl, naphtyl, or $R^{46}$ and $R^{47}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{48}$.

EMBODIMENT 123

A compound according to embodiment 122 wherein $R^{46}$ and $R^{47}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{48}$.

EMBODIMENT 124

A compound according to any one of the embodiments 97 to 123 wherein $R^{48}$ is halogen, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —C(O)—O—$C_{1-6}$-alkyl-aryl, or —$S(O)_2R^{52}$, wherein aryl is phenyl or naphtyl, and heteroaryl is pyridyl or pyrimidyl, and wherein each cyclic moiety is optionally substituted with one or more substituents independently selected from $R^{53}$.

EMBODIMENT 125

A compound according to embodiment 124 wherein $R^{48}$ is halogen, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, or —$S(O)_2R^{52}$, wherein aryl is phenyl or naphtyl, and heteroaryl is pyridyl or pyrimidyl, and wherein each cyclic moiety is optionally substituted with one or more substituents independently selected from $R^{53}$.

EMBODIMENT 126

A compound according to embodiment 125 wherein $R^{41}$ is halogen, carboxy, oxo, —$CF_3$, $C_{1-6}$-alkyl, carboxy-$C_{1-6}$-alkyl, —C(O)—$C_{1-6}$-alkyl, —C(O)—O—$C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —$S(O)_2R^{52}$, wherein aryl is phenyl or naphtyl, and wherein each cyclic moiety is optionally substituted with one or more substituents independently selected from $R^{53}$.

EMBODIMENT 127

A compound according to embodiment 126 wherein $R^{48}$ is halogen, carboxy, oxo, $C_{1-6}$-alkyl, carboxy-$C_{1-6}$-alkyl.

EMBODIMENT 128

A compound according to any one of the embodiments 97 to 127 wherein $R^{49}$ and $R^{50}$ are independently $C_{1-6}$-alkyl, halogen, hydroxy, carboxy, or —$CF_3$.

EMBODIMENT 129

A compound according to embodiment 128 wherein $R^{49}$ and $R^{50}$ are independently methyl, ethyl, propyl, halogen, hydroxy, carboxy, or —$CF_3$.

EMBODIMENT 130

A compound according to any one of the embodiments 97 to 129 wherein $R^{52}$ is $C_{1-6}$-alkyl, $-C_{1-6}$-alkyl-C(O)—O—$C_{1-6}$-alkyl, phenyl, phenyl-$C_{1-6}$-alkyl, heteroaryl optionally substituted with $C_{1-6}$-alkyl or —N(CH$_3$)$_2$, wherein heteroaryl is imidazolyl, pyridyl or pyrimidyl.

EMBODIMENT 131

A compound according to embodiment 130 wherein $R^{52}$ is $C_{1-6}$-alkyl, —$C_{1-6}$-alkyl-C(O)—O—$C_{1-6}$-alkyl, or —N(CH$_3$)$_2$.

EMBODIMENT 132

A compound according to any one of the embodiments 97 to 131 wherein $R^{53}$ is halogen, carboxy, —CF$_3$, $C_{1-6}$-alkyl, or $C_{1-6}$-alkoxy.

EMBODIMENT 133

A compound according to any one of the embodiments 97 to 132 wherein $R^3$, $R^4$, $R^5$, $R^6$, $R^{30}$, $R^{31}$, $R^{32}$ and $R^{33}$ are independently selected from the group consisting of halogen, oxo, cyano, hydroxy, carboxy, —CF$_3$; or —NR$^{10}$R$^{11}$; or $C_{1-6}$-alkyl, $C_{2-6}$-alkenyl, $C_{3-8}$-cycloalkyl, $C_{3-8}$-cycloalkyl-$C_{1-6}$-alkyl, aryl, aryl-$C_{1-6}$-alkyl, $C_{1-6}$-alkoxy, $C_{3-6}$-cycloalkyl-$C_{1-6}$-alkoxy, aryl-$C_{1-6}$-alkoxy, heteroaryl-$C_{1-6}$-alkoxy, $C_{1-6}$-alkylthio, aryloxy, arylthio, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—R$^{27}$, —S(O)$_2$—R$^{27}$, —C(O)—NR$^{13}$R$^{14}$, —S(O)$_2$—NR$^{13}$R$^{14}$, —$C_{1-6}$-alkyl-C(O)—NR$^{13}$R$^{14}$; or two substituents selected from $R^3$, $R^4$, $R^5$ and $R^6$ or $R^{30}$R$^{31}$, $R^{32}$ and $R^{33}$ attached to the same or adjacent atoms together form a radical —O—(CH$_2$)$_{1-3}$—O—.

EMBODIMENT 134

A compound according to embodiment 133 wherein $R^3$, $R^4$, $R^5$, $R^6$, $R^{30}$, $R^{31}$, $R^{32}$ and $R^{33}$ are independently selected from the group consisting of halogen, oxo, —CF$_3$; or —NR$^{10}$R$^{11}$; or $C_{1-6}$-alkyl, $C_{3-8}$-cycloalkyl, $C_{1-6}$-alkoxy, $C_{1-6}$-alkylthio, aryl, aryl-$C_{1-6}$-alkyl, arylthio, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—R$^{27}$, —S(O)$_2$—NR$^{13}$R$^{14}$ or —S(O)$_2$—R$^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—(CH$_2$)$_{1-3}$—O—.

EMBODIMENT 135

A compound according to embodiment 134 wherein $R^3$, $R^4$, $R^5$, $R^6$, $R^{30}$, $R^{31}$, $R^{32}$ and $R^{33}$ are independently selected from the group consisting of halogen, —CF$_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, phenylthio, —C(O)—O—CH$_3$, or —C(O)—O—CH$_2$CH$_3$, each of which is optionally substituted with one or more substituents independently selected from $R^{12}$; or —C(O)—R$^{27}$, —S(O)$_2$—NR$^{13}$R$^{14}$ or —S(O)$_2$—R$^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—(CH$_2$)$_{1-3}$—O—.

EMBODIMENT 136

A compound according to embodiment 135 wherein $R^3$, $R^4$, $R^5$, $R^6$, $R^{30}$, $R^{31}$, $R^{32}$ and $R^{33}$ are independently selected from the group consisting of halogen, —CF$_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, phenylthio, —C(O)—O—CH$_3$, or —C(O)—O—CH$_2$CH$_3$, each of which is optionally substituted with one or more substituents independently selected from $R^{12}$; or —C(O)—R$^{27}$—S(O)$_2$—NR$^{13}$R$^{14}$ or —S(O)$_2$—R$^2$.

EMBODIMENT 137

A compound according to embodiment 136 wherein $R^3$, $R^4$, $R^5$, $R^6$, $R^{30}$, $R^{31}$, $R^{32}$ and $R^{33}$ are independently selected from the group consisting of F, Cl, —CF$_3$, methyl, ethyl, propyl, isopropyl, butyl, tert-butyl, methoxy, ethoxy, propoxy, —C(O)—R$^{27}$, —S(O)$_2$—NR$^{13}$R$^{14}$ or —S(O)$_2$—R$^{27}$.

EMBODIMENT 138

A compound according to any one of the embodiments 97 to 137 wherein $R^{12}$ is halogen, cyano, hydroxy, carboxy, —CF$_3$, $C_{1-6}$-alkyloxy, $C_{3-8}$-cycloalkyloxy, aryloxy, aryl-$C_{1-6}$-alkyloxy or $C_{1-6}$-alkyl.

EMBODIMENT 139

A compound according to embodiment 138 wherein $R^{12}$ is halogen, cyano, hydroxy, carboxy, —CF$_3$, methoxy, ethoxy, propoxy, cyclopropyloxy, cyclobutyloxy, cyclopentyloxy, cyclohexyloxy, cycloheptyloxy, phenyloxy, phenyl-methoxy, phenyl-ethyloxy, phenylpropoxy, methyl, ethyl or propyl.

EMBODIMENT 140

A compound according to embodiment 139 wherein $R^{12}$ is halogen, carboxy, ethoxy, propoxy, cyclopropyloxy, cyclobutyloxy, cyclopentyloxy, cyclohexyloxy, cycloheptyloxy, phenyloxy, phenyl-methoxy, phenyl-ethyloxy, phenyl-propoxy, methyl, ethyl or propyl.

EMBODIMENT 141

A compound according to any one of the embodiments 97 to 140 wherein $R^{10}$ and $R^{11}$ independently represent hydrogen, methyl, ethyl, propyl, —C(O)—CH$_3$, —C(O)—CH$_2$CH$_3$, —CH$_2$C(O)OH, —CH$_2$CH$_2$C(O)OH, —C(O)—CH$_2$—C(O)OH, —C(O)—CH$_2$CH$_2$—C(O)OH, —S(O)$_2$CH$_3$, or phenyl.

EMBODIMENT 142

A compound according to embodiment 141 wherein $R^{10}$ and $R^{11}$ independently represent hydrogen, methyl, ethyl, —C(O)—CH$_3$, —CH$_2$C(O)OH, —C(O)—CH$_2$—C(O)OH, —S(O)$_2$CH$_3$, or phenyl.

EMBODIMENT 143

A compound according to embodiment 142 wherein $R^{10}$ and $R^{11}$ independently represent hydrogen, methyl, ethyl, or phenyl.

EMBODIMENT 144.

A compound according to any one of the embodiments 97 to 143 wherein $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryl-$C_{2-6}$-alkenyl, heteroaryl, heteroaryl-$C_{1-6}$-alkyl, carboxy-$C_{1-6}$-alkyl, $C_{1-6}$-alkoxy-$C_{1-6}$-alkyl, $C_{1-6}$-alkylthio-$C_{1-6}$-alkyl, $R^{10}$HN—$C_{1-6}$-alkyl, $R^{10}R^{11}$N—$C_{1-6}$-alkyl, $R^{10}R^{11}$N—S(O)$_2$—$C_{1-6}$-alkyl, or $R^{10}R^{11}$N—C(O)—$C_{1-6}$-alkyl, each of which is optionally substituted with one or more substituents independently selected from $R^{12}$.

EMBODIMENT 145

A compound according to embodiment 144 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl-$C_{2-6}$-alkenyl, aryl, heteroaryl, heteroaryl-$C_{1-6}$-alkyl, carboxy-$C_{1-6}$-alkyl, carboxy-$C_{1-6}$-alkyl, $C_{1-6}$-alkoxy-$C_{1-6}$-alkyl, $R^{10}$HN—$C_{1-6}$-alkyl, $R^{10}R^{11}$N—$C_{1-6}$-alkyl, $R^{10}R^{11}$N—S(O)$_2$—$C_{1-6}$-alkyl, or $R^{10}R^{11}$N—C(O)—$C_{1-6}$-alkyl, each of which is optionally substituted with one or more substituents independently selected from $R^{12}$.

EMBODIMENT 146

A compound according to embodiment 145 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl, heteroaryl-$C_{1-6}$-alkyl, aryl-$C_{1-6}$-alkyl, $C_{1-6}$-alkoxy-$C_{1-6}$-alkyl, carboxy-$C_{1-6}$-alkyl, or heteroaryl, each of which is optionally substituted with one or more substituents independently selected from $R^{12}$.

EMBODIMENT 147

A compound according to embodiment 146 wherein $R^{27}$ is methyl, ethyl, propyl, n-butyl, isobutyl, 1,1,1-trifluoroethyl, cyclopropyl, cyclopentyl, cyclopropylmethyl, phenyl, pyridyl, thiophene, imidazole, or thiazole, each of which is optionally substituted with one or more substituents independently selected from $R^{12}$.

EMBODIMENT 148

A compound according to embodiment 147 wherein $R^{27}$ is methyl, ethyl, propyl, n-butyl, isobutyl, 1,1,1-trifluoroethyl, cyclopropyl, cyclopentyl, cyclopropylmethyl, phenyl, or pyridyl, thiophene, imidazole, or thiazole.

EMBODIMENT 149

A compound according to embodiment 148 wherein $R^{27}$ is methyl, ethyl, or propyl.

EMBODIMENT 150

A compound according to any one of the embodiments 97 to 149 wherein $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

EMBODIMENT 151

A compound according to embodiment 150 wherein $R^{13}$ and $R^{14}$ are independently selected from the group consisting of hydrogen, methyl, ethyl, propyl, hydroxymethyl, hydroxyethyl, carboxy-methyl, carboxy-ethyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

EMBODIMENT 152

A compound according to embodiment 151 wherein $R^{13}$ and $R^{14}$ are independently selected from the group consisting of hydrogen, methyl, ethyl, propyl, or phenyl, each of which is optionally substituted with one or more substituents independently selected from $R^{15}$.

EMBODIMENT 153

A compound according to any one of the embodiments 97 to 152 wherein $R^{15}$ is halogen, cyano, hydroxy, carboxy, —CF$_3$, methyl, ethyl, or propyl.

EMBODIMENT 154

A compound according to embodiment 153 wherein $R^{15}$ is halogen, hydroxy, carboxy, —CF$_3$, methyl, or ethyl.

EMBODIMENT 155

A compound according to any one of the embodiments 97 to 154 wherein $R^{16}$ is —NR$^{19}$R$^{20}$, —NHS(O)$_2$CF$_3$, —NHS(O)$_2$CH$_2$CF$_3$, or —C(O)NR$^{19}$R$^{20}$.

EMBODIMENT 156

A compound according to any one of the embodiments 97 to 155 wherein $R^{20}$ represents $C_{3-8}$-cycloalkyl optionally substituted with one or more substituents independently selected from $R^{24}$.

EMBODIMENT 157

A compound according to any one of the embodiments 97 to 156 wherein $R^{21}$ is selected from
$C_{3-8}$-cycloalkyl, $C_{3-8}$-cycloalkyl-$C_{1-6}$-alkyl, carboxy-$C_{1-6}$-alkyl, hydroxy-$C_{1-6}$-alkyl, or —$C_{1-6}$-alkyl-NR$^{22}$R$^{23}$ which is substituted with one or more substituents independently selected from $R^{24}$.

EMBODIMENT 158

A compound according to embodiment 157 wherein $R^{21}$ is $C_{3-8}$-cycloalkyl.

EMBODIMENT 159

A compound according to any one of the embodiments 97 to 158 wherein $R^{22}$ and $R^{23}$ are independently selected from hydrogen, $C_{1-6}$-alkyl, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, $C_{3-8}$-cycloalkyl, phenyl, naphtyl, or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

EMBODIMENT 160

A compound according to embodiment 159 wherein $R^{22}$ and $R^{23}$ are independently selected from hydrogen, methyl, ethyl, propyl, butyl, carboxymethyl, carboxyethyl, carboxypropyl, hydroxymethyl, hydroxyethyl, hydroxypropyl, cyclopropyl, cyclobutyl, cyclopentyl, cyclohexyl, cycloheptyl, phenyl, naphtyl, or $R^{22}$ and $R^{23}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

EMBODIMENT 161

A compound according to embodiment 160 wherein $R^{22}$ and $R^{23}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

EMBODIMENT 162

A compound according to embodiment 160 wherein $R^{22}$ and $R^{23}$ are independently hydrogen, methyl, ethyl or propyl.

EMBODIMENT 163

A compound according to any one of the embodiments 97 to 162 wherein $R^{24}$ is halogen, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —C(O)—O—$C_{1-6}$-alkyl-aryl, or —S(O)$_2R^{28}$, wherein aryl is phenyl or naphtyl, and heteroaryl is pyridyl or pyrimidyl, and wherein each cyclic moiety is optionally substituted with one or more substituents independently selected from $R^{29}$.

EMBODIMENT 164

A compound according to embodiment 163 wherein $R^{24}$ is halogen, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, or —S(O)$_2R^{28}$, wherein aryl is phenyl or naphtyl, and heteroaryl is pyridyl or pyrimidyl, and wherein each cyclic moiety is optionally substituted with one or more substituents independently selected from $R^{29}$.

EMBODIMENT 165

A compound according to embodiment 164 wherein $R^{24}$ is halogen, carboxy, oxo, —$CF_3$, $C_{1-6}$-alkyl, carboxy-$C_{1-6}$-alkyl, —C(O)—$C_{1-6}$-alkyl, —C(O)—O—$C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —S(O)$_2R^2$, wherein aryl is phenyl or naphtyl, and wherein each cyclic moiety is optionally substituted with one or more substituents independently selected from $R^{29}$.

EMBODIMENT 166

A compound according to embodiment 165 wherein $R^{24}$ is carboxy, oxo, $C_{1-6}$-alkyl, carboxy-$C_{1-6}$-alkyl, —C(O)—O—$C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —S(O)$_2R^{28}$, wherein aryl is phenyl or naphtyl, and wherein each cyclic moiety is optionally substituted with one or more substituents independently selected from $R^{29}$.

EMBODIMENT 167

A compound according to embodiment 166 wherein $R^{24}$ is carboxy.

EMBODIMENT 168

A compound according to any one of the embodiments 97 to 167 wherein $R^{25}$ is independently $C_{1-6}$-alkyl, halogen, hydroxy, carboxy, or —$CF_3$.

EMBODIMENT 169

A compound according to embodiment 168 wherein $R^{25}$ is independently methyl, ethyl, propyl, halogen, hydroxy, carboxy, or —$CF_3$.

EMBODIMENT 170

A compound according to any one of the embodiments 97 to 169 wherein $R^{28}$ is $C_{1-6}$-alkyl, —$C_{1-6}$-alkyl-C(O)—O—$C_{1-6}$-alkyl, carboxy-$C_{1-6}$-alkyl, phenyl, phenyl-$C_{1-6}$-alkyl, heteroaryl optionally substituted with $C_{1-6}$-alkyl or —N(CH$_3$)$_2$, wherein heteroaryl is imidazolyl, pyridyl or pyrimidyl.

EMBODIMENT 171

A compound according to embodiment 170 wherein $R^{28}$ is $C_{1-6}$-alkyl, carboxy-$C_{1-6}$-alkyl, or —N(CH$_3$)$_2$.

EMBODIMENT 172

A compound according to any one of the embodiments 97 to 171 wherein $R^{29}$ is halogen, carboxy, —$CF_3$, $C_{1-6}$-alkyl, or $C_{1-6}$-alkoxy.

In one aspect the invention provides a compound which is
1,1-Dicyclopentyl-3-thiazol-2-yl-urea
1-Cyclopentyl-1-((R,S)-3,5-dimethyl-cyclohexyl)-3-thiazol-2-yl-urea
1-(1,4-Dioxa-spiro[4.5]dec-8-yl)-1-(4-methyl-cyclohexyl)-3-thiazol-2-yl-urea
1-Cyclopentyl-1-(1,4-dioxa-spiro[4.5]dec-8-yl)-3-thiazol-2-yl-urea
1-(4-Methyl-cyclohexyl)-3-(5-methyl-thiazol-2-yl)-1-(4-oxo-cyclohexyl)-urea Ethyl {2-[3-dicyclohexylureido]-5-[4-methylpiperazin-1-yl]-thiazol-4-yl}-acetate
1,1-Dicyclohexyl-3-(5-imidazol-1-yl-thiazol-2-yl)-urea
3-(5-Chloro-thiazol-2-yl)-1,1-bis-(tetrahydro-pyran-4-yl)-urea
3-[2-(3,3-Dicyclohexyl-ureido)-thiazol-4-ylmethylsulfanyl]-propionic acid
[2-(3,3-Dicyclohexyl-ureido)-thiazol-4-ylmethanesulfonyl]-acetic acid 1-(4-Amino-cyclohexyl)-1-cyclohexyl-3-(5-methyl-thiazol-2-yl)-urea 1-(1-Acetyl-piperidin-4-yl)-1-cyclopentyl-3-thiazol-2-yl-urea trans-3-(5-Chloro-thiazol-2-yl)-1-cyclohexyl-1-[1-(3-phenyl-acryloyl)-piperidin-4-yl]-urea
3-(5-Chloro-thiazol-2-yl)-1-cyclohexyl-1-[1-(2-phenoxy-acetyl)-piperidin-4-yl]-urea
1-(1-Acetyl-piperidin-4-yl)-3-(5-chloro-thiazol-2-yl)-1-cycloheptyl-urea
3-(5-Chloro-thiazol-2-yl)-1-(1-methanesulfonyl-piperidin-4-yl)-1-(trans-4-methyl-cyclohexyl)-urea
3-(5-Chloro-thiazol-2-yl)-1-(1-ethanesulfonyl-piperidin-4-yl)-1-(trans-4-methyl-cyclohexyl)-urea
3-(5-Chloro-thiazol-2-yl)-1-cyclohexyl-1-[1-(propane-1-sulfonyl)-piperidin-4-yl]-urea
2-[2-(3,3-Dicyclohexyl-ureido)-thiazol-5-ylsulfanyl]-2-methyl-propionic acid
2-[2-(3,3-Dicyclohexyl-ureido)-thiazol-5-ylsulfanyl]-propionic acid
[2-(3-Cyclohex-3-enyl-3-cyclohexyl-ureido)-thiazol-5-ylsulfanyl]-acetic acid
{2-[3-Cyclohexyl-3-(1-dimethylsulfamoyl-piperidin-4-yl)-ureido]-thiazol-5-ylsulfanyl}-acetic acid
3-(2-{3-Cyclohexyl-3-[1-(morpholine-4-carbonyl)-piperidin-4-yl]-ureido}-thiazol-5-ylsulfanyl)-propionic acid
(2-{3-Cyclohexyl-3-[1-(morpholine-4-carbonyl)-piperidin-4-yl]-ureido}-thiazol-5-ylsulfanyl)-acetic acid
3-{2-[3-Cyclohexyl-3-(1-dimethylsulfamoyl-piperidin-4-yl)-ureido]-thiazol-5-ylsulfanyl}-propionic acid
{2-[3-Cyclohexyl-3-(1-dimethylcarbamoyl-piperidin-4-yl)-ureido]-thiazol-5-ylsulfanyl}-acetic acid
3-{2-[3-Cyclohexyl-3-(1-dimethylcarbamoyl-piperidin-4-yl)-ureido]-thiazol-5-ylsulfanyl}-propionic acid
6-{4-[3-(5-Chloro-thiazol-2-yl)-1-cyclohexyl-ureido]-piperidin-1-yl}-6-oxo-hex-3-enoic acid
1-(1-Acetyl-piperidin-4-yl)-1-(trans-4-methyl-cyclohexyl)-3-[5-(2-oxo-2-piperidin-1-yl-ethylsulfanyl)-thiazol-2-yl]-urea
2-{2-[3-(1-Acetyl-piperidin-4-yl)-3-(trans-4-methyl-cyclohexyl)-ureido]-thiazol-5-ylsulfanyl}-N,N-diethyl-acetamide
1-(1-Acetyl-piperidin-4-yl)-1-(trans-4-methyl-cyclohexyl)-3-{5-[2-(4-methyl-piperazin-1-yl)-2-oxo-ethylsulfanyl]-thiazol-2-yl}-urea
1-(1-Acetyl-piperidin-4-yl)-1-(trans-4-methyl-cyclohexyl)-3-{5-[2-oxo-2-(4-pyrimidin-2-yl-piperazin-1-yl)-ethylsulfanyl]-thiazol-2-yl}-urea
1-(1-Acetyl-piperidin-4-yl)-1-(trans-4-methyl-cyclohexyl)-3-thiazol-2-yl-urea
{2-[3-Cyclohexyl-3-(trans-4-methoxymethyl-cyclohexyl)-ureido]-thiazol-5-ylsulfanyl}-acetic acid
{2-[3-Cyclopentyl-3-(trans-4-ethyl-cyclohexyl)-ureido]-thiazol-5-ylsulfanyl}-acetic acid
{2-[3-Cyclopentyl-3-(trans-4-isopropyl-cyclohexyl)-ureido]-thiazol-5-ylsulfanyl}-acetic acid
3-{2-[3-Cyclopentyl-3-(trans-4-ethyl-cyclohexyl)-ureido]-thiazol-5-ylsulfanyl}-propionic acid
3-{2-[3-Cyclopentyl-3-(trans-4-isopropyl-cyclohexyl)-ureido]-thiazol-5-ylsulfanyl}-propionic acid
{2-[3-Cyclohexyl-3-(trans-4-ethoxymethyl-cyclohexyl)-ureido]-thiazol-5-ylsulfanyl}-acetic acid
{2-[3-Cyclopentyl-3-(trans-4-methoxy-cyclohexyl)-ureido]-thiazol-5-ylsulfanyl}-acetic acid
{2-[3-Cycloheptyl-3-(trans-4-methoxy-cyclohexyl)-ureido]-thiazol-5-ylsulfanyl}-acetic acid
{2-[3-Cyclopentyl-3-(trans-4-ethoxy-cyclohexyl)-ureido]-thiazol-5-ylsulfanyl}-acetic acid
{2-[3-Cyclohexyl-3-(trans-4-ethoxy-cyclohexyl)-ureido]-thiazol-5-ylsulfanyl}-acetic acid
{2-[3-Cycloheptyl-3-(trans-4-ethoxy-cyclohexyl)-ureido]-thiazol-5-ylsulfanyl}-acetic acid
3-{2-[3-Cyclohexyl-3-(trans-4-methoxymethyl-cyclohexyl)-ureido]-thiazol-5-ylsulfanyl}-propionic acid
{2-[3-(trans-4-tert-Butyl-cyclohexyl)-3-cyclopentyl-ureido]-thiazol-5-ylsulfanyl}-acetic acid
{2-[3-(trans-4-tert-Butyl-cyclohexyl)-3-cyclohexyl-ureido]-thiazol-5-ylsulfanyl}-acetic acid
{2-[3-trans-4-tert-Butyl-cyclohexyl)-3-cycloheptyl-ureido]-thiazol-5-ylsulfanyl}-acetic acid
{2-[3-Cycloheptyl-3-(trans-4-methoxymethyl-cyclohexyl)-ureido]-thiazol-5-ylsulfanyl}-acetic acid
3-{2-[3-Cycloheptyl-3-trans-4-methoxymethyl-cyclohexyl)-ureido]-thiazol-5-ylsulfanyl}-propionic acid
3-{2-[3-Cyclohexyl-3-(trans-4-ethoxymethyl-cyclohexyl)-ureido]-thiazol-5-ylsulfanyl}-propionic acid
3-{2-[3-(trans-4-tert-Butyl-cyclohexyl)-3-cyclopentyl-ureido]-thiazol-5-ylsulfanyl}-propionic acid
3-{2-[3-(trans-4-tert-Butyl-cyclohexyl)-3-cyclohexyl-ureido]-thiazol-5-ylsulfanyl}-propionic acid
3-{2-[3-(trans-4-tert-Butyl-cyclohexyl)-3-cycloheptyl-ureido]-thiazol-5-ylsulfanyl}-propionic acid
2-{2-[3-(trans-4-tert-Butyl-cyclohexyl)-3-cyclopentyl-ureido]-thiazol-5-ylsulfanyl}-2-methyl-propionic acid
2-{2-[3-(trans-4-tert-Butyl-cyclohexyl)-3-cyclohexyl-ureido]-thiazol-5-ylsulfanyl}-2-methyl-propionic acid
{2-[3-Cycloheptyl-3-(trans-4-ethoxymethyl-cyclohexyl)-ureido]-thiazol-5-ylsulfanyl}-acetic acid
{2-[3-Cyclohexyl-3-(trans-4-cyclopropylmethoxy-cyclohexyl)-ureido]-thiazol-5-ylsulfanyl}-acetic acid
3-{2-[-3-Cyclohexyl-3-(trans-4-cyclopropylmethoxy-cyclohexyl)-ureido]-thiazol-5-ylsulfanyl}-propionic acid
3-{2-[3-Cyclopentyl-3-(trans-4-methoxy-cyclohexyl)-ureido]-thiazol-5-ylsulfanyl}-propionic acid
3-{2-[3-Cyclohexyl-3-(trans-4-methoxy-cyclohexyl)-ureido]-thiazol-5-ylsulfanyl}-propionic acid
3-{2-[3-Cycloheptyl-3-(trans-4-methoxy-cyclohexyl)-ureido]-thiazol-5-ylsulfanyl}-propionic acid
3-{2-[3-Cyclopentyl-3-(trans-4-ethoxy-cyclohexyl)-ureido]-thiazol-5-ylsulfanyl}-propionic acid
3-{2-[3-Cyclohexyl-3-(trans-4-ethoxy-cyclohexyl)-ureido]-thiazol-5-ylsulfanyl}-propionic acid
3-{2-[3-Cycloheptyl-3-(trans-4-ethoxy-cyclohexyl)-ureido]-thiazol-5-ylsulfanyl}-propionic acid
(2-{3-Cyclohexyl-3-[trans-4-(2-methoxy-ethoxy)-cyclohexyl]-ureido}-thiazol-5-ylsulfanyl)-acetic acid
3-(2-{3-Cyclohexyl-3-[trans-4-(2-methoxy-ethoxy)-cyclohexyl]-ureido}-thiazol-5-ylsulfanyl)-propionic acid
{2-[3-Cyclopentyl-3-(trans-4-methoxymethyl-cyclohexyl)-ureido]-thiazol-5-ylsulfanyl}-acetic acid
3-{2-[3-Cycloheptyl-3-(trans-4-ethoxymethyl-cyclohexyl)-ureido]-thiazol-5-ylsulfanyl}-propionic acid 3-{2-[3-Cyclopentyl-3-(trans-4-methoxymethyl-cyclohexyl)-ureido]-thiazol-5-ylsulfanyl}-propionic acid
2-{2-[3-Cyclohexyl-3-(trans-4-cyclopropylmethoxy-cyclohexyl)-ureido]-thiazol-5-ylsulfanyl}-2-methyl-propionic acid
2-(2-{3-Cyclohexyl-3-[trans-4-(2-methoxy-ethoxy)-cyclohexyl]-ureido}-thiazol-5-ylsulfanyl)-2-methyl-propionic acid
[2-(3,3-Dicyclohexyl-ureido)-thiazole-5-sulfonylamino]-acetic acid
{2-[3-(1-Acetyl-piperidin-4-yl)-3-cyclohexyl-ureido]-thiazole-5-sulfonylamino}-acetic acid
2-{2-[3-Cycloheptyl-3-(trans-4-ethoxymethyl-cyclohexyl)-ureido]-thiazol-5-ylsulfanyl}-2-methyl-propionic acid
2-{2-[3-Cycloheptyl-3-(trans-4-methoxymethyl-cyclohexyl)-ureido]-thiazol-5-ylsulfanyl}-2-methyl-propionic acid
{2-[3-Cyclohexyl-3-(trans-4-methyl-cyclohexyl)-ureido]-thiazole-5-sulfonylamino}-acetic acid
3-[2-(3,3-Dicyclohexyl-ureido)-thiazole-5-sulfonylamino]-propionic acid
3-{2-[3-Cyclohexyl-3-(trans-4-methyl-cyclohexyl)-ureido]-thiazole-5-sulfonylamino}-propionic acid
{[2-(3,3-Dicyclohexyl-ureido)-thiazole-5-sulfonyl]-methyl-amino}-acetic acid
({2-[3-Cyclohexyl-3-(trans-4-methyl-cyclohexyl)-ureido]-thiazole-5-sulfonyl}-methyl-amino)-acetic acid
(S)-1-[2-(3,3-Dicyclohexyl-ureido)-thiazole-5-sulfonyl]-pyrrolidine-2-carboxylic acid
(S)-1-{2-[3-Cyclohexyl-3-(trans-4-methyl-cyclohexyl)-ureido]-thiazole-5-sulfonyl}-pyrrolidine-2-carboxylic acid
{2-[3-Cycloheptyl-3-(trans-4-propoxy-cyclohexyl)-ureido]-thiazol-5-ylsulfanyl}-acetic acid
{2-[3-Cyclopentyl-3-(trans-4-propoxy-cyclohexyl)-ureido]-thiazol-5-ylsulfanyl}-acetic acid
{2-[3-Cyclohexyl-3-(trans-4-isobutoxy-cyclohexyl)-ureido]-thiazol-5-ylsulfanyl}-acetic acid
2-{2-[3-Cyclohexyl-3-(trans-4-propoxy-cyclohexyl)-ureido]-thiazol-5-ylsulfanyl}-2-methyl-propionic acid
3-{2-[3-Cyclohexyl-3-(trans-4-isobutoxy-cyclohexyl)-ureido]-thiazol-5-ylsulfanyl}-propionic acid
3-{2-[3-Cycloheptyl-3-(trans-4-propoxy-cyclohexyl)-ureido]-thiazol-5-ylsulfanyl}-propionic acid
3-{2-[3-Cyclopentyl-3-(trans-4-propoxy-cyclohexyl)-ureido]-thiazol-5-ylsulfanyl}-propionic acid
2-{2-[3-Cyclohexyl-3-(trans-4-ethoxymethyl-cyclohexyl)-ureido]-thiazol-5-ylsulfanyl}-2-methyl-propionic acid
{2-[3-Cyclohexyl-3-(trans-4-phenyl-cyclohexyl)-ureido]-thiazol-5-ylsulfanyl}-acetic acid
3-{2-[3-Cyclohexyl-3-(trans-4-phenyl-cyclohexyl)-ureido]-thiazol-5-ylsulfanyl}-propionic acid
{2-[3-Cycloheptyl-3-(trans-4-phenyl-cyclohexyl)-ureido]-thiazol-5-ylsulfanyl}-acetic acid
3-{2-[3-Cycloheptyl-3-(trans-4-phenyl-cyclohexyl)-ureido]-thiazol-5-ylsulfanyl}-propionic acid
2-{2-[3-Cyclohexyl-3-(4-phenyl-cyclohexyl)-ureido]-thiazol-5-ylsulfanyl}-2-methyl-propionic acid
2-{2-[3-Cycloheptyl-3-(4-phenyl-cyclohexyl)-ureido]-thiazol-5-ylsulfanyl}-2-methyl-propionic acid
(E)-6-[4-(1-Cyclohexyl-3-thiazol-2-yl-ureido)-piperidin-1-yl]-6-oxo-hex-3-enoic acid
{2-[3-Cyclohexyl-3-(trans-4-isopropyl-cyclohexyl)-ureido]-thiazol-5-ylsulfanyl}-acetic acid
{2-[3-Cycloheptyl-3-(trans-4-isopropyl-cyclohexyl)-ureido]-thiazol-5-ylsulfanyl}-acetic acid
{2-[3-Cyclohexyl-3-(trans-4-ethyl-cyclohexyl)-ureido]-thiazol-5-ylsulfanyl}-acetic acid
{2-[3-Cyclohexyl-3-(trans-4-propoxy-cyclohexyl)-ureido]-thiazole-5-sulfonylamino}-acetic acid
3-{2-[3-Cyclohexyl-3-(trans-4-propoxy-cyclohexyl)-ureido]-thiazole-5-sulfonylamino}-propionic acid
({2-[3-Cyclohexyl-3-(trans-4-propoxy-cyclohexyl)-ureido]-thiazole-5-sulfonyl}-methyl-amino)-acetic acid
{2-[3-(trans-4-tert-Butoxy-cyclohexyl)-3-cycloheptyl-ureido]-thiazol-5-ylsulfanyl}-acetic acid
{2-[3-(trans-4-tert-Butoxy-cyclohexyl)-3-cyclohexyl-ureido]-thiazol-5-ylsulfanyl}-acetic acid
3-{2-[3-(trans-4-tert-Butoxy-cyclohexyl)-3-cycloheptyl-ureido]-thiazol-5-ylsulfanyl}-propionic acid
3-{2-[3-(trans-4-tert-Butoxy-cyclohexyl)-3-cyclohexyl-ureido]-thiazol-5-ylsulfanyl}-propionic acid
{2-[3-(trans-4-Benzyloxy-cyclohexyl)-3-cyclohexyl-ureido]-thiazol-5-ylsulfanyl}-acetic acid
{2-[3-(trans-4-Benzyloxy-cyclohexyl)-3-cycloheptyl-ureido]-thiazol-5-ylsulfanyl}-acetic acid
3-{2-[3-(trans-4-Benzyloxy-cyclohexyl)-3-cyclohexyl-ureido]-thiazol-5-ylsulfanyl}-propionic acid
3-{2-[3-(trans-4-Benzyloxy-cyclohexyl)-3-cycloheptyl-ureido]-thiazol-5-ylsulfanyl}-propionic acid
2-{2-[3-Cyclohexyl-3-(trans-4-methyl-cyclohexyl)-ureido]-thiazole-5-sulfonylamino}-2-methyl-propionic acid
(R)-1-{2-[3-Cyclohexyl-3-(trans-4-methyl-cyclohexyl)-ureido]-thiazole-5-sulfonyl}-pyrrolidine-2-carboxylic acid
2-{2-[3-Cyclohexyl-3-(trans-4-propoxy-cyclohexyl)-ureido]-thiazole-5-sulfonylamino}-2-methyl-propionic acid
(R)-1-{2-[3-Cyclohexyl-3-(trans-4-propoxy-cyclohexyl)-ureido]-thiazole-5-sulfonyl}-pyrrolidine-302-carboxylic acid
{2-[3-Cyclohexyl-3-(trans-4-isopropoxy-cyclohexyl)-ureido]-thiazol-5-ylsulfanyl}-acetic acid
{2-[3-Cycloheptyl-3-(trans-4-isopropoxy-cyclohexyl)-ureido]-thiazol-5-ylsulfanyl}-acetic acid
3-{2-[3-Cyclohexyl-3-(trans-4-isopropoxy-cyclohexyl)-ureido]-thiazol-5-ylsulfanyl}-propionic acid
3-{2-[3-Cycloheptyl-3-(trans-4-isopropoxy-cyclohexyl)-ureido]-thiazol-5-ylsulfanyl}-propionic acid
3-(2-{3-Cyclohexyl-3-[4-(trans-2-methoxy-ethoxymethyl)-cyclohexyl]-ureido}-thiazol-5-ylsulfanyl)-acetic acid
3-(2-{3-Cyclohexyl-3-[4-(trans-2-methoxy-ethoxymethyl)-cyclohexyl]-ureido}-thiazol-5-ylsulfanyl)-propionic acid
(2-{3-Cycloheptyl-3-[4-(trans-2-methoxy-ethoxymethyl)-cyclohexyl]-ureido}-thiazol-5-ylsulfanyl)-acetic acid
3-(2-{3-Cycloheptyl-3-[4-(trans-2-methoxy-ethoxymethyl)-cyclohexyl]-ureido}-thiazol-5-ylsulfanyl)-propionic acid
(2-{3-Cyclohexyl-3-[4-(trans-2,2,2-trifluoro-ethoxyethyl)-cyclohexyl]-ureido}-thiazol-5-ylsulfanyl)-acetic acid
(2-{2-[3-Cyclohexyl-3-(trans-4-propoxy-cyclohexyl)-ureido]-thiazol-5-ylsulfanyl}-acetyl)-methanesulfonamide
2-(2-{3-Cyclohexyl-3-[4-(trans-2-methoxy-ethoxymethyl)-cyclohexyl]-ureido}-thiazol-5-ylsulfanyl)-2-methyl-propionic acid
2-(2-{3-Cycloheptyl-3-[4-(trans-2-methoxy-ethoxymethyl)-cyclohexyl]-ureido}-thiazol-5-ylsulfanyl)-2-methyl-propionic acid
2-{2-[3-Cyclohexyl-3-(trans-4-methoxymethyl-cyclohexyl)-ureido]-thiazol-5-ylsulfanyl}-2-methyl-propionic acid
{2-[3-Cyclohexyl-3-(cis-4-propoxy-cyclohexyl)-ureido]-thiazol-5-ylsulfanyl}-acetic acid
{2-[3-Cyclohexyl-3-(trans-4-phenoxy-cyclohexyl)-ureido]-thiazol-5-ylsulfanyl}-acetic acid
(2-{3-Cyclohexyl-3-[trans-4-(pyridin-2-yloxy)-cyclohexyl]-ureido}-thiazol-5-ylsulfanyl)-acetic acid 3-(2-{3-Cyclohexyl-3-[trans-4-(pyridin-2-yloxy)-cyclohexyl]-ureido}-thiazol-5-ylsulfanyl)-propionic acid
(2-{3-Cyclohexyl-3-[trans-4-(2,2,2-trifluoro-ethoxy)-cyclohexyl]-ureido}-thiazol-5-ylsulfanyl)-acetic acid
2-[3-Cyclohexyl-3-(trans-4-methyl-cyclohexyl)-ureido]-thiazole-5-sulfonic acid methylamide In another aspect the invention provides a compound which is 2-(3,3-Dicyclohexylureido)-4-methylthiazole-5-carboxylic acid (2-hydroxyethyl)amide
(2-{3-Cyclohexyl-3-[-4-(2-methyl-allyloxy)-cyclohexyl]-ureido}-thiazol-5-ylsulfanyl)-acetic acid
3-(2-{3-Cyclohexyl-3-[trans-4-(2-methyl-allyloxy)-cyclohexyl]-ureido}-thiazol-5-ylsulfanyl)-propionic acid
2-(2-{3-Cyclohexyl-3-[trans-4-(2-methyl-allyloxy)-cyclohexyl]-ureido}-thiazol-5-ylsulfanyl)-2-methyl-propionic acid
{2-[3-Cyclohexyl-3-(trans-4-phenoxymethyl-cyclohexyl)-ureido]-thiazol-5-ylsulfanyl}-acetic acid
3-{2-[3-Cyclohexyl-3-(trans-4-cyclopropylmethoxymethyl-cyclohexyl)-ureido]-thiazol-5-ylsulfanyl}-propionic acid
3-{2-[3-Cycloheptyl-3-(trans-4-cyclopropylmethoxymethyl-cyclohexyl)-ureido]-thiazol-5-ylsulfanyl}-propionic acid
(2-{3-Cyclohexyl-3-[4-(trans-4-methoxy-phenoxymethyl)-cyclohexyl]-ureido}-thiazol-5-ylsulfanyl)-acetic acid
(2-{3-Cyclohexyl-3-[trans-4-(4-fluoro-phenoxymethyl)-cyclohexyl]-ureido}-thiazol-5-ylsulfanyl)-acetic acid
(2-{3-Cyclohexyl-3-[trans-4-(4-imidazol-1-yl-phenoxymethyl)-cyclohexyl]-ureido}-thiazol-5-ylsulfanyl)-acetic acid
2-({2-[3-Cyclohexyl-3-(trans-4-methyl-cyclohexyl)-ureido]-thiazole-5-sulfonyl}-methyl-amino)-N,N-diethyl-acetamide
1-{2-[3-Cyclohexyl-3-(trans-4-methyl-cyclohexyl)-ureido]-thiazole-5-sulfonylamino}-cyclobutanecarboxylic acid
1-{2-[3-Cyclohexyl-3-(trans-4-methyl-cyclohexyl)-ureido]-thiazole-5-sulfonylamino}-cyclopropanecarboxylic acid
1-{2-[3-Cyclohexyl-3-(trans-4-propoxy-cyclohexyl)-ureido]-thiazole-5-sulfonylamino}-cyclobutanecarboxylic acid
{2-[3-Cyclohexyl-3-(trans-4-cyclopropylmethoxymethyl-cyclohexyl)-ureido]-thiazol-5-ylsulfanyl}-acetic acid
{2-[3-Cycloheptyl-3-(trans-4-cyclopropylmethoxymethyl-cyclohexyl)-ureido]-thiazol-5-ylsulfanyl}-acetic acid
{2-[3-(trans-4-Benzyloxymethyl-cyclohexyl)-3-cyclohexyl-ureido]-thiazol-5-ylsulfanyl}-acetic acid
{2-[3-Cycloheptyl-3-(trans-4-phenoxymethyl-cyclohexyl)-ureido]-thiazol-5-ylsulfanyl}-acetic acid
(2-{3-Cycloheptyl-3-[trans-4-(4-methoxy-phenoxymethyl)-cyclohexyl]-ureido}-thiazol-5-ylsulfanyl)-acetic acid
(2-{3-Cycloheptyl-3-[trans-4-(4-fluoro-phenoxymethyl)-cyclohexyl]-ureido}-thiazol-5-ylsulfanyl)-acetic acid
(2-{3-Cycloheptyl-3-[trans-4-(4-trifluoromethyl-phenoxymethyl)-cyclohexyl]-ureido}-thiazol-5-ylsulfanyl)-acetic acid
(2-{3-Cyclohexyl-3-[trans-4-(4-trifluoromethyl-phenoxymethyl)-cyclohexyl]-ureido}-thiazol-5-ylsulfanyl)-acetic acid
3-{2-[3-Cyclohexyl-3-(trans-4-phenoxymethyl-cyclohexyl)-ureido]-thiazol-5-ylsulfanyl}-propionic acid
3-(2-{3-Cyclohexyl-3-[trans-4-(4-methoxy-phenoxymethyl)-cyclohexyl]-ureido}-thiazol-5-ylsulfanyl)-propionic acid
3-(2-{3-Cyclohexyl-3-[trans-4-(4-fluoro-phenoxymethyl)-cyclohexyl]-ureido}-thiazol-5-ylsulfanyl)-propionic acid
2-{2-[3-Cyclohexyl-3-(trans-4-cyclopropylmethoxymethyl-cyclohexyl)-ureido]-thiazol-5-ylsulfanyl}-2-methyl-propionic acid
2-{2-[3-Cyclohexyl-3-(trans-4-methyl-cyclohexyl)-ureido]-thiazole-5-sulfonylamino}-N,N-diethyl-acetamide
2-{2-[3-Cyclohexyl-3-(trans-4-methyl-cyclohexyl)-ureido]-thiazole-5-sulfonylamino}-N-methyl-acetamide
2-{2-[3-Cyclohexyl-3-(trans-4-methyl-cyclohexyl)-ureido]-thiazole-5-sulfonylamino}-N-isopropyl-acetamide
2-[3-Cyclohexyl-3-(trans-4-methyl-cyclohexyl)-ureido]-thiazole-5-sulfonic acid (2-morpholin-4-yl-2-oxo-ethyl)-amide In another aspect the invention provides a compound which is 1,1-Dicyclopentyl-3-thiazol-2-yl-urea
1-Cyclopentyl-1-((R,S)-3,5-dimethyl-cyclohexyl)-3-thiazol-2-yl-urea
1-(1,4-Dioxa-spiro[4.5]dec-8-yl)-1-(4-methyl-cyclohexyl)-3-thiazol-2-yl-urea
1-Cyclopentyl-1-(1,4-dioxa-spiro[4.5]dec-8-yl)-3-thiazol-2-yl-urea
1-(4-Methyl-cyclohexyl)-3-(5-methyl-thiazol-2-yl)-1-(4-oxo-cyclohexyl)-urea
Ethyl {2-[3-dicyclohexylureido]-5-[4-methylpiperazin-1-yl]-thiazol-4-yl}-acetate
1,1-Dicyclohexyl-3-(5-imidazol-1-yl-thiazol-2-yl)-urea
3-(5-Chloro-thiazol-2-yl)-1,1-bis-(tetrahydro-pyran-4-yl)-urea
3-[2-(3,3-Dicyclohexyl-ureido)-thiazol-4-ylmethylsulfanyl]-propionic acid
[2-(3,3-Dicyclohexyl-ureido)-thiazol-4-ylmethanesulfonyl]-acetic acid
1-(4-Amino-cyclohexyl)-1-cyclohexyl-3-(5-methyl-thiazol-2-yl)-urea
1-(1-Acetyl-piperidin-4-yl)-1-cyclopentyl-3-thiazol-2-yl-urea trans-3-(5-Chloro-thiazol-2-yl)-1-cyclohexyl-1-[1-(3-phenyl-acryloyl)-piperidin-4-yl]-urea
3-(5-Chloro-thiazol-2-yl)-1-cyclohexyl-1-[1-(2-phenoxy-acetyl)-piperidin-4-yl]-urea
1-(1-Acetyl-piperidin-4-yl)-3-(5-chloro-thiazol-2-yl)-1-cycloheptyl-urea
3-(5-Chloro-thiazol-2-yl)-1-(1-methanesulfonyl-piperidin-4-yl)-1-(trans-4-methyl-cyclohexyl)-urea
3-(5-Chloro-thiazol-2-yl)-1-(1-ethanesulfonyl-piperidin-4-yl)-1-(trans-4-methyl-cyclohexyl)-urea
3-(5-Chloro-thiazol-2-yl)-1-cyclohexyl-1-[1-(propane-1-sulfonyl)-piperidin-4-yl]-urea
2-[2-(3,3-Dicyclohexyl-ureido)-thiazol-5-ylsulfanyl]-2-methyl-propionic acid
2-[2-(3,3-Dicyclohexyl-ureido)-thiazol-5-ylsulfanyl]-propionic acid
[2-(3-Cyclohex-3-enyl-3-cyclohexyl-ureido)-thiazol-5-ylsulfanyl]-acetic acid
{2-[3-Cyclohexyl-3-(1-dimethylsulfamoyl-piperidin-4-yl)-ureido]-thiazol-5-ylsulfanyl}-acetic acid
3-(2-{3-Cyclohexyl-3-[1-(morpholine-4-carbonyl)-piperidin-4-yl]-ureido}-thiazol-5-ylsulfanyl)-propionic acid
(2-{3-Cyclohexyl-3-[1-(morpholine-4-carbonyl)-piperidin-4-yl]-ureido}-thiazol-5-ylsulfanyl)-acetic acid
3-{2-[3-Cyclohexyl-3-(1-dimethylsulfamoyl-piperidin-4-yl)-ureido]-thiazol-5-ylsulfanyl}-propionic acid
{2-[3-Cyclohexyl-3-(1-dimethylcarbamoyl-piperidin-4-yl)-ureido]-thiazol-5-ylsulfanyl}-acetic acid
3-{2-[3-Cyclohexyl-3-(1-dimethylcarbamoyl-piperidin-4-yl)-ureido]-thiazol-5-ylsulfanyl}-propionic acid
6-{4-[3-(5-Chloro-thiazol-2-yl)-1-cyclohexyl-ureido]-piperidin-1-yl}-6-oxo-hex-3-enoic acid 1-(1-Acetyl-piperidin-4-yl)-1-(trans-4-methyl-cyclohexyl)-3-[5-(2-oxo-2-piperidin-1-yl-ethylsulfanyl)-thiazol-2-yl]-urea 2-{2-[3-(1-Acetyl-piperidin-4-yl)-3-(trans-4-methyl-cyclohexyl)-ureido]-thiazol-5-ylsulfanyl}-N,N-diethyl-acetamide 1-(1-Acetyl-piperidin-4-yl)-1-(trans-4-methyl-cyclohexyl)-3-{5-[2-(4-methyl-piperazin-1-yl)-2-oxo-ethylsulfanyl]-thiazol-2-yl}-urea 1-(1-Acetyl-piperidin-4-yl)-1-(trans-4-methyl-cyclohexyl)-3-{5-[2-oxo-2-(4-pyrimidin-2-yl-piperazin-1-yl)-ethylsulfanyl]-thiazol-2-yl}-urea 1-(1-Acetyl-piperidin-4-yl)-1-(trans-4-methyl-cyclohexyl)-3-thiazol-2-yl-urea {2-[3-Cyclohexyl-3-(trans-4-methoxymethyl-cyclohexyl)-ureido]-thiazol-5-ylsulfanyl}-acetic acid {2-[3-Cyclopentyl-3-(trans-4-ethyl-cyclohexyl)-ureido]-thiazol-5-ylsulfanyl}-acetic acid {2-[3-Cyclopentyl-3-(trans-4-isopropyl-cyclohexyl)-ureido]-thiazol-5-ylsulfanyl}-acetic acid 3-{2-[3-Cyclopentyl-3-(trans-4-ethyl-cyclohexyl)-ureido]-thiazol-5-ylsulfanyl}-propionic acid 3-{2-[3-Cyclopentyl-3-(trans-4-isopropyl-cyclohexyl)-ureido]-thiazol-5-ylsulfanyl}-propionic acid {2-[3-Cyclohexyl-3-(trans-4-ethoxymethyl-cyclohexyl)-ureido]-thiazol-5-ylsulfanyl}-acetic acid {2-[3-Cyclopentyl-3-(trans-4-methoxy-cyclohexyl)-ureido]-thiazol-5-ylsulfanyl}-acetic acid

{2-[3-Cycloheptyl-3-(trans-4-methoxy-cyclohexyl)-ureido]-thiazol-5-ylsulfanyl}-acetic acid {2-[3-Cyclopentyl-3-(trans-4-ethoxy-cyclohexyl)-ureido]-thiazol-5-ylsulfanyl}-acetic acid {2-[3-Cyclohexyl-3-(trans-4-ethoxy-cyclohexyl)-ureido]-thiazol-5-ylsulfanyl}-acetic acid {2-[3-Cycloheptyl-3-(trans-4-ethoxy-cyclohexyl)-ureido]-thiazol-5-ylsulfanyl}-acetic acid 3-{2-[3-Cyclohexyl-3-(trans-4-methoxymethyl-cyclohexyl)-ureido]-thiazol-5-ylsulfanyl}-propionic acid {2-[3-(trans-4-tert-Butyl-cyclohexyl)-3-cyclopentyl-ureido]-thiazol-5-ylsulfanyl}-acetic acid {2-[3-(trans-4-tert-Butyl-cyclohexyl)-3-cyclohexyl-ureido]-thiazol-5-ylsulfanyl}-acetic acid

{2-[3-trans-4-tert-Butyl-cyclohexyl)-3-cycloheptyl-ureido]-thiazol-5-ylsulfanyl}-acetic acid {2-[3-Cycloheptyl-3-(trans-4-methoxymethyl-cyclohexyl)-ureido]-thiazol-5-ylsulfanyl}-acetic acid 3-{2-[3-Cycloheptyl-3-trans-4-methoxymethyl-cyclohexyl)-ureido]-thiazol-5-ylsulfanyl}-propionic acid 3-{2-[3-Cyclohexyl-3-(trans-4-ethoxymethyl-cyclohexyl)-ureido]-thiazol-5-ylsulfanyl}-propionic acid 3-{2-[3-(trans-4-tert-Butyl-cyclohexyl)-3-cyclopentyl-ureido]-thiazol-5-ylsulfanyl}-propionic acid 3-{2-[3-(trans-4-tert-Butyl-cyclohexyl)-3-cyclohexyl-ureido]-thiazol-5-ylsulfanyl}-propionic acid 3-{2-[3-(trans-4-tert-Butyl-cyclohexyl)-3-cycloheptyl-ureido]-thiazol-5-ylsulfanyl}-propionic acid 2-{2-[3-(trans-4-tert-Butyl-cyclohexyl)-3-cyclopentyl-ureido]-thiazol-5-ylsulfanyl}-2-methyl-propionic acid 2-{2-[3-(trans-4-tert-Butyl-cyclohexyl)-3-cyclohexyl-ureido]-thiazol-5-ylsulfanyl}-2-methyl-propionic acid {2-[3-Cycloheptyl-3-(trans-4-ethoxymethyl-cyclohexyl)-ureido]-thiazol-5-ylsulfanyl}-acetic acid {2-[3-Cyclohexyl-3-(trans-4-cyclopropylmethoxy-cyclohexyl)-ureido]-thiazol-5-ylsulfanyl}-acetic acid 3-{2-[-3-Cyclohexyl-3-(trans-4-cyclopropylmethoxy-cyclohexyl)-ureido]-thiazol-5-ylsulfanyl}-propionic acid 3-{2-[3-Cyclopentyl-3-(trans-4-methoxy-cyclohexyl)-ureido]-thiazol-5-ylsulfanyl}-propionic acid 3-{2-[3-Cyclohexyl-3-(trans-4-methoxy-cyclohexyl)-ureido]-thiazol-5-ylsulfanyl}-propionic acid 3-{2-[3-Cycloheptyl-3-(trans-4-methoxy-cyclohexyl)-ureido]-thiazol-5-ylsulfanyl}-propionic acid 3-{2-[3-Cyclopentyl-3-(trans-4-ethoxy-cyclohexyl)-ureido]-thiazol-5-ylsulfanyl}-propionic acid 3-{2-[3-Cyclohexyl-3-(trans-4-ethoxy-cyclohexyl)-ureido]-thiazol-5-ylsulfanyl}-propionic acid 3-{2-[3-Cycloheptyl-3-(trans-4-ethoxy-cyclohexyl)-ureido]-thiazol-5-ylsulfanyl}-propionic acid (2-{3-Cyclohexyl-3-[trans-4-(2-methoxy-ethoxy)-cyclohexyl]-ureido}-thiazol-5-ylsulfanyl)-acetic acid 3-(2-{3-Cyclohexyl-3-[trans-4-(2-methoxy-ethoxy)-cyclohexyl]-ureido}-thiazol-5-ylsulfanyl)-propionic acid {2-[3-Cyclopentyl-3-(trans-4-methoxymethyl-cyclohexyl)-ureido]-thiazol-5-ylsulfanyl}-acetic acid 3-{2-[3-Cycloheptyl-3-(trans-4-ethoxymethyl-cyclohexyl)-ureido]-thiazol-5-ylsulfanyl}-propionic acid 3-{2-[3-Cyclopentyl-3-(trans-4-methoxymethyl-cyclohexyl)-ureido]-thiazol-5-ylsulfanyl}-propionic acid 2-{2-[3-Cyclohexyl-3-(trans-4-cyclopropylmethoxy-cyclohexyl)-ureido]-thiazol-5-ylsulfanyl}-2-methyl-propionic acid 2-(2-{3-Cyclohexyl-3-[trans-4-(2-methoxy-ethoxy)-cyclohexyl]-ureido}-thiazol-5-ylsulfanyl)-2-methyl-propionic acid

[2-(3,3-Dicyclohexyl-ureido)-thiazole-5-sulfonylamino]-acetic acid

{2-[3-(1-Acetyl-piperidin-4-yl)-3-cyclohexyl-ureido]-thiazole-5-sulfonylamino}-acetic acid 2-{2-[3-Cycloheptyl-3-(trans-4-ethoxymethyl-cyclohexyl)-ureido]-thiazol-5-ylsulfanyl}-2-methyl-propionic acid 2-{2-[3-Cycloheptyl-3-(trans-4-methoxymethyl-cyclohexyl)-ureido]-thiazol-5-ylsulfanyl}-2-methyl-propionic acid {2-[3-Cyclohexyl-3-(trans-4-methyl-cyclohexyl)-ureido]-thiazole-5-sulfonylamino}-acetic acid 3-[2-(3,3-Dicyclohexyl-ureido)-thiazole-5-sulfonylamino]-propionic acid 3-{2-[3-Cyclohexyl-3-(trans-4-methyl-cyclohexyl)-ureido]-thiazole-5-sulfonylamino}-propionic acid {[2-(3,3-Dicyclohexyl-ureido)-thiazole-5-sulfonyl]-methyl-amino}-acetic acid ({2-[3-Cyclohexyl-3-(trans-4-methyl-cyclohexyl)-ureido]-thiazole-5-sulfonyl}-methyl-amino)-acetic acid (S)-1-[2-(3,3-Dicyclohexyl-ureido)-thiazole-5-sulfonyl]-pyrrolidine-2-carboxylic acid (S)-1-{2-[3-Cyclohexyl-3-(trans-4-methyl-cyclohexyl)-ureido]-thiazole-5-sulfonyl}-pyrrolidine-2-carboxylic acid {2-[3-Cycloheptyl-3-(trans-4-propoxy-cyclohexyl)-ureido]-thiazol-5-ylsulfanyl}-acetic acid {2-[3-Cyclopentyl-3-(trans-4-propoxy-cyclohexyl)-ureido]-thiazol-5-ylsulfanyl}-acetic acid {2-[3-Cyclohexyl-3-(trans-4-isobutoxy-cyclohexyl)-ureido]-thiazol-5-ylsulfanyl}-acetic acid 2-{2-[3-Cyclohexyl-3-(trans-4-propoxy-cyclohexyl)-ureido]-thiazol-5-ylsulfanyl}-2-methyl-propionic acid 3-{2-[3-Cyclohexyl-3-(trans-4-isobutoxy-cyclohexyl)-ureido]-thiazol-5-ylsulfanyl}-propionic acid 3-{2-[3-Cycloheptyl-3-(trans-4-propoxy-cyclohexyl)-ureido]-thiazol-5-ylsulfanyl}-propionic acid 3-{2-[3-Cyclopentyl-3-(trans-4-propoxy-cyclohexyl)-ureido]-thiazol-5-ylsulfanyl}-propionic acid 2-{2-[3-Cyclohexyl-3-(trans-4-ethoxymethyl-cyclohexyl)-ureido]-thiazol-5-ylsulfanyl}-2-methyl-propionic acid {2-[3-Cyclohexyl-3-(trans-4-phenyl-cyclohexyl)-ureido]-thiazol-5-ylsulfanyl}-acetic acid
3-{2-[3-Cyclohexyl-3-(trans-4-phenyl-cyclohexyl)-ureido]-thiazol-5-ylsulfanyl}-propionic acid
{2-[3-Cycloheptyl-3-(trans-4-phenyl-cyclohexyl)-ureido]-thiazol-5-ylsulfanyl}-acetic acid
3-{2-[3-Cycloheptyl-3-(trans-4-phenyl-cyclohexyl)-ureido]-thiazol-5-ylsulfanyl}-propionic acid
2-{2-[3-Cyclohexyl-3-(4-phenyl-cyclohexyl)-ureido]-thiazol-5-ylsulfanyl}-2-methyl-propionic acid
2-{2-[3-Cycloheptyl-3-(4-phenyl-cyclohexyl)-ureido]-thiazol-5-ylsulfanyl}-2-methyl-propionic acid
(E)-6-[4-(1-Cyclohexyl-3-thiazol-2-yl-ureido)-piperidin-1-yl]-6-oxo-hex-3-enoic acid
{2-[3-Cyclohexyl-3-(trans-4-isopropyl-cyclohexyl)-ureido]-thiazol-5-ylsulfanyl}-acetic acid
{2-[3-Cycloheptyl-3-(trans-4-isopropyl-cyclohexyl)-ureido]-thiazol-5-ylsulfanyl}-acetic acid
{2-[3-Cyclohexyl-3-(trans-4-ethyl-cyclohexyl)-ureido]-thiazol-5-ylsulfanyl}-acetic acid
{2-[3-Cyclohexyl-3-(trans-4-propoxy-cyclohexyl)-ureido]-thiazole-5-sulfonylamino}-acetic acid
3-{2-[3-Cyclohexyl-3-(trans-4-propoxy-cyclohexyl)-ureido]-thiazole-5-sulfonylamino}-propionic acid
({2-[3-Cyclohexyl-3-(trans-4-propoxy-cyclohexyl)-ureido]-thiazole-5-sulfonyl}-methyl-amino)-acetic acid
{2-[3-(trans-4-tert-Butoxy-cyclohexyl)-3-cycloheptyl-ureido]-thiazol-5-ylsulfanyl}-acetic acid
{2-[3-(trans-4-tert-Butoxy-cyclohexyl)-3-cyclohexyl-ureido]-thiazol-5-ylsulfanyl}-acetic acid
3-{2-[3-(trans-4-tert-Butoxy-cyclohexyl)-3-cycloheptyl-ureido]-thiazol-5-ylsulfanyl}-propionic acid
3-{2-[3-(trans-4-tert-Butoxy-cyclohexyl)-3-cyclohexyl-ureido]-thiazol-5-ylsulfanyl}-propionic acid
{2-[3-(trans-4-Benzyloxy-cyclohexyl)-3-cyclohexyl-ureido]-thiazol-5-ylsulfanyl}-acetic acid
{2-[3-(trans-4-Benzyloxy-cyclohexyl)-3-cycloheptyl-ureido]-thiazol-5-ylsulfanyl}-acetic acid
3-{2-[3-(trans-4-Benzyloxy-cyclohexyl)-3-cyclohexyl-ureido]-thiazol-5-ylsulfanyl}-propionic acid
3-{2-[3-(trans-4-Benzyloxy-cyclohexyl)-3-cycloheptyl-ureido]-thiazol-5-ylsulfanyl}-propionic acid
2-{2-[3-Cyclohexyl-3-(trans-4-methyl-cyclohexyl)-ureido]-thiazole-5-sulfonylamino}-2-methyl-propionic acid
(R)-1-{2-[3-Cyclohexyl-3-(trans-4-methyl-cyclohexyl)-ureido]-thiazole-5-sulfonyl}-pyrrolidine-352-carboxylic acid
2-{2-[3-Cyclohexyl-3-(trans-4-propoxy-cyclohexyl)-ureido]-thiazole-5-sulfonylamino}-2-methyl-propionic acid
(R)-1-{2-[3-Cyclohexyl-3-(trans-4-propoxy-cyclohexyl)-ureido]-thiazole-5-sulfonyl}-pyrrolidine-2-carboxylic acid
{2-[3-Cyclohexyl-3-(trans-4-isopropoxy-cyclohexyl)-ureido]-thiazol-5-ylsulfanyl}-acetic acid
{2-[3-Cycloheptyl-3-(trans-4-isopropoxy-cyclohexyl)-ureido]-thiazol-5-ylsulfanyl}-acetic acid
3-{2-[3-Cyclohexyl-3-(trans-4-isopropoxy-cyclohexyl)-ureido]-thiazol-5-ylsulfanyl}-propionic acid
3-{2-[3-Cycloheptyl-3-(trans-4-isopropoxy-cyclohexyl)-ureido]-thiazol-5-ylsulfanyl}-propionic acid
3-(2-{3-Cyclohexyl-3-[4-(trans-2-methoxy-ethoxymethyl)-cyclohexyl]-ureido}-thiazol-5-ylsulfanyl)-acetic acid
3-(2-{3-Cyclohexyl-3-[4-(trans-2-methoxy-ethoxymethyl)-cyclohexyl]-ureido}-thiazol-5-ylsulfanyl)-propionic acid
(2-{3-Cycloheptyl-3-[4-(trans-2-methoxy-ethoxymethyl)-cyclohexyl]-ureido}-thiazol-5-ylsulfanyl)-acetic acid
3-(2-{3-Cycloheptyl-3-[4-(trans-2-methoxy-ethoxymethyl)-cyclohexyl]-ureido}-thiazol-5-ylsulfanyl)-propionic acid
(2-{3-Cyclohexyl-3-[4-(trans-2,2,2-trifluoro-ethoxymethyl)-cyclohexyl]-ureido}-thiazol-5-ylsulfanyl)-acetic acid
(2-{2-[3-Cyclohexyl-3-(trans-4-propoxy-cyclohexyl)-ureido]-thiazol-5-ylsulfanyl}-acetyl)-methanesulfonamide
2-(2-{3-Cyclohexyl-3-[4-(trans-2-methoxy-ethoxymethyl)-cyclohexyl]-ureido}-thiazol-5-ylsulfanyl)-2-methyl-propionic acid
2-(2-{3-Cycloheptyl-3-[4-(trans-2-methoxy-ethoxymethyl)-cyclohexyl]-ureido}-thiazol-5-ylsulfanyl)-2-methyl-propionic acid
2-{2-[3-Cyclohexyl-3-(trans-4-methoxymethyl-cyclohexyl)-ureido]-thiazol-5-ylsulfanyl}-2-methyl-propionic acid
{2-[3-Cyclohexyl-3-(cis-4-propoxy-cyclohexyl)-ureido]-thiazol-5-ylsulfanyl}-acetic acid
{2-[3-Cyclohexyl-3-(trans-4-phenoxy-cyclohexyl)-ureido]-thiazol-5-ylsulfanyl}-acetic acid
(2-{3-Cyclohexyl-3-[trans-4-(pyridin-2-yloxy)-cyclohexyl]-ureido}-thiazol-5-ylsulfanyl)-acetic acid
3-(2-{3-Cyclohexyl-3-[trans-4-(pyridin-2-yloxy)-cyclohexyl]-ureido}-thiazol-5-ylsulfanyl)-propionic acid
(2-{3-Cyclohexyl-3-[trans-4-(2,2,2-trifluoro-ethoxy)-cyclohexyl]-ureido}-thiazol-5-ylsulfanyl)-acetic acid
2-[3-Cyclohexyl-3-(trans-4-methyl-cyclohexyl)-ureido]-thiazole-5-sulfonic acid methylamide
2-{2-[3-Cycloheptyl-3-(trans-4-methoxy-cyclohexyl)-ureido]-thiazol-5-ylsulfanyl}-2-methyl-propionic acid
2-{2-[3-Cyclohexyl-3-(trans-4-methoxy-cyclohexyl)-ureido]-thiazol-5-ylsulfanyl}-2-methyl-propionic acid
2-{2-[3-Cycloheptyl-3-(trans-4-ethoxy-cyclohexyl)-ureido]-thiazol-5-ylsulfanyl}-2-methyl-propionic acid In another embodiment, the present invention provides a novel pharmaceutical composition, comprising: a pharmaceutically acceptable carrier and a compound of the present invention, or a pharmaceutically acceptable salt thereof.

In another embodiment, the present invention provides a novel method of treating type 2 diabetes, comprising: administering to a subject in need thereof a therapeutically effective amount of a compound of the present invention.

In one aspect the invention provides a method of preventing hypoglycaemia comprising administration of a compound according to the present invention.

In another aspect the invention provides the use of a compound according to the present invention for the preparation of a medicament for the prevention of hypoglycaemia.

In another aspect the invention provides a compound as described herein, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

In another aspect the invention provides a compound which is
5-[3-Cyclohexyl-3-(trans-4-methyl-cyclohexyl)-ureido]-[1,3,4]thiadiazole-2-sulfonic acid methylamide
{5-[3-Cyclohexyl-3-(trans-4-methyl-cyclohexyl)-ureido]-[1,3,4]thiadiazole-2-sulfonylamino}-acetic acid
({5-[3-Cyclohexyl-3-(trans-4-methyl-cyclohexyl)-ureido]-[1,3,4]thiadiazole-2-sulfonyl}-methylamino)-acetic acid
2-[3-Cyclohexyl-3-(trans-4-methyl-cyclohexyl)-ureido]-4-methyl-thiazole-5-sulfonic acid methylamide
{2-[3-Cyclohexyl-3-(trans-4-methyl-cyclohexyl)-ureido]-4-methyl-thiazole-5-sulfonylamino}-acetic acid
({2-[3-Cyclohexyl-3-(trans-4-methyl-cyclohexyl)-ureido]-4-methyl-thiazole-5-sulfonyl}-methylamino)-acetic acid 1-Cyclohexyl-1-(trans-4-methyl-cyclohexyl)-3-[5-(piperidine-1-sulfonyl)-[1,3,4]thiadiazol-2-yl]-urea
5-[3-Cyclohexyl-3-(trans-4-methyl-cyclohexyl)-ureido]-[1,3,4]thiadiazole-2-sulfonic acid (2-methoxy-ethyl)-amide
5-[3-Cyclohexyl-3-(trans-4-methyl-cyclohexyl)-ureido]-[1,3,4]thiadiazole-2-sulfonic acid isopropylamide
5-[3-Cyclohexyl-3-(trans-4-methyl-cyclohexyl)-ureido]-[1,3,4]thiadiazole-2-sulfonic acid phenylamide
1-Cyclohexyl-1-(trans-4-methyl-cyclohexyl)-3-[5-(piperidine-1-sulfonyl)-thiazol-2-yl]-urea
2-[3-Cyclohexyl-3-(trans-4-methyl-cyclohexyl)-ureido]-thiazole-5-sulfonic acid isopropylamide
1-Cyclohexyl-3-[5-(cis-2,6-dimethyl-piperidine-1-sulfonyl)-thiazol-2-yl]-1-(trans-4-methyl-cyclohexyl)-urea
2-[3-Cyclohexyl-3-(trans-4-methyl-cyclohexyl)-ureido]-thiazole-5-sulfonic acid tert-butylamide In another aspect the invention provides a compound as described herein for use as a medicament.

In another aspect the invention provides a compound as described herein for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

In another aspect the invention provides a pharmaceutical composition comprising, as an active ingredient, at least one compound as described herein together with one or more pharmaceutically acceptable carriers or excipients.

In one embodiment such a pharmaceutical composition may be in unit dosage form, comprising from about 0.05 mg to about 1000 mg, preferably from about 0.1 mg to about 500 mg and especially preferred from about 0.5 mg to about 200 mg of the compound according to the present invention.

In another aspect the invention provides the use of a compound according to the invention for increasing the activity of glucokinase.

In another aspect the invention provides the use of a compound according to the invention for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins. In another aspect the invention provides the use of a compound according to the invention for the preparation of a medicament for the adjuvant treatment of type 1 diabetes for preventing the onset of diabetic complications.

In another aspect the invention provides the use of a compound according to the invention for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome. In one embodiment the invention provides any of the above uses in a regimen which comprises treatment with a further antidiabetic agent.

In a further aspect the invention provides the use of a compound according to the invention or a pharmaceutical composition as described above for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behaviour, or for enhancing the secretion of enteroincretins.

In a further aspect the invention provides the use of a compound according to the invention or a pharmaceutical composition as described above for the adjuvant treatment of type 1 diabetes for preventing the onset of diabetic complications.

In a further aspect the invention provides the use of a compound according to the invention or a pharmaceutical composition as described above for increasing the number and/or the size of beta cells in a mammalian subject, for treatment of beta cell degeneration, in particular apoptosis of beta cells, or for treatment of functional dyspepsia, in particular irritable bowel syndrome.

In another embodiment the invention provides a for the treatment of a glucokinase-deficiency mediated condition/disease which is caused by a glucokinase mutation.

In another embodiment the invention provides a method wherein the glucokinase-deficiency mediated condition/disease is Maturity-Onset Diabetes of the Young, Neonatal Diabetes Mellitus, or Persistent Neonatal Diabetes Mellitus.

In another embodiment the invention provides a method for preventing or ameliorating the development of diabetes in subjects exhibiting symptoms of Impaired Glucose Tolerance, Gestational Diabetes Mellitus, Polycystic Ovarian Syndrome, Cushings syndrome or Metabolic Syndrome comprising administering to a subject in need of such treatment a compound according to the invention or pharmaceutical composition thereof, wherein blood glucose normalization occurs with reduced risk of hypoglycemia.

In another embodiment the invention provides a method for preventing or ameliorating microvascular diseases comprising administering to a subject in need of such treatment a compound according to the invention or pharmaceutical composition thereof.

In another embodiment the invention provides a method for preventing macrovascular diseases in subjects exhibiting symptoms of Impaired Glucose Tolerance, Gestational Diabetes Mellitus, or Metabolic Syndrome, comprising administering to a subject in need of such treatment a compound according to the invention or pharmaceutical composition thereof, alone or in combination with lipid-lowering drugs, wherein blood glucose normalization occurs with reduced risk of hypoglycemia.

In another embodiment the invention provides a method for the preservation of beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method for preventing amyloid beta peptide induced cell death comprising administering to a subject in need of such treatment a compound according to the invention or pharmaceutical composition thereof, wherein blood glucose normalization occurs with reduced risk of hypoglycemia.

In another embodiment the invention provides a method wherein the subject is a veterinary subject.

In another embodiment the invention provides a method wherein a compound according to the invention is administered as a food additive.

In another embodiment the invention provides a method for the treatment of hepatic conditions benefiting from blood glucose normalization comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions benefiting from improved liver function comprising administering to a subject in need of such treatment a compound according to the invention or pharmaceutical composition thereof.

In another embodiment the invention provides a method for the treatment of hyperglycemic conditions that result from critical illness, or as a consequence of therapeutic intervention comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions that result from critical illness like cancer, or are a consequence of therapy, for example cancer therapy or HIV-treatment, comprising administering to a subject in need of such treatment a compound according to the invention or pharmaceutical composition thereof.

In another embodiment the invention provides a method of treatment adjuvant to insulin in insulin-requiring diabetes type 2, or as replacement for insulin comprising administering to a subject in need of such treatment a compound according to the invention or pharmaceutical composition thereof, wherein blood glucose normalization occurs with reduced risk of hypoglycemia.

In another embodiment the invention provides a method for the treatment of lipodistrophy comprising administering to a subject in need of such treatment a compound according to the invention or pharmaceutical composition thereof, wherein blood glucose normalization occurs with reduced risk of hypoglycemia.

In another embodiment the invention provides a method for the treatment of hyperglycemia resulting from severe physical stress without signs of liver failure comprising administering to a subject in need of such treatment a compound according to the invention or pharmaceutical composition thereof, wherein blood glucose normalization occurs with reduced risk of hypoglycemia.

In another embodiment the invention provides a method wherein the severe physical stress is multiple trauma, or diabetic ketoacidosis.

In another embodiment the invention provides a method for preventing apoptotic liver damage comprising administering to a subject in need of such treatment a compound according to the invention or pharmaceutical composition thereof.

In another embodiment the invention provides a method for preventing hypoglycemia comprising administering to a subject in need of such treatment a compound according to the invention or pharmaceutical composition thereof, wherein blood glucose normalization occurs with reduced risk of hypoglycemia.

In another embodiment the invention provides a method for increasing beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method of preventing type 1 diabetes comprising administering to a subject in need of such treatment a compound according to the invention or pharmaceutical composition thereof, wherein blood glucose normalization occurs with reduced risk of hypoglycemia.

In another embodiment the invention provides a method of preserving and/or increasing beta-cell mass and function in patients having undergone pancreatic islet transplantation comprising administering to a subject in need of such treatment a compound according to the invention or pharmaceutical composition thereof.

In another embodiment the invention provides a method of improving glucose control during and after surgery comprising administering to a subject in need of such treatment a compound according to the invention or pharmaceutical composition thereof.

In another embodiment the invention provides a method of improving liver function and/or survival in patients undergoing liver transplantation comprising administering to a subject in need of such treatment a compound according to the invention or pharmaceutical composition thereof. In another embodiment hereof the invention provides a method wherein the administration occurs before, during or after transplantation, or any combination thereof.

In another embodiment the invention provides a method of obtaining blood glucose normalization comprising administering to a subject in need of such treatment a compound according to the invention or pharmaceutical composition thereof, wherein blood glucose normalization occurs with reduced risk of hypoglycemia.

In another embodiment the invention provides a method of preventing or ameliorating diabetic late complications comprising administering to a subject in need of such treatment a compound according to the invention or pharmaceutical composition thereof.

In another embodiment the invention provides a method of treating type 1 or 2 diabetes comprising administering to a subject in need of such treatment a compound according to the invention or pharmaceutical composition thereof, wherein the treatment does not result in a weight gain.

In another embodiment the invention provides a method of preventing diabetic ketoacidosis comprising administering to a subject in need of such treatment a compound according to the invention or pharmaceutical composition thereof.

Combination Treatment

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, a-glucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one embodiment of the present invention, the present compounds are administered in combination with a sulphonylurea eg tolbutamide, chlorpropamide, tolazamide, glibenclamide, glipizide, glimepiride, glicazide or glyburide.

In one embodiment of the present invention, the present compounds are administered in combination with a biguanide eg metformin.

In one embodiment of the present invention, the present compounds are administered in combination with a meglitinide eg repaglinide or senaglinide/nateglinide.

In one embodiment of the present invention, the present compounds are administered in combination with a thiazolidinedione insulin sensitizer eg troglitazone, ciglitazone, pioglitazone, rosiglitazone, isaglitazone, darglitazone, englitazone, CS-011/C1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one embodiment of the present invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one embodiment of the present invention the present compounds are administered in combination with an α-glucosidase inhibitor eg voglibose, emiglitate, miglitol or acarbose.

In one embodiment of the present invention the present compounds are administered in combination with a glycogen phosphorylase inhibitor eg the compounds described in WO 97/09040 (Novo Nordisk A/S).

In one embodiment of the present invention the present compounds are administered in combination with an agent acting on the ATP-dependent potassium channel of the pancreatic β-cells eg tolbutamide, glibenclamide, glipizide, glicazide, BTS-67582 or repaglinide.

In one embodiment of the present invention the present compounds are administered in combination with nateglinide.

In one embodiment of the present invention the present compounds are administered in combination with an antihyperlipidemic agent or a antilipidemic agent eg cholestyramine, colestipol, clofibrate, gemfibrozil, lovastatin, pravastatin, simvastatin, probucol or dextrothyroxine.

Furthermore, the compounds according to the invention may be administered in combination with one or more anti-obesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further antiobesity agents are bupropion (antidepressant), topiramate (anticonvulsant), ecopipam (dopamine D1/D5 antagonist) and naltrexone (opioid antagonist).

In one embodiment of the present invention the antiobesity agent is leptin.

In one embodiment of the present invention the antiobesity agent is a serotonin and norepinephrine reuptake inhibitor eg sibutramine.

In one embodiment of the present invention the antiobesity agent is a lipase inhibitor eg orlistat.

In one embodiment of the present invention the antiobesity agent is an adrenergic CNS stimulating agent eg dexamphetamine, amphetamine, phentermine, mazindol phendimetrazine, diethylpropion, fenfluramine or dexfenfluramine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In one embodiment of the present invention, the present compounds are administered in combination with insulin, insulin derivatives or insulin analogues.

In one embodiment of the invention the insulin is an insulin derivative is selected from the group consisting of B29-N$^\epsilon$-myristoyl-des(B30) human insulin, B29-N$^\epsilon$-palmitoyl-des (B30) human insulin, B29-N$^\epsilon$-myristoyl human insulin, B29-N$^\epsilon$-palmitoyl human insulin, B28-N'-myristoyl Lys$^{B28}$ Pro$^{B29}$ human insulin, B28-N'-palmitoyl Lys$^{B28}$ Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-lithocholyl-γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

In another embodiment of the invention the insulin derivative is B29-N'-myristoyl-des(B30) human insulin.

In a further embodiment of the invention the insulin is an acid-stabilised insulin. The acid-stabilised insulin may be selected from analogues of human insulin having one of the following amino acid residue substitutions:

A21G

A21G, B28K, B29P

A21G, B28D

A21G, B28E

A21G, B3K, B29E

A21G, desB27

A21G, B9E

A21G, B9D

A21G, B10E insulin.

In a further embodiment of the invention the insulin is an insulin analogue. The insulin analogue may be selected from the group consisting of An analogue wherein position B28 is Asp, Lys, Leu, Val, or Ala and position B29 is Lys or Pro; and des(B28-B30), des(B27) or des(B30) human insulin.

In another embodiment the analogue is an analogue of human insulin wherein position B28 is Asp or Lys, and position B29 is Lys or Pro.

In another embodiment the analogue is des(B30) human insulin.

In another embodiment the insulin analogue is an analogue of human insulin wherein position B28 is Asp.

In another embodiment the analogue is an analogue wherein position B3 is Lys and position B29 is Glu or Asp.

In another embodiment the GLP-1 derivative to be employed in combination with a compound of the present invention refers to GLP-1 (1-37), exendin-4(1-39), insulinotropic fragments thereof, insulinotropic analogues thereof and insulinotropic derivatives thereof. Insulinotropic fragments of GLP-1 (1-37) are insulinotropic peptides for which the entire sequence can be found in the sequence of GLP-1 (1-37) and where at least one terminal amino acid has been deleted. Examples of insulinotropic fragments of GLP-1 (1-37) are GLP-1 (7-37) wherein the amino acid residues in positions 1-6 of GLP-1 (1-37) have been deleted, and GLP-1 (7-36) where the amino acid residues in position 1-6 and 37 of GLP-1 (1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1 (1-37) are e.g. Met$^8$-GLP-1 (7-37) wherein the alanine in position 8 has been replaced by methionine and the amino acid residues in position 1 to 6 have been deleted, and Arg$^{34}$-GLP-1 (7-37) wherein the valine in position 34 has been replaced with arginine and the amino acid residues in position 1 to 6 have been deleted. An example of an insulinotropic analogue of exendin-4(1-39) is Ser$^2$Asp$^3$-exendin-4 (1-39) wherein the amino acid residues in position 2 and 3 have been replaced with serine and aspartic acid, respectively (this particular analogue also being known in the art as exendin-3). Insulinotropic derivatives of GLP-1 (1-37), exendin-4(1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1 (1-37), exendin-4(1-39) and analogues thereof are GLP-1 (7-36)-amide, Arg$^{34}$, Lys$^{26}$(NE-(γ-Glu(N$^\alpha$-hexadecanoyl)))-GLP-1 (7-37) and Tyr$^{31}$-exendin-4 (1-31)-amide. Further examples of GLP-1 (1-37), exendin-4 (1-39), insulinotropic fragments thereof, insulinotropic analogues thereof and insulinotropic derivatives thereof are described in WO 98/08871, WO 99/43706, U.S. Pat. No. 5,424,286 and WO 00/09666.

In another aspect of the present invention, the present compounds are administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In one embodiment of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg. For parenteral routes such as intravenous, intrathecal, intramuscular and similar administration, typically doses are in the order of about half the dose employed for oral administration. The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds of this invention which are generally prepared by reacting the free base with a suitable organic or inorganic acid or by reacting the acid with a suitable organic or inorganic base.

When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further aspect of the present invention.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452;

and 4,265,874, incorporated herein by reference, to form osmotic therapeutic tablets for controlled release. Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present. The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the pre-sent invention.

Thus, in a further embodiment, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the present invention may comprise a compound according to the present invention in combination with further active substances such as those described in the foregoing.

The present invention also provides a method for the synthesis of compounds useful as intermediates in the preparation of compounds of formula (I) along with methods for the preparation of compounds of formula (I). The compounds can be prepared readily according to the following reaction Schemes (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

Pharmacological Methods

Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM $MgCl_2$, 2 mM dithiothreitol, 0.6 mM NADP, 1 mM ATP, 0.195 µM G-6-P dehydrogenase (from Roche, 127 671), 15 nM recombinant human glucokinase. The glucokinase is human liver glucokinase N-terminally truncated with an N-terminal His-tag $((His)_8$-VEQILA . . . Q466) and is expressed in E. coli as a soluble protein with enzymatic activity comparable to liver extracted GK.

The purification of His-tagged human glucokinase (hGK) was performed as follows: The cell pellet from 50 ml E. coli culture was resuspended in 5 ml extraction buffer A (25 mM HEPES, pH 8.0, 1 mM $MgCl_2$, 150 mM NaCl, 2 mM mercaptoethanol) with addition of 0.25 mg/ml lysozyme and 50 µg/ml sodium azide. After 5 minutes at room temperature 5 ml of extraction buffer B (1.5 M NaCl, 100 mM $CaCl_2$, 100 mM $MgCl_2$, 0.02 mg/ml DNase 1, protease inhibitor tablet (Complete® 1697498): 1 tablet pr. 20 ml buffer) was added. The extract was then centrifugated at 15.000 g for 30 minutes. The resulting supernatant was loaded on a 1 ml Metal Chelate Affinity Chromatography (MCAC) Column charged with $Ni^{2+}$. The column is washed with 2 volumes buffer A containing 20 mM imidazole and the bound his-tagged hGK is subsequently eluted using a 20 minute gradient of 20 to 500 mM imidazol in buffer A. Fractions are examined using SDS-gel-electrophoresis, and fractions containing hGK (MW: 52 KDa) are pooled. Finally a gelfiltration step is used for final polishing and buffer exhange. hGK containing fractions are loaded onto a Superdex 75 (16/60) gelfiltration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 ml E. coli culture is generally approximately 2-3 mg hGK with a purity >90%.

The compound to be tested is added into the well in final 2.5% DMSO concentration in an amount sufficient to give a desired concentration of compound, for instance 1, 5, 10, 25 or 50 µM. The reaction starts after glucose is added to a final concentration of 2, 5, 10 or 15 mM. The assay uses a 96-well UV plate and the final assay volume used is 200 µl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibits activation of glucokinase in this assay. A compound, which at a concentration of at or below 30 µM gives 1.5-fold higher glucokinase activity than the result from the assay without compound, is deemed to be an activator of glucokinase.

The glucose sensitivity of the compounds are measured at a compound concentration of 10 µM and at glucose concentrations of 5 and 15 mM.

Glucokinase Activity Assay (II)

Determination of glycogen deposition in isolated rat hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 µM dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $Mg_2SO_4$, 1.5 mM $KH_2PO_4$, 20 mM HEPES, 9 mM $NaHCO_3$, 0.1% w/v HSA, and 2.25 mM $CaCl_2$, pH 7.4 at 37° C.) and incubated in 100 µl buffer A containing 15 mM glucose and increasing concentrations of the test compound, such as for instance 1, 5, 10, 25, 50 or 100 µM, for 180 minutes. Glycogen content is measured using standard procedures(Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)

Stimulation of insulin secretion by glucokinase activators in INS-1 E cells The glucose responsive β-cell line INS-1 E is cultivated as described by Asfari M et al., Endocrinology, 130, 167-178 (1992). The cells are then seeded into 96 well cell culture plates and grown to a density of approximately $5 \times 10^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 µM, and the supernatants collected for measurements of insulin concentrations by ELISA (n=4). A compound, which when used in this assay gives an significant increase in insulin secretion in response to glucose compared to the result from the assay without compound, is deemed to have activity in this assay.

While the invention has been described and illustrated with reference to certain preferred embodiments thereof, those skilled in the art will appreciate that various changes, modifications and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

EXAMPLES

Abbreviations used in the Schemes and Examples are as Follows

| | |
|---|---|
| d = | day(s) |
| g = | gram(s) |
| h = | hour(s) |
| MHz = | mega hertz |
| L = | liter(s) |
| M = | molar |
| mg = | milligram(s) |
| min = | minute(s) |
| mL = | milliliter(s) |
| mM = | millimolar |
| mmol = | millimole(s) |
| mol = | mole(s) |
| N = | normal |
| ppm = | parts per million |
| i.v. = | intravenous |
| m/z = | mass to charge ratio |
| mp = | melting point |
| MS = | mass spectrometry |
| HPLC = | high pressure liquid chromatography |
| HPLC-MS = | high pressure liquid chromatography—mass spectrometry |
| NMR = | nuclear magnetic resonance spectroscopy |
| p.o. = | per oral |
| $R_t$ = | retention time |
| rt = | room temperature |
| s.c. = | subcutaneous |
| TLC = | thin layer chromatography |
| BuOK = | Potassium tert-butoxide |
| Boc = | tert-Butyloxcarbonyl |
| CDI = | carbonyldiimidazole |
| DBU = | 1,8-Diazabicyclo[5.4.0]-undec-7-en |
| DCM ($CH_2Cl_2$) = | dichloromethane, methylenechloride |
| DHOBt = | 3,4-Dihydro-3-hydroxy-4-oxo-1,2,3-benzotriazine |
| DIC = | 1,3-Diisopropyl carbodiimide |
| DCC = | 1,3-Dicyclohexyl carbodiimide |
| DIEA = | N,N-diisopropylethylamine |
| DIPEA = | N,N-diisopropylethylamine |
| DMA = | N,N-dimethylacetamide |
| DMAP = | 4-(N,N-dimethylamino)pyridine |
| DMF = | N,N-dimethylformamide |
| DMF = | N,N-dimethylformamide |
| DMPU = | N,N'-dimethylpropyleneurea, 1,3-dimethyl-2-oxohexa-hydropyrimidine |
| EDAC = | 1-(3-Dimethylaminopropyl)-3-ethyl-carbodiimide hydrochloride |
| $Et_2O$ = | diethyl ether |
| EtOAc = | ethyl acetate |
| HMPA = | hexamethylphosphoric acid triamide |
| HOBt = | N-Hydroxybenzotriazole |
| HOAt = | 7-Aza-1-Hydroxybenzotriazole |
| LAH, ($LiAlH_4$) = | Lithiumaluminium hydride |
| LDA = | lithium diisopropylamide |
| MeCN = | acetonitrile |
| MeOH = | methanol |
| NMP = | N-methylpyrrolidin-2-one |
| NaH = | Sodium Hydride |
| $NH_2OH$ = | Hydoxylamine |
| PyBroP = | Bromotrispyrrolidinophosphonium hexafluorophosphate |
| TEA ($Et_3N$) = | triethylamine |
| TFA = | trifluoroacetic acid |
| THF = | tetrahydrofuran |
| $CDCl_3$ = | deuterio chloroform |
| $CD_3OD$ = | tetradeuterio methanol |
| DMSO-$d_6$ = | hexadeuterio dimethylsulfoxide |

NMR

Proton NMR spectra were recorded at ambient temperature using a Brucker Avance DPX 200 (200 MHz), Brucker Avance DPX 300 (300 MHz) and Brucker Avance DPX 400 (400 MHz) with tetramethylsilane as an internal standard. Chemical shifts ($\delta$) are given in ppm

HPLC-MS

The following instrumentation is used:

Hewlett Packard series 1100 G1312A Bin Pump

Hewlett Packard series 1100 Column compartment

Hewlett Packard series 1100 G1315A DAD diode array detector

Hewlett Packard series 1100 MSD

Sedere 75 Evaporative Light Scattering detector

The instrument is controlled by HP Chemstation software.

The HPLC pump is connected to two eluent reservoirs containing:

| | |
|---|---|
| A: | 0.01% TFA in water |
| B: | 0.01% TFA in acetonitrile |

The analysis is performed at 40° C. by injecting an appropriate volume of the sample (preferably 1 µl) onto the column which is eluted with a gradient of acetonitrile.

The HPLC conditions, detector settings and mass spectrometer settings used are given in the following table.

| | |
|---|---|
| Column | Waters Xterra MS C-18 × 3 mm id 5 µm |
| Gradient | 5%-100% acetonitrile linear during 7.5 min at 1.5 mL/min |
| Detection | 210 nm (analogue output from DAD) |
| | ELS (analogue output from ELS) |
| MS | ionisation mode API-ES |
| | Scan 100-1000 amu step 0.1 amu |

After the DAD the flow is divided yielding approximately 1 mL/min to the ELS and 0.5 mL/min to the MS.

Preparative HPLC Methods

HPLC Method 1

The RP-purification was performed on a Gilson system (3 Gilson 306 pumps, Gilson 170 DAD detector and a Gilson 215 liquidhandler) using a Waters X-terra RP (10 µm, 30 mm×150 mm) with gradient elution, 5% to 95% solvent B (0.05% TFA in acetonitrile) in solvent A (0.05% TFA in water) within 15 min, 40 mL/min, detection at 210 nm, temperature rt. The pooled fractions are either evaporated to dryness in vacuo, or evaporated in vacuo until the acetonitrile is removed, and then frozen and freeze dried.

HPLC-MS Method 2

The RP-analysis was performed on an Agilent HPLC system (1100 degasser, 1100 pump, 1100 injector and a 1100 DAD) fitted with an Agilent MS detector system Model SL (MW 0-3000) and a S.E.D.E.R.E Model Sedex 75 ELS detector system using a Waters X-terra MS C18 column (5 µm, 3.0 mm×50 mm) with gradient elution, 5% to 100% solvent B (0.05% TFA in acetonitrile) in solvent A (0.05% TFA in water) within 6.75 min, 1.5 mL/min, temperature 25° C.

General

The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General procedures A through G described herein.

The structures of the compounds are confirmed by either by nuclear magnetic resonance (NMR) and/or by HPLS-MS.

General Procedure (A)

Compounds of the formula (Ia) according to the invention wherein $R^1$, $R^2$ and A are as defined for formula (I) can be prepared as outlined below:

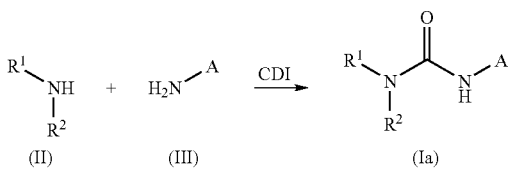

Step 1.

The aminoheterocycle ($NH_2A$) (III) wherein A is as defined for formula (I), can be converted using standard literature procedures (for example WO 2004/002481) to an acyl imidazonium intermediate with carbonyl diimidazole (CDI) or an equivalent of this in a solvent such as dichloromethane, dichloroethane, tetrahydrofuran, or DMF. Treatment with $R^1R^2NH$ (II), wherein $R^1$ and $R^2$ are as defined above, gives the compound of formula (Ia). The aminoheterocycle ($NH_2A$) or secondary amine ($R^1R^2NH$) can be either commercially available compounds or compounds that can be prepared following procedures described in the literature or prepared as described in the relevant example and general procedures.

Step 2.

In some cases it might be more convenient to generate the final substituents on $R^1$, $R^2$ and A after the urea formation. If in example the substituent on A in formula (Ia) contains an ester functionality this can be hydrolysed to the corresponding carboxylic acid using standard conditions for hydrolysis of esters. Suitable bases for the hydrolysis are NaOH and LiOH or equivalents of these in solvents like dioxane, THF, EtOH, MeOH and water or mixtures of these. The reactions can be performed at room temperature or at elevated temperatures.

Other examples are described in general procedure I and J.

General Procedure (B)

The desired amines $R^1R^2NH$ described in General procedure (A) can be prepared by a reductive amination by reaction of primary amine $R^1NH_2$ and a ketone $R^2$=O or an aldehyde with a reducing agent such as sodium cyanoborohydride in a solvent such as tetrahydrofuran as shown below, following procedures described in the literature (Org. Prep. Proced. Int. 1979, 11, 201).

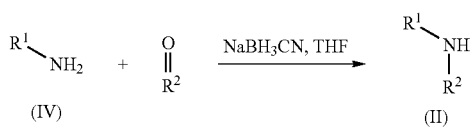

The primary amine, ketone and aldehyde can be either commercially available compounds or compounds that can be prepared following procedures described in the literature or prepared as described in the relevant example and general procedures.

General Procedure (C)

Preparation of trans-alkoxymethylcyclohexylamine and the Like

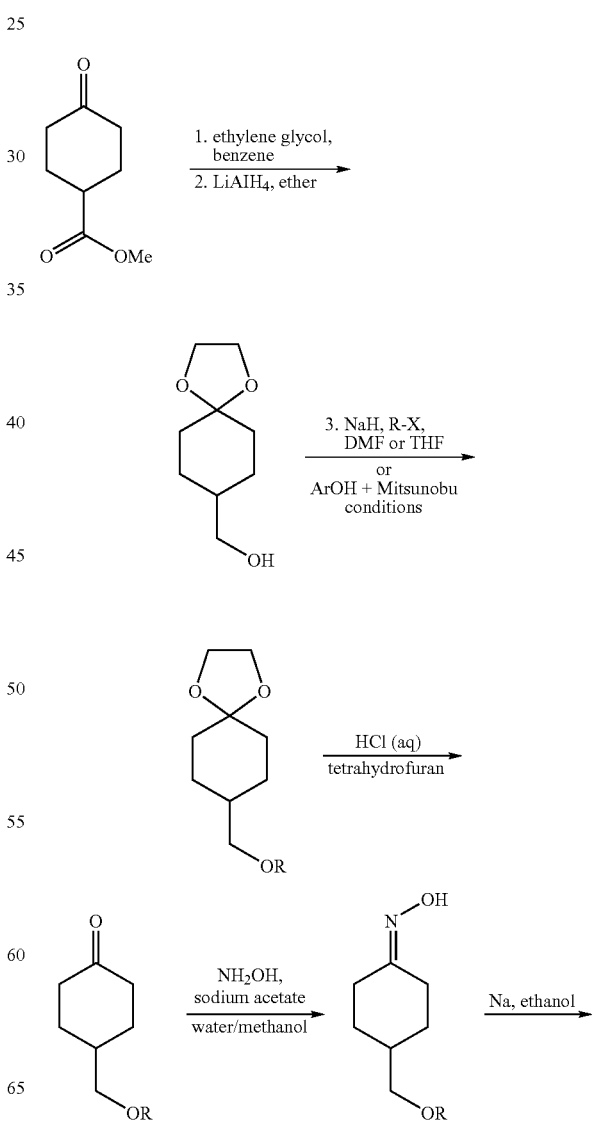

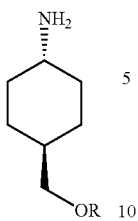

The carbonyl group of 4-oxo-cyclohexanone carboxylic acid methyl ester can be protected as a ketal by reaction with ethylene glycol in benzene with azeotropic removal of water. The ester group can then be reduced with lithium aluminium hydride in a suitable solvent such as diethyl ether or tetrahydrofuran. The alcohol can be alkylated using sodium hydride and a suitable alkyl halide (R—X, wherein R is a an appropriate radical) in a solvent such as tetrahydrofuran or DMF, or it can be converted to an aryl- or heteroaryl-ether under Mitsunobu conditions (Mitsunobu, 1981, 1, 1-28). Ketal deprotection of the product of formula Insulin Receptor Antagonist under standard acidic conditions gives a ketone which can be converted to the corresponding oxime upon treatment with hydroxylamine and a suitable base (for example sodium acetate). Reduction of the oxime using sodium in ethanol affords the trans-amine as the major isomer, which, if necessary can be purified by recrystallisation of the corresponding HCl salt.

General Procedure (D)

Reductive Amination of trans-alkoxymethylcyclohexylamine and the Like

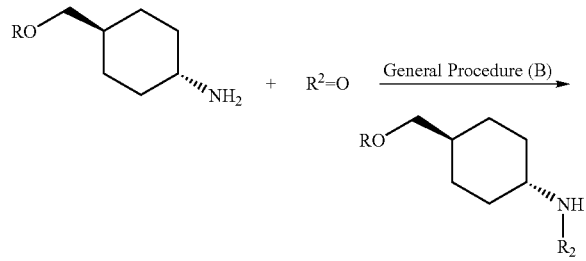

Reductive amination of the amine (wherein R is a an appropriate radical) with a ketone or an aldehyde $R^2$=O using general procedure (B) affords a trans-alkoxymethylcyclohexylamine.

General Procedure (E)

Preparation of 2-Amino-thiazole-5-sulfonic acid amides

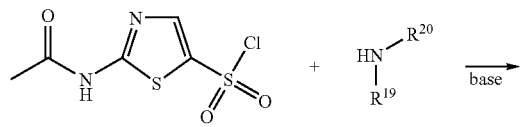

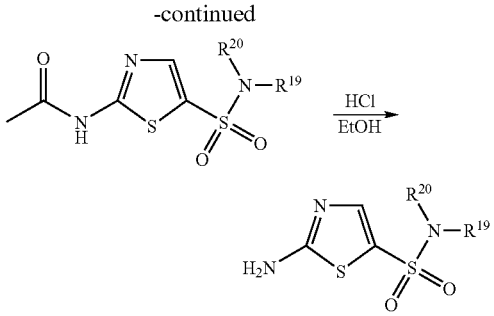

A mixture of an amine $NHR^{19}R^{20}$, wherein $R^{19}$ and $R^{20}$ are as defined for formula (I)), protected amino acid or the like is reacted with 2-acetylamino-thiazole-5-sulfonyl chloride prepared as described in *J. Am. Chem. Soc,* 1947, 69, 2063,) in the precence of a base such as DIPEA in DCM. N-Deacetylation of the intermediate can be achieved upon heating in the presence of HCl in dioxane/EtOH to give the required sulfonamido-2-aminothiazole.

General Procedure (F)

Preparation of trans-aryloxycyclohexylamines and the Like

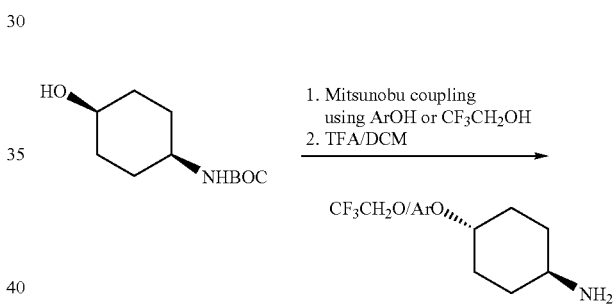

N-Boc protected cis-4-hydroxycyclohexylamine (prepared as described in WO 2005/019222) can be converted to in example the corresponding trans-trifluoroethoxy or appropriate aryloxy-cyclohexylamines under Mitsunobu conditions e.g. $PBu_3$/ADDP or DEAD/$PPh_3$ and subsequent N-deprotection in TFA/DCM.

General Procedure (G)

Preparation of cycloalkyl-[trans-4-(alkoxy)-cycloalkyl]-amines and the Like

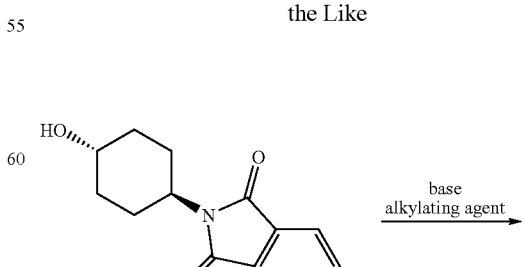

-continued

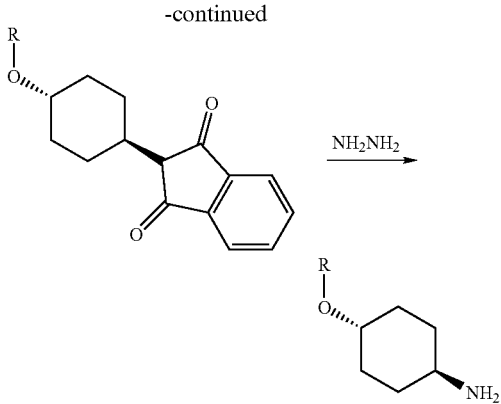

2-(trans-4-Hydroxy-cyclohexyl)-isoindole-1,3-dione (Glennon et al. *J. Med. Chem.* 1996, 39, 1, 314-322) can be alkylated with an alkylating agent R-halides or an equivalent of this using a base such as NaH, potassium tert-butoxid, DBU or the like in a solvent like DMF, NMP, DMSO, THF at temperatures from −10 to 120° C. Deprotection of in example trans-4-alkoxy-cyclohexyl-isoindole-1,3-dione can be achieve using hydrazine in ethanol at room temperature or at elevated temperatures. Alkylation of the trans-alkoxy-cyclohexylamine can be achieved using reductive amination with an appropriate ketone and a reducing agent such as sodium cyoanoborohydride or an equivalent of this. The reaction can be performed in solvents like THF, EtOH or MeOH or mixtures of these, using a dehydrating agent such as molecular sieves or $MgSO_4$, or in the presence of acetic acid. The reaction can be performed at temperatures from −10 to 120° C.

General Procedure (H)

Preparation of trans-4-alkyl-cyclohexylamines and the Like

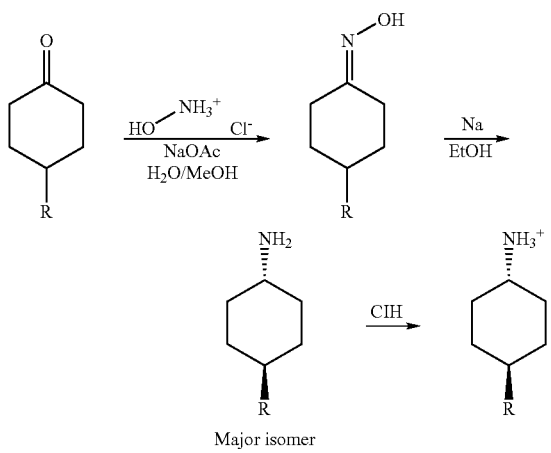

A 4-substituted cyclohexanone (wherein the substituent R is an appropriate radical) can be converted to the corresponding oxime upon treatment with hydroxylamine hydrochloride and a suitable base such as sodium acetate in a solvent mixture such as water/MeOH at elevated temperature. Reduction of the oxime using sodium in ethanol at elevated temperatures affords in example the trans-4-alkyl/aryl-cyclohexylamine as the major isomer, which, if necessary can be purified by recrystallisation of the corresponding HCl salt.

General Procedure (I)

Synthesis of Acyl- or Sulfonyl-piperidinyl-(thiazolyl)-cycloalkyl ureas

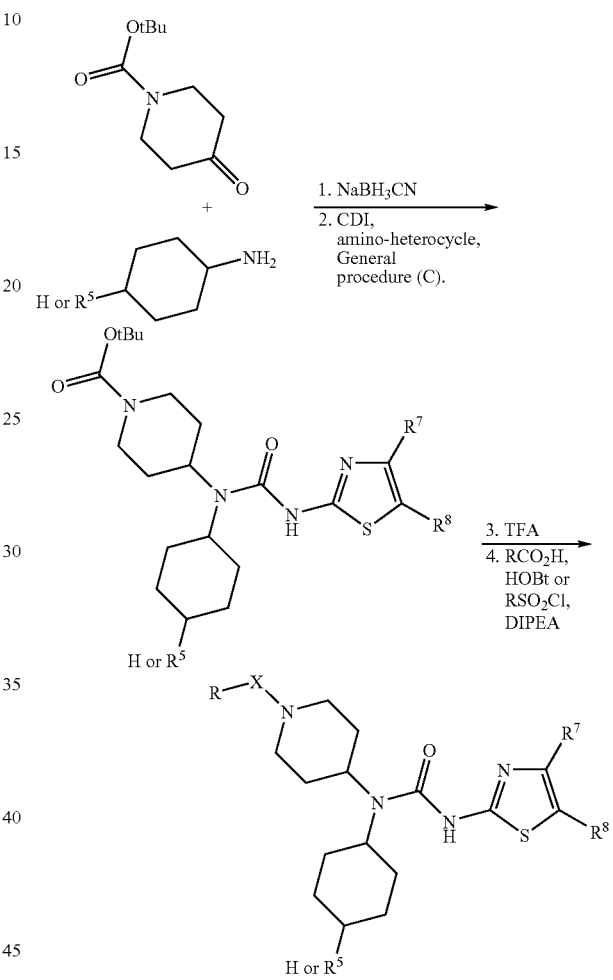

X = CO or $SO_2$
R = Alkyl, aryl etc

Step 1.

To N-Boc-piperidin-4-one (10 g) in a mixture of methanol (50 ml) and tetrahydrofuran (50 ml) is added an equimolar amount of a cycloalkylamine (4.5 g) at room temperature. Sodium cyanoborohydride (6.3 g, 2 eq) is added and the reaction stirred at room temperature overnight. The crude product is filtered through celite, concentrated in vacuo, redissolved/suspended in ether, stirred for 1 h, and decanted. This procedure is repeated 4 times and the combined ether-phases are concentrated in vacuo to afford the appropriate 4-cycloalkylamino-piperidine-1-carboxylic acid tert-butyl ester as a pale yellow oil which is used directly in step 2.

Step 2.

A equimolar mixture of 1,1-carbonyldiimidazole, amino-heteroaryl compound wherein $R^7$ and $R^8$ are as defined as for formula (I) (for example 5-methyl-2-aminothiazole) and 4-dimethylaminopyridine (5 mol %) in dichloroethane is heated for 4 h at 80° C. then cooled to room temperature. The amine product (1 equivalent) from Step 1 is added and the reaction is stirred overnight. Work up and chromatography (5% ethyl acetate in hexane) affords the desired Boc protected urea.

Step 3.

Boc deprotection is performed using trifluoroacetic acid (TFA) in DCM for 2 h at room temperature. Excess TFA and DCM are removed in vacuo to give the crude amine which is used directly in the next Step.

Step 4.

Acylation with either an HOBt activated carboxylic acid (RCO$_2$H), or a sulfonylchloride (RSO$_2$Cl), wherein R is an appropriate radical affords the required amide or sulfonamide respectively via established literature procedures.

Step 5.

If the substituent on the aminoheteroaryl moiety contains an ester functionality this can be hydrolysed using lithium hydroxide in methanol to give the corresponding acid.

General Procedure (J)

Conversion of Thiazolemercaptoacetic, Propionic Acids and the Like to Amides

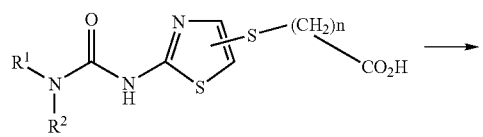

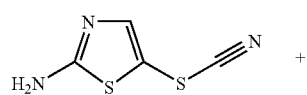

The carboxylic acid is initially treated with suitable amide coupling reagents, for example DHOBt and EDAC in a solvent such as dimethylformamide. A primary or secondary amine together with an equivalent of base (for example DIPEA) can then be added to give the desired amide, after purification by HPLC or flash chromatography.

General Procedure (K)

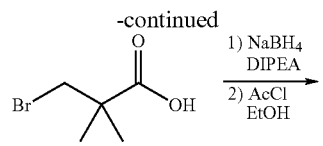

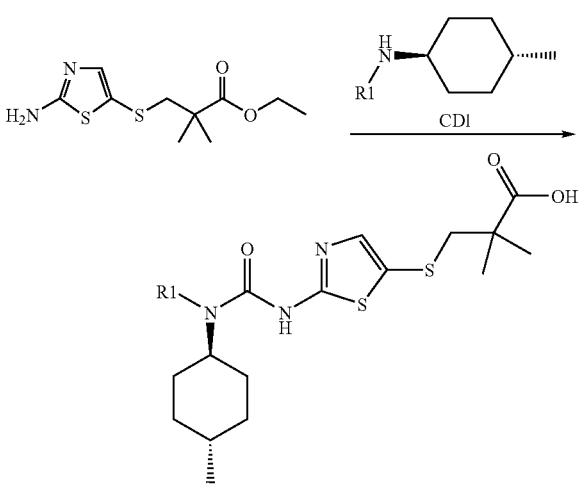

3-(2-Amino-thiazol-5-ylsulfanyl)-2,2-dimethyl-propionic acid ethyl ester can be prepared from 5-thiocyanato-thiazol-2-ylamine by treatment with sodium borohydride in MeOH followed by addition of 3-bromo-2,2-dimethyl-propionic acid. After aquous work up the intermediate acid can be treated with HCl in EtOH to give the 3-(2-amino-thiazol-5-ylsulfanyl)-2,2-dimethyl-propionic acid ethyl ester.

The aminothiazole ester can be coupled to the final urea derivative following the general procedure (A).

Example 1

1,1-Dicyclopentyl-3-thiazol-2-yl-urea

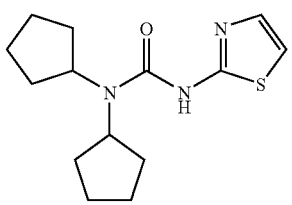

To a solution of 2-aminothiazole (50 mg, 0.5 mmol) in dichloromethane was added carbonyldiimidazole (81 mg, 0.5 mmol) and dimethylaminopyridine (3 mg) and the solution stirred 1 h at room temperature. Dicyclopentylamine (77 mg) was then added and the reaction stirred overnight at room temperature. The reaction mixture is then diluted with ethyl acetate (8 mL), washed successively with 10% sodiumhydrogensulphate (3 mL), water (3 mL), dried over magnesium sulphate, concentrated in vacuo, and the residue purified by flash chlomatography (eluant 7 ethyl acetate:3 heptane)

HPLC-MS: m/z=280 (M+H)

Example 2

1-Cyclopentyl-1-((3S,5R)-3,5-dimethyl-cyclohexyl)-3-thiazol-2-yl-urea

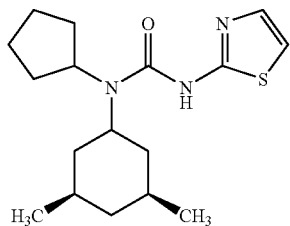

Cyclopentyl-((3S,5R)-3,5-dimethyl-cyclohexyl)-amine was prepared as described in General Procedure (B). The urea coupling was performed in an similar manner to the synthesis of 1,1-dicyclopentyl-3-thiazol-2-yl-urea, using carbonyl imidazole and 2-aminothiazole as starting material.

HPLC-MS: m/z=322 (M+H)

Example 3

1-(1,4-Dioxa-spiro[4.5]dec-8-yl)-1-(4-methyl-cyclohexyl)-3-thiazol-2-yl-urea

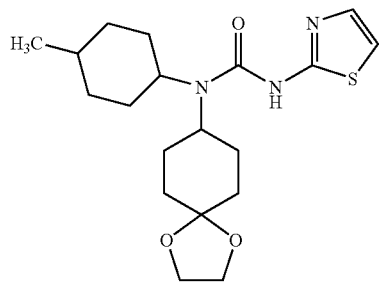

Prepared in an similar manner to example 2 according to general procedures (A) and (B) using 1,4-dioxaspiro[4.5]decan-8-one, 4-methylcyclohexylamine and 2-aminothiazole as starting material.

HPLC-MS: m/z=380 (M+H)

Example 4

1-Cyclopentyl-1-(1,4-dioxa-spiro[4.5]dec-8-yl)-3-thiazol-2-yl-urea

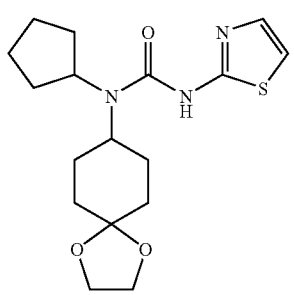

Prepared in an similar manner to example 2 according to general procedures (A) and (B) using 1,4-dioxaspiro[4.5]decan-8-one, cyclopentanone and 2-aminothiazole as starting material.

HPLC-MS: m/z=352 (M+H)

Example 5

1-(4-Methyl-cyclohexyl)-3-(5-methyl-thiazol-2-yl)-1-(4-oxo-cyclohexyl)-urea

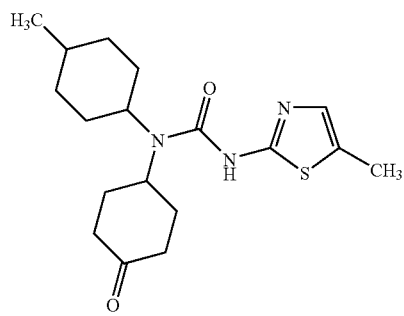

1-(1,4-Dioxa-spiro[4.5]dec-8-yl)-1-(4-methyl-cyclohexyl)-3-(5-methyl-thiazol-2-yl)-urea was prepared in an similar manner to example 2 according to general procedures (A) and (B) using 1,4-dioxaspiro[4.5]decan-8-one, 4-methylcyclohexylamine and 2-amino-5-methylthiazole. The acetale was then hydrolysed in the following way:

A solution of 1-(1,4-dioxa-spiro[4.5]dec-8-yl)-1-(4-methyl-cyclohexyl)-3-(5-methyl-thiazol-2-yl)-urea (100 mg, 0.25 mmol) in 80% aqueous acetic acid (1.15 mL) was heated at 60° C. for 3½ h. The reaction mixture was evaporated to dryness in vacuo to give a golden oil. The crude product was purified by HPLC to give the title compound.

$^1$H-NMR (CDCl$_3$): δ 7.02 (d, 1H), 3.66 (broad s, 2H), 2.66 (m, 3H), 2.46 (m, 3H), 2.37 (s, 3H), 1.98 (m, 4H), 1.76 (m, 3H), 1.59 (m, 2H), 1.39 (m, 2H), 1.05 (d, 1H), 0.91 (d, 2H).

HPLC-MS: m/z=350 (M+H)

Example 6

Ethyl {2-[3,3-dicyclohexylureido]-5-[4-methylpiperazin-1-yl]-thiazol-4-yl}-acetate

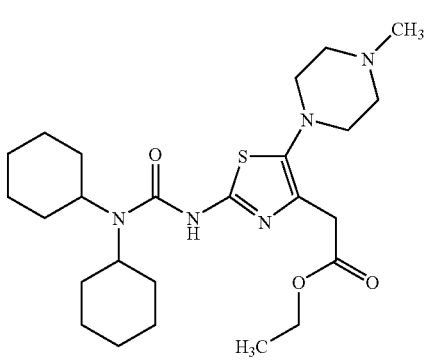

Step 1.

[2-(3,3-Dicyclohexyl-ureido)-thiazol-4-yl]-acetic acid ethyl ester was prepared in an similar manner to the synthesis of 1,1-dicyclopentyl-3-thiazol-2-yl-urea, using dicyclohexylamine, carbonyldiimidazole and ethyl 2-amino-4-thiazole acetate.

Step 2.

To a solution of 2-(3,3-dicyclohexyl-ureido)-thiazol-4-yl]-acetic acid ethyl ester (3.0 g, 7.62 mmol) in acetic acid (250 mL) was added N-chlorosuccinimide (1.32 g, 9.91 mmol). The reaction mixture was stirred at room temperature and under a nitrogen atmosphere for 20 h. The mixture was evaporated to dryness in vacuo. The residue dissolved in methylene chloride (100 mL), washed with 10% aqueous sodium hydrogensulfate (50 mL), saturated sodium hydrogencarbonate (50 mL), dried over magnesium sulfate, and evaporated to dryness in vacuo to give the crude intermediate. This was further purified on a silica gel column (eluent: ethyl acetate/heptane (1:4)) to give ethyl {5-chloro-2-[3-dicyclohexylureido]-thiazol-4-yl}-acetate as yellow crystals (Yield: 1.89 g (58%)). The crystals contain approx. 10% of ethyl chloro-{2-[3-dicyclohexylureido]-thiazol-4-yl}-acetate.

Step 3.

DIPEA (60 μl, 0.35 mmol) and N-methylpiperazine (33 μl, 0.298) were added to a solution of ethyl {5-chloro-2-[3,3-dicyclohexylureido]-thiazol-4-yl}-acetate (100 mg, 0.234 mmol) in methylene chloride (5 mL). The reaction mixture was stirred at room temperature for 48 h, filtered and evaporated to dryness in vacuo. The crude product was purified by HPLC to give ethyl {2-[3,3-dicyclohexylureido]-5-[4-methylpiperazin-1-yl]-thiazol-4-yl}-acetate. Yield: 13 mg (11%).

$^1$H-NMR (CD$_3$OD): δ4.15 (q, 2H), 3.67 (s, 2H), 3.55 (m, 2H), 3.47 (m, 2CH), 3.28 (m, 2H), 3.06 (t, 2H), 2.96 (s, 3H), 1.96 (m, 4H), 1.82 (broad d, 5H), 1.66 (broad d, 6H), 1.32-1.40 (4H, m), 1.25 (t, 3H), 1.10-1.30 (m, 1H).

HPLC-MS: m/z=492 (M+H)

Example 7

1,1-Dicyclohexyl-3-(5-imidazol-1-yl-thiazol-2-yl)-urea

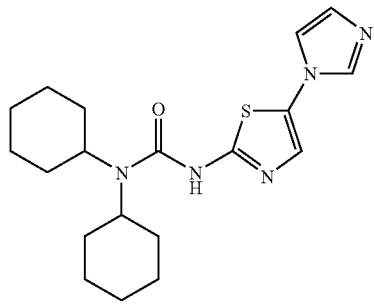

Step 1.

A mixture of 2-amino-5-bromothiazole hydrobromide (0.5 g, 1.92 mmol), DMF (6 mL), potassium carbonate (1.0 g, 7.2 mmol), and imidazole (132 mg, 1.94 mmol) was stirred at room temperature for 6 h. The mixture was filtered and the filtrate evaporated to dryness in vacuo. The crude product was purified on a silica gel column (eluent: gradient from 100% methylene chloride to 100% isopropanol) to give 5-imidazol-1-yl-thiazol-2-ylamine. Yield: 0.16 g (50

Step 2.

Urea coupling in an identical manner to Example 1 using carbonyldiimidazole, 2-amino-5-imidazol-thiazole, and dicyclohexylamine gave 1,1-dicyclohexyl-3-(5-imidazol-1-yl-thiazol-2-yl)-urea.

$^1$H-NMR (CDCl$_3$): δ7.96 (broad s, 1H), 7.69 (s, 1H), 7.32 (s, 1H), 7.17 (s, 1H), 7.13 (s, 1H), 3.43 (m, 2H), 1.95-1.60 (m, 14H), 1.40-1.10 (m, 6H).

HPLC-MS: m/z=375 (M+H)

Example 8

3-(5-Chloro-thiazol-2-yl)-1,1-bis-(tetrahydro-pyran-4-yl)-urea

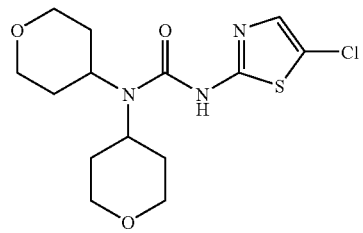

Prepared in an similar manner to example 2 according to general procedures (A) and (B) using tetrahydropyrane-4-one, 4-aminotetrahydropyran and 5-chloro-2-aminothiazole.

HPLC-MS: m/z=346 (M+H)

Example 9

3-[2-(3,3-Dicyclohexyl-ureido)-thiazol-4-ylmethylsulfanyl]-propionic acid

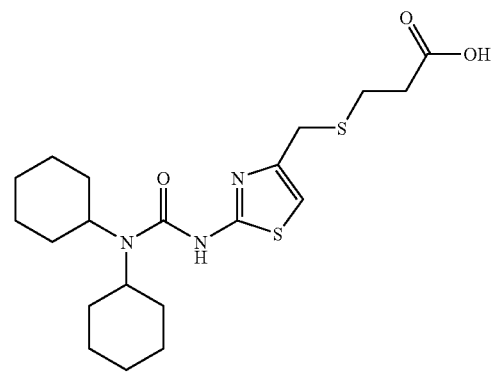

Prepared in accordance with the procedure for the synthesis of {2-[3-cyclopentyl-3-(trans-4-methoxy-cyclohexyl)-ureido]-thiazol-5-ylsulfanyl}-acetic acid using dicyclohexylamine and 3-(2-amino-thiazol-4-ylmethylsulfanyl)-propionic acid ethyl ester prepared in analogy to the methyl ester described in WO 2004/002481).

HPLC-MS: m/z 426 (M+H).

Example 10

[2-(3,3-Dicyclohexyl-ureido)-thiazol-4-ylmethane-sulfonyl]-acetic acid

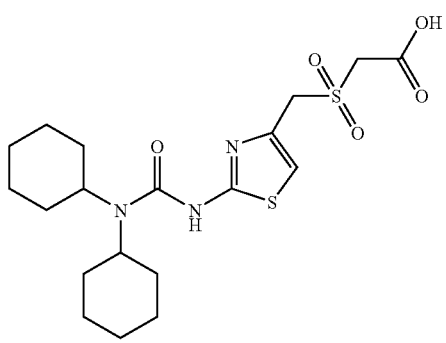

Montmorillonite (161 mg) and water (38 μL) was stirred for 10 min before oxone (187 mg, 0.30 mmol) and DCM (200 μL) was added. A solution of 3-[2-(3,3-dicyclohexyl-ureido)-thiazol-4-ylmethylsulfanyl]-propionic acid (50 mg, 0.12 mmol) in DCM (1 mL) was then added and the reaction mixture was stirred for 3 days at room temperature. The solid was filtered off and washed with MeOH and the filtrate was concentrated in vacuo. The crude product was purified on prep. HPLC to give 20 mg of [2-(3,3-dicyclohexyl-ureido)-thiazol-4-ylmethanesulfonyl]-acetic acid.

HPLC-MS: m/z 444 (M+H)

Example 11

1-(4-Amino-cyclohexyl)-1-cyclohexyl-3-(5-methyl-thiazol-2-yl)-urea

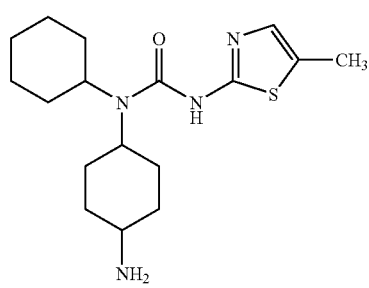

Prepared in accordance with the procedure for the synthesis of {2-[3-cyclopentyl-3-(trans-4-methoxy-cyclohexyl)-ureido]-thiazol-5-ylsulfanyl}-acetic acid using 4-tert-butyloxycarbonylamine-cyclohexanone, cyclohexylamine and 5-methyl-thiazole-2-ylamine HPLC-MS: m/z 337(M+H)

Example 12

1-(1-Acetyl-piperidin-4-yl)-1-cyclopentyl-3-thiazol-2-yl-urea

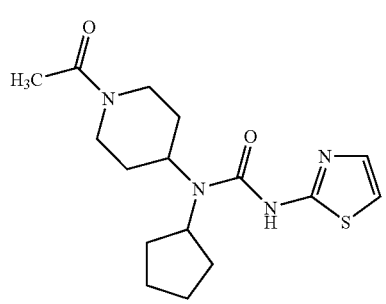

Prepared according to general procedure (I). To a mixture of N-acetyl-piperidone (1.4 g) and cyclopentylamine (0.9 g) and molecular sieves (5 g) in THF (8 mL) and methanol (8 mL) was added sodium cyanoborohydride (2.1 g) and the reaction was stirred overnight at room temperature. Insoluble material was removed by filtration and after removal of solvent in vacuo the crude secondary amine (0.57 g) was isolated. The urea coupling was performed in an similar manner to the synthesis of 1,1-dicyclopentyl-3-thiazol-2-yl-urea using carbonyl imidazole and 2-aminothiazole as starting material.

HPLC-MS: m/z=359 (M+Na)

Example 13 trans-3-(5-Chloro-thiazol-2-yl)-1-cyclohexyl-1-[1-(3-phenyl-acryloyl)-piperidin-4-yl]-urea

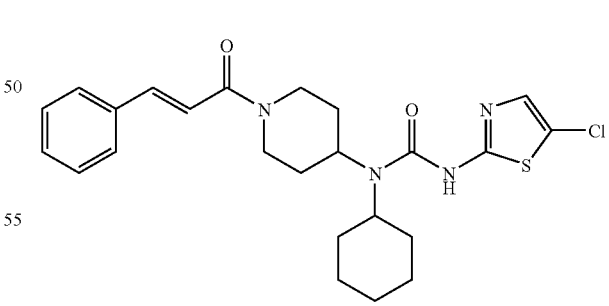

Prepared in a similar manner to the synthesis of example 12 according to general procedure (I) using 4-Boc-amino piperidone, cyclohexylamine, 5-chloro-2-aminothiazole and cinnamic acid as starting material.

HPLC-MS: m/z=495 (M+Na)

Example 14

3-(5-Chloro-thiazol-2-yl)-1-cyclohexyl-1-[1-(2-phenoxy-acetyl)-piperidin-4-yl]-urea

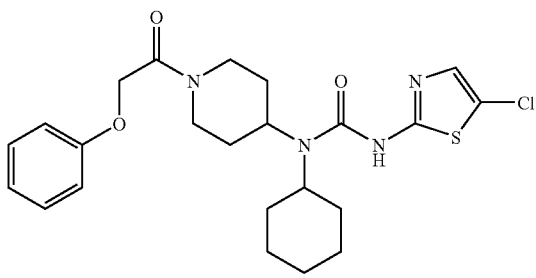

Prepared in a similar manner to the synthesis of example 12 according to general procedure (I) using 4-Boc-amino piperidone, cyclohexylamine, 5-chloro-2-aminothiazole and phenoxyacetic acid as starting material.

HPLC-MS: m/z=477 (M+Na)

Example 15

2-(3,3-Dicyclohexylureido)-4-methylthiazole-5-carboxylic acid (2-hydroxyethyl)amide

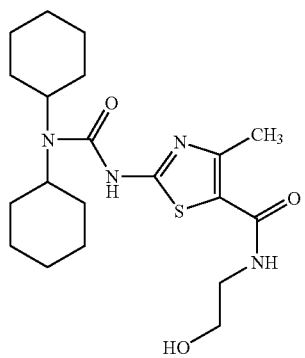

To a mixture of 2-amino-4-methyl-thiazole-carboxylic acid (2-hydroxyethyl)-amide (0.2 g) in dichloromethane was added N,O-bis-(trimethylsilyl)-acetamide (0.2 g) and the mixture stirred for 12 h. CDI (0.16 g) and DMAP (6 mg) was then added and the mixture stirred for 12 h before addition of dicyclohexylamine (0.18 g). After stirring overnight waster was added and the aqueous phase extracted with dichloromethane, concentrated and purified by chromatography to give the title compound.

$^1$H NMR (DMSO): δ 0.95-2.18 (m, 20H), 3.20-3.60 (m, 6H), 2.42 (s, 3H), 10.80-11-03 (bs, 1H).

Example 16

1-(1-Acetyl-piperidin-4-yl)-3-(5-chloro-thiazol-2-yl)-1-cycloheptyl-urea

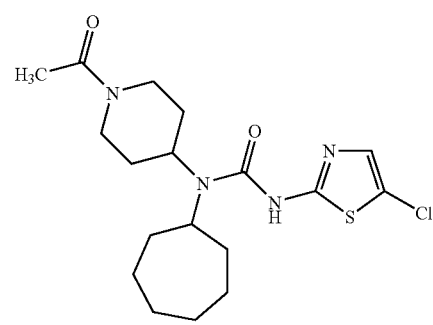

Prepared in a similar manner to the synthesis of example 12 according to general procedure (I) using 4-acetyl-amino-piperidine, cycloheptanone and 5-chloro-2-aminothiazole as starting material.

$^1$H NMR (CDCl$_3$): δ 1.37-2.18 (m, 16H), 2.13 (s, 3H), 2.49-2.67 (m, 1H), 3.07-3.22 (m, 1H), 3.33-3.43 (m, 1H), 3.85-3.96 (1H, m), 3.97-4.28 (m, 1H), 4.70-4.81 (m, 1H), 7.17 (s, 1H).

HPLC-MS: m/z=399 (M+H)

Example 17

3-(5-Chloro-thiazol-2-yl)-1-(1-methanesulfonyl-piperidin-4-yl)-1-(trans-4-methyl-cyclohexyl)-urea

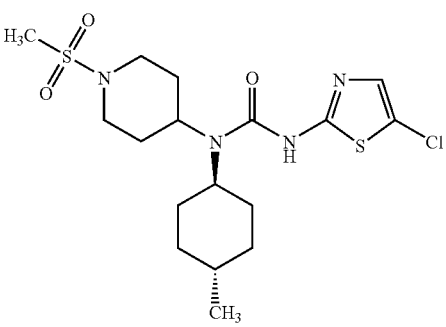

Prepared in a similar manner to the synthesis of example 12 according to general procedure (I) using 4-Boc-amino piperidone, trans-4-methylcyclohexylamine, 5-chloro-2-aminothiazole and methanesulfonylchloride as starting material.

HPLC-MS: m/z=435 (M+H)

Example 18

3-(5-Chloro-thiazol-2-yl)-1-(1-ethanesulfonyl-piperidin-4-yl)-1-(trans-4-methyl-cyclohexyl)-urea

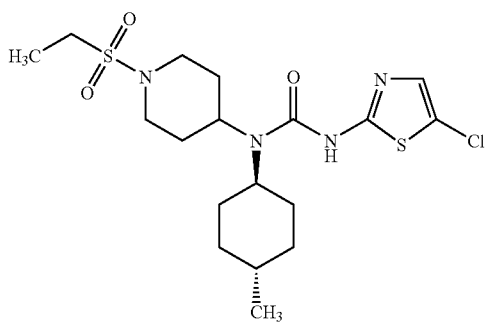

Prepared in a similar manner to the synthesis of example 12 according to general procedure (I) using 4-Boc-amino piperidone, trans-4-methylcyclohexylamine, 5-chloro-2-aminothiazole and ethanesulfonylchloride as starting material.

HPLC-MS: m/z=453 (M+H)

Example 19

3-(5-Chloro-thiazol-2-yl)-1-cyclohexyl-1-[1-(propane-1-sulfonyl)-piperidin-4-yl]-urea

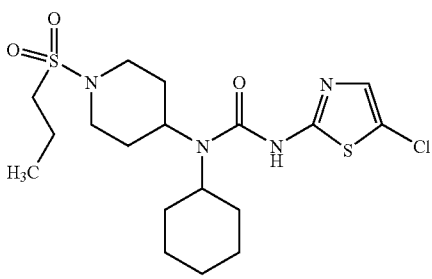

Prepared in a similar manner to the synthesis of example 12 according to general procedure (I) using 4-Boc-amino piperidine, cyclohexanone, 5-chloro-2-aminothiazole and propanesul-fonylchloride as starting material.

HPLC-MS: m/z=449 (M+H)

Example 20

2-[2-(3,3-Dicyclohexyl-ureido)-thiazol-5-ylsulfanyl]-2-methyl-propionic acid

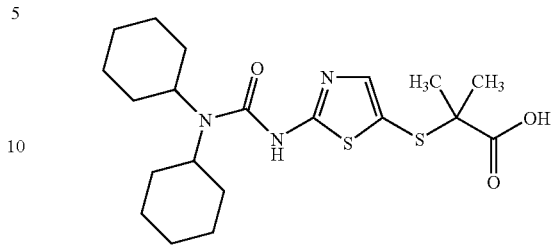

Step 1.

An equimolar mixture of 1,1-carbonyldiimidazole, 5-thiocyanato-thiazol-2-ylamine (commercial available or prepared as described in *J. Am. Chem. Soc* 71, 4007, 1949 or *J. Med. Chem.*, 20, 572, 1977) and DMAP (5 mol %) in THF was heated for 2 h at 60-70° C. and then cooled to room temperature. Dicyclohexyl amine (1 equivalent) was added and the reaction is stirred overnight at room temperature. The reaction mixture was quenched with water. The organic phase was isolated and the aqueous phase was extracted with $CH_2Cl_2$, and the combined organic phases were dried and concentrated in vacuo. The crude product was purified by flash chromatography (heptane:EtOAc 100:0 50:50) affording 1,1-dicyclohexyl-3-(5-thiocyanato-thiazol-2-yl)-urea as an oil.

Step 2.

An equimolar mixture of 1,4-dithiothreitol (DTT) and 1,1-dicyclohexyl-3-(5-thiocyanato-thiazol-2-yl)-urea (prepared as described in Step 1) in MeOH (4 mL/mmol) was stirred in a nitrogen atmosphere at room temperature for 2 h. Addition of $K_2CO_3$ (3 equiv) and ethyl 2-bromo-2-methylproprionate (1.1 equivalents). The reaction mixture was stirred at room temperature over night and quenched with water. Addition of $CH_2Cl_2$. The organic phase was isolated and the aqueous phase was extracted with $CH_2Cl_2$, and the combined organic phases were concentrated in vacuo. The crude product was dissolved in MeCN and purified by reverse phase preparative (HPLC method 1) to give 2-[2-(3,3-dicyclohexyl-ureido)-thiazol-5-ylsulfanyl]-2-methyl-propionic acid ethyl ester as an oil. This material was dissolved in MeOH and treated with 20 equivalents of 1N NaOH and stirred over night at room temperature. MeOH was removed by evaporation. Addition of 1N HCl to pH<1 caused precipitation. The precipitate was isolated by filtration, washed with water and dried to give the title compound.

HPLC-MS method 2: m/z=426 (M+H).

$^1$H NMR (CDCl$_3$) δ 7.09 (s, 1H), 3.50 (br s, 2H), 1.87-1.12 (m, 20H), 1.60 (s, 6H).

Example 21

2-[2-(3,3-Dicyclohexyl-ureido)-thiazol-5-ylsulfanyl]-propionic acid

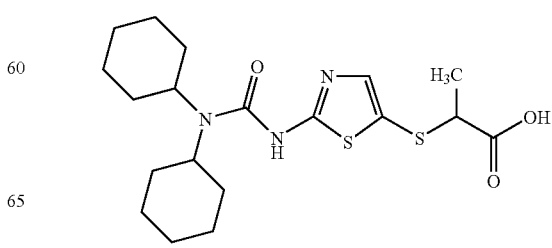

The title compound was prepared in a similar manner to 2-[2-(3,3-dicyclohexyl-ureido)-thiazol-5-ylsulfanyl]-2-methyl-propionic acid using ethyl 2-bromoproprionate as the alkylating agent.

HPLC-MS method 2: m/z=412 (M+H).

$^1$H NMR (CDCl$_3$) δ 7.11 (s, 1H), 3.62 (q, 1H), 3.44 (br s, 2H), 1.86-1.12 (m, 20H), 1.48 (d, 3H).

Example 22

[2-(3-Cyclohex-3-enyl-3-cyclohexyl-ureido)-thiazol-5-ylsulfanyl]-acetic acid

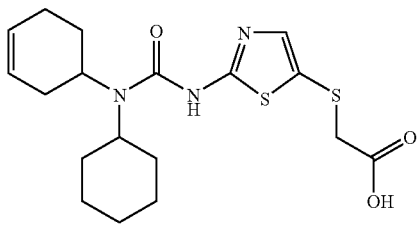

Prepared in accordance with the procedure for the synthesis of {2-[3-cyclopentyl-3-(trans-4-methoxy-cyclohexyl)-ureido]-thiazol-5-ylsulfanyl}-acetic acid using cyclohex-3-enylamine, cyclohexanone and (2-amino-thiazol-5-ylsulfanyl)-acetic acid ethyl ester as starting material.

HPLC-MS: m/z 396 (M+H).

Example 23

{2-[3-Cyclohexyl-3-(1-dimethylsulfamoyl-piperidin-4-yl)-ureido]-thiazol-5-ylsulfanyl}-acetic acid

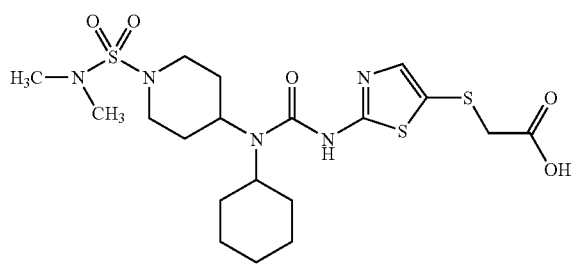

{2-[3-Cyclohexyl-3-piperidin-4-yl-ureido]-thiazol-5-ylsulfanyl}-acetic acid ethyl ester was pre-pared in a similar manner to the synthesis of example 12 from N-Boc piperidone, cyclo-hexylamine and (2-amino-thiazol-5-ylsulfanyl)-acetic acid ethyl, Boc deprotection, reaction with dimethylsulfamoyl chloride and hydrolysis of the ester moiety as described in general procedure (I) gave the title compound.

$^1$H NMR (CDCl$_3$): δ 1.11-1.88 (m, 14H), 2.85 (s, 6H), 2.85-3.04 (m, 4H), 3.37 (s, 2H), 3.72-3.85 (m, 2H), 7.30 (s, 1H).

HPLC-MS: m/z 506(M+H).

Example 24

3-(2-{3-Cyclohexyl-3-[1-(morpholine-4-carbonyl)-piperidin-4-yl]-ureido}-thiazol-5-ylsulfanyl)-propionic acid

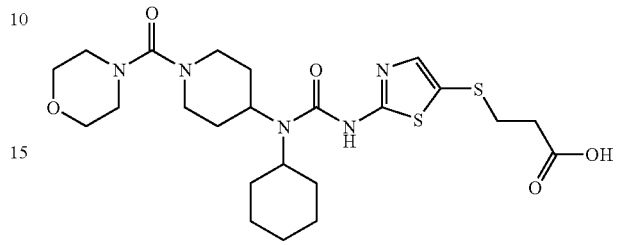

{2-[3-Cyclohexyl-3-piperidin-4-yl-ureido]-thiazol-5-ylsulfanyl}-propionic acid ethyl ester was prepared in a similar manner to the synthesis of example 12 from N-Boc piperidone, cyclo-hexylamine and (2-amino-thiazol-5-ylsulfanyl)-acetic acid ethyl ester, Boc deprotection, reaction with 4-morpholine carbonyl chloride and hydrolysis of the ester moiety as described in general procedure (I) gave the title compound.

$^1$H NMR (CDCl$_3$): δ 1.11-1.95 (m, 14H), 2.68-3.03 (m, 6H), 3.25-3.34 (m, 4H), 3.65-3.85 (m, 8H), 7.32 (s, 1H).

HPLC-MS: m/z 527 (M+H).

Example 25

(2-{3-Cyclohexyl-3-[1-(morpholine-4-carbonyl)-piperidin-4-yl]-ureido}-thiazol-5-ylsulfanyl)-acetic acid

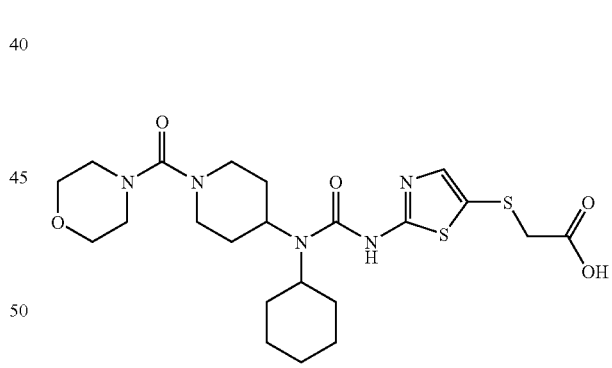

{2-[3-Cyclohexyl-3-piperidin-4-yl-ureido]-thiazol-5-ylsulfanyl}-acetic acid ethyl ester was pre-pared in a similar manner to the synthesis of example 12 from N-Boc piperidone, cyclohexylamine and (2-amino-thiazol-5-ylsulfanyl)-acetic acid ethyl ester, Boc deprotection, reaction with 4-morpholine carbonyl chloride and hydrolysis of the ester moiety as described in general procedure (I) gave the title compound.

$^1$H NMR (CDCl$_3$): δ 1.05-1.95 (m, 14H), 2.78-3.03 (m, 2H), 3.22-3.33 (m, 4H), 3.36 (s, 2H), 3.62-3.74 (4H, m), 3.75-3.83 (m, 4H), 7.32 (s, 1H).

HPLC-MS: m/z 512 (M+H).

Example 26

3-{2-[3-Cyclohexyl-3-(1-dimethylsulfamoyl-piperidin-4-yl)-ureido]-thiazol-5-ylsulfanyl}-propionic acid

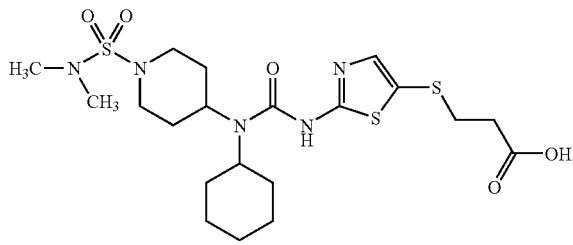

{2-[3-Cyclohexyl-3-piperidin-4-yl-ureido]-thiazol-5-ylsulfanyl}-propionic acid ethyl ester was prepared in a similar manner to the synthesis of example 12 from N-Boc piperidone, cyclohexylamine and (2-amino-thiazol-5-ylsulfanyl)-acetic acid ethyl ester, Boc deprotection, reaction with dimethylsulfamoyl chloride and hydrolysis of the ester moiety as described in general procedure (I) gave the title compound.

$^1$H NMR (CDCl$_3$): δ 1.11-2.00 (m, 14H), 2.85 (s, 6H), 2.70-3.24 (m, 6H), 3.69-3.90 (m, 4H), 7.29 (s, 1H).

HPLC-MS: m/z 520(M+H).

Example 27

{2-[3-Cyclohexyl-3-(1-dimethylcarbamoyl-piperidin-4-yl)-ureido]-thiazol-5-ylsulfanyl}-acetic acid

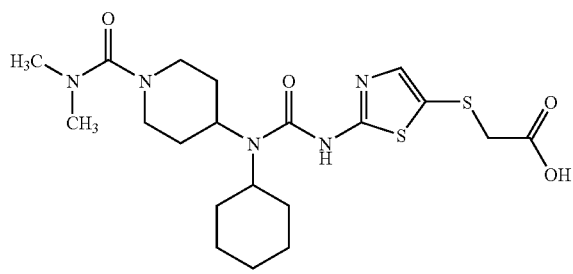

{2-[3-Cyclohexyl-3-piperidin-4-yl-ureido]-thiazol-5-ylsulfanyl}-acetic acid ethyl ester was pre-pared in a similar manner to the synthesis of example 12 from N-Boc piperidone, cyclohexyl-amine and (2-amino-thiazol-5-ylsulfanyl)-acetic acid ethyl ester, Boc deprotection, reaction with dimethylcarbamoyl chloride and hydrolysis of the ester moiety as described in general procedure (I) gave the title compound.

$^1$H NMR (CDCl$_3$): δ 1.11-1.88 (m, 14H), 2.85 (s, 6H), 2.85-3.04 (m, 4H), 3.34 (s, 2H), 3.72-3.85 (m, 2H), 7.30 (s, 1H).

HPLC-MS: m/z 471 (M+H).

Example 28

3-{2-[3-Cyclohexyl-3-(1-dimethylcarbamoyl-piperidin-4-yl)-ureido]-thiazol-5-ylsulfanyl}-propionic acid

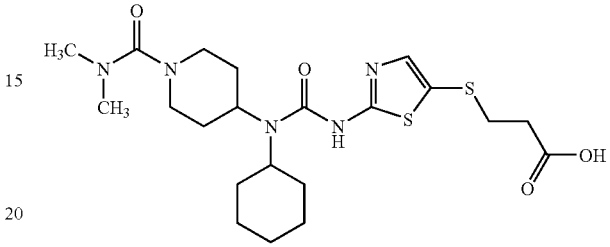

{2-[3-Cyclohexyl-3-piperidin-4-yl-ureido]-thiazol-5-ylsulfanyl}-propionic acid ethyl ester was prepared from N-Boc piperidone, cyclohexylamine and (2-amino-thiazol-5-ylsulfanyl)-acetic acid ethyl ester, Boc deprotection, reaction with dimethylcarbamoyl chloride and hydrolysis of the ester moiety as described in general procedure (I) gave the title compound.

HPLC-MS: m/z 485 (M+H).

Example 29

6-{4-[3-(5-Chloro-thiazol-2-yl)-1-cyclohexyl-ureido]-piperidin-1-yl}-6-oxo-hex-3-enoic acid

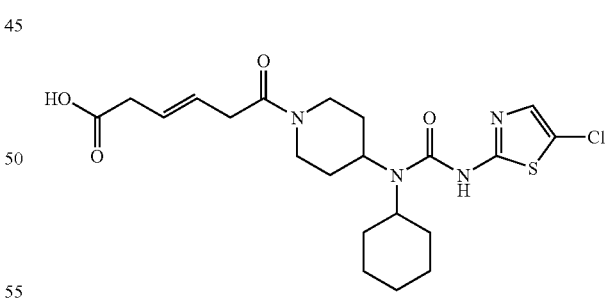

Prepared as described in general procedure (I) using 3-(5-chloro-thiazol-2-yl)-1-(trans-4-methyl-cyclohexyl)-1-piperidin-4-yl-urea and trans-2-butene-1,4-dicarboxylic acid.

$^1$H NMR (CDCl$_3$): δ 1.10-2.00 (m, 14H), 2.80-3.40 (m, 6H), 3.75 (d, 2H), 4.65 (d, 2H), 5.52-5.63 (m, 1H), 5.35-5.85 (m, 1H), 7.10 (s, 1H).

HPLC-MS: m/z 469 (M+H).

Example 30

1-(1-Acetyl-piperidin-4-yl)-1-(trans-4-methyl-cyclohexyl)-3-[5-(2-oxo-2-piperidin-1-yl-ethylsulfanyl)-thiazol-2-yl]-urea

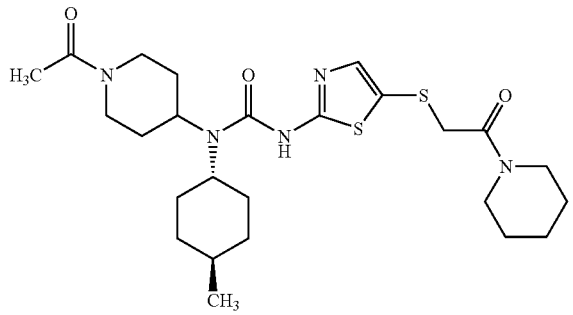

{2-[3-(1-Acetyl-piperidin-4-yl)-3-(trans-4-methyl-cyclohexyl)-ureido]-thiazol-5-ylsulfanyl}-acetic acid was prepared from 1-[4-(trans-4-methyl-cyclohexylamino)-piperidin-1-yl]-ethanone and (2-amino-thiazol-5-ylsulfanyl)-acetic acid ethyl ester as described in general procedure (I). Amide coupling was then performed as follows using general procedure (J): {2-[3-(1-Acetyl-piperidin-4-yl)-3-(trans-4-methyl-cyclohexyl)-ureido]-thiazol-5-ylsulfanyl}-acetic acid is dissolved/suspended in 1 ml of DMF in a 4 ml glass vial equipped with a magnetic stirring bar and a screw cap. 0.015 g (0.088 mmol) of DHOBt+0.017 g (0.088 mmol) of EDAC is added, stirred for 1 h at room temperature (clear yellow mixture) after which 0.088 mmol of piperidine and 0.015 ml (0.088 mmol) of diisopropylethylamine is added. Stirred for 3 days at room temperature and purification by HPLC gave the title compound.

HPLC-MS: m/z 522 (M+H).

Example 31

2-{2-[3-(1-Acetyl-piperidin-4-yl)-3-(trans-4-methyl-cyclohexyl)-ureido]-thiazol-5-ylsulfanyl}-N,N-diethyl-acetamide

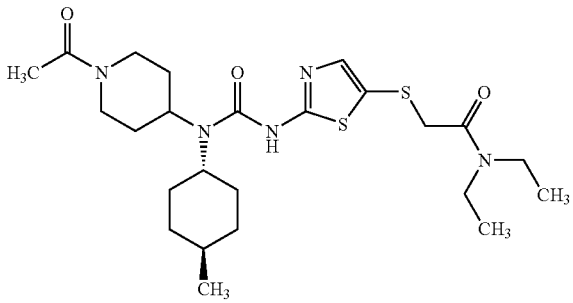

Prepared in a similar manner to 1-(1-acetyl-piperidin-4-yl)-1-(trans-4-methyl-cyclohexyl)-3-[5-(2-oxo-2-piperidin-1-yl-ethylsulfanyl)-thiazol-2-yl]-urea using {2-[3-(1-acetyl-piperidin-4-yl)-3-(trans-4-methyl-cyclohexyl)-ureido]-thiazol-5-ylsulfanyl}-acetic acid and diethylamine.

HPLC-MS: m/z 510 (M+H).

Example 32

1-(1-Acetyl-piperidin-4-yl)-1-(trans-4-methyl-cyclohexyl)-3-{5-[2-(4-methyl-piperazin-1-yl)-2-oxo-ethylsulfanyl]-thiazol-2-yl}-urea

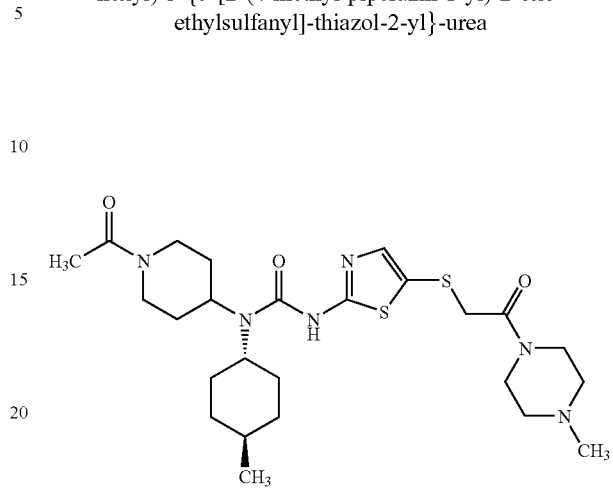

Prepared in a similar manner to 1-(1-acetyl-piperidin-4-yl)-1-(trans-4-methyl-cyclohexyl)-3-[5-(2-oxo-2-piperidin-1-yl-ethylsulfanyl)-thiazol-2-yl]-urea using {2-[3-(1-acetyl-piperidin-4-yl)-3-(trans-4-methyl-cyclohexyl)-ureido]-thiazol-5-ylsulfanyl}-acetic acid and N-methylpipeazine.

HPLC-MS: m/z 537 (M+H).

Example 33

1-(1-Acetyl-piperidin-4-yl)-1-(trans-4-methyl-cyclohexyl)-3-{5-[2-oxo-2-(4-pyrimidin-2-yl-piperazin-1-yl)-ethylsulfanyl]-thiazol-2-yl}-urea

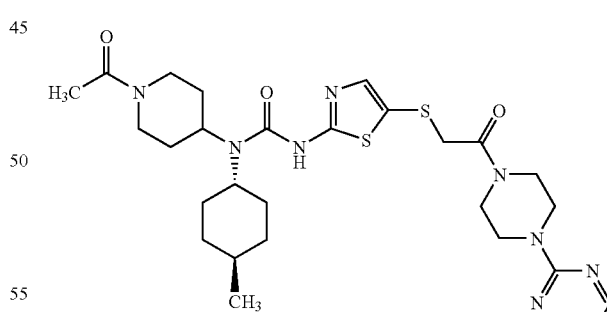

Prepared in a similar manner to 1-(1-acetyl-piperidin-4-yl)-1-(trans-4-methyl-cyclohexyl)-3-[5-(2-oxo-2-piperidin-1-yl-ethylsulfanyl)-thiazol-2-yl]-urea using {2-[3-(1-acetyl-piperidin-4-yl)-3-(trans-4-methyl-cyclohexyl)-ureido]-thiazol-5-ylsulfanyl}-acetic acid and 2-(piperazinyl)pyrimidine.

HPLC-MS: m/z 601 (M+H).

Example 34

1-(1-Acetyl-piperidin-4-yl)-1-(trans-4-methyl-cyclohexyl)-3-thiazol-2-yl-urea

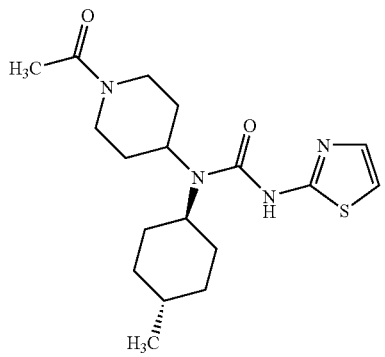

Prepared in a similar manner to the synthesis of example 12 using general method (I) from 1-[4-(trans-4-methyl-cyclohexylamino)-piperidin-1-yl]-ethanone and aminothiazole.

$^1$H-NMR (CDCl$_3$): δ8.36 (broad s, 1H), 7.33 (d, 1H), 6.85 (d, 1H), 4.76 (dm, 1H), 3.89 (dm, 1H), 3.78 (m, 1H), 3.30 (m, 1H), 3.08 (dt, 1H), 2.53 (dt, 1H), 2.1-2.2 (m, 2H), 2.12 (s, 3H), 1.95-1.64 (m, 8H), 1.36-1.45 (m, 1H), 1.04 (m, 2H), 0.92 (d, 3H).

HPLC-MS: m/z 365 (M+H).

Example 35

(2-{3-Cyclohexyl-3-[trans-4-(2-methyl-allyloxy)-cyclohexyl]-ureido}-thiazol-5-ylsulfanyl)-acetic acid

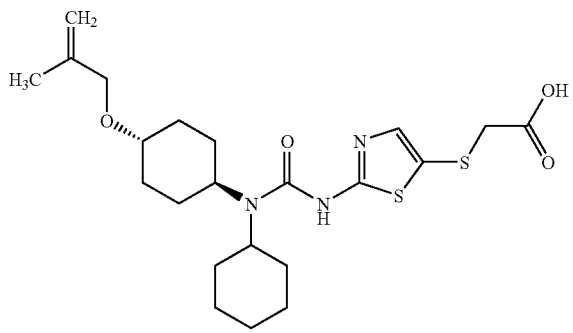

Prepared according to the procedure for the synthesis of {2-[3-cyclopentyl-3-(trans-4-methoxy-cyclohexyl)-ureido]-thiazol-5-ylsulfanyl}-acetic acid.

Step 1.
Cyclohexyl-[trans-4-(2-methyl-allyloxy)-cyclohexyl]-amine was prepare using (trans-4-hydroxy-cyclohexyl)-isoindole-1,3-dione, 3-bromo-2-methyl-propene and cyclohexanone Step 2.
(2-{3-Cyclohexyl-3-[trans-4-(2-methyl-allyloxy)-cyclohexyl]-ureido}-thiazol-5-ylsulfanyl)-acetic acid was prepared using cyclohexyl-[trans-4-(2-methyl-allyloxy)-cyclohexyl]-amine and amino-thiazol-5-ylsulfanyl)-acetic acid ethyl ester.

$^1$H NMR (CDCl$_3$) δ 7.25 (s, 1H), 4.98 (s, 1H), 4.90 (s, 1H), 3.92 (s, 2H), 3.6-3.2 (m, 3H), 3.32 (s, 2H), 2.5-1.0 (m, 21H).

HPLC-MS: m/z 469 (M+H).

Example 36

3-(2-{3-Cyclohexyl-3-[trans-4-(2-methyl-allyloxy)-cyclohexyl]-ureido}-thiazol-5-ylsulfanyl)-propionic acid

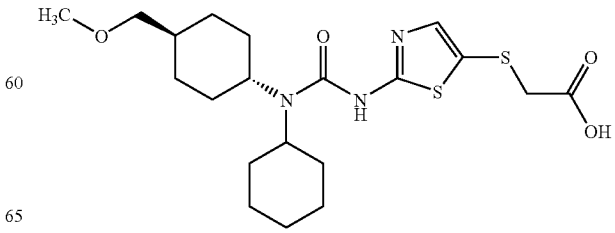

Prepared according to the procedure for the synthesis of {2-[3-cyclopentyl-3-(trans-4-methoxy-cyclohexyl)-ureido]-thiazol-5-ylsulfanyl}-acetic acid.

Step 1.
Cyclohexyl-[trans-4-(2-methyl-allyloxy)-cyclohexyl]-amine was prepare using (trans-4-hydroxy-cyclohexyl)-isoindole-1,3-dione, 3-bromo-2-methyl-propene and cyclohexanone Step 2.
3-(2-{3-Cyclohexyl-3-[trans-4-(2-methyl-allyloxy)-cyclohexyl]-ureido}-thiazol-5-ylsulfanyl)-propionic acid was prepared using cyclohexyl-[trans-4-(2-methyl-allyloxy)-cyclohexyl]-amine and amino-thiazol-5-ylsulfanyl)-propionic acid ethyl ester.

$^1$H NMR (400 MHz, DMSO-d$_6$) δ7.39 (s, 1H), 4.92 (s, 1H), 4.82 (s, 1H), 3.87 (s, 2H), 3.7-3.3 (m, 2H), 3.30-3.10 (m, 1H), 2.85 (t, 2H), 2.50 (t, 2H), 2.2-1.0 (m, 18H), 1.65 (s, 3H).

HPLC-MS: m/z 483 (M+H).

Example 37

{2-[3-Cyclohexyl-3-(trans-4-methoxymethyl-cyclohexyl)-ureido]-thiazol-5-ylsulfanyl}-acetic acid Prepared as follows using general Procedures (C), (D) and (A).

Steps 1 and 2.

A mixture of 4-carboxymethylcyclohexanone (21 g), ethylene glycol (19 g), conc. sulphuric acid (0.3 mL) and benzene (250 mL) was heated at reflux for 20 h with Dean Stark azeotropic removal of water. After cooling the solution was washed with sodium bicarbonate solution, dried over magnesium sulphate and concentrated. The crude ketal was then taken up in diethyl ether (250 mL) and lithium aluminium hydride (7 g) was added. The mixture was stirred overnight and then water (20 mL), 10% sodium hydroxide (30 mL) and water (30 mL) was added carefully. Sodium sulphate (30 g) was then added and the mixture stirred for 20 min, The insoluble material was removed by filtration and the organic phase concentrated in vacuo to give (1,4-dioxa-spiro[4.5]dec-8-yl)-methanol (21 g).

$^1$H NMR (CDCl$_3$): δ1.20-1.80, (m, 10H), 3.45 (d, 2H), 3.95 (s, 4H).

Steps 3 and 4.

To (1,4-Dioxa-spiro[4.5]dec-8-yl)-methanol (10 g) in tetrahydrofuran (300 mL) in an ice bath was added sodium hydride (3.6 g of 60% in mineral oil) and the mixture stirred for 30 min. Methyl iodide 7.8 mL in THF (20 mL) was added dropwise and the reaction was allowed to warm slowly to room temperature overnight. Water (20 mL) was added and the reaction mixture partially concentrated, then partitioned between water (100 mL) and diethyl ether (300 mL). The organic phase was isolated, dried and concentrated in vacuo. The crude was then taken up in tetrahydrofuran (250 mL) and 40 mL of 3N aqueous HCl was added. The reaction was stirred for 2 h at room temperature, partially concentrated and then the crude product was extracted with diethyl ether, dried, concentrated and purified by flash chromatography (eluant 4 hexane: 1 ethyl acetate) to give 4-methoxymethyl-cyclohexanone 4.9 g.

$^1$H NMR (CDCl$_3$): δ1.40-1.55 (m, 2H), 1.98-2.15 (m, 3H), 2.20-2.45 (m, 4H), (d, 2H), 3.36 (d, 4H), 3.31 (s. 3H).

Steps 5 and 6.

A mixture of 4-methoxymethyl-cyclohexanone (5 g), hydroxylamine hydrochloride (4.7 g), and sodium acetate (5.6 g) in water (125 mL) and methanol (25 mL) was heated to 60° C. for 18 h. Ether was added and the organic phase isolated, washed with saturated sodium bicarbonate, dried over magnesium sulphate and concentrated in vacuo. Ethanol was added and then sodium (8 g) was added portionwise. The mixture was then heated to 65° C. for 1.5 h, cooled in an ice bath and water (10 mL) was carefully added. The reaction was partially concentrated, water (30 mL) was added and the aqueous phase was extracted with diethyl ether and concentrated to give the crude product. Addition of 6N HCl afforded the corresponding HCl salt which was recrystallised from acetonitrile to give trans-4-methoxymethyl-cyclohexylamine hydrochloride (3 g).

$^1$H NMR (DMSO-d$_6$): δ0.90-1.15 (m, 2H), 1.20-1.37 (m, 2H), 1.38-1.54 (m, 1H), 1.73 (d, 2H), 1.95 (d, 2H), 2.80-2.95 (m, 1H), 3.12 (d, 2H), 3.22 (s. 3H), 8.21 (s, 3H).

Step 7.

To a mixture of trans-4-methoxymethyl-cyclohexylamine hydrochloride (0.7 g), cyclohexanone (0.4 g), diisoropylethylamine (0.5 g) and molecular sieves (3 g) in THF (5 mL) and methanol (5 mL) was added sodium cyanoborohydride (0.49 g) and the mixture stirred overnight at room temperature. Insoluble material was removed by filtration and the crude product purified by flash chromatography to give cyclohexyl-(trans-4-methoxymethyl-cyclohexyl)-amine (0.29 g).

HPLC-MS: m/z 227 (M+H).

Step 8.

A mixture of (2-amino-thiazol-5-ylsulfanyl)-acetic acid ethyl ester, carbonyl diimidazole (0.34 g) and 4-dimethylaminopyridine (12 mg) in dichloromethane (10 mL) and tetrahydrofuran (10 mL) was stirred at room temperature for 5 h. Cyclohexyl-(trans-4-methoxymethyl-cyclohexyl)-amine was added and the reaction stirred overnight at room temperature. Purification by flash chromatography gave {2-[3-cyclohexyl-3-(trans-4-methoxymethyl-cyclohexyl)-ureido]-thiazol-5-ylsulfanyl}-acetic acid ethyl ester.

HPLC-MS: m/z 471 (M+H).

Step 9

{2-[3-Cyclohexyl-3-(trans-4-methoxymethyl-cyclohexyl)-ureido]-thiazol-5-ylsulfanyl}-acetic acid ethyl ester was dissolved in methanol (10 mL) and 1N sodium hydroxide (5 mL) was added. Stirred at room temperature for 3 h then acidified with 1N hydrochloric acid. The white precipitate was filtered and dried to give the title compound (97 mg).

$^1$H NMR (CDCl$_3$): δ 1.0-2.0 (m, 19H), 3.15-3.50 (2H, m), 3.21 (d, 2H), 3.35 (s, 3H), 3.34 (s, 2H), 7.28 (s, 1H).

HPLC-MS: m/z 443 (M+H).

Example 38

{2-[3-Cyclopentyl-3-(trans-4-ethyl-cyclohexyl)-ureido]-thiazol-5-ylsulfanyl}-acetic acid

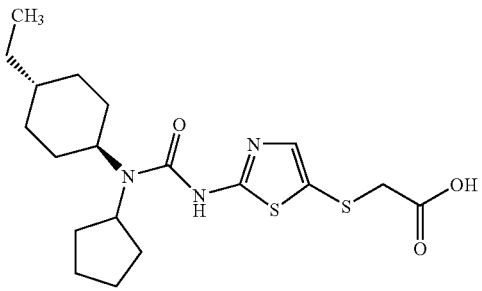

Step 1.

Sodium (45 g, 1.96 mol) was slowly added to a solution of 4-ethylcyclohexanone oxime (33 g, 0.23 mol) (prepared according to lit. R. O. Hutchins et al. J. Org. Chem. 60 (1995) 7396-7405)) in 99.9% ethanol (500 mL) while keeping the temperature below 65° C. The reaction mixture was heated at reflux temperature for 1½ h and then stirred at room temperature for further 16 h. A mixture of water (500 mL) and ethanol (100 mL) was added and the mixture was extracted with diethyl ether (3×250 mL). The combined organic phases was washed with brine (150 mL), dried over anhydrous magnesium sulphate and evaporated to dryness. The residue was dissolved in ethanol (100 mL), pH was adjusted to approx. 3 with 4 N hydrochloric acid (60 mL) and the solution was evaporated to dryness in vacuo to give crude ethylcyclohexylamine. The product was purified by recrystallization from ethanol/acetonitrile (4:1) to give 4-trans-ethylcyclohexylamine, hydrochloride as white crystalls.

Step 2.

An equimolar mixture of 4-trans-ethylcyclohexylamine, hydrochloride (prepared in Step 1), diisopropylethyl amine and cyclohexanone in THF:MeOH (1:1, 2 mL/mmol) and 3 Å molsieves was added sodium cyanoborohydride (2 equiv) and the mixture was stirred at room temperature overnight, filtered through celite, added DCM and water. The organic phase was isolated and washed with water and added 4N HCl and subsequently evaporated to dryness in vacuo. Addition of MeOH and evaporation to dryness gave the crude secondary amine cyclopentyl-(trans-4-ethyl-cyclohexyl)-amine which was used in the next step without further purification.

Step 3.

An equimolar mixture of 1,1-carbonyldiimidazole, (2-amino-thiazol-5-ylsulfanyl)-acetic acid ethyl ester and DMAP (5 mol %) in THF was heated for 5 h at 50-60° C. and then cooled to room temperature. Then cyclopentyl-(trans-4-ethyl-cyclohexyl)-amine (1 equivalent; see Step 2) was added and the reaction is stirred overnight at room temperature. The reaction mixture was quenched with water. The organic phase was isolated and the aqueous phase was extracted with $CH_2Cl_2$, and the combined organic phases were dried and concentrated in vacuo. The crude product was dissolved in MeCN and purified (HPLC method 1) to give {2-[3-cyclopentyl-3-(trans-4-ethyl-cyclohexyl)-ureido]-thiazol-5-ylsulfanyl}-acetic acid ethyl ester. This material was dissolved in MeOH and treated with 15 equivalents of 1N NaOH over night at room temperature. MeOH was removed by evaporation. Addition of 1N HCl to pH<1 caused precipitation. The precipitate was isolated by filtration, washed with water and dried to give the title compound.

HPLC-MS method 2: m/z=412 (M+H).

$^1$H NMR (DMSO-$d_6$) δ 12.0 (br s, 1H), 7.40 (s, 1H), 3.85 (br s, 1H), 3.60 (br s, 1H), 3.48 (s, 2H), 1.88-1.42 (m, 14H), 1.25-0.99 (m, 5H), 0.86 (t, 3H).

Example 39

{2-[3-Cyclopentyl-3-(trans-4-isopropyl-cyclohexyl)-ureido]-thiazol-5-ylsulfanyl}-acetic acid

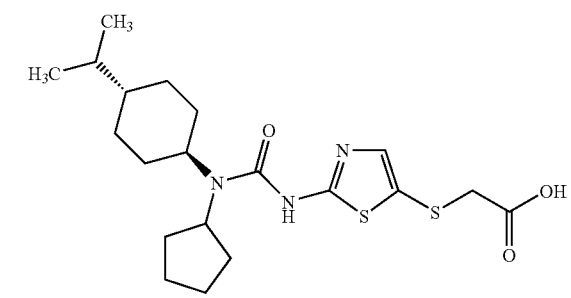

Prepared in a similar manner to {2-[3-cyclopentyl-3-(trans-4-ethyl-cyclohexyl)-ureido]-thiazol-5-ylsulfanyl}-acetic acid via cyclopentyl-(trans-4-isopropyl-cyclohexyl)-amine and (2-amino-thiazol-5-ylsulfanyl)-acetic acid ethyl ester to give the title compound.

HPLC-MS method 2: m/z=426 (M+H).

$^1$H NMR (DMSO-$d_6$) δ 12.35 (br s, 1H), 7.39 (s, 1H), 3.84 (br s, 1H), 3.61 (br s, 1H), 3.48 (s, 2H), 1.90-1.40 (m, 15H), 1.20-0.99 (m, 3H), 0.86 (d, 6H).

Example 40

3-{2-[3-Cyclopentyl-3-(trans-4-ethyl-cyclohexyl)-ureido]-thiazol-5-ylsulfanyl}-propionic acid

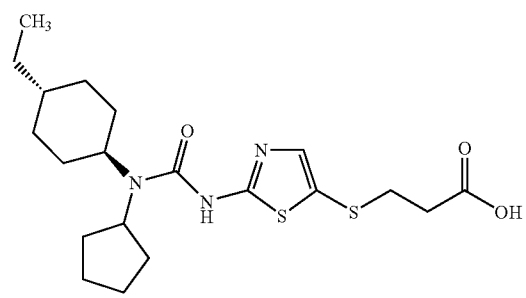

Prepared in a similar manner to {2-[3-cyclopentyl-3-(trans-4-ethyl-cyclohexyl)-ureido]-thiazol-5-ylsulfanyl}-acetic acid via cyclopentyl-(trans-4-ethyl-cyclohexyl)-amine and 3-(2-amino-thiazol-5-ylsulfanyl)-propionic acid ethyl ester to give the title compound.

HPLC-MS method 2: m/z=426 (M+H).

$^1$H NMR (DMSO-$d_6$) δ 11.8 (br s, 1H), 7.38 (s, 1H), 3.86 (br s, 1H), 3.62 (br s, 1H), 2.85 (t, 2H), 2.50 (t, 2H), 1.89-1.44 (m, 14H), 1.24-0.99 (m, 5H), 0.87 (t, 3H).

Example 41

3-{2-[3-Cyclopentyl-3-(trans-4-isopropyl-cyclohexyl)-ureido]-thiazol-5-ylsulfanyl}-propionic acid

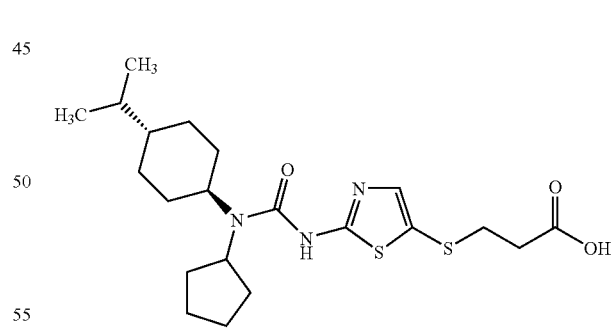

Prepared in a similar manner to {2-[3-cyclopentyl-3-(trans-4-ethyl-cyclohexyl)-ureido]-thiazol-5-ylsulfanyl}-acetic acid via cyclopentyl-(trans-4-isopropyl-cyclohexyl)-amine and 3-(2-amino-thiazol-5-ylsulfanyl)-propionic acid ethyl ester to give the title compound.

HPLC-MS method 2: m/z=440 (M+H).

$^1$H NMR (DMSO-$d_6$) δ 11.6 (br s, 1H), 7.38 (s, 1H), 3.86 (br s, 1H), 3.62 (br s, 1H), 2.85 (t, 2H), 2.50 (t, 2H), 1.91-1.39 (m, 15H), 1.20-0.99 (m, 3H), 0.85 (d, 6H).

Example 42

{2-[3-Cyclohexyl-3-(trans-4-ethoxymethyl-cyclohexyl)-ureido]-thiazol-5-ylsulfanyl}-acetic acid

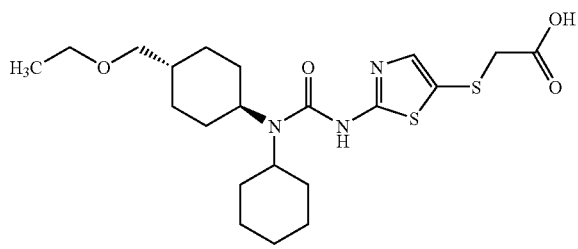

Prepared in an similar manner to {2-[3-cyclohexyl-3-(trans-4-methoxymethyl-cyclohexyl)-ureido]-thiazol-5-ylsulfanyl}-acetic acid via cyclohexyl-(trans-4-ethoxymethyl-cyclohexyl)-amine and (2-amino-thiazol-5-ylsulfanyl)-acetic acid ethyl ester to give the title compound.

$^1$H NMR (CDCl$_3$): δ1.2 (t, 3H), 1.0-2.0 (m, 19H), 3.20-3.50 (2H, m), 3.22 (d, 2H), 3.30 (s, 2H), 3.41 (q, 2H), 7.22 (s, 1H).

HPLC-MS: m/z 456 (M+H).

Example 43

{2-[3-Cyclopentyl-3-(trans-4-methoxy-cyclohexyl)-ureido]-thiazol-5-ylsulfanyl}-acetic acid

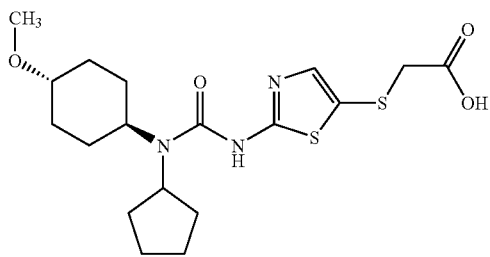

Step 1 (preparation of the secondary amine):

To a solution of 2-(trans-4-hydroxy-cyclohexyl)-isoindole-1,3-dione (Glennon et al. *J. Med. Chem.* 1996, 39, 1, 314-322) (1.0 g, 40.77 mmol) in DMF (4.0 mL) was added NaH (60% in oil, 0.41 g, 10.2 mmol) followed by iodomethane (5.79 g, 40.7 mmol). The reaction mixture was stirred for 16 h before water (15 mL) and ethyl acetate (25 mL) was added and the phases were separated. The organic phase was washed with water (2×10 mL), dried over MgSO$_4$ and the solvent was removed in cacuo. The residue was purified on silica gel (EtOAc-heptane) to give 0.810 g (77%) 2-(trans-4-methoxy-cyclohexyl)-isoindole-1,3-dione.

2-(trans-4-methoxy-cyclohexyl)-isoindole-1,3-dione (0.710 g, 2.74 mmol) in absolute ethanol (10 mL) was added hydrazine hydrate (0.130 g, 4.11 mmol) and the reaction mixture was stirred for 2 h at 50° C. The oilbath was removed and the mixture was stirred for 16 h at room temperature. The volatiles were removed in vacuo and the residue was added NaOH (20 mL, 10 N) and extracted with diethyl ether (3×10 mL). The organic phase was dried with MgSO$_4$ and concentrated in vacuo to give 0.300 g (85%) of 4-trans-methoxy-cyclohexy-lamine. 4-Trans-methoxy-cyclohexylamine (100 mg, 0.78 mmol) and cyclopentanone (72 mg, 0.85 mmol) in THF-MeOH 2:1 (2 mL) and acetic acid (0.1 mL) was added sodium cyanoborohydride (73 mg, 1.02 mmol) in small portions over 15 min. The reaction mixture was stirred for 16 h before the volatiles were removed in vacuo. The residue was added HCl (1N, 50 mL) and stirred for 16 h at rt. The mixture was added NaOH (10N, 2.5 mL), extracted with diethyl ether (2×10 mL) and dried over MgSO$_4$. The solvent was removed in vacuo to give 134 mg (88%) of cyclopentyl-(4-methoxy-cyclohexyl)-amine.

Step 2 (coupling and hydrolysis):

Amino-thiazol-5-ylsulfanyl)-acetic acid ethyl ester (110 mg, 0.51 mmol)) in THF (5, mL) was added CDI (82 mg, 0.51 mmol) and DMAP (2 mg, 0.017 mmol) and the reaction mixture was stirred for 2 h at rt before cyclopentyl-(4-methoxy-cyclohexyl)-amine (66.5 mg, 0.34 mmol) was added. The reaction mixture was stirred for 16 h before the solvent was removed in vacuo. The residue added ethyl acetate (25 mL) and washed with HCl (1N, 2×10 mL) and dried over MgSO4. The sovent was removed in vacuo and the residue was purified on preparative HPLC methode 1 to give 35 mg (24%) of {2-[3-cyclopentyl-3-(trans-4-methoxy-cyclohexyl)-ureido]-thiazol-5-ylsulfanyl}-acetic acid ethyl ester.

{2-[3-Cyclopentyl-3-(trans-4-methoxy-cyclohexyl)-ureido]-thiazol-5-ylsulfanyl}-acetic acid ethyl ester (30 mg, 0.068 mmol) in acetonitrile (1 mL) was added NaOH (1N, 0.3 mL) and the reaction mixture was stirred for 2 h at rt before the solvent was removed in vacuo. HCl (1N, 2.5 mL) was added under stirring and the precipitate was collected, washed with water (3×2.5 mL) and dried in vacuo to give 18 mg (64%) of {2-[3-cyclopentyl-3-(trans-4-methoxy-cyclohexyl)-ureido]-thiazol-5-ylsulfanyl}-acetic acid.

$^1$H NMR (400 MHz, DMSO-d$_6$) δ 7.4 (s, 1H), 3.87 (bs, 1H), 3.60 (bs, 1H), 3.49 (s, 2H), 3.22 (s, 3H), 3.15-3.04 (m, 1H), 2.05-1.40 (m, 14H), 1.32-1.18 (m, 2H).

HPLC-MS: m/z 414(M+H).

Example 44

{2-[3-Cycloheptyl-3-(trans-4-methoxy-cyclohexyl)-ureido]-thiazol-5-ylsulfanyl}-acetic acid

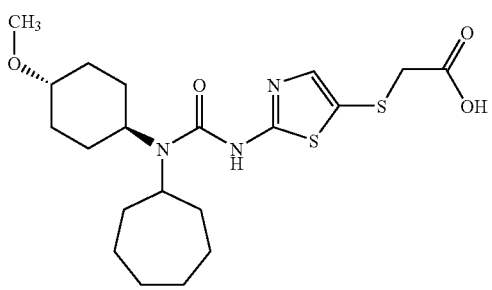

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-methoxy-cyclohexyl]-amine was prepare using (trans-4-hydroxy-cyclohexyl)-isoindole-1,3-dione, iodomethane and cycloheptanone.

Step 2: {2-[3-Cycloheptyl-3-(trans-4-methoxy-cyclohexyl)-ureido]-thiazol-5-ylsulfanyl}-acetic acid was prepared using cycloheptyl-[trans-4-methoxy-cyclohexyl]-amine and amino-thiazol-5-ylsulfanyl)-acetic acid ethyl ester.

$^{1}$H NMR (DMSO-d$_{6}$) δ 7.40 (s, 1H), 3.9-3.4 (bm, 2H), 3.47 (s, 2H), 3.22 (s, 3H), 3.15-3.05 (m, 1H), 2.10-1.18 (m, 20H).
HPLC-MS: m/z 442 (M+H).

Example 45

{2-[3-Cyclopentyl-3-(trans-4-ethoxy-cyclohexyl)-ureido]-thiazol-5-ylsulfanyl}-acetic acid

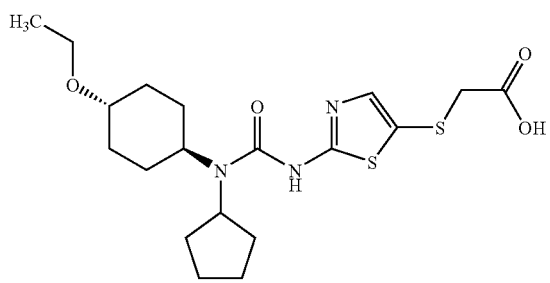

Prepared according to the procedure for the synthesis of {2-[3-cyclopentyl-3-(trans-4-methoxy-cyclohexyl)-ureido]-thiazol-5-ylsulfanyl}-acetic acid.
Step 1: Cyclopentyl-[trans-4-ethoxy-cyclohexyl]-amine was prepare using (trans-4-hydroxy-cyclohexyl)-isoindole-1,3-dione, iodoethane and cyclopentanone.
Step 2: {2-[3-Cyclopentyl-3-(trans-4-ethoxy-cyclohexyl)-ureido]-thiazol-5-ylsulfanyl}-acetic acid was prepared using cyclopentyl-[trans-4-ethoxy-cyclohexyl]-amine and amino-thiazol-5-ylsulfanyl)-acetic acid ethyl ester.

$^{1}$H NMR (DMSO-d$_{6}$) δ 7.40 (s, 1H), 3.9 (bs, 1H), 3.6 (bs, 1H), 3.47 (s, 2H), 3.42 (q, 2H), 3.25-3.15 (m, 1H), 2.0-1.2 (m, 16H), 1.08 (t, 3H).
HPLC-MS: m/z 428 (M+H).

Example 46

{2-[3-Cyclohexyl-3-(trans-4-ethoxy-cyclohexyl)-ureido]-thiazol-5-ylsulfanyl}-acetic acid

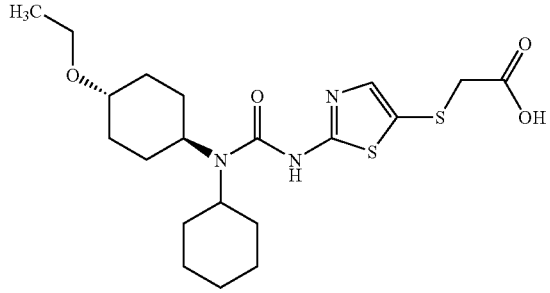

Prepared according to the procedure for the synthesis of {2-[3-cyclopentyl-3-(trans-4-methoxy-cyclohexyl)-ureido]-thiazol-5-ylsulfanyl}-acetic acid.
Step 1: Cyclohexyl-[trans-4-ethoxy-cyclohexyl]-amine was prepare using (trans-4-hydroxy-cyclohexyl)-isoindole-1,3-dione, iodoethane and cyclohexanone.

Step 2: {2-[3-Cyclohexyl-3-(trans-4-ethoxy-cyclohexyl)-ureido]-thiazol-5-ylsulfanyl}-acetic acid was prepared using cyclohexyl-[trans-4-ethoxy-cyclohexyl]-amine and amino-thiazol-5-ylsulfanyl)-acetic acid ethyl ester.

$^{1}$H NMR (DMSO-d$_{6}$) δ 7.40 (s, 1H), 3.7-3.3 (m, 2H), 3.49 (s, 2H), 3.40 (q, 2H), 3.20 (m, 1H), 2.15-1.15 (m, 18), 1.10 (t, 3H).
HPLC-MS: m/z 442 (M+H).

Example 47

{2-[3-Cycloheptyl-3-(trans-4-ethoxy-cyclohexyl)-ureido]-thiazol-5-ylsulfanyl}-acetic acid

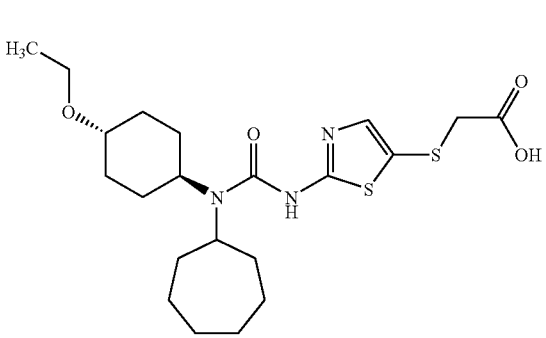

Prepared according to the procedure for the synthesis of {2-[3-cyclopentyl-3-(trans-4-methoxy-cyclohexyl)-ureido]-thiazol-5-ylsulfanyl}-acetic acid.
Step 1: Cycloheptyl-[trans-4-ethoxy-cyclohexyl]-amine was prepare using (trans-4-hydroxy-cyclohexyl)-isoindole-1,3-dione, iodoethane and cycloheptanone.
Step 2: {2-[3-Cycloheptyl-3-(trans-4-ethoxy-cyclohexyl)-ureido]-thiazol-5-ylsulfanyl}-acetic acid was prepared using cycloheptyl-[trans-4-ethoxy-cyclohexyl]-amine and amino-thiazol-5-ylsulfanyl)-acetic acid ethyl ester.
HPLC-MS: m/z 456 (M+H).

Example 48

3-{2-[3-Cyclohexyl-3-(trans-4-methoxymethyl-cyclohexyl)-ureido]-thiazol-5-ylsulfanyl}-propionic acid

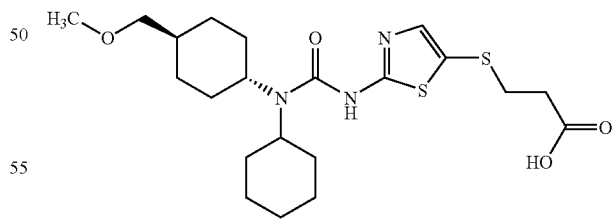

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-methoxymethyl-cyclohexyl)-amine and (2-amino-thiazol-5-ylsulfanyl)-propionic acid ethyl ester to give the title compound.

$^{1}$H NMR (CDCl$_{3}$): δ1.0-2.0 (m, 19H), 2.68-2.76 (m, 2H), 2.95-3.03 (m, 2H), 3.24 (d, 2H), 3.10-3.70 (m, 2H), 3.36 (s, 3H), 7.30 (s, 1H).
HPLC-MS: m/z 456 (M+H).

Example 49

{2-[3-(trans-4-tert-Butyl-cyclohexyl)-3-cyclopentyl-ureido]-thiazol-5-ylsulfanyl}-acetic acid

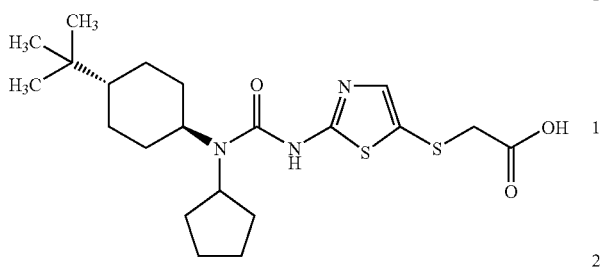

Prepared in a similar manner to {2-[3-cyclopentyl-3-(trans-4-ethyl-cyclohexyl)-ureido]-thiazol-5-ylsulfanyl}-acetic acid via (4-tert-butyl-cyclohexyl)-cyclopentyl-amine and (2-amino-thiazol-5-ylsulfanyl)-acetic acid ethyl ester to give the title compound.

HPLC-MS method 2: m/z=440 (M+H).

$^1$H NMR (DMSO-$d_6$) δ 11.5 (br s, 1H), 7.40 (s, 1H), 3.82 (br s, 1H), 3.63 (br s, 1H), 3.48 (s, 2H), 1.90-1.44 (m, 14H), 1.20-0.93 (m, 3H), 0.85 (s, 9H).

Example 50

{2-[3-(trans-4-tert-Butyl-cyclohexyl)-3-cyclohexyl-ureido]-thiazol-5-ylsulfanyl}-acetic acid

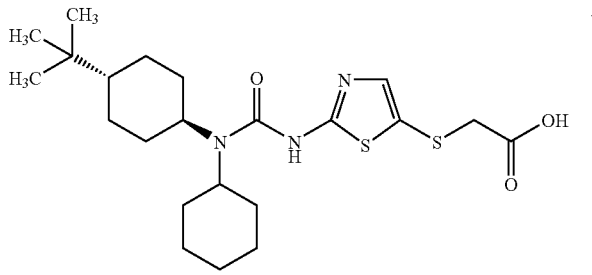

Prepared in a similar manner to {2-[3-cyclopentyl-3-(trans-4-ethyl-cyclohexyl)-ureido]-thiazol-5-ylsulfanyl}-acetic acid via (4-tert-butyl-cyclohexyl)-cyclohexyl-amine and (2-amino-thiazol-5-ylsulfanyl)-acetic acid ethyl ester to give the title compound.

HPLC-MS method 2: m/z=454 (M+H).

$^1$H NMR (DMSO-$d_6$) δ 11.5 (br s, 1H), 7.40 (s, 1H), 3.65 (br s, 2H), 3.48 (s, 2H), 2.05-0.95 (m, 19H), 0.84 (s, 9H).

Example 51

{2-[3-(trans-4-tert-Butyl-cyclohexyl)-3-cycloheptyl-ureido]-thiazol-5-ylsulfanyl}-acetic acid

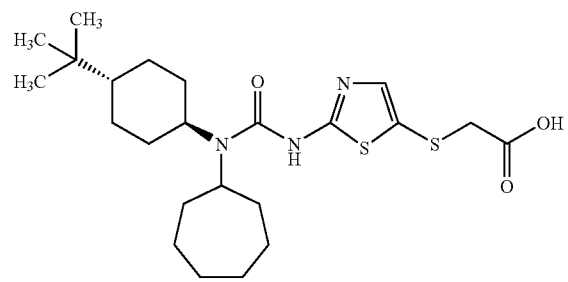

Prepared in a similar manner to {2-[3-cyclopentyl-3-(trans-4-ethyl-cyclohexyl)-ureido]-thiazol-5-ylsulfanyl}-acetic acid via (4-tert-butyl-cyclohexyl)-cycloheptyl-amine and (2-amino-thiazol-5-ylsulfanyl)-acetic acid ethyl ester to give the title compound.

HPLC-MS method 2: m/z=468 (M+H).

$^1$H NMR (DMSO-$d_6$) δ 11.5 (br s, 1H), 7.41 (s, 1H), 4.20 (br s, 2H), 3.50 (s, 2H), 2.15 (br s, 2H), 1.68-0.97 (m, 19H), 0.85 (s, 9H).

Example 52

{2-[3-Cycloheptyl-3-(trans-4-methoxymethyl-cyclohexyl)-ureido]-thiazol-5-ylsulfanyl}-acetic acid

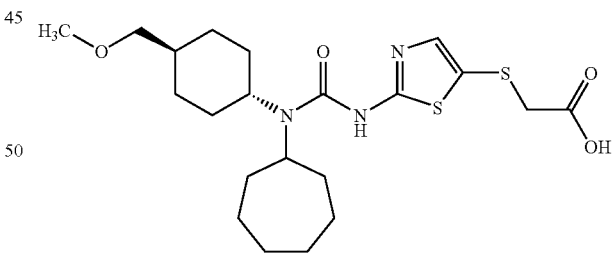

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-methoxymethyl-cycloheptyl)-amine and (2-amino-thiazol-5-ylsulfanyl)-acetic acid ethyl ester to give the title compound.

$^1$H NMR (CDCl$_3$): δ1.0-2.0 (m, 21H), 3.21 (d, 2H), 3.37 (s, 3H), 3.39 (s, 2H), 3.15-3-35 (m, 1H), 3.55-3.85 (m, 1H), 7.27 (s, 1H).

HPLC-MS: m/z 456 (M+H).

Example 53

3-{2-[3-Cycloheptyl-3-(trans-4-methoxymethyl-cyclohexyl)-ureido]-thiazol-5-ylsulfanyl}-propionic acid

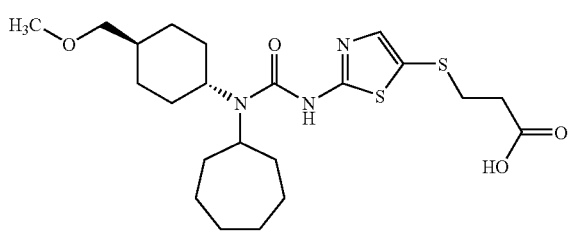

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-methoxymethyl-cycloheptyl)-amine and (2-amino-thiazol-5-ylsulfanyl)-propionic acid ethyl ester to give the title compound.

$^1$H NMR (CDCl$_3$): δ1.0-2.0 (m, 21H), 2.69-2.75 (m, 2H), 2.91-3.04 (m, 2H), 3.20-3.23 (d, 2H), 3.10-3.30 (m, 1H), 3.34 (s, 3H), 3.50-3.80 (m, 1H), 7.27 (s, 1H).

HPLC-MS: m/z 470 (M+H).

Example 54

3-{2-[3-Cyclohexyl-3-(trans-4-ethoxymethyl-cyclohexyl)-ureido]-thiazol-5-ylsulfanyl}-propionic acid

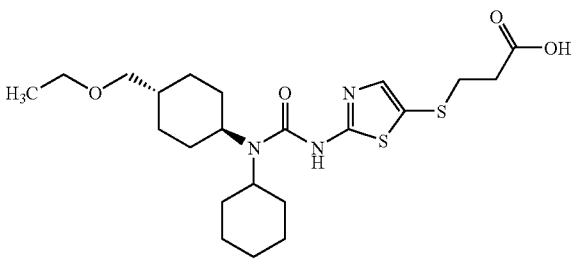

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-ethoxymethyl-cyclohexyl)-amine and (2-amino-thiazol-5-ylsulfanyl)-propionic acid ethyl ester to give the title compound.

$^1$H NMR (CDCl$_3$): δ1.2 (t, 3H), 1.0-2.0 (m, 19H), 2.69-2.81 (m, 2H), 2.91-3.05 (2H, m), 3.25 (d, 2H), 3.10-3.60 (m, 2H), 3.38 (q, 2H), 7.22 (s, 1H).

HPLC-MS: m/z 470 (M+H).

Example 55

3-{2-[3-(trans-4-tert-Butyl-cyclohexyl)-3-cyclopentyl-ureido]-thiazol-5-ylsulfanyl}-propionic acid

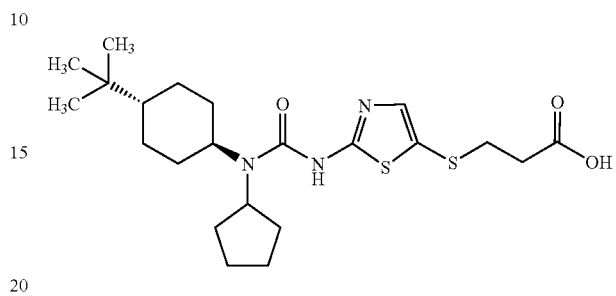

Prepared in a similar manner to {2-[3-cyclopentyl-3-(trans-4-ethyl-cyclohexyl)-ureido]-thiazol-5-ylsulfanyl}-acetic acid via (4-tert-butyl-cyclohexyl)-cyclopentyl-amine and 3-(2-amino-thiazol-5-ylsulfanyl)-propionic acid ethyl ester to give the title compound.

HPLC-MS method 2: m/z=454 (M+H).

$^1$H NMR (DMSO-d$_6$) δ 11.5 (br s, 1H), 7.38 (s, 1H), 3.83 (br s, 1H), 3.64 (br s, 1H), 2.85 (t, 2H), 2.49 (t, 2H), 1.91-1.44 (m, 14H), 1.23-0.93 (m, 3H), 0.85 (s, 9H).

Example 56

3-{2-[3-(trans-4-tert-Butyl-cyclohexyl)-3-cyclohexyl-ureido]-thiazol-5-ylsulfanyl}-propionic acid

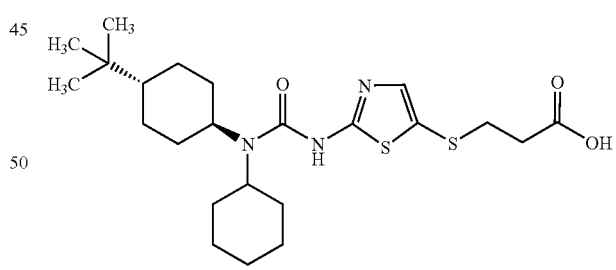

Prepared in a similar manner to {2-[3-cyclopentyl-3-(trans-4-ethyl-cyclohexyl)-ureido]-thiazol-5-ylsulfanyl}-acetic acid via (4-tert-butyl-cyclohexyl)-cyclohexyl-amine and 3-(2-amino-thiazol-5-ylsulfanyl)-propionic acid ethyl ester to give the title compound.

HPLC-MS method 2: m/z=468 (M+H).

$^1$H NMR (DMSO-d$_6$) δ 11.5 (br s, 1H), 7.38 (s, 1H), 3.55 (br s, 2H), 2.85 (t, 2H), 2.49 (t, 2H), 2.05-0.95 (m, 19H), 0.85 (s, 9H).

Example 57

3-{2-[3-(trans-4-tert-Butyl-cyclohexyl)-3-cycloheptyl-ureido]-thiazol-5-ylsulfanyl}-propionic acid

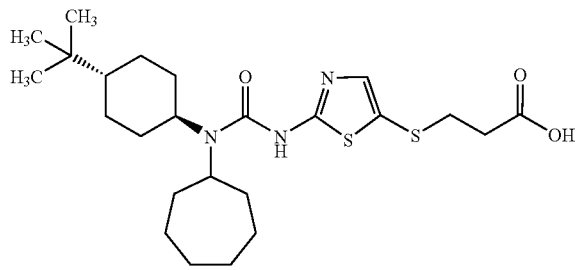

Prepared in a similar manner to {2-[3-cyclopentyl-3-(trans-4-ethyl-cyclohexyl)-ureido]-thiazol-5-ylsulfanyl}-acetic acid via (4-tert-butyl-cyclohexyl)-cycloheptyl-amine and 3-(2-amino-thiazol-5-ylsulfanyl)-propionic acid ethyl ester to give the title compound.

HPLC-MS method 2: m/z=482 (M+H).

$^1$H NMR (DMSO-$d_6$) δ 11.5 (br s, 1H), 7.38 (s, 1H), 3.80 (br s, 2H), 2.84 (t, 2H), 2.49 (t, 2H), 2.16 (br s, 2H), 1.68-0.96 (m, 19H), 0.85 (s, 9H).

Example 58

2-{2-[3-(trans-4-tert-Butyl-cyclohexyl)-3-cyclopentyl-ureido]-thiazol-5-ylsulfanyl}-2-methyl-propionic acid

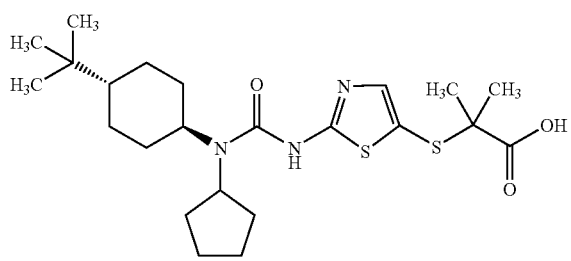

Prepared in a similar manner to {2-[3-cyclopentyl-3-(trans-4-ethyl-cyclohexyl)-ureido]-thiazol-5-ylsulfanyl}-acetic acid (Example 38) via (4-tert-butyl-cyclohexyl)-cyclopentyl-amine and 2-(2-amino-thiazol-5-ylsulfanyl)-2-methyl-propionic acid ethyl ester to give the title compound.

HPLC-MS method 2: m/z=468 (M+H).

$^1$H NMR (DMSO-$d_6$) δ 12.6 (br s, 1H), 11.1 (br s, 1H), 7.38 (s, 1H), 3.83 (br s, 1H), 3.63 (br s, 1H), 1.93-1.43 (m, 14H), 1.40 (s, 6H), 1.23-0.94 (m, 3H), 0.85 (s, 9H).

Example 59

2-{2-[3-(trans-4-tert-Butyl-cyclohexyl)-3-cyclohexyl-ureido]-thiazol-5-ylsulfanyl}-2-methyl-propionic acid

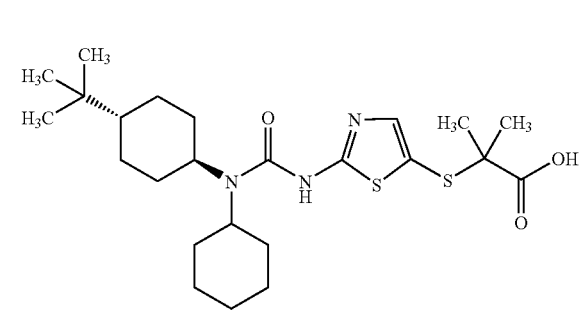

Prepared in a similar manner to {2-[3-cyclopentyl-3-(trans-4-ethyl-cyclohexyl)-ureido]-thiazol-5-ylsulfanyl}-acetic acid (Example 38) via (4-tert-butyl-cyclohexyl)-cyclohexyl-amine and 2-(2-amino-thiazol-5-ylsulfanyl)-2-methyl-propionic acid ethyl ester to give the title compound.

HPLC-MS method 2: m/z=482 (M+H).

$^1$H NMR (DMSO-$d_6$) δ 12.6 (br s, 1H), 11.1 (br s, 1H), 7.38 (s, 1H), 3.40 (br s, 2H), 2.05-0.95 (m, 19H), 1.40 (s, 6H), 0.85 (s, 9H).

Example 60

{2-[3-Cycloheptyl-3-(trans-4-ethoxymethyl-cyclohexyl)-ureido]-thiazol-5-ylsulfanyl}-acetic acid

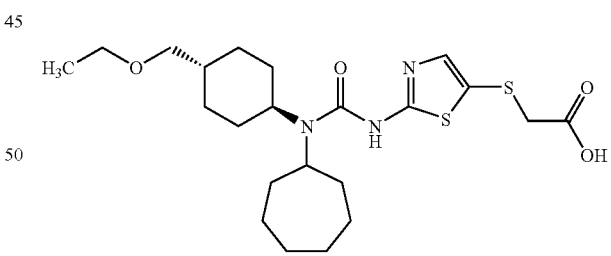

Prepared in an similar manner to {2-[3-cyclohexyl-3-(trans-4-methoxymethyl-cyclohexyl)-ureido]-thiazol-5-ylsulfanyl}-acetic acid via cyclohexyl-(trans-4-ethoxymethyl-cycloheptyl)-amine and (2-amino-thiazol-5-ylsulfanyl)-acetic acid ethyl ester to give the title compound.

$^1$H NMR (CDCl$_3$): δ1.21 (t, 3H), 1.0-2.4 (m, 21H), 3.23 (d, 2H), 3.33 (s, 2H), 3.30-3.70 (m, 2H), 3.43 (q, 2H), 7.22 (s, 1H,)

HPLC-MS: m/z 470 (M+H).

Example 61

{2-[3-Cyclohexyl-3-(trans-4-cyclopropyl methoxy-cyclohexyl)-ureido]-thiazol-5-ylsulfanyl}-acetic acid

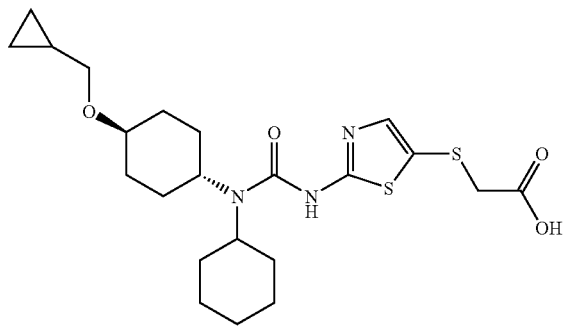

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-cyclopropylmethoxy-cyclohexyl]-amine was prepare using (trans-4-hydroxy-cyclohexyl)-isoindole-1,3-dione, cyclopropylmethylbromide and cyclohexanone.

Step 2: {2-[3-Cyclohexyl-3-(trans-4-cyclopropylmethoxy-cyclohexyl)-ureido]-thiazol-5-ylsulfanyl}-acetic acid was prepared using cyclohexyl-[trans-4-cyclopropylmethoxy-cyclohexyl]-amine and amino-thiazol-5-ylsulfanyl)-acetic acid ethyl ester.

$^1$H NMR (DMSO-$d_6$) δ 7.40 (s, 1H), 3.6-3.2 (m, 3H), 3.47 (s, 2H), 3.23 (d, 3H), 2.2-0.9 (m, 19H), 0.45 (m, 2H), 0.14 (m, 2H).

HPLC-MS: m/z 468 (M+H).

Example 62

3-{2-[-3-Cyclohexyl-3-(trans-4-cyclopropyl methoxy-cyclohexyl)-ureido]-thiazol-5-ylsulfanyl}-propionic acid

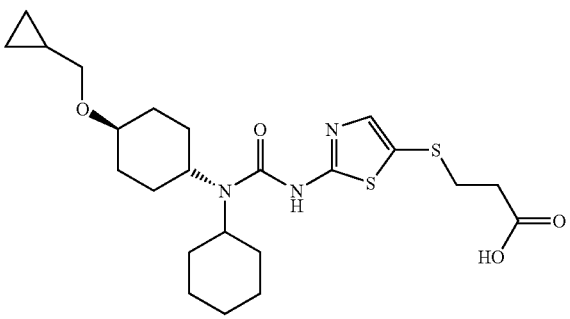

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-cyclopropylmethoxy-cyclohexyl]-amine was prepare using (trans-4-hydroxy-cyclohexyl)-isoindole-1,3-dione, cyclopropylmethylbromide and cyclohexanone.

Step 2: {2-[3-Cyclohexyl-3-(trans-4-cyclopropylmethoxy-cyclohexyl)-ureido]-thiazol-5-ylsulfanyl}-propionic acid was prepared using cyclohexyl-[trans-4-cyclopropylmethoxy-cyclohexyl]-amine and amino-thiazol-5-ylsulfanyl)-propionic acid ethyl ester.

$^1$H NMR (DMSO-$d_6$) δ 7.37 (s, 1H), 3.7-3.2 (m, 3H), 3.24 (d, 3H), 2.85 (t, 2H), 2.50 (t, 2H), 2.2-0.9 (m, 19H), 0.45 (m, 2H), 0.14 (m, 2H).

HPLC-MS: m/z 482(M+H).

Example 63

3-{2-[3-Cyclopentyl-3-(trans-4-methoxy-cyclohexyl)-ureido]-thiazol-5-ylsulfanyl}-propionic acid

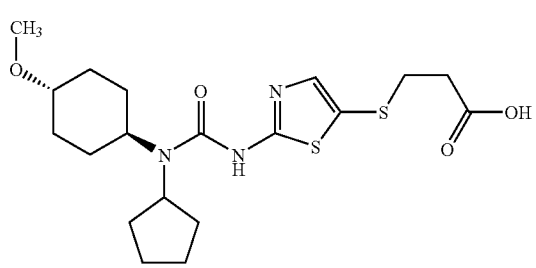

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclopentyl-[trans-4-methoxy-cyclohexyl]-amine was prepare using (trans-4-hydroxy-cyclohexyl)-isoindole-1,3-dione, iodomethane and cyclopentanone.

Step 2: 3-{2-[3-Cyclopentyl-3-(trans-4-methoxy-cyclohexyl)-ureido]-thiazol-5-ylsulfanyl}-propionic acid was prepared using cyclopentyl-[trans-4-methoxy-cyclohexyl]-amine and amino-thiazol-5-ylsulfanyl)-propionic acid ethyl ester.

$^1$H NMR (DMSO-$d_6$) δ 7.38 (s, 1H), 3.87 (m, 1H), 3.60 (m, 1H), 3.33 (s, 3H), 3.10 (m, 1H), 2.85 (t, 2H), 2.50 (t, 2H), 2.1-1.4 (m, 14H), 1.31-1.15 (m, 2H).

HPLC-MS: m/z 428 (M+H).

Example 64

3-{2-[3-Cyclohexyl-3-(trans-4-methoxy-cyclohexyl)-ureido]-thiazol-5-ylsulfanyl}-propionic acid

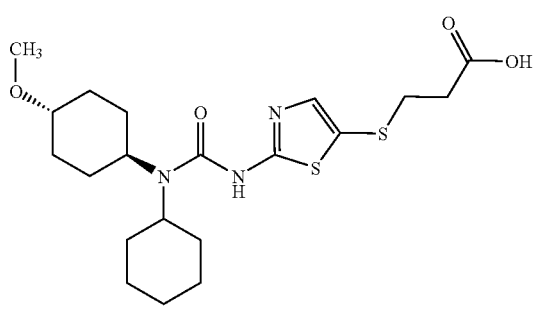

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-methoxy-cyclohexyl]-amine was prepare using (trans-4-hydroxy-cyclohexyl)-isoindole-1,3-dione, iodomethane and cyclohexanone.

Step 2: 3-{2-[3-Cyclohexyl-3-(trans-4-methoxy-cyclohexyl)-ureido]-thiazol-5-ylsulfanyl}-propionic acid was prepared using cyclohexyl-[trans-4-methoxy-cyclohexyl]-amine and amino-thiazol-5-ylsulfanyl)-propionic acid ethyl ester.

$^1$H NMR (DMSO-$d_6$) δ 7.32 (s, 1H), 3.65-3.20 (m, 2H) 3.20 (s, 2H), 3.05 (m, 1H), 2.80 (t, 2H), 2.45 (t, 2H), 2.15-1.00 (m, 18H).

HPLC-MS: m/z 442 (M+H).

Example 65

3-{2-[3-Cycloheptyl-3-(trans-4-methoxy-cyclohexyl)-ureido]-thiazol-5-ylsulfanyl}-propionic acid

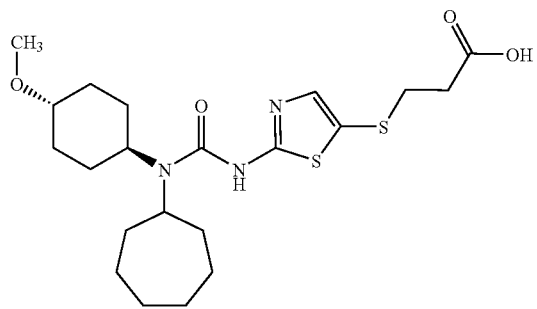

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-methoxy-cyclohexyl]-amine was prepare using (trans-4-hydroxy-cyclohexyl)-isoindole-1,3-dione, iodomethane and cycloheptanone.

Step 2: 3-{2-[3-Cycloheptyl-3-(trans-4-methoxy-cyclohexyl)-ureido]-thiazol-5-ylsulfanyl}-propionic acid was prepared using cycloheptyl-[trans-4-methoxy-cyclohexyl]-amine and amino-thiazol-5-ylsulfanyl)-propionic acid ethyl ester.

$^1$H NMR (DMSO-$d_6$) δ 7.32 (s, 1H), 3.20 (s, 3H), 3.08 (m, 1H), 2.79 (t, 2H), 2.47 (t, 2H), 2.25-1.10 (m, 20H).

HPLC-MS: m/z 456 (M+H).

Example 66

3-{2-[3-Cyclopentyl-3-(trans-4-ethoxy-cyclohexyl)-ureido]-thiazol-5-ylsulfanyl}-propionic acid

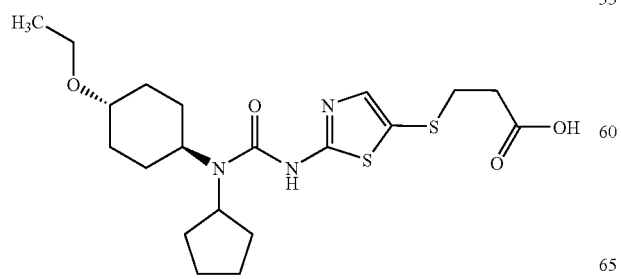

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclopentyl-[trans-4-ethoxy-cyclohexyl]-amine was prepare using (trans-4-hydroxy-cyclohexyl)-isoindole-1,3-dione, iodoethane and cyclopentanone.

Step 2: 3-{2-[3-Cyclopentyl-3-(trans-4-ethoxy-cyclohexyl)-ureido]-thiazol-5-ylsulfanyl}-propionic acid was prepared using cyclopentyl-[trans-4-ethoxy-cyclohexyl]-amine and amino-thiazol-5-ylsulfanyl)-propionic acid ethyl ester.

$^1$H NMR (400 MHz, DMSO-$d_6$) δ 7.33 (s, 1H); 3.82 (m, 1H), 3.55 (M, 1H), 3.40 (q, 2H), 3.15 (m, 1H), 2.80 (t, 2H), 2.45 (t, 2H), 2.05-1.10 (m, 16H), 1.05 (t, 3H).

HPLC-MS: m/z 442 (M+H).

Example 67

3-{2-[3-Cyclohexyl-3-(trans-4-ethoxy-cyclohexyl)-ureido]-thiazol-5-ylsulfanyl}-propionic acid

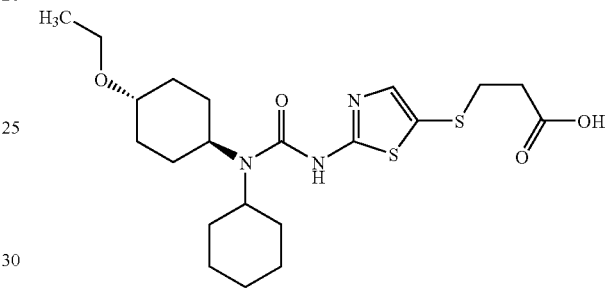

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-ethoxy-cyclohexyl]-amine was prepare using (trans-4-hydroxy-cyclohexyl)-isoindole-1,3-dione, iodoethane and cyclohexanone.

Step 2: {2-[3-Cyclohexyl-3-(trans-4-ethoxy-cyclohexyl)-ureido]-thiazol-5-ylsulfanyl}-propionic acid was prepared using cyclohexyl-[trans-4-ethoxy-cyclohexyl]-amine and amino-thiazol-5-ylsulfanyl)-propionic acid ethyl ester.

$^1$H NMR (DMSO-$d_6$) δ 11.8 (bs, 1H), 7.38 (s, 1H), 3.7-3.2 (m, 2H), 3.40 (q, 2H), 3.20 (m, 1H), 2.84 (t, 2H), 2.50 (t, 2H), 2.20-1.15 (m, 18H), 1.10 (t, 3H).

HPLC-MS: m/z 456 (M+H).

Example 68

3-{2-[3-Cycloheptyl-3-(trans-4-ethoxy-cyclohexyl)-ureido]-thiazol-5-ylsulfanyl}-propionic acid

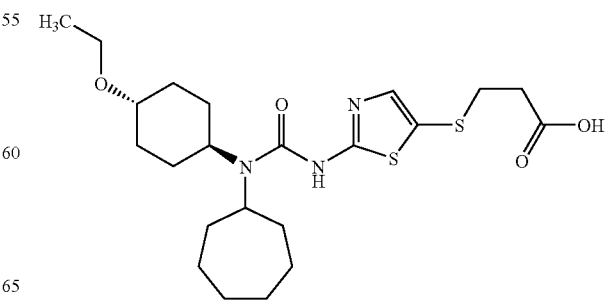

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-ethoxy-cyclohexyl]-amine was prepare using (trans-4-hydroxy-cyclohexyl)-isoindole-1, 3-dione, iodoethane and cycloheptanone.

Step 2: {2-[3-Cycloheptyl-3-(trans-4-ethoxy-cyclohexyl)-ureido]-thiazol-5-ylsulfanyl}-propionic acid was prepared using cycloheptyl-[trans-4-ethoxy-cyclohexyl]-amine and amino-thiazol-5-ylsulfanyl)-propionic acid ethyl ester.

$^1$H NMR (DMSO-d$_6$) δ 7.32 (s, 1H), 3.7-3.3 (m, 2H), 3.38 (q, 2H), 3.15 (m, 1H), 2.80 (t, 2H), 2.45 (t, 2H), 2.2-1.1 (m, 20H), 1.03 (t, 3H).

HPLC-MS: m/z 470 (M+H).

Example 69

(2-{3-Cyclohexyl-3-[trans-4-(2-methoxy-ethoxy)-cyclohexyl]-ureido}-thiazol-5-ylsulfanyl)-acetic acid

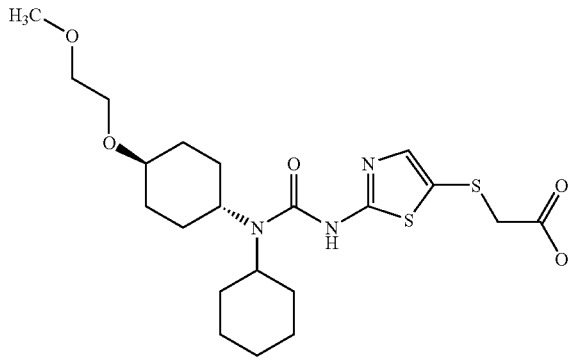

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-(2-methoxy-ethoxy)-cyclohexyl]-amine was prepare using (trans-4-hydroxy-cyclohexyl)-isoindole-1,3-dione, 1-bromo-2-methoxyethane and cyclohexanone.

Step 2: (2-{3-Cyclohexyl-3-[trans-4-(2-methoxy-ethoxy)-cyclohexyl]-ureido}-thiazol-5-ylsulfanyl)-acetic acid was prepared using cyclohexyl-[trans-4-(2-methoxy-ethoxy)-cyclohexyl]-amine and amino-thiazol-5-ylsulfanyl)-acetic acid ethyl ester.

HPLC-MS: m/z 472(M+H).

Example 70

3-(2-{3-Cyclohexyl-3-[trans-4-(2-methoxy-ethoxy)-cyclohexyl]-ureido}-thiazol-5-ylsulfanyl)-propionic acid

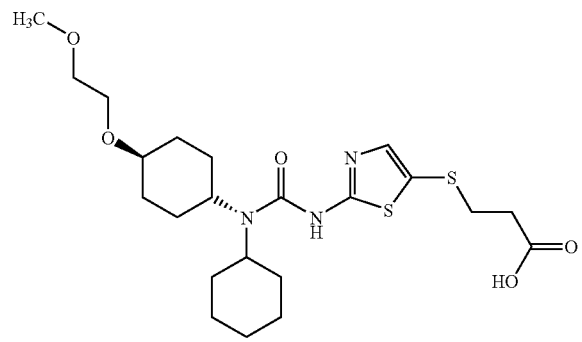

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-(2-methoxy-ethoxy)-cyclohexyl]-amine was prepare using (trans-4-hydroxy-cyclohexyl)-isoindole-1,3-dione, 1-bromo-2-methoxyethane and cyclohexanone.

Step 2: (2-{3-Cyclohexyl-3-[trans-4-(2-methoxy-ethoxy)-cyclohexyl]-ureido}-thiazol-5-ylsulfanyl)-propionic acid was prepared using cyclohexyl-[trans-4-(2-methoxy-ethoxy)-cyclohexyl]-amine and amino-thiazol-5-ylsulfanyl)-propionic acid ethyl ester.

1H NMR (400 MHz, DMSO-d$_6$) δ 7.37 (s, 1H), 3.7-3.3 (m, 2H), 3.52 (t, 2H), 3.42 (t, 2H), 3.25 (s, 3H), 3.3-3.18 (m, 1H), 2.85 (t, 2H), 2.50 (t, 2H), 2.2-1.0 (m, 18H).

HPLC-MS: m/z 486 (M+H).

Example 71

{2-[3-Cyclopentyl-3-(trans-4-methoxymethyl-cyclohexyl)-ureido]-thiazol-5-ylsulfanyl}-acetic acid

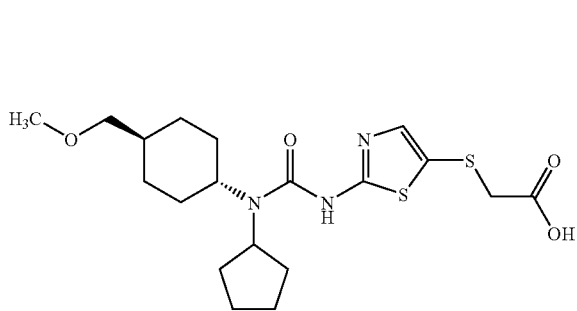

Prepared in an similar manner to {2-[3-cyclohexyl-3-(trans-4-methoxymethyl-cyclohexyl)-ureido]-thiazol-5-ylsulfanyl}-acetic acid via cyclohexyl-(trans-4-methoxymethyl-cyclopentyl)-amine and (2-amino-thiazol-5-ylsulfanyl)-acetic acid ethyl ester to give the title compound.

$^1$H NMR (CDCl$_3$): δ 1.10-2.00 (m, 17H), 3.21 (d, 2H), 3.32 (s, 3H), 3.34 (s, 2H), 3.35-3.50 (1H, m), 3.70-3.85 (m, 1H), 7.28 (s, 1H).

HPLC-MS: m/z 428 (M+H).

Example 72

3-{2-[3-Cycloheptyl-3-(trans-4-ethoxymethyl-cyclohexyl)-ureido]-thiazol-5-ylsulfanyl}-propionic acid

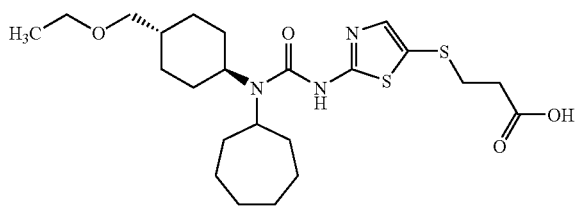

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-ethoxymethyl-cycloheptyl)-amine and (2-amino-thiazol-5-ylsulfanyl)-propionic acid ethyl ester to give the title compound.

$^1$H NMR (CDCl$_3$): δ1.22 (t, 3H), 1.0-2.4 (m, 21H), 2.65-2.76 (2H, m), 2.91-3.03 (m, 2H), 3.23 (d, 2H), 3.1-3.6 (m, 2H), 3.44 (q, 2H), 7.22 (s, 1H).

HPLC-MS: m/z 484 (M+H).

Example 73

3-{2-[3-Cyclopentyl-3-(trans-4-methoxymethyl-cyclohexyl)-ureido]-thiazol-5-ylsulfanyl}-propionic acid

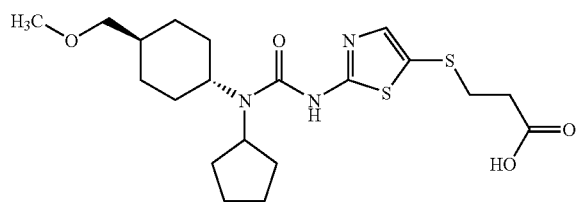

Prepared in an similar manner to {2-[3-cyclohexyl-3-(trans-4-methoxymethyl-cyclohexyl)-ureido]-thiazol-5-ylsulfanyl}-acetic acid via cyclohexyl-(trans-4-methoxymethyl-cyclopentyl)-amine and (2-amino-thiazol-5-ylsulfanyl)-propionic acid ethyl ester to give the title compound.

$^1$H NMR (CDCl$_3$): δ 1.10-2.00 (m, 17H), 2.69-2.76 (m, 2H), 2.91-3.01 (m, 2H), 3.21 (d, 2H), 3.32 (s, 3H), 3.25-3.48 (1H, m), 3.60-3.85 (m, 1H), 7.26 (s, 1H).

HPLC-MS: m/z 443 (M+H).

Example 74

2-{2-[3-Cyclohexyl-3-(trans-4-cyclopropyl methoxy-cyclohexyl)-ureido]-thiazol-5-ylsulfanyl}-2-methyl-propionic acid

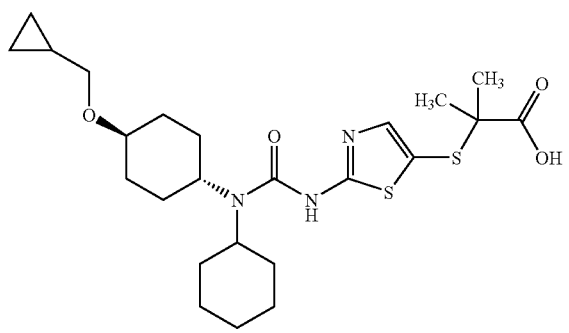

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-cyclopropylmethoxy-cyclohexyl]-amine was prepare using (trans-4-hydroxy-cyclohexyl)-isoindole-1,3-dione, cyclopropylmethylbromide and cyclohexanone.

Step 2: {2-[3-Cyclohexyl-3-(trans-4-cyclopropylmethoxy-cyclohexyl)-ureido]-thiazol-5-ylsulfanyl}-acetic acid was prepared using cyclohexyl-[trans-4-cyclopropylmethoxy-cyclohexyl]-amine and 2-(2-amino-thiazol-5-ylsulfanyl)-2-methyl-propionic acid ethyl ester.

HPLC-MS: m/z 496 (M+H).

Example 75

2-(2-{3-Cyclohexyl-3-[trans-4-(2-methoxy-ethoxy)-cyclohexyl]-ureido}-thiazol-5-ylsulfanyl)-2-methyl-propionic acid

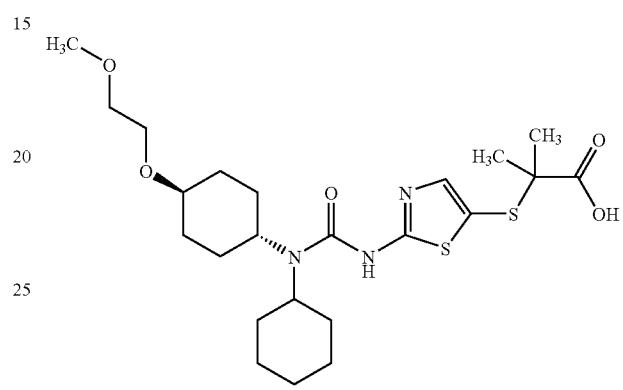

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-(2-methoxy-ethoxy)-cyclohexyl]-amine was prepare using (trans-4-hydroxy-cyclohexyl)-isoindole-1,3-dione, 1-bromo-2-methoxyethane and cyclohexanone.

Step 2: 2-(2-{3-Cyclohexyl-3-[trans-4-(2-methoxy-ethoxy)-cyclohexyl]-ureido}-thiazol-5-ylsulfanyl)-2-methyl-propionic acid was prepared using cyclohexyl-[trans-4-(2-methoxy-ethoxy)-cyclohexyl]-amine and 2-(2-amino-thiazol-5-ylsulfanyl)-2-methyl-propionic acid ethyl ester.

HPLC-MS: m/z 500 (M+H).

Example 76

[2-(3,3-Dicyclohexyl-ureido)-thiazole-5-sulfonylamino]-acetic acid

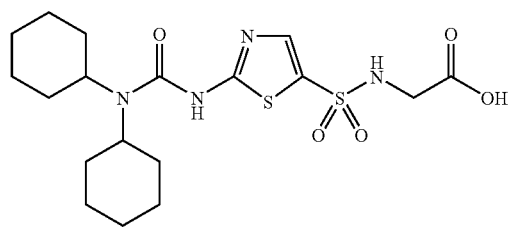

Step 1.

A mixture of glycine ethylester hydrochloride (15 mmol), 2-acetylamino-thiazole-5-sulfonyl chloride (12 mmol) (prepared as described in *J. Am. Chem. Soc* 69, 2063, 1947), DIPEA (35 mmol) in DCM (50 mL) was stirred at room temperature over night. Addition of water and 1N HCl to pH 2 resulted in precipitation. The precipitate was isolated by filtration, washed with water and dried to give (2-acetylamino-thiazole-5-sulfonylamino)-acetic acid ethyl ester (64%) as crystals. This was suspended in EtOH (15 mL) and added 4N HCl in dioxane (15 mL) and heated for 4 h at 80° C. and then cooled to room temperature. Addition of aqueous NaHCO₃ to neutral pH. The organic phase was isolated and the aqueous phase was extracted with CH₂Cl₂, and the combined organic phases were dried and concentrated in vacuo to give (2-amino-thiazole-5-sulfonylamino)-acetic acid ethyl ester (80%) as colourless crystals.

Step 2.

An equimolar mixture of 1,1-carbonyldiimidazole, (2-amino-thiazole-5-sulfonylamino)-acetic acid ethyl ester and DMAP (5 mol %) in THF was heated for 2 h at 50-60° C. and then cooled to room temperature. Then dicyclohexylamine (1 equivalent) was added and the reaction is stirred overnight at room temperature. The reaction mixture was quenched with water. The organic phase was isolated and the aqueous phase was extracted with CH₂Cl₂, and the combined organic phases were dried and concentrated in vacuo. The crude product was dissolved in MeCN and purified (HPLC method 1) to give [2-(3,3-dicyclohexyl-ureido)-thiazole-5-sulfonylamino]-acetic acid ethyl ester. This material was dissolved in MeOH and treated with 20 equivalents of 1N NaOH over night at room temperature. MeOH was removed by evaporation. Addition of 1N HCl to pH<1 caused precipitation. The precipitate was isolated by filtration, washed with water and dried to give title compound.

HPLC-MS method 2: m/z=445 (M+H).

$^1$H NMR (CDCl₃+2 dr CD₃OD) δ 7.79 (s, 1H), 3.80 (s, 2H), 3.40 (br s, 2H), 1.90-1.64 (m, 13H), 1.42-1.13 (m, 7H).

Example 77

{2-[3-(1-Acetyl-piperidin-4-yl)-3-cyclohexyl-ureido]-thiazole-5-sulfonylamino}-acetic acid

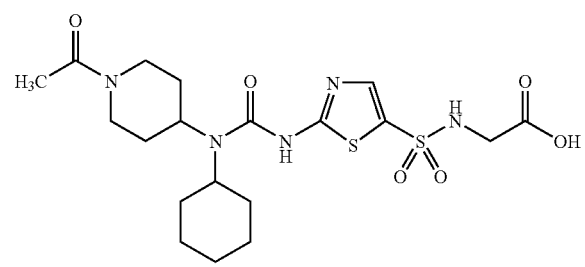

Prepared in a similar manner to [2-(3,3-dicyclohexyl-ureido)-thiazole-5-sulfonylamino]-acetic acid via 1-(4-cyclohexylamino-piperidin-1-yl)-ethanone (General procedure 1) and (2-amino-thiazole-5-sulfonylamino)-acetic acid ethyl ester to give the title compound.

$^1$H NMR (DMSO-d₆) δ 12.7 (br s, 1H), 11.4 (br s, 1H), 8.16 (br t, 1H), 8.78 (s, 1H), 4.45 (br d, 1H), 3.85 (br d, 1H), 3.63 (d, 2H), 3.10 (t, 1H), 2.59-2.45 (m, 1H), 2.25-1.05 (m, 16H), 2.02 (s, 3H).

Example 78

2-{2-[3-Cycloheptyl-3-(trans-4-ethoxymethyl-cyclohexyl)-ureido]-thiazol-5-ylsulfanyl}-2-methyl-propionic acid

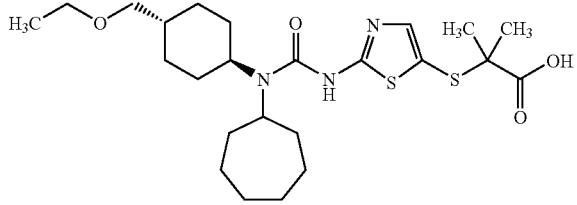

Prepared in a similar manner to {2-[3-cyclohexyl-3-(trans-4-methoxymethyl-cyclohexyl)-ureido]-thiazol-5-ylsulfanyl}-acetic acid via cycloheptyl-(trans-4-ethoxymethyl-cycloheptyl)-amine and 2-(2-amino-thiazol-5-ylsulfanyl)-2-methyl-propionic acid ethyl ester to give the title compound.

$^1$H NMR (CDCl₃): δ 1.19 (t, 3H), 1.10-2.00 (m, 21H), 3.23 (d, 2H), 3.4 (q, 2H), 3.15-3.30 (m, 1H), 3.70-3.95 (m, 1H), 7.10 (s, 1H,)

HPLC-MS: m/z 498 (M+H).

Example 79

2-{2-[3-Cycloheptyl-3-(trans-4-methoxymethyl-cyclohexyl)-ureido]-thiazol-5-ylsulfanyl}-2-methyl-propionic acid

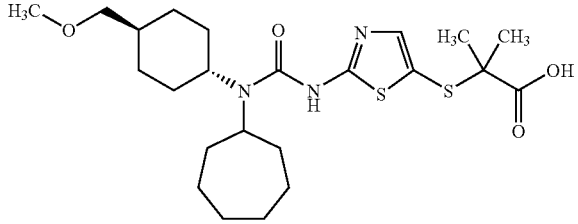

Prepared in a similar manner to {2-[3-cyclohexyl-3-(trans-4-methoxymethyl-cyclohexyl)-ureido]-thiazol-5-ylsulfanyl}-acetic acid via cycloheptyl-(trans-4-methoxymethyl-cycloheptyl)-amine and 2-(2-amino-thiazol-5-ylsulfanyl)-2-methyl-propionic acid ethyl ester to give the title compound.

$^1$H NMR (CDCl₃): δ 1.00-2.00 (m, 21H), 3.18 (d, 2H), 3.32 (s, 3H), 3.10-3.30 (m, 1H), 3.65-3.95 (m, 1H), 7.08 (s, 1H).

HPLC-MS: m/z 485 (M+H).

Example 80

{2-[3-Cyclohexyl-3-(trans-4-methyl-cyclohexyl)-ureido]-thiazole-5-sulfonylamino}-acetic acid

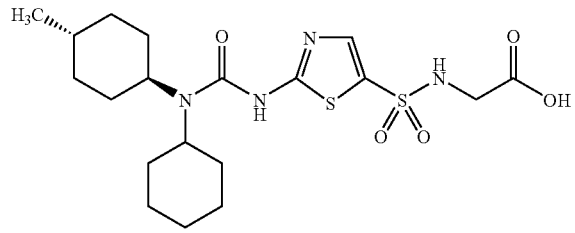

Prepared in a similar manner to [2-(3,3-dicyclohexyl-ureido)-thiazole-5-sulfonylamino]-acetic acid (Example 76) via cyclohexyl-(trans-4-methyl-cyclohexyl)-amine (General procedure 1) and (2-amino-thiazole-5-sulfonylamino)-acetic acid ethyl ester to give the title compound.

HPLC-MS method 2: m/z=460 (M+H).

$^1$H NMR (DMSO-d$_6$) δ12.7 (br s, 1H), 11.35 (br s, 1H), 8.15 (t, 1H), 7.76 (s, 1H), 3.62 (d, 2H), 3.45 (br s, 2H), 1.74-1.02 (m, 19H), 0.88 (d, 3H).

Example 81

3-[2-(3,3-Dicyclohexyl-ureido)-thiazole-5-sulfonylamino]-propionic acid

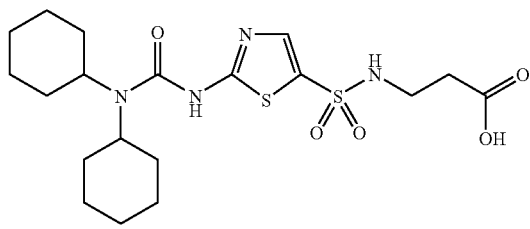

Prepared in a similar manner to [2-(3,3-dicyclohexyl-ureido)-thiazole-5-sulfonylamino]-acetic acid via dicyclohexylamine and 3-(2-amino-thiazole-5-sulfonylamino)-propionic acid ethyl ester to give the title compound.

$^1$H NMR (DMSO-d$_6$) δ 12.05 (br s, 2H), 7.79 (s, 1H), 7.75 (t, 1H), 3.48 (br s, 2H), 3.02 (q, 2H), 2.42 (t, 2H), 2.06-1.04 (m, 20H).

Example 82

3-{2-[3-Cyclohexyl-3-(trans-4-methyl-cyclohexyl)-ureido]-thiazole-5-sulfonylamino}-propionic acid

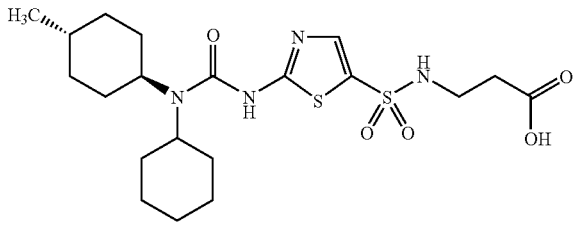

Prepared in a similar manner to [2-(3,3-dicyclohexyl-ureido)-thiazole-5-sulfonylamino]-acetic acid via cyclohexyl-(trans-4-methyl-cyclohexyl)-amine and 3-(2-amino-thiazole-5-sulfonylamino)-propionic acid ethyl ester to give the title compound.

$^1$H NMR (DMSO-d$_6$) δ 12.3 (br s, 1H), 11.5 (br s, 1H), 7.78 (s, 1H), 7.75 (t, 1H), 3.5 (br s, 2H), 3.01 (q, 2H), 2.41 (t, 2H), 2.10-1.05 (m, 19H), 0.87 (d, 3H).

Example 83

{[2-(3,3-Dicyclohexyl-ureido)-thiazole-5-sulfonyl]-methyl-amino}-acetic acid

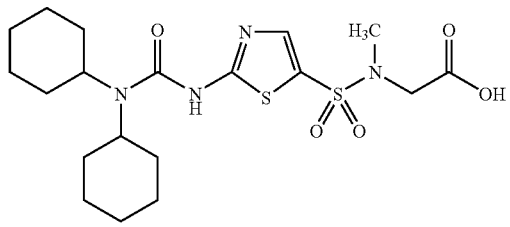

Prepared in a similar manner to [2-(3,3-dicyclohexyl-ureido)-thiazole-5-sulfonylamino]-acetic acid via dicyclohexylamine and [(2-amino-thiazole-5-sulfonyl)-methyl-amino]-acetic acid methyl ester to give the title compound.

HPLC-MS method 2: m/z=459 (M+H).

$^1$H NMR (CDCl$_3$) δ 7.68 (s, 1H), 4.14 (s, 2H), 3.37 (br s, 2H), 3.10 (s, 3H), 1.86-1.12 (m, 20H).

Example 84

({2-[3-Cyclohexyl-3-(trans-4-methyl-cyclohexyl)-ureido]-thiazole-5-sulfonyl}-methyl-amino)-acetic acid

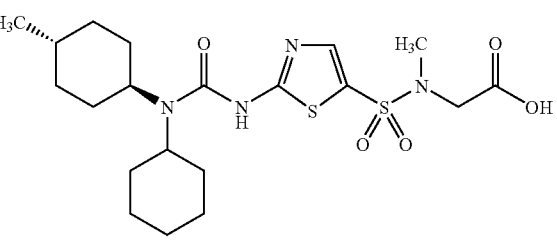

Prepared in a similar manner to [2-(3,3-dicyclohexyl-ureido)-thiazole-5-sulfonylamino]-acetic acid via cyclohexyl-(trans-4-methyl-cyclohexyl)-amine and [(2-amino-thiazole-5-sulfonyl)-methyl-amino]-acetic acid methyl ester to give the title compound.

HPLC-MS method 2: m/z=473 (M+H).

$^1$H NMR (DMSO-d$_6$) δ 12.8 (br s, 1H), 11.5 (br s, 1H), 7.87 (s, 1H), 3.87 (s, 2H), 3.48 (br s, 2H), 2.81 (s, 3H), 1.95 (br s, 3H), 1.76-0.99 (m, 16H), 0.87 (d, 3H).

Example 85

(S)-1-[2-(3,3-Dicyclohexyl-ureido)-thiazole-5-sulfonyl]-pyrrolidine-2-carboxylic acid

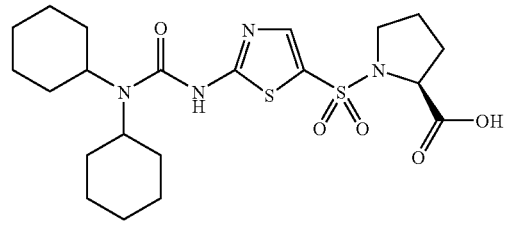

Prepared in a similar manner to [2-(3,3-dicyclohexyl-ureido)-thiazole-5-sulfonylamino]-acetic acid via dicyclohexylamine and (S)-1-(2-amino-thiazole-5-sulfonyl)-pyrrolidine-2-carboxylic acid methyl ester to give the title compound.

HPLC-MS method 2: m/z=485 (M+H).

$^1$H NMR (DMSO-d$_6$) δ 12.78 (br s, 1H), 11.48 (br s, 1H), 7.92 (s, 1H), 4.02 (dd, 1H), 3.57-3.18 (m, 4H), 2.07-1.05 (m, 24H).

Example 86

(S)-1-{2-[3-Cyclohexyl-3-(trans-4-methyl-cyclohexyl)-ureido]-thiazole-5-sulfonyl}-pyrrolidine-2-carboxylic acid

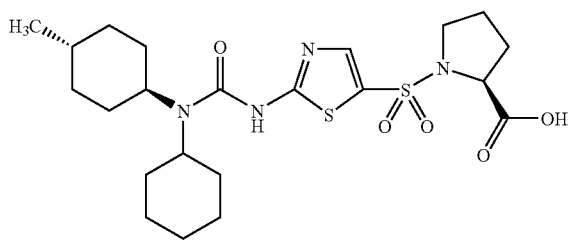

Prepared in a similar manner to [2-(3,3-dicyclohexyl-ureido)-thiazole-5-sulfonylamino]-acetic acid via cyclohexyl-(trans-4-methyl-cyclohexyl)-amine and (S)-1-(2-amino-thiazole-5-sulfonyl)-pyrrolidine-2-carboxylic acid methyl ester to give the title compound.

HPLC-MS method 2: m/z=499 (M+H).

$^1$H NMR (DMSO-d$_6$) δ 12.78 (br s, 1H), 11.46 (br s, 1H), 7.92 (s, 1H), 4.02 (dd, 1H), 3.60-3.18 (m, 4H), 2.06-0.99 (m, 23H), 0.88 (d, 3H).

Example 87

{2-[3-Cycloheptyl-3-(trans-4-propoxy-cyclohexyl)-ureido]-thiazol-5-ylsulfanyl}-acetic acid

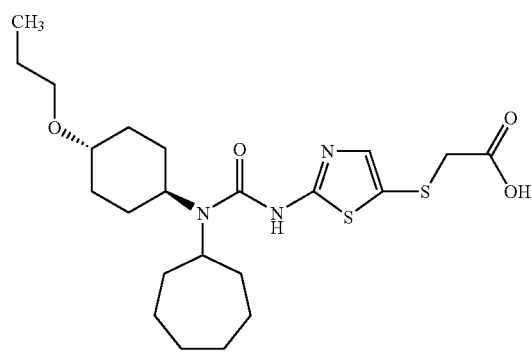

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-propoxy-cyclohexyl]-amine was prepare using (trans-4-hydroxy-cyclohexyl)-isoindole-1,3-dione, 1-bromopropane and cycloheptanone.

Step 2: {2-[3-Cycloheptyl-3-(trans-4-propoxy-cyclohexyl)-ureido]-thiazol-5-ylsulfanyl}-acetic acid was prepared using cycloheptyl-[trans-4-propoxy-cyclohexyl]-amine and amino-thiazole-5-ylsulfanyl)-acetic acid ethyl ester.

$^1$H NMR (DMSO-d$_6$) δ 7.39 (s, 1H), 3.70-3.15 (m, 3H), 3.48 (s, 2H), 2.20-1.15 (m, 20), 0.87 (t, 3H).

HPLC-MS: m/z 470 (M+H).

Example 88

{2-[3-Cyclopentyl-3-(trans-4-propoxy-cyclohexyl)-ureido]-thiazol-5-ylsulfanyl}-acetic acid

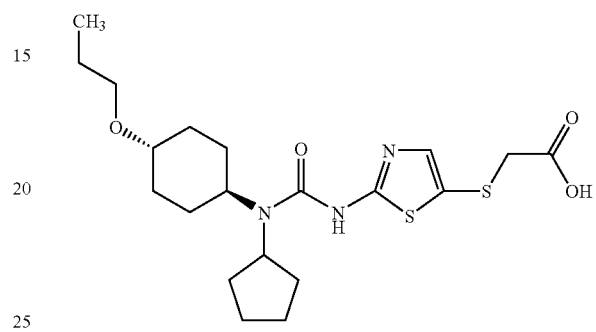

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclopentyl-[trans-4-propoxy-cyclohexyl]-amine was prepare using (trans-4-hydroxy-cyclohexyl)-isoindole-1,3-dione, 1-bromopropane and cyclopentanone.

Step 2: {2-[3-Cyclopentyl-3-(trans-4-propoxy-cyclohexyl)-ureido]-thiazol-5-ylsulfanyl}-acetic acid was prepared using cyclopentyl-[trans-4-propoxy-cyclohexyl]-amine and amino-thiazole-5-ylsulfanyl)-acetic acid ethyl ester.

$^1$H NMR (DMSO-d$_6$) δ 7.35 (s, 1H), 3.82 (m, 1H), 3.55 (m, 1H), 3.42 (s, 2H), 3.28 (t, 2H), 3.12 (m, 1H), 2.1-1.1 (m, 16H), 0.8 (t, 3H).

HPLC-MS: m/z 442 (M+H).

Example 89

{2-[3-Cyclohexyl-3-(trans-4-isobutoxy-cyclohexyl)-ureido]-thiazol-5-ylsulfanyl}-acetic acid

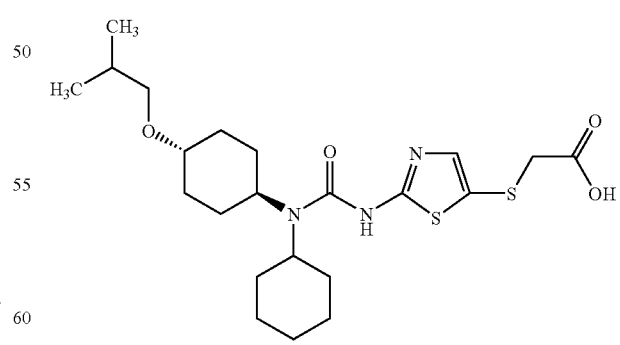

Prepared according to the procedure for the synthesis of {2-[3-cyclopentyl-3-(trans-4-methoxy-cyclohexyl)-ureido]-thiazol-5-ylsulfanyl}-acetic acid using 2-(trans-4-hydroxy-cyclohexyl)-isoindole-1,3-dione, 3-bromo-2-methylpropene cycloheptanone and 2-(2-amino-thiazol-5-ylsulfanyl)-2-methyl-acetic acid ethyl ester. The intermediate cyclohexyl-[trans-4-(2-methyl-allyloxy)-cyclohexyl]-amine was hydrogenated using the following procedure: Cyclo-hexyl-[4-(2-methyl-allyloxy)-cyclohexyl]-amine (540 mg, 2.15 mmol) was dissolved in 10 mL AcOH and the setup was flushed with N$_2$ before 50 mg Pd/C was added. A balloon was charged with N$_2$ and connected to the setup. The reaction mixture was stirred for three days at room temperature before the Pd was filtered off using a pad of celite. The filtrate was poured on 1 N NaOH (pH>12) and the mixture was extracted 3× with diethylether (50 mL), and dried (MgSO$_4$) to give cyclohexyl-(trans-4-isobutoxy-cyclohexyl)-amine which was transformed to the title compound according to the procedure for the synthesis of {2-[3-cyclopentyl-3-(trans-4-methoxy-cyclohexyl)-ureido]-thiazol-5-ylsulfanyl}-acetic acid.

$^1$H NMR (DMSO-d$_6$) δ 7.35 (s, 1H), 3.7-3.1 (m, 3H), 3.43 (s, 2H), 3.13 (d, 2H), 2.2-0.9 (m, 18H), 0.82 (d, 6H).

HPLC-MS: m/z 470 (M+H).

Example 90

2-(2-{3-Cyclohexyl-3-[trans-4-(2-methyl-allyloxy)-cyclohexyl]-ureido}-thiazol-5-ylsulfanyl)-2-methyl-propionic acid

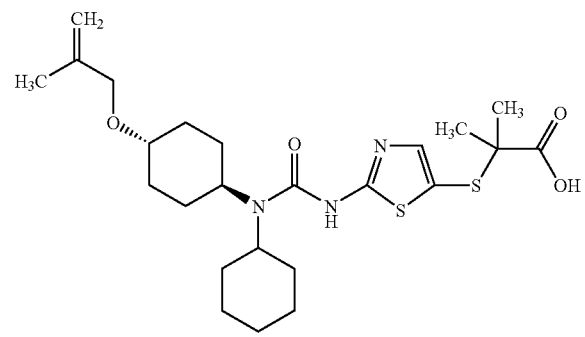

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-(2-methyl-allyloxy)-cyclohexyl]-amine was prepare using (trans-4-hydroxy-cyclohexyl)-isoindole-1,3-dione, 3-bromo-2-methyl-propene and cyclohexanone Step 2: 2-(2-{3-Cyclohexyl-3-[trans-4-(2-methyl-allyloxy)-cyclohexyl]-ureido}-thiazol-5-ylsulfanyl)-2-methyl-propionic acid was prepared using cyclohexyl-[trans-4-(2-methyl-allyloxy)-cyclohexyl]-amine and 2-(2-amino-thiazol-5-ylsulfanyl)-2-methyl-propionic acid ethyl ester.

HPLC-MS: m/z 496 (M+H).

Example 91

2-{2-[3-Cyclohexyl-3-(ltrans-4-propoxy-cyclohexyl)-ureido]-thiazol-5-ylsulfanyl}-2-methyl-propionic acid

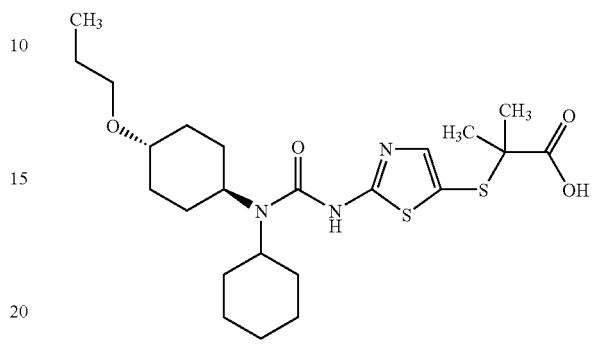

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-propoxy-cyclohexyl]-amine was prepare using (trans-4-hydroxy-cyclohexyl)-isoindole-1,3-dione, 1-bromopropane and cyclohexanone.

Step 2: 2-{2-[3-Cyclohexyl-3-(trans-4-propoxy-cyclohexyl)-ureido]-thiazol-5-ylsulfanyl}-2-methyl-propionic acid was prepared using cyclohexyl-[trans-4-propoxy-cyclohexyl]-amine and 2-(2-amino-thiazol-5-ylsulfanyl)-2-methyl-propionic acid ethyl ester.

1H NMR (DMSO-d$_6$) δ 7.38 (s, 1H), 3.7-3.2 (m, 2H), 3.50 (t, 2H), 3.18 (m, 1H), 2.2-1.0 (m, 18H), 1.39 (s, 6H), 0.85 (t, 3H).

HPLC-MS: m/z 484 (M+H).

Example 92

3-{2-[3-Cyclohexyl-3-(trans-4-isobutoxy-cyclohexyl)-ureido]-thiazol-5-ylsulfanyl}-propionic acid

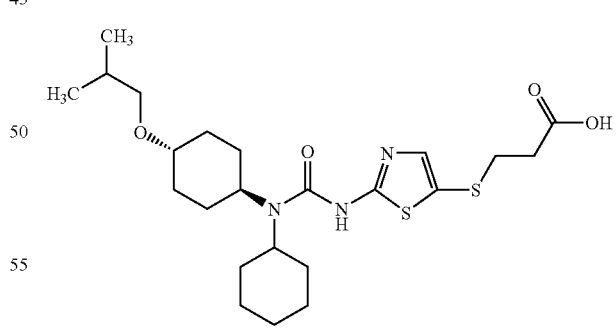

Prepared as described for the synthesis of {2-[3-cyclohexyl-3-(trans-4-isobutoxy-cyclohexyl)-ureido]-thiazol-5-ylsulfanyl}-acetic acid using 2-(2-amino-thiazol-5-ylsulfanyl)-2-methyl-acetic acid ethyl ester in the coupling step.

$^1$H NMR (DMSO-d$_6$) δ 7.32 (s, 1H), 4.0-3.2 (m, 3H), 3.12 (d, 2H), 2.80 (t, 2H), 2.48 (t, 2H), 2.2-0.9 (m, 18H), 0.80 (d, 6H).

HPLC-MS: m/z 484 (M+H).

Example 93

3-{2-[3-Cycloheptyl-3-(trans-4-propoxy-cyclohexyl)-ureido]-thiazol-5-ylsulfanyl}-propionic acid

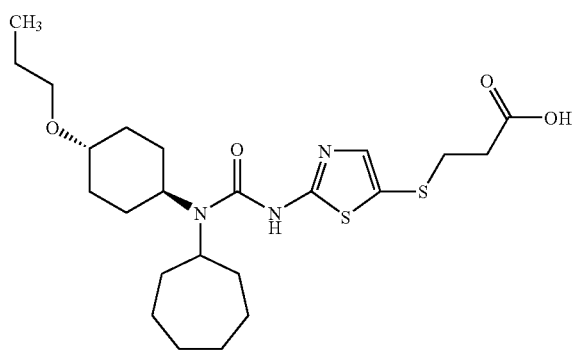

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-propoxy-cyclohexyl]-amine was prepare using (trans-4-hydroxy-cyclohexyl)-isoindole-1,3-dione, 1-bromopropane and cycloheptanone.

Step 2: 3-{2-[3-Cycloheptyl-3-(trans-4-propoxy-cyclohexyl)-ureido]-thiazol-5-ylsulfanyl}-propionic acid was prepared using cycloheptyl-[trans-4-propoxy-cyclohexyl]-amine and amino-thiazol-5-ylsulfanyl)-propionic acid ethyl ester.

1H NMR (DMSO-$d_6$) δ 7.32 (s, 1H), 3.7-3.2 (m, 3H), 3.30 (t, 2H), 2.80 (t, 2H), 2.45 (t, 2H), 2.3-1.0 (m, m, 20H), 0.82 (t, 3H).

HPLC-MS: m/z 484 (M+H).

Example 94

3-{2-[3-Cyclopentyl-3-(trans-4-propoxy-cyclohexyl)-ureido]-thiazol-5-ylsulfanyl}-propionic acid

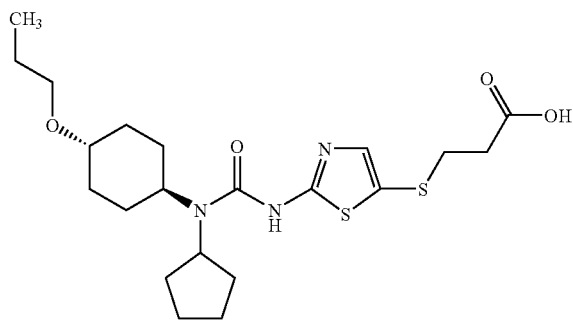

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclopentyl-[trans-4-propoxy-cyclohexyl]-amine was prepare using (trans-4-hydroxy-cyclohexyl)-isoindole-1,3-dione, 1-bromopropane and cyclopentanone.

Step 2: 3-{2-[3-Cyclopentyl-3-(trans-4-propoxy-cyclohexyl)-ureido]-thiazol-5-ylsulfanyl}-propionic acid was prepared using cyclopentyl-[trans-4-propoxy-cyclohexyl]-amine and amino-thiazol-5-ylsulfanyl)-propionic acid ethyl ester.

$^1$H NMR (DMSO-$d_6$) δ 7.32 (s, 1H), 3.9-2.9 (m, 3H), 2.80 (t, 2H), 2.44 (t, 2H), 2.1-1.0 (m, 16H), 0.80 (t, 3H).

HPLC-MS: m/z 456 (M+H).

Example 95

2-{2-[3-Cyclohexyl-3-(trans-4-ethoxymethyl-cyclohexyl)-ureido]-thiazol-5-ylsulfanyl}-2-methyl-propionic acid

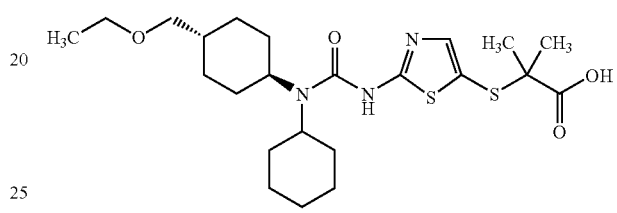

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-ethoxymethyl-cyclohexyl)-amine and 2-(2-amino-thiazol-5-ylsulfanyl)-2-methyl-propionic acid ethyl ester to give the title compound.

$^1$H NMR (CDCl$_3$): δ1.05-1.95 (19H, m), 1.18 (t, 3H), 1.58 (6H, s), 1.0-2.4 (m, 21H), 3.15-3.55 (m, 2H), 3.23 (d, 2H), 3.46 (q, 2H), 7.09 (s, 1H).

HPLC-MS: m/z 485 (M+H).

Example 96

{2-[3-Cyclohexyl-3-(trans-4-phenyl-cyclohexyl)-ureido]-thiazol-5-ylsulfanyl}-acetic acid

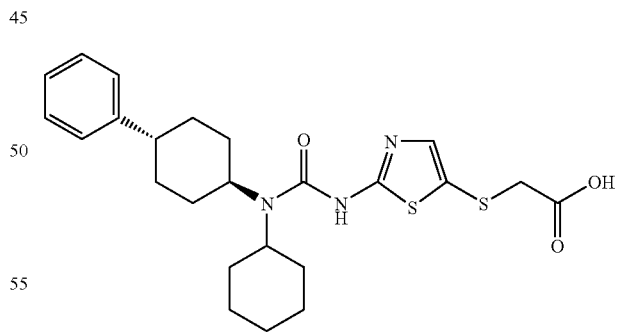

Prepared in a similar manner to {2-[3-cyclopentyl-3-(trans-4-ethyl-cyclohexyl)-ureido]-thiazol-5-ylsulfanyl}-acetic acid (Example 38) via cyclohexyl-(4-phenyl-cyclohexyl)-amine and (2-amino-thiazol-5-ylsulfanyl)-acetic acid ethyl ester to give the title compound.

HPLC-MS method 2: m/z=474 (M+H).

$^1$H NMR (DMSO) δ 12.4 (br s, 1H), 7.41 (s, 1H), 7.31-7.16 (m, 5H), 3.58 (br s, 2H), 3.49 (s, 2H), 2.25-1.10 (m, 19H).

Example 97

3-{2-[3-Cyclohexyl-3-(trans-4-phenyl-cyclohexyl)-ureido]-thiazol-5-ylsulfanyl}-propionic acid

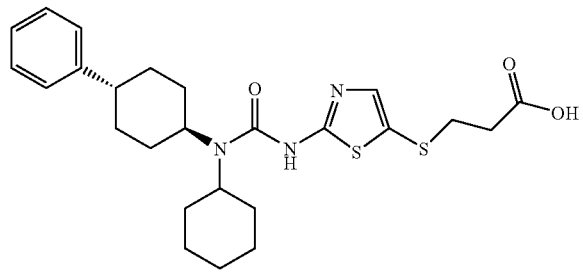

Prepared in a similar manner to {2-[3-cyclopentyl-3-(trans-4-ethyl-cyclohexyl)-ureido]-thiazol-5-ylsulfanyl}-acetic acid via cyclohexyl-(4-phenyl-cyclohexyl)-amine and 3-(2-amino-thiazol-5-ylsulfanyl)-propionic acid ethyl ester to give the title compound.

HPLC-MS method 2: m/z=488 (M+H).

$^1$H NMR (DMSO-d$_6$) δ 11.8 (br s, 1H), 7.39 (s, 1H), 7.30-7.17 (m, 5H), 3.55 (br s, 2H), 2.87 (t, 2H), 2.50 (t, 2H), 2.25-1.07 (m, 19H).

Example 98

{2-[3-Cycloheptyl-3-(trans-4-phenyl-cyclohexyl)-ureido]-thiazol-5-ylsulfanyl}-acetic acid

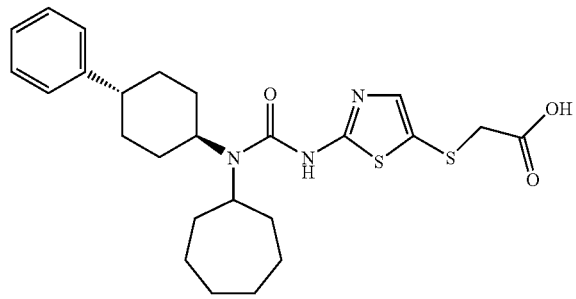

Prepared in a similar manner to {2-[3-cyclopentyl-3-(trans-4-ethyl-cyclohexyl)-ureido]-thiazol-5-ylsulfanyl}-acetic acid via cycloheptyl-(4-phenyl-cyclohexyl)-amine and (2-amino-thiazol-5-ylsulfanyl)-acetic acid ethyl ester to give the title compound.

HPLC-MS method 2: m/z=488 (M+H).

$^1$H NMR (DMSO-d$_6$) δ 11.4 (br s, 1H), 7.41 (s, 1H), 7.32-7.16 (m, 5H), 3.55 (br s, 2H), 3.48 (s, 2H), 2.58-1.42 (m, 21H).

Example 99

3-{2-[3-Cycloheptyl-3-(4-phenyl-cyclohexyl)-ureido]-thiazol-5-ylsulfanyl}-propionic acid

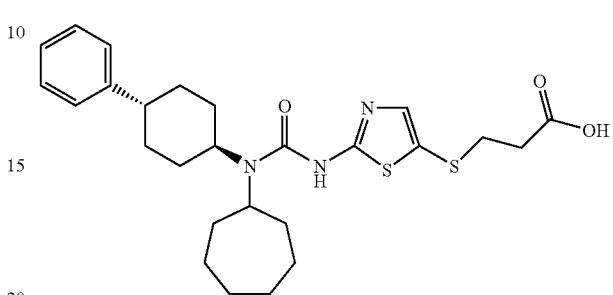

Prepared in a similar manner to {2-[3-cyclopentyl-3-(trans-4-ethyl-cyclohexyl)-ureido]-thiazol-5-ylsulfanyl}-acetic acid via cycloheptyl-(4-phenyl-cyclohexyl)-amine and 3-(2-amino-thiazol-5-ylsulfanyl)-propionic acid ethyl ester to give the title compound.

HPLC-MS method 2: m/z=502 (M+H).

$^1$H NMR (DMSO-d$_6$) δ 11.8 (br s, 1H), 7.39 (s, 1H), 7.31-7.17 (m, 5H), 3.87 (br s, 2H), 2.85 (t, 2H), 2.50 (t, 2H), 2.25-1.45 (m, 21H).

Example 100

2-{2-[3-Cyclohexyl-3-(4-phenyl-cyclohexyl)-ureido]-thiazol-5-ylsulfanyl}-2-methyl-propionic acid

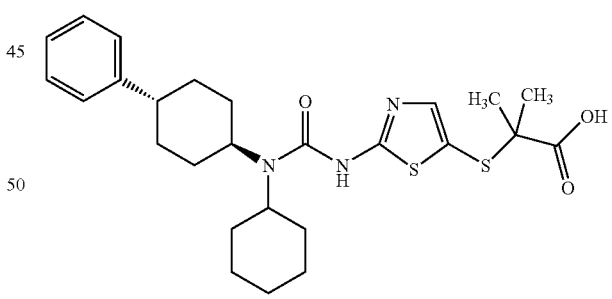

Prepared in a similar manner to {2-[3-cyclopentyl-3-(trans-4-ethyl-cyclohexyl)-ureido]-thiazol-5-ylsulfanyl}-acetic acid via cyclohexyl-(4-phenyl-cyclohexyl)-amine and 2-(2-amino-thiazol-5-ylsulfanyl)-2-methyl-propionic acid ethyl ester.

HPLC-MS method 2: m/z=502 (M+H).

$^1$H NMR (DMSO-d$_6$) δ12.2 (br s, 1H), 7.40 (s, 1H), 7.31-7.17 (m, 5H), 3.60 (br s, 2H), 2.25-1.08 (m, 19H), 1.41 (s, 6H).

Example 101

2-{2-[3-Cycloheptyl-3-(4-phenyl-cyclohexyl)-ureido]-thiazol-5-ylsulfanyl}-2-methyl-propionic acid

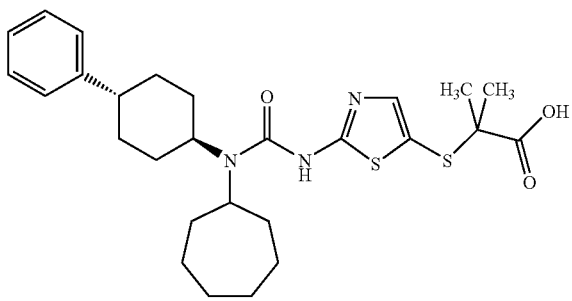

Prepared in a similar manner to {2-[3-cyclopentyl-3-(trans-4-ethyl-cyclohexyl)-ureido]-thiazol-5-ylsulfanyl}-acetic acid (via cycloheptyl-(4-phenyl-cyclohexyl)-amine and 2-(2-amino-thiazol-5-ylsulfanyl)-2-methyl-propionic acid ethyl ester.

HPLC-MS method 2: m/z=516 (M+H).

$^1$H NMR (DMSO-d$_6$) δ 12.6 (br s, 1H), 11.2 (br s, 1H), 7.40 (s, 1H), 7.31-7.17 (m, 5H), 3.90 (br s, 2H), 2.60-1.42 (m, 21H), 1.40 (s, 6H).

Example 102

{2-[3-Cyclohexyl-3-(trans-4-phenoxymethyl-cyclohexyl)-ureido]-thiazol-5-ylsulfanyl}-acetic acid

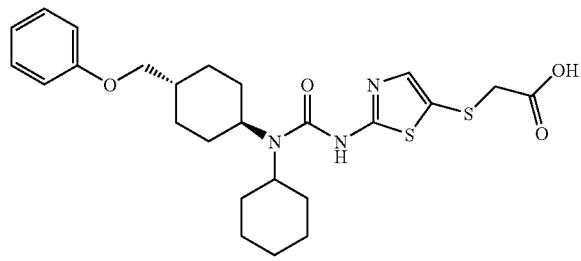

Step 1, 0.50 g of tert-butyl-trans-(4-hydroxymethylcyclohexyl) carbamate is dissolved in 30 mL of tetrahydrofuran and 0,881 g (4.36 mmol) of tributylphoshine is added. The mixture is cooled in an ice bath and 1.10 g of 1,1-(azodicarbonyl)dipiperidine is added, stirred for 10 min. and 0,226 g of phenol is added. The reaction is stirred while the ice bath is allowed to reach room temperature over approx. 2 h then stirred overnight at room temperature.

50 mL of water is added and the aqueous layer extracted with ethyl acetate, washed with 10% NaHSO4, 20 mL of sat. NaHCO$_3$, 20 ml of brine, dried (MgSO$_4$), filtered and concentrated in vacuo, filtered through a pad of silica using ethyl acetate and hexane as eluant and concentrated in vacuo to afford 0.6 g (trans-4-phenoxymethyl-cyclohexyl)-carbamic acid tert-butyl ester a white solid.

HPLC-MS: m/z 328 (M+Na).

Step 2.

380 mg of (trans-4-phenoxymethyl-cyclohexyl)-carbamic acid tert-butyl ester is dissolved in 5 mL of dichloromethane and 5 ml of trifluoroacetic acid is added. The mixture is stirred for 2 h, concentrated in vacuo and stripped twice from dichloromethane to afford 250 mg of trans-4-phenoxymethylcyclohexylamine trifluoroacetate as a white solid.

HPLC-MS: m/z 205 (M+H).

Step 3.

Trans-4-phenoxymethylcyclohexylamine trifluoroacetate (1.2 mmol) is dissolved in a mixture of 4 ml of THF and 4 mL of MeOH in a 20 ml glass vial equipped with a magnetic stirrer and a screw cap. 117 mg of cyclohexanone and 3 g of 3 Å molecular sieves are added. The mixture is stirred for 10 min. after which 2.4 mL of 1N sodiumcyanoborohydride in tetrahydrofuran is added. The reaction stirred 4 days at room temperature then filtered through celite washing through with 30 mL of dichloromethane. The organic phase is washed with 10 mL of water, 10 mL of brine, dried (MgSO$_4$), filtered and concentrated in vacuo to give 300 mg of cyclohexyl-(trans-4-phenoxymethyl-cyclohexyl)-amine.

HPLC-MS: m/z 288 (M+H).

Step 4.

A mixture of (2-amino-thiazol-5-ylsulfanyl)-acetic acid ethyl ester (0.13 g), carbonyl diimidazole (0.11 g) and 4-dimethylaminopyridine (4 mg) in tetrahydrofuran (10 mL) and tetrahydrofuran (10 mL) was stirred at room temperature for 2 h. Cyclohexyl-(trans-4-phenoxymethyl-cyclohexyl)-amine was added and the reaction stirred overnight at room temperature. Purification by flash chromatography gave 80 mg {2-[3-cyclohexyl-3-(trans-4-phenoxymethyl-cyclohexyl)-ureido]-thiazol-5-ylsulfanyl}-acetic acid ethyl ester HPLC-MS: m/z 532 (M+H).

Step 5.

80 mg of {2-[3-cyclohexyl-3-(trans-4-phenoxymethyl-cyclohexyl)-ureido]-thiazol-5-ylsulfanyl}-acetic acid ethyl ester was dissolved in tetrahydrofuran (1 mL) and 1N sodium hydroxide (1 mL) was added. Stirred at room temperature for 2 h then acidified with 1N hydrochloric acid. White precipitate filtered and dried to give the title compound (73 mg)

$^1$H NMR (DMSO-d$_6$): δ1.0-2.2 (m, 19H), 3.30-3.50 (m, 2H), 3.49 (s, 2H), 3.80 (d, 2H), 6.85-6.95 (m, 3H), 7.25-7.33 (m, 2H), 7.39 (s, 1H).

HPLC-MS: m/z 504 (M+H).

Example 103

(E)-6-[4-(1-Cyclohexyl-3-thiazol-2-yl-ureido)-piperidin-1-yl]-6-oxo-hex-3-enoic acid

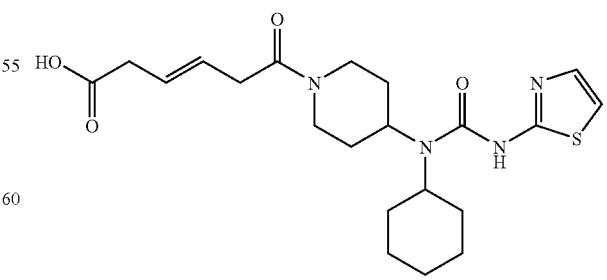

Prepared as described in general procedure (I) using 1-cyclohexyl-1-piperidin-4-yl-3-thiazol-2-yl-urea trans-2-butene-1,4-dicarboxylic acid.

¹H NMR (CDCl₃): δ 1.00-2.80 (m, 14H), 3.00-3.25 (4H, m), 3.15-3.40 (m, 1H), 3.80-3.95 (m, 3H), 4.65-4.80 (m, 2H), 5.60-5.70 (m, 1H), 5.73-5.85 (m, 1H), 6.88 (d, 1H), 7.35 (d, 1H).

HPLC-MS: m/z 435(M+H).

Example 104

{2-[3-Cyclohexyl-3-(trans-4-isopropyl-cyclohexyl)-ureido]-thiazol-5-ylsulfanyl}-acetic acid

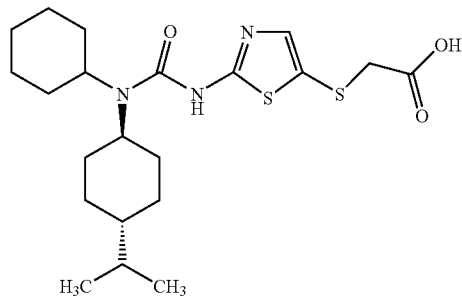

Prepared in a similar manner to {2-[3-cyclopentyl-3-(trans-4-ethyl-cyclohexyl)-ureido]-thiazol-5-ylsulfanyl}-acetic acid via cyclohexyl-(trans-4-isopropyl-cyclohexyl)-amine and (2-amino-thiazol-5-ylsulfanyl)-acetic acid ethyl ester to give the title compound.

HPLC-MS: m/z=440 (M+H).

¹H NMR (CDCl₃) δ 7.30 (s, 1H), 3.38 (br s, 2H), 3.35 (s, 2H), 2.12-1.08 (m, 20H), 0.87 (d, 6H).

Example 105

{2-[3-Cycloheptyl-3-(trans-4-isopropyl-cyclohexyl)-ureido]-thiazol-5-ylsulfanyl}-acetic acid

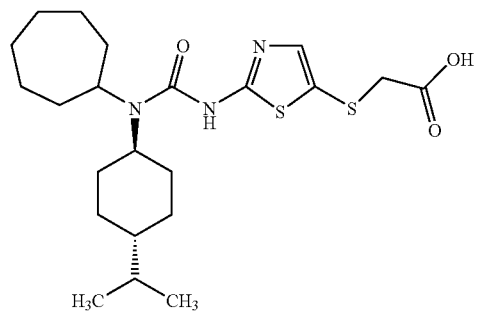

Prepared in a similar manner to {2-[3-cyclopentyl-3-(trans-4-ethyl-cyclohexyl)-ureido]-thiazol-5-ylsulfanyl}-acetic acid (Example 38) via cycloheptyl-(trans-4-isopropyl-cyclohexyl)-amine and (2-amino-thiazol-5-ylsulfanyl)-acetic acid ethyl ester to give the title compound.

HPLC-MS: m/z=454 (M+H).

¹H NMR (CDCl₃) δ 7.29 (s, 1H), 3.68 (br s, 1H), 3.34 (s, 2H), 3.25 (br s, 1H), 2.38 (br s, 2H), 1.82-1.04 (m, 20H), 0.89 (d, 6H).

Example 106

{2-[3-Cyclohexyl-3-(trans-4-ethyl-cyclohexyl)-ureido]-thiazol-5-ylsulfanyl}-acetic acid

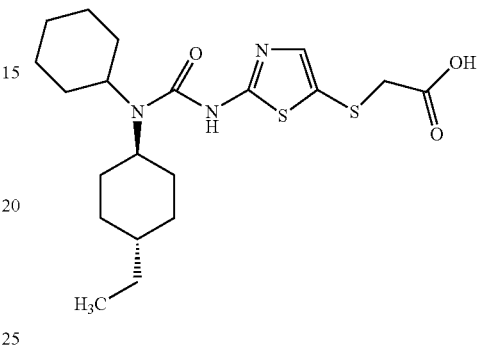

Prepared in a similar manner to {2-[3-cyclopentyl-3-(trans-4-ethyl-cyclohexyl)-ureido]-thiazol-5-ylsulfanyl}-acetic acid via cyclohexyl-(trans-4-ethyl-cyclohexyl)-amine and (2-amino-thiazol-5-ylsulfanyl)-acetic acid ethyl ester to give the title compound.

HPLC-MS: m/z=426 (M+H).

¹H NMR (400 MHz, CDCl₃) δ 7.34 (s, 1H), 3.42 (br s, 2H), 3.37 (s, 2H), 2.20-1.00 (m, 21H), 0.90 (t, 3H).

Example 107

{2-[3-Cyclohexyl-3-(trans-4-propoxy-cyclohexyl)-ureido]-thiazole-5-sulfonylamino}-acetic acid

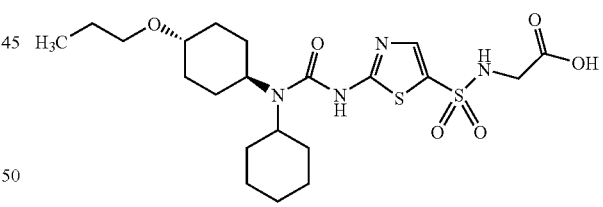

Prepared in a similar manner to [2-(3,3-dicyclohexyl-ureido)-thiazole-5-sulfonylamino]-acetic acid via cyclohexyl-(trans-4-propoxy-cyclohexyl)-amine (prepared according to the procedure described for the synthesis of {2-[3-cyclopentyl-3-(trans-4-methoxy-cyclohexyl)-ureido]-thiazol-5-ylsulfanyl}-acetic acid (Step 1) using (trans-4-hydroxy-cyclohexyl)-isoindole-1,3-dione, 1-bromopropane and cyclohexanone) and (2-amino-thiazole-5-sulfonylamino)-acetic acid ethyl ester to give the title compound.

HPLC-MS method 2: m/z=503 (M+H).

¹H NMR (DMSO-d₆) δ12.7 (br s, 1H), 11.4 (br s, 1H), 8.16 (t, 1H), 7.78 (s, 1H), 3.62 (d, 2H), 3.45 (br s, 2H), 3.35 (t, 2H), 3.22-3.15 (m, 1H), 2.25-1.5 (m, 20H), 0.86 (t, 3H).

Example 108

3-{2-[3-Cyclohexyl-3-(trans-4-propoxy-cyclohexyl)-ureido]-thiazole-5-sulfonylamino}-propionic acid

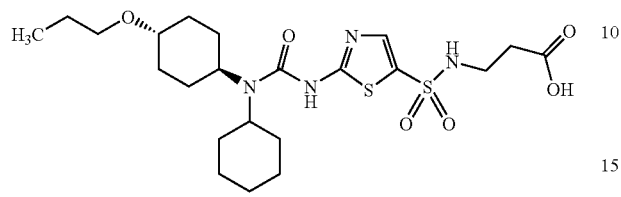

Prepared in a similar manner to [2-(3,3-dicyclohexyl-ureido)-thiazole-5-sulfonylamino]-acetic acid via cyclohexyl-(trans-4-propoxy-cyclohexyl)-amine (prepared according to the procedure described for the synthesis of {2-[3-cyclopentyl-3-(trans-4-methoxy-cyclohexyl)-ureido]-thiazol-5-ylsulfanyl}-acetic acid (Step 1) using (trans-4-hydroxy-cyclohexyl)-isoindole-1,3-dione, 1-bromopropane and cyclohexanone) and 3-(2-amino-thiazole-5-sulfonylamino)-propionic acid ethyl ester to give the title compound.

HPLC-MS method 2: m/z=517 (M+H).

$^1$H NMR (CDCl$_3$) δ 7.78 (s, 1H), 6.54 (br t, 1H), 3.58-3.19 (m, 5H), 3.41 (t, 2H), 2.55 (t, 2H), 2.20-1.11 (m, 20H), 0.92 (t, 3H).

Example 109

({2-[3-Cyclohexyl-3-(trans-4-propoxy-cyclohexyl)-ureido]-thiazole-5-sulfonyl}-methyl-amino)-acetic acid

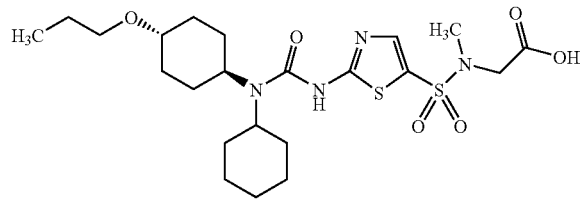

Prepared in a similar manner to [2-(3,3-dicyclohexyl-ureido)-thiazole-5-sulfonylamino]-acetic acid via cyclohexyl-(trans-4-propoxy-cyclohexyl)-amine (prepared according to the procedure described for the synthesis of {2-[3-cyclopentyl-3-(trans-4-methoxy-cyclohexyl)-ureido]-thiazol-5-ylsulfanyl}-acetic acid (Step 1) using (trans-4-hydroxy-cyclohexyl)-isoindole-1,3-dione, 1-bromopropane and cyclohexanone) and [(2-amino-thiazole-5-sulfonyl)-methyl-amino]-acetic acid methyl ester to give the title compound.

HPLC-MS method 2: m/z=517 (M+H).

$^1$H NMR (CDCl$_3$) δ 7.78 (s, 1H), 3.86 (s, 2H), 3.58-3.32 (m, 2H), 3.41 (t, 2H), 3.28 (br t, 1H), 2.90 (s, 3H), 2.20-1.11 (m, 20H), 0.91 (t, 3H).

Example 110

3-{2-[3-Cyclohexyl-3-(trans-4-cyclopropyl methoxymethyl-cyclohexyl)-ureido]-thiazol-5-ylsulfanyl}-propionic acid

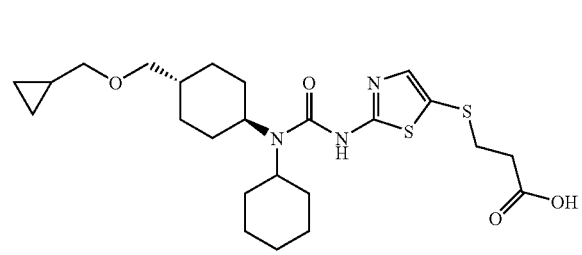

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-cyclopropyl-methoxymethyl-cyclohexyl)-amine and (2-amino-thiazol-5-ylsulfanyl)-propionic acid ethyl ester to give the title compound.

$^1$H NMR (CDCl$_3$): δ0.08-0.15 (m, 2H), 0.40-0.46 (m, 2H), 0.75-1.80-2.4 (m, 20H), 2.49-2.53 (m, 2H), 2.70-2.85 (m, 2H), 3.00-3.15 (m, 6H), 7.15 (s, 1H).

HPLC-MS: m/z 497 (M+H).

Example 111

3-{2-[3-Cycloheptyl-3-(trans-4-cyclopropylmethoxymethyl-cyclohexyl)-ureido]-thiazol-5-ylsulfanyl}-propionic acid

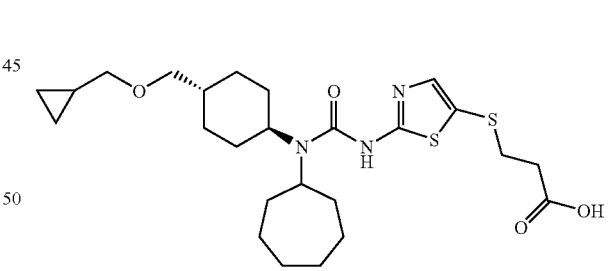

Prepared in a similar manner to {2-[3-cyclohexyl-3-(trans-4-methoxymethyl-cyclohexyl)-ureido]-thiazol-5-ylsulfanyl}-acetic acid via cycloheptyl-(trans-4-cyclopropyl-methoxymethyl-cyclohexyl)-amine and (2-amino-thiazol-5-ylsulfanyl)-propionic acid ethyl ester to give the title compound.

$^1$H NMR (CDCl$_3$): δ0.08-0.14 (m, 2H), 0.39-0.46 (m, 2H), 0.75-1.80-2.4 (m, 22H), 2.45-2.55 (m, 2H), 2.70-2.86 (m, 2H), 3.00-3.15 (m, 6H), 7.16 (s, 1H).

HPLC-MS: m/z 511 (M+H).

Example 112

(2-{3-Cyclohexyl-3-[4-(trans-4-methoxy-phenoxymethyl)-cyclohexyl]-ureido}-thiazol-5-ylsulfanyl)-acetic acid

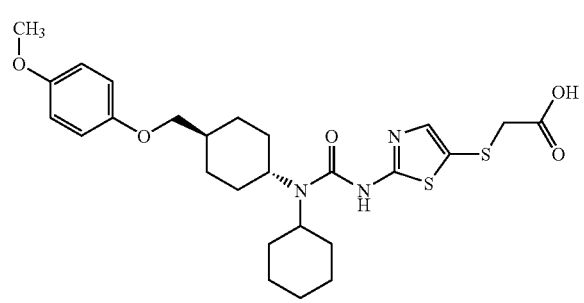

Prepared in a similar manner to {2-[3-cyclohexyl-3-(trans-4-phenoxymethyl-cyclohexyl)-ureido]-thiazol-5-ylsulfanyl}-acetic acid via cyclohexyl-[trans-4-(4-methoxy-phenoxymethyl)-cyclohexyl]-amine and (2-amino-thiazol-5-ylsulfanyl)-acetic acid ethyl ester to give the title compound.

$^1$H NMR (DMSO-$d_6$): δ1.0-2.2 (m, 19H), 3.30-3.50 (m, 2H), 3.47 (s, 2H), 3.68 (s, 3H), 3.72 (d, 2H), 6.80-6.90 (m, 4H), 7.22 (s, 1H).

HPLC-MS: m/z 534 (M+H).

Example 113

(2-{3-Cyclohexyl-3-[trans-4-(4-fluoro-phenoxymethyl)-cyclohexyl]-ureido}-thiazol-5-ylsulfanyl)-acetic acid

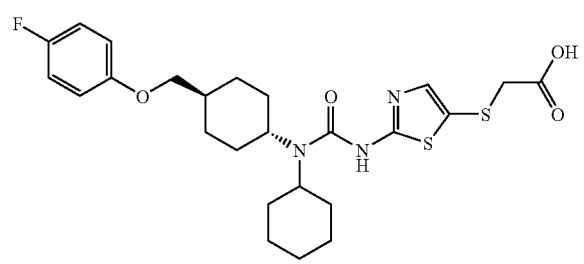

Prepared in a similar manner to {2-[3-cyclohexyl-3-(trans-4-phenoxymethyl-cyclohexyl)-ureido]-thiazol-5-ylsulfanyl}-acetic acid via cyclohexyl-[trans-4-(4-fluoro-phenoxymethyl)-cyclohexyl]-amine and (2-amino-thiazol-5-ylsulfanyl)-acetic acid ethyl ester to give the title compound.

$^1$H NMR (DMSO-$d_6$): δ1.0-2.2 (m, 19H), 3.30-3.65 (m, 2H), 3.52 (s, 2H), 3.76 (d, 2H), 6.90-6.99 (m, 2H), 7.05-7.15 (m, 2H), 7.22 (s, 1H).

HPLC-MS: m/z 522 (M+H).

Example 114

(2-{3-Cyclohexyl-3-[trans-4-(4-imidazol-1-yl-phenoxymethyl)-cyclohexyl]-ureido}-thiazol-5-ylsulfanyl)-acetic acid

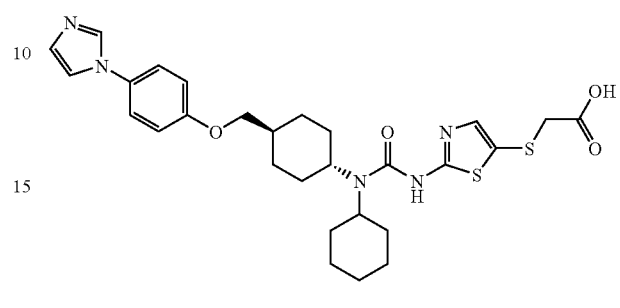

Prepared in an similar manner to {2-[3-cyclohexyl-3-(trans-4-phenoxymethyl-cyclohexyl)-ureido]-thiazol-5-ylsulfanyl}-acetic acid via cyclohexyl-[trans-4-(4-imidazol-1-yl-phenoxymethyl)-cyclohexyl]-amineand (2-amino-thiazol-5-ylsulfanyl)-acetic acid ethyl ester to give the title compound.

$^1$H NMR (DMSO-$d_6$): δ1.0-2.2 (m, 19H), 3.30-3.66 (m, 6H), 6.90-6.99 (m, 2H), 7.19 (d, 2H), 7.38 (s, 1H,) 7.71 (d, 2H), 7.81 (s, 1H), 8.20 (s, 1H), 9.59 (s, 1H).

HPLC-MS: m/z 570 (M+H).

Example 115

{2-[3-(trans-4-tert-Butoxy-cyclohexyl)-3-cycloheptyl-ureido]-thiazol-5-ylsulfanyl}-acetic acid

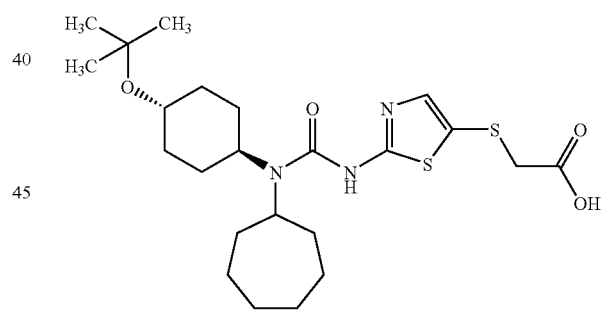

Prepared according to the procedure for the synthesis of {2-[3-cyclopentyl-3-(trans-4-methoxy-cyclohexyl)-ureido]-thiazol-5-ylsulfanyl}-acetic acid.

Step 1.

Cycloheptyl-[trans-4-tert-butoxy-cyclohexyl]-amine was prepare using trans-4-tert-butoxy-cyclohexylamine and cyclohexanone.

Step 2.

{2-[3-(trans-4-tert-Butoxy-cyclohexyl)-3-cycloheptyl-ureido]-thiazol-5-ylsulfanyl}-acetic acid was prepared using cycloheptyl-[trans-4-tert-butoxy-cyclohexyl]-amine and amino-thiazol-5-ylsulfanyl)-acetic acid ethyl ester.

$^1$H NMR (CDCl$_3$) δ 7.30 (s, 1H), 3.7-3.3 (m, 3H), 3.35 (s, 2H), 1.95-1.3 (m, 20H), 1.20 (s, 9H).

HPLC-MS: m/z 484 (M+H).

Example 116

{2-[3-(4-tert-Butoxy-cyclohexyl)-3-cyclohexyl-ureido]-thiazol-5-ylsulfanyl}-acetic acid

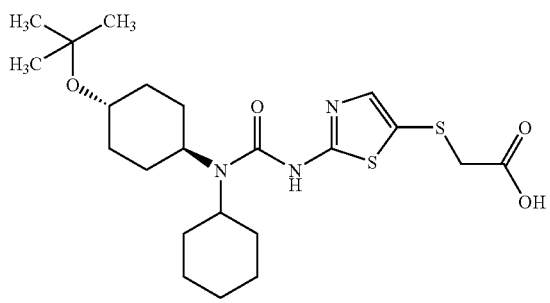

Prepared according to the procedure for the synthesis of {2-[3-cyclopentyl-3-(trans-4-methoxy-cyclohexyl)-ureido]-thiazol-5-ylsulfanyl}-acetic acid.

Step 1.
Cyclohexyl-[trans-4-tert-butoxy-cyclohexyl]-amine was prepare using trans-4-tert-butoxy-cyclohexylamine and cyclohexanone.

Step 2.
{2-[3-(4-tert-Butoxy-cyclohexyl)-3-cyclohexyl-ureido]-thiazol-5-ylsulfanyl}-acetic acid was prepared using cyclohexyl-[trans-4-tert-butoxy-cyclohexyl]-amine and amino-thiazol-5-ylsulfanyl)-acetic acid ethyl ester.

$^1$H NMR (DMSO-$d_6$) δ7.39 (s, 1H), 3.7-3.3 (m, 3H), 3.48 (s, 2H), 2.2-1.2 (m, 18H), 1.13 (s, 9H).
HPLC-MS: m/z 470 (M+H).

Example 117

3-{2-[3-(trans-4-tert-Butoxy-cyclohexyl)-3-cycloheptyl-ureido]-thiazol-5-ylsulfanyl}-propionic acid

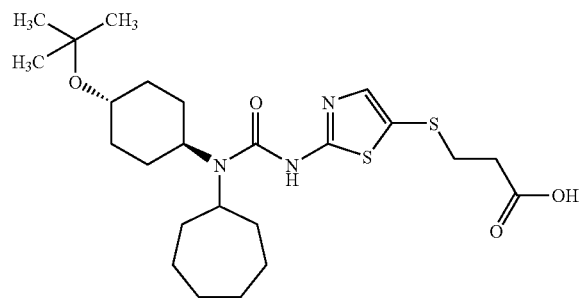

Prepared according to the procedure for the synthesis of {2-[3-cyclopentyl-3-(trans-4-methoxy-cyclohexyl)-ureido]-thiazol-5-ylsulfanyl}-acetic acid.
Step 1: Cycloheptyl-[trans-4-tert-butoxy-cyclohexyl]-amine was prepare using trans-4-tert-butoxy-cyclohexylamine and cycloheptanone.
Step 2: 3-{2-[3-(trans-4-tert-Butoxy-cyclohexyl)-3-cycloheptyl-ureido]-thiazol-5-ylsulfanyl}-propionic acid was prepared using cycloheptyl-[trans-4-tert-butoxy-cyclohexyl]-amine and amino-thiazol-5-ylsulfanyl)-propionic acid ethyl ester.

1H NMR (DMSO-$d_6$) δ7.38 (s, 1H), 3.7-3.3 (m, 2H), 3.33 (s, 2H), 2.84 (t, 2H), 2.50 (t, 2H), 2.2-1.2 (m, 20H), 1.13 (s, 9H).
HPLC-MS: m/z 498 (M+H).

Example 118

3-{2-[3-(4-tert-Butoxy-cyclohexyl)-3-cyclohexyl-ureido]-thiazol-5-ylsulfanyl}-propionic acid

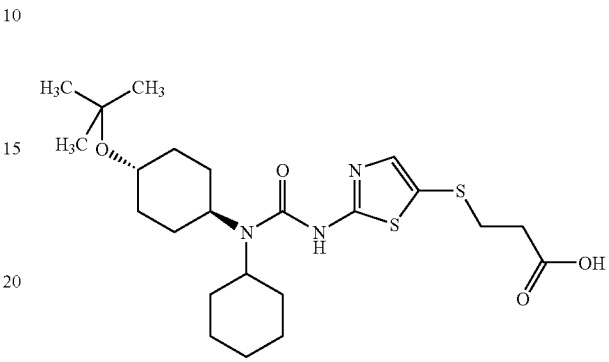

Prepared according to the procedure for the synthesis of {2-[3-cyclopentyl-3-(trans-4-methoxy-cyclohexyl)-ureido]-thiazol-5-ylsulfanyl}-acetic acid.
Step 1: Cyclohexyl-[trans-4-tert-butoxy-cyclohexyl]-amine was prepare using trans-4-tert-butoxy-cyclohexylamine and cyclohexanone.
Step 2: 3-{2-[3-(4-tert-Butoxy-cyclohexyl)-3-cyclohexyl-ureido]-thiazol-5-ylsulfanyl}-propionic acid was prepared using cyclohexyl-[trans-4-tert-butoxy-cyclohexyl]-amine and amino-thiazol-5-ylsulfanyl)-propionic acid ethyl ester.

$^1$H NMR (DMSO-$d_6$) δ 7.38 (s, 1H), 3.7-3.2 (m, 3H), 3.30 (s, 2H), 2.84 (t, 2H), 2.2-1.2 (m, 18H), 1.15 (s, 9H).
HPLC-MS: m/z 485 (M+H).

Example 119

{2-[3-(trans-4-Benzyloxy-cyclohexyl)-3-cyclohexyl-ureido]-thiazol-5-ylsulfanyl}-acetic acid

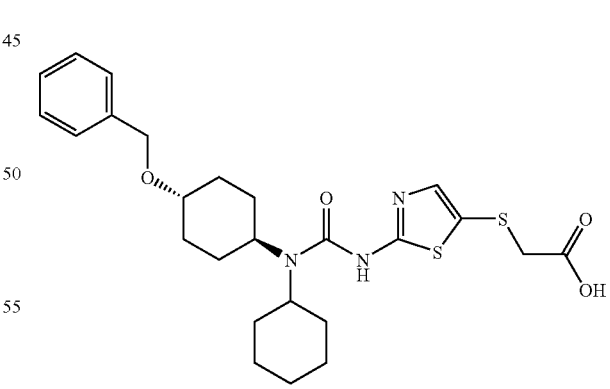

Prepared according to the procedure for the synthesis of {2-[3-cyclopentyl-3-(trans-4-methoxy-cyclohexyl)-ureido]-thiazol-5-ylsulfanyl}-acetic acid.
Step 1: Cyclohexyl-[trans-4-benzyloxy-cyclohexyl]-amine was prepare using (trans-4-hydroxy-cyclohexyl)-isoindole-1,3-dione, benzyl bromide and cyclohexanone.
Step 2: {2-[3-(trans-4-Benzyloxy-cyclohexyl)-3-cyclohexyl-ureido]-thiazol-5-ylsulfanyl}-acetic acid was prepared using cyclohexyl-[trans-4-benzyloxy-cyclohexyl]-amine and amino-thiazol-5-ylsulfanyl)-acetic acid ethyl ester.

$^1$H NMR (DMSO-d$_6$) δ 7.39 (s, 1H), 7.39-7.22 (m, 5H), 4.50 (s, 2H), 3.7-3.2 (m, 3H), 3.48 (s, 2H), 2.2-1.0 (m, 18H). HPLC-MS: m/z 504 (M+H).

Example 120

{2-[3-(trans-4-Benzyloxy-cyclohexyl)-3-cycloheptyl-ureido]-thiazol-5-ylsulfanyl}-acetic acid

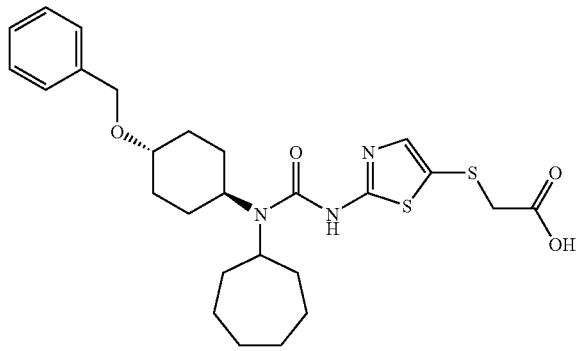

Prepared according to the procedure for the synthesis of {2-[3-cyclopentyl-3-(trans-4-methoxy-cyclohexyl)-ureido]-thiazol-5-ylsulfanyl}-acetic acid.

Step 1.
Cycloheptyl-[trans-4-benzyloxy-cyclohexyl]-amine was prepare using (trans-4-hydroxy-cyclohexyl)-isoindole-1,3-dion, benzyl bromide and cycloheptanone.

Step 2.
{2-[3-(trans-4-Benzyloxy-cyclohexyl)-3-cycloheptyl-ureido]-thiazol-5-ylsulfanyl}-acetic acid was prepared using cycloheptyl-[trans-4-benzyloxy-cyclohexyl]-amine and amino-thiazol-5-ylsulfanyl)-acetic acid ethyl ester.

$^1$H NMR (DMSO-d$_6$) δ 7.39 (s, 1H), 7.4-7.2 (m, 5H), 4.51 (s, 2H), 3.48 (s, 2H), 3.7-3.2 (m, 3H), 2.2-1.1 (m, 20H). HPLC-MS: m/z 518 (M+H).

Example 121

3-{2-[3-(trans-4-Benzyloxy-cyclohexyl)-3-cyclohexyl-ureido]-thiazol-5-ylsulfanyl}-propionic acid

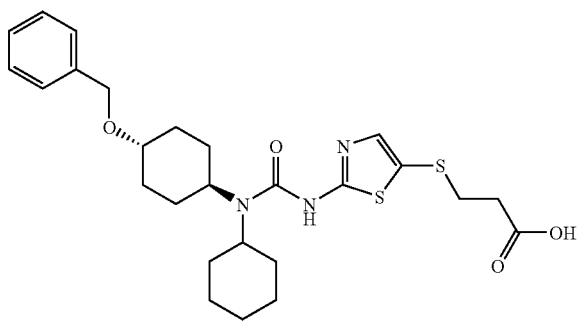

Prepared according to the procedure for the synthesis of {2-[3-cyclopentyl-3-(trans-4-methoxy-cyclohexyl)-ureido]-thiazol-5-ylsulfanyl}-acetic acid.

Step 1.
Cyclohexyl-[trans-4-benzyloxy-cyclohexyl]-amine was prepare using (trans-4-hydroxy-cyclohexyl)-isoindole-1,3-dione, benzyl bromide and cyclohexanone.

Step 2.
3-{2-[3-(trans-4-Benzyloxy-cyclohexyl)-3-cyclohexyl-ureido]-thiazol-5-ylsulfanyl}-propionic acid was prepared using cyclohexyl-[trans-4-benzyloxy-cyclohexyl]-amine and amino-thiazol-5-ylsulfanyl)-propionic acid ethyl ester.

$^1$H NMR (DMSO-d$_6$) δ 7.40-7.24 (m, 6H), 4.51 (s; 2H), 3.7-3.3 (m, 3H), 2.84 (t, 2H), 2.50 (t, 2H), 2.2-1.0 (m, 18H). HPLC-MS: m/z 518 (M+H).

Example 122

3-{2-[3-(trans-4-Benzyloxy-cyclohexyl)-3-cycloheptyl-ureido]-thiazol-5-ylsulfanyl}-propionic acid

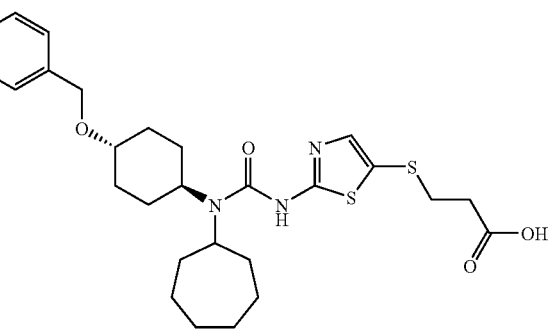

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-benzyloxy-cyclohexyl]-amine was prepare using (trans-4-hydroxy-cyclohexyl)-isoindole-1,3-dione, benzyl bromide and cycloheptanone.

Step 2: 3-{2-[3-(trans-4-Benzyloxy-cyclohexyl)-3-cycloheptyl-ureido]-thiazol-5-ylsulfanyl}-propionic acid was prepared using cycloheptyl-[trans-4-benzyloxy-cyclohexyl]-amine and amino-thiazol-5-ylsulfanyl)-propionic acid ethyl ester.

$^1$H NMR (DMSO-d$_6$) δ 7.40-7.23 (m, 6H), 4.50 (s, 2H), 3.7-3.2 (m, 3H), 2.83 (t, 2H), 2.49 (t, 2H), 2.2-1.2 (m, 20H) HPLC-MS: m/z 532 (M+H).

Example 123

2-({2-[3-Cyclohexyl-3-(trans-4-methyl-cyclohexyl)-ureido]-thiazole-5-sulfonyl}-methyl-amino)-N,N-diethyl-acetamide

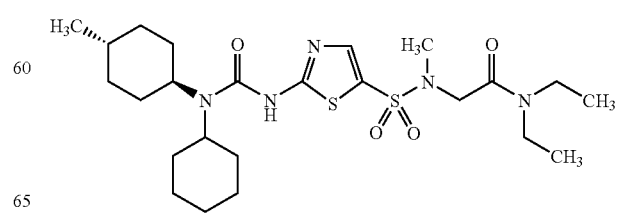

An equimolar mixture of HOBt, ({2-[3-cyclohexyl-3-(trans-4-methyl-cyclohexyl)-ureido]-thiazole-5-sulfonyl}-methyl-amino)-acetic acid was added EDAC (1.5 eq) and diisopropylethyl amine (1.2 eq) and dry DMF (10 mL/mmol). The solution was stirred 30 min at rt and then diethyl amine (1.5 eq) was added and stirring was continued over night.

The reaction mixture was quenched with water. The organic phase was isolated and the aqueous phase was extracted with $CH_2Cl_2$, and the combined organic phases were dried and concentrated in vacuo. The crude product was dissolved in MeCN and purified (HPLC method 1) to give the title compound.

HPLC-MS method 2: m/z=528 (M+H).

$^1$H NMR (CDCl$_3$) δ 7.79 (s, 1H), 3.92 (s, 2H), 3.44-3.33 (m, 6H), 2.90 (s, 3H), 1.95-1.75 (m, 13H), 1.47-1.03 (m, 12H), 0.92 (d, 3H).

Example 124

2-{2-[3-Cyclohexyl-3-(trans-4-methyl-cyclohexyl)-ureido]-thiazole-5-sulfonylamino}-2-methyl-propionic acid

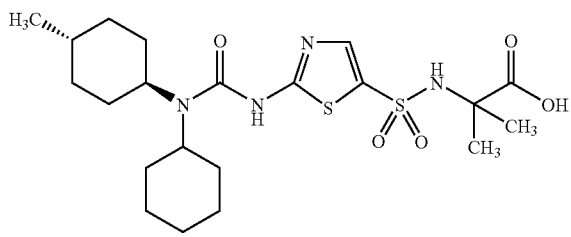

Prepared in a similar manner to [2-(3,3-dicyclohexyl-ureido)-thiazole-5-sulfonylamino]-acetic acid via cyclohexyl-(trans-4-methyl-cyclohexyl)-amine and 2-(2-amino-thiazole-5-sulfonylamino)-2-methyl-propionic acid methyl ester to give the title compound.

HPLC-MS method 2: m/z=487 (M+H).

$^1$H NMR (CDCl$_3$) δ 7.67 (s, 1H), 5.65 (br s, 1H), 5.20 (br s, 1H), 3.60-3.05 (m, 2H), 2.22-1.02 (m, 19H), 1.60 (s, 6H), 0.92 (d, 3H).

Example 125

1-{2-[3-Cyclohexyl-3-(trans-4-methyl-cyclohexyl)-ureido]-thiazole-5-sulfonylamino}-cyclobutanecarboxylic acid

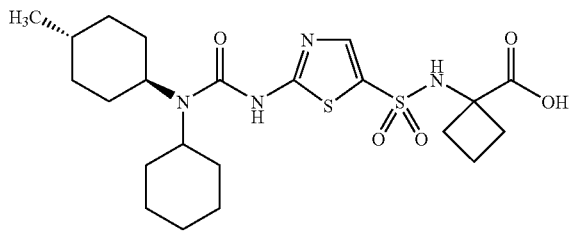

Prepared in a similar manner to [2-(3,3-dicyclohexyl-ureido)-thiazole-5-sulfonylamino]-acetic acid via cyclohexyl-(trans-4-methyl-cyclohexyl)-amine and 1-(2-amino-thiazole-5-sulfonylamino)-cyclobutanecarboxylic acid methyl ester to give the title compound.

HPLC-MS method 2: m/z=500 (M+H).

$^1$H NMR (CDCl$_3$) δ 7.60 (s, 1H), 5.23 (br s, 1H), 3.55 (br s, 1H), 3.05 (br s, 1H), 2.68-2.52 (m, 5H), 2.18-1.05 (m, 20H), 0.91 (d, 3H).

Example 126

1-{2-[3-Cyclohexyl-3-(trans-4-methyl-cyclohexyl)-ureido]-thiazole-5-sulfonylamino}-cyclopropanecarboxylic acid

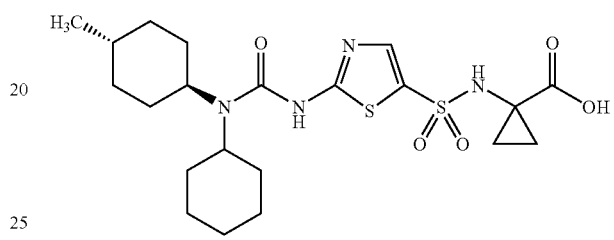

Prepared in a similar manner to [2-(3,3-dicyclohexyl-ureido)-thiazole-5-sulfonylamino]-acetic acid via cyclohexyl-(trans-4-methyl-cyclohexyl)-amine and 1-(2-amino-thiazole-5-sulfonylamino)-cyclopropanecarboxylic acid ethyl ester to give the title compound.

HPLC-MS method 2: m/z=485 (M+H).

$^1$H NMR (DMSO-d6) δ 12.5 (br s, 1H), 11.32 (br s, 1H), 8.68 (s, 1H), 7.68 (s, 1H), 2.07-1.00 (m, 25H), 0.87 (d, 3H).

Example 127

(R)-1-{2-[3-Cyclohexyl-3-(trans-4-methyl-cyclohexyl)-ureido]-thiazole-5-sulfonyl}-pyrrolidine-2-carboxylic acid

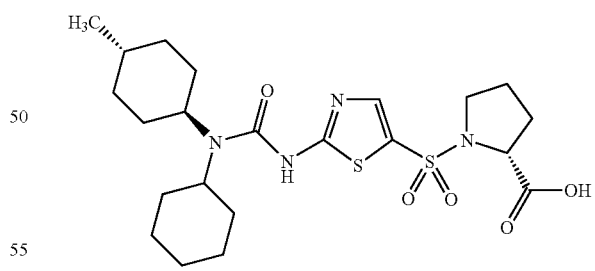

Prepared in a similar manner to [2-(3,3-dicyclohexyl-ureido)-thiazole-5-sulfonylamino]-acetic acid via cyclohexyl-(trans-4-methyl-cyclohexyl)-amine and (R)-1-(2-amino-thiazole-5-sulfonyl)-pyrrolidine-2-carboxylic acid methyl ester to give the title compound.

HPLC-MS method 2: m/z=499 (M+H).

$^1$H NMR identical to that of (S)-1-{2-[3-cyclohexyl-3-(trans-4-methyl-cyclohexyl)-ureido]-thiazole-5-sulfonyl}-pyrrolidine-2-carboxylic acid.

Example 128

1-{2-[3-Cyclohexyl-3-(trans-4-propoxy-cyclohexyl)-ureido]-thiazole-5-sulfonylamino}-cyclobutanecarboxylic acid

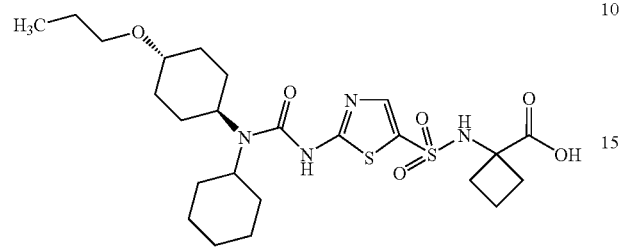

Prepared in a similar manner to [2-(3,3-dicyclohexyl-ureido)-thiazole-5-sulfonylamino]-acetic acid via cyclohexyl-(trans-4-propoxy-cyclohexyl)-amine (prepared according to the procedure described for the synthesis of {2-[3-cyclopentyl-3-(trans-4-methoxy-cyclohexyl)-ureido]-thiazol-5-ylsulfanyl}-acetic acid (Step 1) using (trans-4-hydroxy-cyclohexyl)-isoindole-1,3-dione, 1-bromopropane and cyclohexanone) and 1-(2-amino-thiazole-5-sulfonylamino)-cyclobutanecarboxylic acid methyl ester to give the title compound.

HPLC-MS method 2: m/z=543 (M+H).

$^1$H NMR (CDCl$_3$) δ 7.60 (s, 1H), 5.50 (br s, 1H), 3.59 (br s, 1H), 3.42 (t, 2H), 3.31-3.22 (m, 1H), 2.68-2.51 (m, 4H), 2.18-1.11 (m, 22H), 0.93 (t, 3H).

Example 129

{2-[3-Cyclohexyl-3-(trans-4-cyclopropyl methoxymethyl-cyclohexyl)-ureido]-thiazol-5-ylsulfanyl}-acetic acid

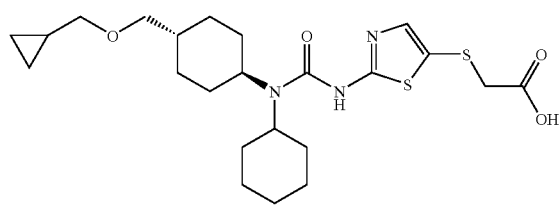

Prepared in an similar manner to {2-[3-cyclohexyl-3-(trans-4-methoxymethyl-cyclohexyl)-ureido]-thiazol-5-ylsulfanyl}-acetic acid via cyclohexyl-(trans-4-cyclopropylmethoxymethyl-cyclohexyl)-amine and (2-amino-thiazol-5-ylsulfanyl)-acetic acid ethyl ester to give the title compound.

$^1$H NMR (CDCl$_3$): δ0.08-0.15 (m, 2H), 0.40-0.50 (m, 2H), 0.80-2.00 (m, 20H), 2.80-3.50 (2H, m), 3.13 (d, 2H), 3.18 (d, 2H), 7.25 (s, 1H).

HPLC-MS: m/z 483 (M+H).

Example 130

{2-[3-Cycloheptyl-3-(trans-4-cyclopropyl methoxymethyl-cyclohexyl)-ureido]-thiazol-5-ylsulfanyl}-acetic acid

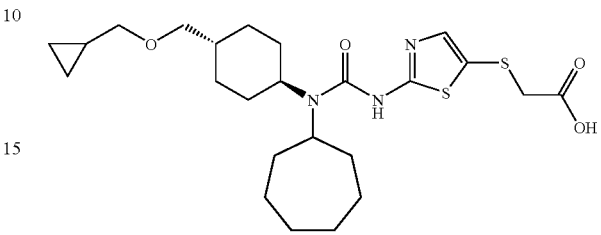

Prepared in an similar manner to {2-[3-cyclohexyl-3-(trans-4-methoxymethyl-cyclohexyl)-ureido]-thiazol-5-ylsulfanyl}-acetic acid via cycloheptyl-(trans-4-cyclopropyl-methoxymethyl-cyclohexyl)-amine and (2-amino-thiazol-5-ylsulfanyl)-acetic acid ethyl ester to give the title compound.

$^1$H NMR (CDCl$_3$): δ0.08-0.15 (m, 2H), 0.40-0.50 (m, 2H), 0.80-1.90 (m, 20H), 2.80-3.50 (2H, m), 3.13 (d, 2H), 3.15 (d, 2H), 3.30-(s, 2H), 7.20 (s, 1H).

HPLC-MS: m/z 497 (M+H).

Example 131

2-{2-[3-Cyclohexyl-3-(trans-4-propoxy-cyclohexyl)-ureido]-thiazole-5-sulfonylamino}-2-methyl-propionic acid

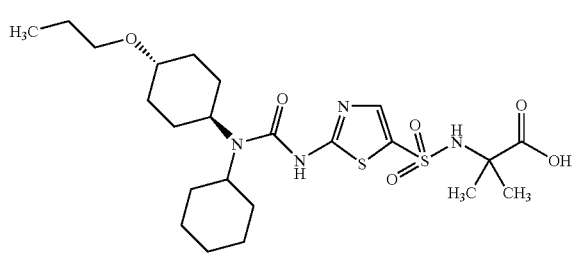

Prepared in a similar manner to [2-(3,3-dicyclohexyl-ureido)-thiazole-5-sulfonylamino]-acetic acid via cyclohexyl-(trans-4-propoxy-cyclohexyl)-amine (prepared according to the procedure described for the synthesis of {2-[3-cyclopentyl-3-(trans-4-methoxy-cyclohexyl)-ureido]-thiazol-5-ylsulfanyl}-acetic acid (Step 1) using (trans-4-hydroxy-cyclohexyl)-isoindole-1,3-dione, 1-bromopropane and cyclohexanone) and 2-(2-amino-thiazole-5-sulfonylamino)-2-methyl-propionic acid methyl ester to give the title compound.

HPLC-MS method 2: m/z=531 (M+H).

$^1$H NMR (400 MHz, CDCl$_3$) δ 7.65 (s, 1H), 5.28 (br s, 1H), 3.60 (br s, 1H), 3.42 (t, 2H), 3.30-3.02 (m, 2H), 2.47-1.11 (m, 20H), 1.61 (s, 6H), 0.92 (d, 3H).

Example 132

(R)-1-{2-[3-Cyclohexyl-3-(trans-4-propoxy-cyclohexyl)-ureido]-thiazole-5-sulfonyl}-pyrrolidine-2-carboxylic acid

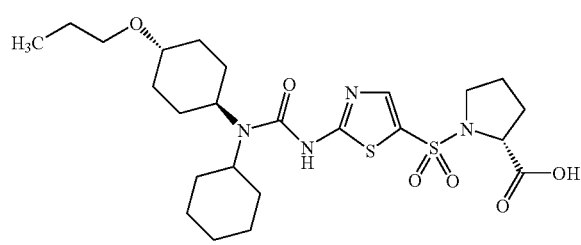

Prepared in a similar manner to [2-(3,3-dicyclohexyl-ureido)-thiazole-5-sulfonylamino]-acetic acid via cyclohexyl-(trans-4-propoxy-cyclohexyl)-amine (prepared according to the procedure described for the synthesis of {2-[3-cyclopentyl-3-(trans-4-methoxy-cyclohexyl)-ureido]-thiazol-5-ylsulfanyl}-acetic acid (Step 1) using (trans-4-hydroxy-cyclohexyl)-isoindole-1,3-dione, 1-bromopropane and cyclohexanone) and (R)-1-(2-amino-thiazole-5-sulfonyl)-pyrrolidine-2-carboxylic acid methyl ester to give the title compound.

HPLC-MS method 2: m/z=543 (M+H).

$^1$H NMR (400 MHz, CDCl$_3$) δ 7.83 (s, 1H), 4.18 (dd, 1H), 3.63-3.23 (m, 8H), 2.27-1.11 (m, 27H), 0.92 (d, 3H).

Example 133

{2-[3-(trans-4-Benzyloxymethyl-cyclohexyl)-3-cyclohexyl-ureido]-thiazol-5-ylsulfanyl}-acetic acid

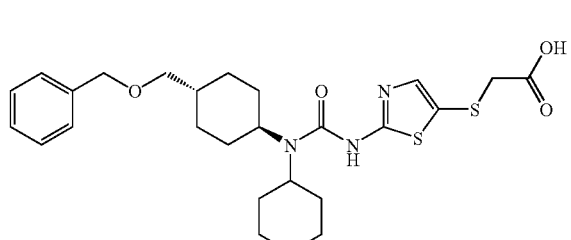

Prepared in a similar manner to {2-[3-cyclohexyl-3-(trans-4-methoxymethyl-cyclohexyl)-ureido]-thiazol-5-ylsulfanyl}-acetic acid via (trans-4-benzyloxymethyl-cyclohexyl)-cyclohexyl-amine and (2-amino-thiazol-5-ylsulfanyl)-acetic acid ethyl ester to give the title compound.

$^1$H NMR (DMSO-d$_6$): δ1.00-2.10 (m, 19H), 3.15-3.55 (m, 2H), 3.20 (d, 2H), 3.47 (s, 2H), 4.45 (s, 2H), 7.20-7.45 (m, 6H).

HPLC-MS: m/z 518 (M+H).

Example 134

{2-[3-Cyclohexyl-3-(trans-4-isopropoxy-cyclohexyl)-ureido]-thiazol-5-ylsulfanyl}-acetic acid

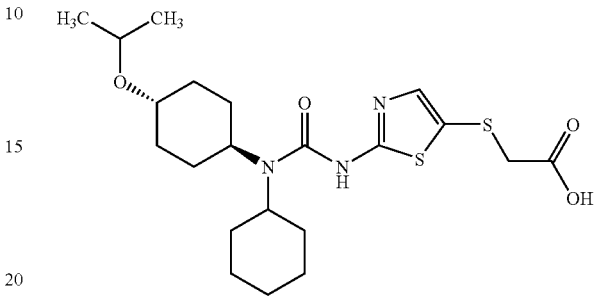

Prepared according to the procedure for the synthesis of {2-[3-cyclopentyl-3-(trans-4-methoxy-cyclohexyl)-ureido]-thiazol-5-ylsulfanyl}-acetic acid using cyclohexyl-(4-isopropoxy-cyclohexyl)-amine and amino-thiazol-5-ylsulfanyl)-acetic acid ethyl ester.

$^1$H NMR (400 MHz, DMSO-d$_6$) δ 7.39 (s, 1H), 3.65 (h, 1H), 3.6-3.2 (m, 3H), 3.48 (s, 2H), 2.2-1.0 (m, 18H), 1.07 (d, 6H).

HPLC-MS: m/z 457 (M+H).

Example 135

{2-[3-Cycloheptyl-3-(trans-4-isopropoxy-cyclohexyl)-ureido]-thiazol-5-ylsulfanyl}-acetic acid

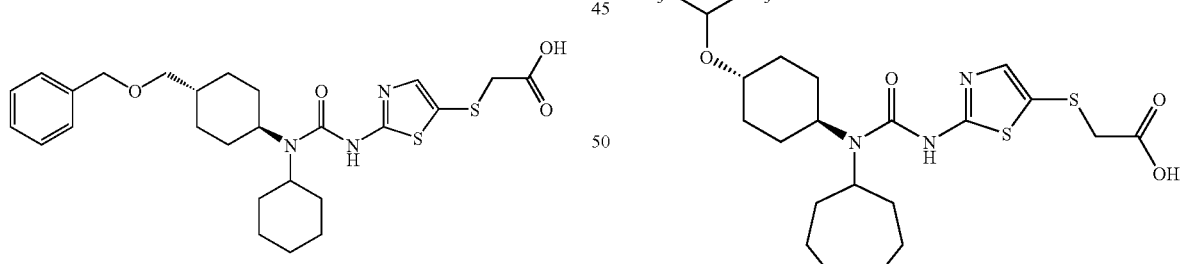

Prepared according to the procedure for the synthesis of {2-[3-cyclopentyl-3-(trans-4-methoxy-cyclohexyl)-ureido]-thiazol-5-ylsulfanyl}-acetic acid using cycloheptyl-(4-isopropoxy-cyclohexyl)-amine and amino-thiazol-5-ylsulfanyl)-acetic acid ethyl ester.

$^1$H NMR (DMSO-d$_6$) δ 7.39 (s, 1H), 3.68 (h, 1H), 3.6-3.2 (m, 3H), 3.48 (s, 2H), 2.2-1.1 (m, 20H), 1.08 (d, 6H).

HPLC-MS: m/z 471 (M+H).

Example 136

{2-[3-Cycloheptyl-3-(trans-4-phenoxymethyl-cyclohexyl)-ureido]-thiazol-5-ylsulfanyl}-acetic acid

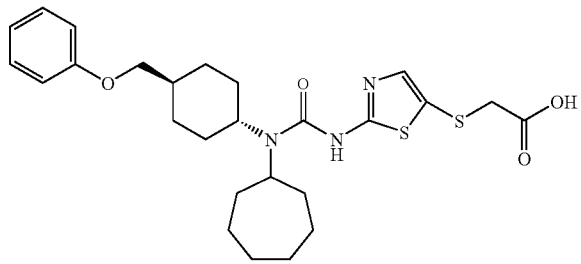

Prepared in an similar manner to {2-[3-cyclohexyl-3-(trans-4-phenoxymethyl-cyclohexyl)-ureido]-thiazol-5-ylsulfanyl}-acetic acid via cycloheptyl-(trans-4-phenoxymethyl-cyclohexyl)-amine and (2-amino-thiazol-5-ylsulfanyl)-acetic acid ethyl ester to give the title compound.

$^1$H NMR (DMSO-$d_6$): δ1.10-2.15 (m, 21H), 3.30-3.50 (m, 2H), 3.48 (s, 2H), 3.79 (d, 2H), 6.87-6.95 (m, 3H), 7.27 (d, 2H,), 7.39 (s, 1H).

HPLC-MS: m/z 518 (M+H).

Example 137

(2-{3-Cycloheptyl-3-[trans-4-(4-methoxy-phenoxymethyl)-cyclohexyl]-ureido}-thiazol-5-ylsulfanyl)-acetic acid

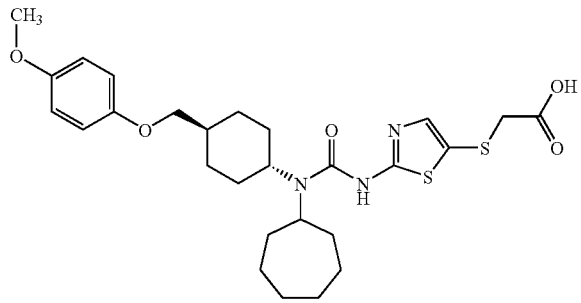

Prepared in a similar manner to {2-[3-cyclohexyl-3-(trans-4-phenoxymethyl-cyclohexyl)-ureido]-thiazol-5-ylsulfanyl}-acetic acid via cycloheptyl-[trans-4-(4-methoxy-phenoxymethyl)-cyclohexyl]-amine and (2-amino-thiazol-5-ylsulfanyl)-acetic acid ethyl ester to give the title compound.

$^1$H NMR (DMSO-$d_6$): δ1.0-2.2 (m, 21H), 3.30-3.50 (m, 2H), 3.45 (s, 2H), 3.69 (s, 3H), 3.72 (d, 2H), 6.80-6.90 (m, 4H), 7.40 (s, 1H).

HPLC-MS: m/z 548 (M+H).

Example 138

(2-{3-Cycloheptyl-3-[trans-4-(4-fluoro-phenoxymethyl)-cyclohexyl]-ureido}-thiazol-5-ylsulfanyl)-acetic acid

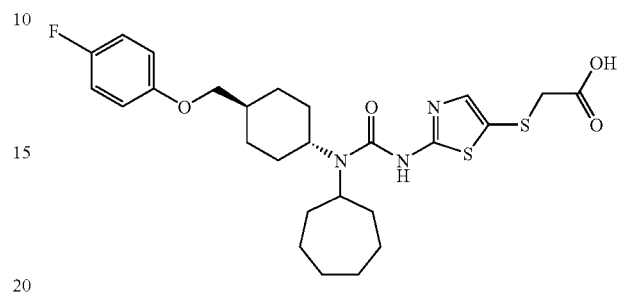

Prepared in a similar manner to {2-[3-cyclohexyl-3-(trans-4-phenoxymethyl-cyclohexyl)-ureido]-thiazol-5-ylsulfanyl}-acetic acid via cycloheptyl-[trans-4-(4-fluoro-phenoxymethyl)-cyclohexyl]-amine and (2-amino-thiazol-5-ylsulfanyl)-acetic acid ethyl ester to give the title compound.

$^1$H NMR (DMSO-$d_6$): δ1.15-2.20 (m, 21H), 3.20-3.50 (m, 2H), 3.46 (s, 2H), 3.80 (d, 2H), 6.93 (d, 2H), 7.37 (t, 2H), 7.39 (s, 1H).

HPLC-MS: m/z 536 (M+H).

Example 139

(2-{3-Cycloheptyl-3-[trans-4-(4-trifluoromethyl-phenoxymethyl)-cyclohexyl]-ureido}-thiazol-5-ylsulfanyl)-acetic acid

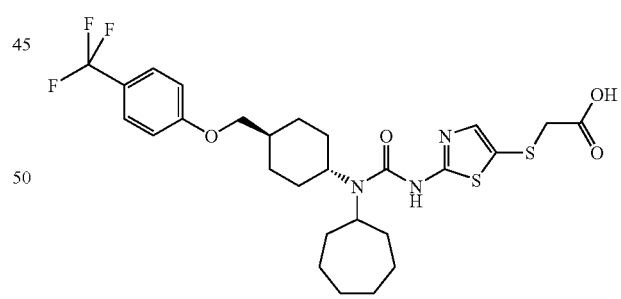

Prepared in an similar manner to {2-[3-cyclohexyl-3-(trans-4-phenoxymethyl-cyclohexyl)-ureido]-thiazol-5-ylsulfanyl}-acetic acid via cycloheptyl-[trans-4-(4-trifluoromethyl-phenoxymethyl)-cyclohexyl]-amine and (2-amino-thiazol-5-ylsulfanyl)-acetic acid ethyl ester to give the title compound.

$^1$H NMR (DMSO-$d_6$): δ1.15-2.20 (m, 21H), 3.20-4.00 (m, 2H), 3.46 (s, 2H), 3.75 (d, 2H), 6.95 (dd, 2H), 7.12 (t, 2H), 7.40 (s, 1H).

HPLC-MS: m/z 586 (M+H).

Example 140

(2-{3-Cyclohexyl-3-[trans-4-(4-trifluoromethyl-phenoxymethyl)-cyclohexyl]-ureido}-thiazol-5-ylsulfanyl)-acetic acid

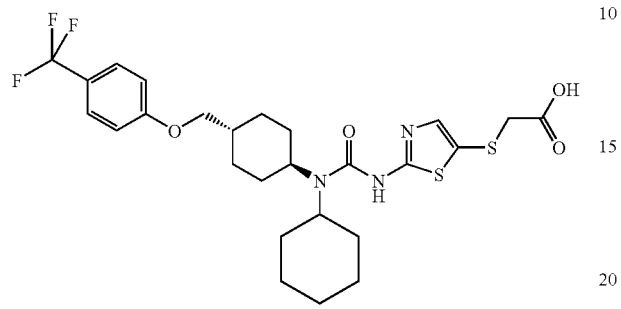

Prepared in an similar manner to {2-[3-cyclohexyl-3-(trans-4-phenoxymethyl-cyclohexyl)-ureido]-thiazol-5-ylsulfanyl}-acetic acid via cyclohexyl-[trans-4-(4-trifluoromethyl-phenoxymethyl)-cyclohexyl]-amine and (2-amino-thiazol-5-ylsulfanyl)-acetic acid ethyl ester to give the title compound.

$^1$H NMR (DMSO): δ1.15-2.20 (m, 19H), 3.10-3.60 (m, 2H), 3.48 (s, 2H), 3.88 (d, 2H), 7.12 (d, 2H), 7.40 (s, 1H), 7.61 (d, 2H).

HPLC-MS: m/z 572 (M+H).

Example 141

3-{2-[3-Cyclohexyl-3-(trans-4-phenoxymethyl-cyclohexyl)-ureido]-thiazol-5-ylsulfanyl}-propionic acid

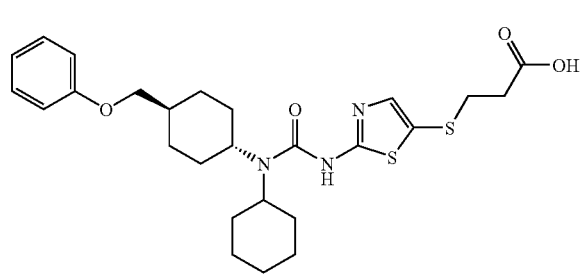

Prepared in an similar manner to {2-[3-cyclohexyl-3-(trans-4-phenoxymethyl-cyclohexyl)-ureido]-thiazol-5-ylsulfanyl}-acetic acid via cyclohexyl-(trans-4-phenoxymethyl-cyclohexyl)-amine and (2-amino-thiazol-5-ylsulfanyl)-propionic acid ethyl ester to give the title compound.

$^1$H NMR (DMSO-$d_6$): δ1.05-2.00 (m, 19H), 2.50 (t, 2H), 2.82 (t, 2H), 3.30-3.50 (m, 2H), 3.78 (d, 2H), 6.91 (d, 3H), 7.25 (d, 2H), 7.38 (s, 1H).

Example 142

3-(2-{3-Cyclohexyl-3-[trans-4-(4-methoxy-phenoxymethyl)-cyclohexyl]-ureido}-thiazol-5-ylsulfanyl)-propionic acid

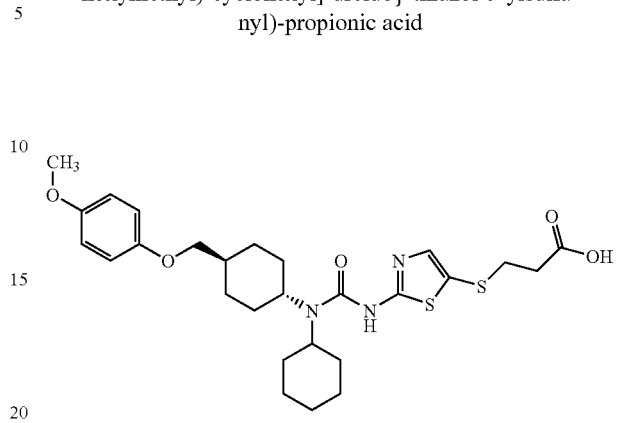

Prepared in an similar manner to {2-[3-cyclohexyl-3-(trans-4-phenoxymethyl-cyclohexyl)-ureido]-thiazol-5-ylsulfanyl}-acetic acid via cyclohexyl-[trans-4-(4-methoxy-phenoxymethyl)-cyclohexyl]-amine and (2-amino-thiazol-5-ylsulfanyl)-propionic acid ethyl ester to give the title compound.

$^1$H NMR (DMSO-$d_6$): δ1.0-2.2 (m, 19H), 2.50 (t, 2H), 2.82 (t, 2H), 3.20-3.90 (m, 2H), 3.68 (s, 3H), 3.72 (d, 2H), 6.82 (m, 4H), 7.37 (s, 1H).

HPLC-MS: m/z 548 (M+H).

Example 143

3-(2-{3-Cyclohexyl-3-[trans-4-(4-fluoro-phenoxymethyl)-cyclohexyl]-ureido}-thiazol-5-ylsulfanyl)-propionic acid

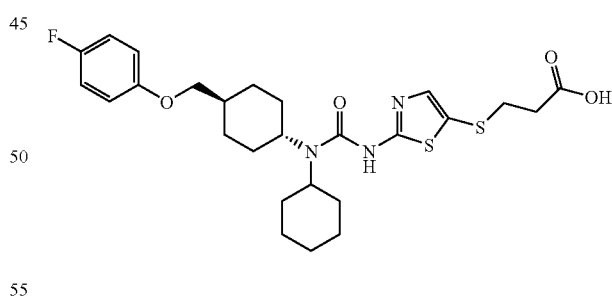

Prepared in a similar manner to {2-[3-cyclohexyl-3-(trans-4-phenoxymethyl-cyclohexyl)-ureido]-thiazol-5-ylsulfanyl}-acetic acid via cyclohexyl-[trans-4-(4-fluoro-phenoxymethyl)-cyclohexyl]-amine and (2-amino-thiazol-5-ylsulfanyl)-propionic acid ethyl ester to give the title compound.

$^1$H NMR (DMSO-$d_6$): δ1.05-2.20 (m, 19H), 2.50 (t, 2H), 2.82 (t, 2H), 3.20-3.90 (m, 2H), 3.72 (d, 2H), 6.92 (dd, 2H), 7.10 (t, 2H), 7.38 (s, 1H).

HPLC-MS: m/z 536 (M+H).

Example 144

3-{2-[3-Cyclohexyl-3-(trans-4-isopropoxy-cyclohexyl)-ureido]-thiaol-5-ylsulfanyl}-propionic acid

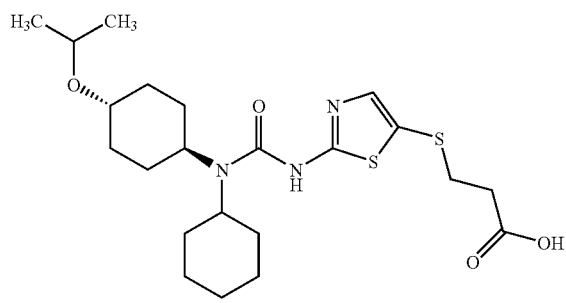

Prepared according to the procedure for the synthesis of {2-[3-cyclopentyl-3-(trans-4-methoxy-cyclohexyl)-ureido]-thiazol-5-ylsulfanyl}-acetic acid using cyclohexyl-(4-isopropoxy-cyclohexyl)-amine and amino-thiazol-5-ylsulfanyl)-propionic acid ethyl ester.

$^1$H NMR (400 MHz, DMSO-$d_6$) δ 7.38 (s, 2H), 3.68 (h, 1H), 3.6-3.2 (m, 3H), 2.83 (t, 2H), 2.50 (t, 2H), 2.2-1.0 (m, 18H), 1.05 (d, 6H).

HPLC-MS: m/z 470 (M+H).

Example 145

3-{2-[3-Cycloheptyl-3-(trans-4-isopropoxy-cyclohexyl)-ureido]-thiazol-5-ylsulfanyl}-propionic acid

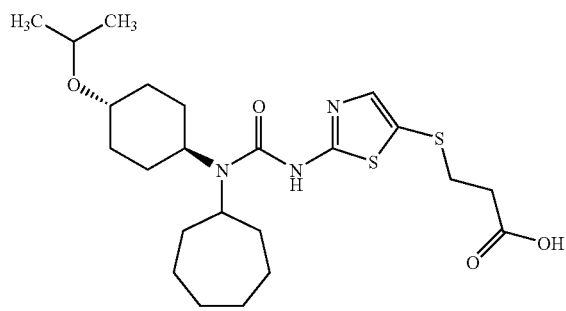

Prepared according to the procedure for the synthesis of {2-[3-cyclopentyl-3-(trans-4-methoxy-cyclohexyl)-ureido]-thiazol-5-ylsulfanyl}-acetic acid using cycloheptyl-(4-isopropoxy-cyclohexyl)-amine and amino-thiazol-5-ylsulfanyl)-propionic acid ethyl ester.

$^1$H NMR (DMSO-$d_6$) δ 7.38 (s, 1H), 3.68 (h, 1H), 3.8-3.1 (m, 3H), 2.85 (t, 2H), 2.50 (t, 2H), 2.2-1.12 (m, 20H), 1.08 (d, 6H).

HPLC-MS: m/z 484 (M+H).

Example 146

3-(2-{3-Cyclohexyl-3-[4-(trans-2-methoxy-ethoxymethyl)-cyclohexyl]-ureido}-thiazol-5-ylsulfanyl)-acetic acid

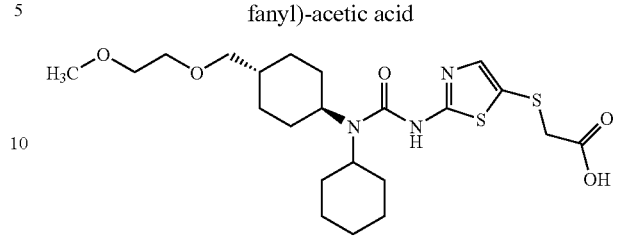

Prepared in an similar manner to {2-[3-cyclohexyl-3-(trans-4-methoxymethyl-cyclohexyl)-ureido]-thiazol-5-ylsulfanyl}-acetic acid via cyclohexyl-[4-(trans-2-methoxy-ethoxymethyl)-cyclohexyl]-amine and (2-amino-thiazol-5-ylsulfanyl)-acetic acid ethyl ester to give the title compound.

$^1$H NMR (CDCl$_3$): δ 1.0-2.0 (m, 19H), 3.0-3.60 (m, 2H), 3.28 (d, 2H), 3.39 (s, 3H), 3.50-3.60 (m, 4H), 7.36 (m, 1H).

HPLC-MS: m/z 487 (M+H).

Example 147

3-(2-{3-Cyclohexyl-3-[4-(trans-2-methoxy-ethoxymethyl)-cyclohexyl]-ureido}-thiazol-5-ylsulfanyl)-propionic acid

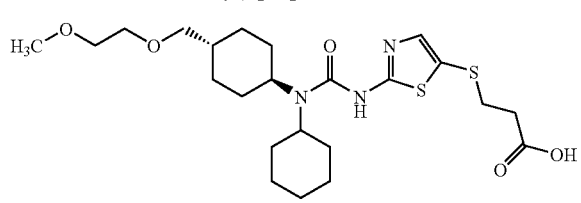

Prepared in an similar manner to {2-[3-cyclohexyl-3-(trans-4-methoxymethyl-cyclohexyl)-ureido]-thiazol-5-ylsulfanyl}-acetic acid via cyclohexyl-[4-(trans-2-methoxy-ethoxymethyl)-cyclohexyl]-amine and (2-amino-thiazol-5-ylsulfanyl)-propionic acid ethyl ester to give the title compound.

$^1$H NMR (CDCl$_3$): δ 1.0-2.0 (m, 19H), 2.9-3.60 (m, 2H), 2.70 (t, 2H), 2.95-3.03 (m, 2H), 3.30 (d, 2H), 3.40 (s, 3H), 3.50-3.60 (m, 4H), 7.31 (m, 1H).

HPLC-MS: m/z 501 (M+H).

Example 148

(2-{3-Cycloheptyl-3-[4-(trans-2-methoxy-ethoxymethyl)-cyclohexyl]-ureido}-thiazol-5-ylsulfanyl)-acetic acid

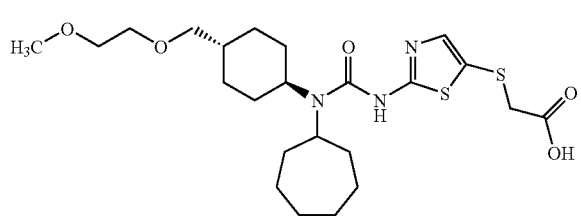

Prepared in a similar manner to {2-[3-cyclohexyl-3-(trans-4-methoxymethyl-cyclohexyl)-ureido]-thiazol-5-ylsulfanyl}-acetic acid via cycloheptyl-[4-(trans-2-methoxyethoxymethyl)-cyclohexyl]-amine and (2-amino-thiazol-5-ylsulfanyl)-acetic acid ethyl ester to give the title compound.

$^1$H NMR (CDCl$_3$): δ1.0-2.0 (m, 21H), 3.0-3.60 (m, 2H), 3.30 (d, 2H), 3.33-3.38 (m, 2H), 3.39 (s, 3H), 3.50-3.60 (m, 4H), 7.32 (bs, 1H).

HPLC-MS: m/z 500 (M+H).

Example 149

3-(2-{3-Cycloheptyl-3-[4-(trans-2-methoxyethoxymethyl)-cyclohexyl]-ureido}-thiazol-5-ylsulfanyl)-propionic acid

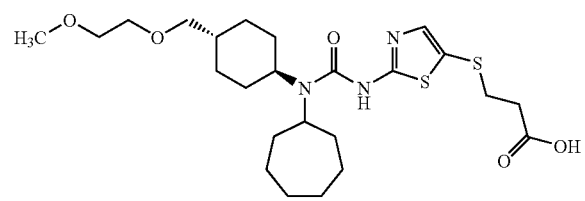

Prepared in a similar manner to {2-[3-cyclohexyl-3-(trans-4-methoxymethyl-cyclohexyl)-ureido]-thiazol-5-ylsulfanyl}-acetic acid via cycloheptyl-[4-(trans-2-methoxyethoxymethyl)-cyclohexyl]-amine and (2-amino-thiazol-5-ylsulfanyl)-propionic acid ethyl ester to give the title compound.

$^1$H NMR (CDCl$_3$): δ1.0-2.0 (m, 21H), 2.9-3.80 (m, 2H), 2.71 (t, 2H), 2.95-3.00 (m, 2H), 3.32 (d, 2H), 3.40 (s, 3H), 3.51-3.60 (m, 4H), 7.30 (m, 1H).

HPLC-MS: m/z 515 (M+H).

Example 150

(2-{3-Cyclohexyl-3-[4-(trans-2,2,2-trifluoro-ethoxymethyl)-cyclohexyl]-ureido}-thiazol-5-ylsulfanyl)-acetic acid

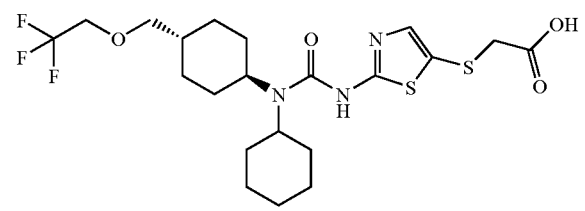

Prepared in an similar manner to {2-[3-cyclohexyl-3-(trans-4-phenoxymethyl-cyclohexyl)-ureido]-thiazol-5-ylsulfanyl}-acetic acid via cyclohexyl-[trans-4-(2,2,2-trifluoro-ethoxymethyl)-cyclohexyl]-amine and (2-amino-thiazol-5-ylsulfanyl)-acetic acid ethyl ester to give the title compound.

$^1$H NMR (CDCl$_3$): δ1.11-2.25 (m, 19H), 3.28-3.50 (m, 2H), 3.34 (s, 2H), 3.44 (d, 2H), 3.81 (q, 2H), 7.27 (s, 1H).

HPLC-MS: m/z 511 (M+H).

Example 151

(2-{2-[3-Cyclohexyl-3-(trans-4-propoxy-cyclohexyl)-ureido]-thiazol-5-ylsulfanyl}-acetyl)-methanesulfonamide

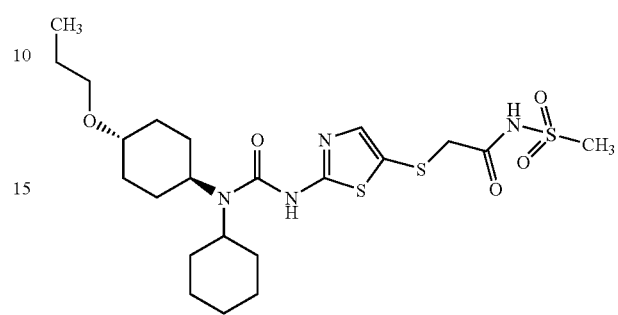

{2-[3-Cyclohexyl-3-(4-propoxy-cyclohexyl)-ureido]-thiazol-5-ylsulfanyl}-acetic acid was pre-pared in a similar manner to {2-[3-cyclopentyl-3-(trans-4-methoxy-cyclohexyl)-ureido]-thiazol-5-ylsulfanyl}-acetic acid via cyclohexyl-(trans-4-propoxy-cyclohexyl)-amine (prepared according to the procedure described for the synthesis of {2-[3-cyclopentyl-3-(trans-4-methoxy-cyclohexyl)-ureido]-thiazol-5-ylsulfanyl}-acetic acid (Step 1) using (trans-4-hydroxy-cyclohexyl)-isoindole-1,3-dione, 1-bromopropane and cyclohexanone) and (2-amino-thiazol-5-ylsulfanyl)-acetic acid ethyl ester. {2-[3-Cyclohexyl-3-(4-propoxy-cyclohexyl)-ureido]-thiazol-5-ylsulfanyl}-acetic acid (0.5 mmol), 1,1'-carbonyldiimidazole (0.51 mmol) and 4-dimethylpyridine (0.05 mmol) was dissolved in anhydrous THF (3 mL). The mixture was stirred at room temperature for 1 hour. To this solution was added methansulfonamide (0.95 mmol) and stirred for 2-3 minutes. A solution of 1,8-diazabicyclo[5.4.0]undece-7-ene (0.6 mmol) in THF (0.5 mL) was added and the mixture was stirred at room temperature for 2 hours and concentrated. The crude product was purified by HPLC (method 1) to give the title compound in 45% yield.

$^1$H NMR (CDCl$_3$): δ 7.44 (s, 1H), 3.49 (s, 2H), 3.41 (m, 3H), 3.33 (s, 3H), 3.23 (m, 2H), 2.30-2.09 (m, 4H), 1.85-1.65 (m, 10H), 1.57 (sextet, 2H), 1.42-1.30 (m, 4H), 1.15 (m, 1H), 0.91 (t, 3H).

HPLC-MS: m/z 534 (M+1)

Example 152

2-{2-[3-Cyclohexyl-3-(trans-4-cyclopropyl methoxymethyl-cyclohexyl)-ureido]-thiazol-5-ylsulfanyl}-2-methyl-propionic acid

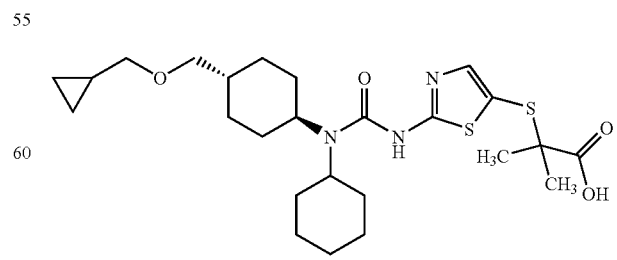

Prepared in a similar manner to {2-[3-cyclohexyl-3-(trans-4-methoxymethyl-cyclohexyl)-ureido]-thiazol-5-ylsulfanyl}-acetic acid via cyclohexyl-(trans-4-cyclopropyl-methoxymethyl-cyclohexyl)-amine and (2-amino-thiazol-5-ylsulfanyl)-2-methyl-propionic acid ethyl ester to give the title compound.

$^{1}$H NMR (CDCl$_{3}$): δ 0.15-0.20 (m, 2H), 0.47-0.54 (m, 2H), 0.75-1.80-2.4 (m, 26H), 3.00-3.60 (m, 6H), 7.15 (s, 1H).

HPLC-MS: m/z 511 (M+H).

Example 153

2-(2-{3-Cyclohexyl-3-[4-(trans-2-methoxy-ethoxymethyl)-cyclohexyl]-ureido}-thiazol-5-ylsulfanyl)-2-methyl-propionic acid

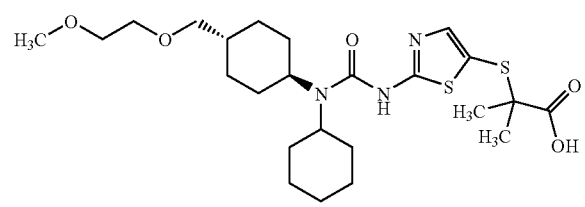

Prepared in a similar manner to {2-[3-cyclohexyl-3-(trans-4-methoxymethyl-cyclohexyl)-ureido]-thiazol-5-ylsulfanyl}-acetic acid via cyclohexyl-[4-(trans-2-methoxy-ethoxymethyl)-cyclohexyl]-amine and (2-amino-thiazol-5-ylsulfanyl)-2-methyl-propionic acid ethyl ester to give the title compound.

$^{1}$H NMR (CDCl$_{3}$): δ1.0-2.0 (m, 25H), 3.0-3.85 (m, 2H), 3.29 (d, 2H), 3.39 (s, 3H), 3.52-3.59 (m, 4H), 7.06 (bs, 1H).

HPLC-MS: m/z 515 (M+H).

Example 154

2-(2-{3-Cycloheptyl-3-[4-(trans-2-methoxy-ethoxymethyl)-cyclohexyl]-ureido}-thiazol-5-ylsulfanyl)-2-methyl-propionic acid

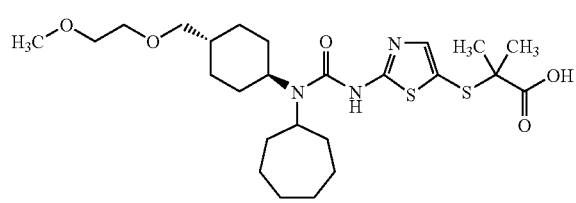

Prepared in a similar manner to {2-[3-cyclohexyl-3-(trans-4-methoxymethyl-cyclohexyl)-ureido]-thiazol-5-ylsulfanyl}-acetic acid via cycloheptl-[4-(trans-2-methoxy-ethoxymethyl)-cyclohexyl]-amine and (2-amino-thiazol-5-ylsulfanyl)-2-methyl-propionic acid ethyl ester to give the title compound.

$^{1}$H NMR (CDCl$_{3}$): δ 1.0-2.0 (m, 27H), 3.0-3.85 (m, 2H), 3.27 (d, 2H), 3.38 (s, 3H), 3.52-3.60 (m, 4H), 7.15 (bs, 1H).

HPLC-MS: m/z 528 (M+H).

Example 155

2-{2-[3-Cyclohexyl-3-(trans-4-methoxymethyl-cyclohexyl)-ureido]-thiazol-5-ylsulfanyl}-2-methyl-propionic acid

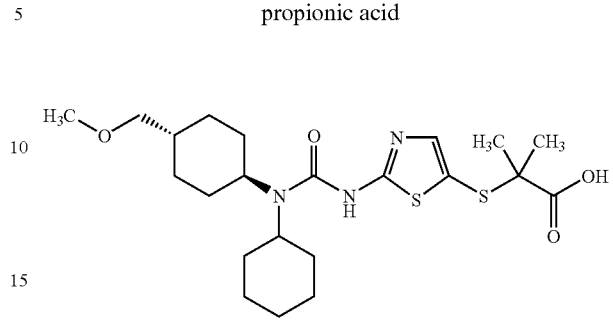

Prepared in an similar manner to {2-[3-cyclohexyl-3-(trans-4-methoxymethyl-cyclohexyl)-ureido]-thiazol-5-ylsulfanyl}-acetic acid via cyclohexyl-(trans-4-methoxymethyl-cycloheptyl)-amine and 2-(2-amino-thiazol-5-ylsulfanyl)-2-methyl-propionic acid ethyl ester to give the title compound.

$^{1}$H NMR (CDCl$_{3}$): δ 1.0-2.0 (m, 25H), 3.15-3.70 (2H, m), 3.21 (d, 2H), 3.33 (s, 3H), 7.10 (s, 1H).

HPLC-MS: m/z 470 (M+H).

Example 156

{2-[3-Cyclohexyl-3-(cis-4-propoxy-cyclohexyl)-ureido]-thiazol-5-ylsulfanyl}-acetic acid

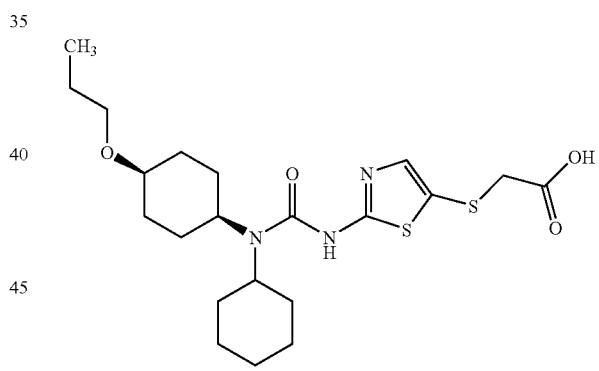

Step 1.

A mixture of cis-4-aminocyclohexanol hydrochloride (4 mmol) and cyclohexanone (8 mmol) and molecular sieves (3 Å, 1 g) in anhydrous MeOH (10 mL) was stirred under N$_{2}$ at room temperature for 10 min. The mixture was added NaBH$_{3}$CN (8 mmol) and glacial AcOH (0.1 mL) and stirred for further 24 h. Addition of NaBH$_{4}$ (1.3 mmol) followed by stirring for another 10 min. The mixture was filtered and the residue was extracted with MeOH (10 mL) and the combined filtrates were evaporated to dryness. The residue was dissolved in 1 M aqueous HCl (15 mL) and washed with TBME (15 mL). The aqueous phase was added 10% aqueous NaOH until pH 14 and extracted with TBME (15 mL). The organic phase was washed with H$_{2}$O (10 ml), dried (Na$_{2}$SO$_{4}$), and evaporated to dryness under reduced pressure affording crude cyclohexyl-cis-(4-hydroxycyclohexyl)amine which was used in the next step without further purification.

Step 2.

A mixture of NaH (60% susp., 1.4 mmol) and ethylene glycol dimethylether (3 mL) was added cyclohexyl-cis-(4-hydroxycyclohexyl)-amine (0.36 mmol) and the mixture was stirred under $N_2$ at rt for 5 min followed by addition of propylbromide (5.5 mmol). The mixture was refluxed for 18 h under $N_2$. The reaction mixture was cooled to rt and quenched with anhydrous EtOH (0.5 mL). The mixture was filtered and the residue was extracted with ethylene glycol di-methylether (2 mL). The organic phase was evaporated to dryness under reduced pressure and co-evaporated with toluene (10 LI). The residue was added HCl in MeOH (1.25 M, 5 mL) and evaporated under reduced pressure affording a white solid. The solid was washed with TBME (2 mL) and dissolved in a mixture of DCM (5 mL) and 1 M aqueous NaOH (5 mL). The organic phase was washed with $H_2O$ (5 mL), dried ($Na_2SO_4$), and evaporated under reduced pressure to give the desired cyclohexyl-cis-(4-propoxycyclohexyl)amine as an oil which was used in the next step without further purification.

Step 3 (Coupling and Hydrolysis).

The title compound was prepared in a similar manner as {2-[3-cyclopentyl-3-(trans-4-methoxy-cyclohexyl)-ureido]-thiazol-5-ylsulfanyl}-acetic acid using cyclohexyl-cis-(4-propoxycyclohexyl)-amine and amino-thiazol-5-ylsulfanyl)-acetic acid ethyl ester.

$^1$H-NMR (DMSO-$d_6$) δ 11.50 (br s, 1H), 7.38 (s, 1H), 3.64 (m, 1H), 3.46 (s, 2H), 3.45-3.25 (m, 4H), 2.14-1.93 (m, 4H), 1.92-1.84 (m, 2H), 1.78-1.69 (m, 2H), 1.60-1.40 (m, 7H), 1.36-1.18 (m, 4H), 1.16-1.03 (m, 1H), 0.93 (t, 3H).

Example 157

{2-[3-Cyclohexyl-3-(trans-4-phenoxy-cyclohexyl)-ureido]-thiazol-5-ylsulfanyl}-acetic acid

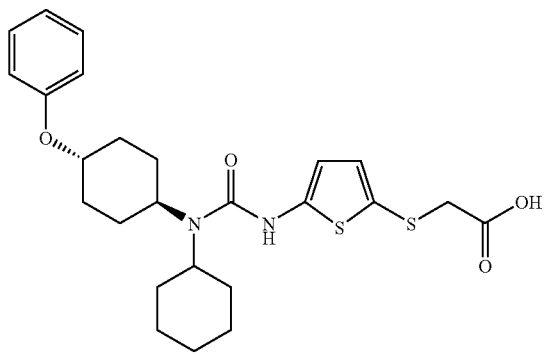

Step 1.

A stirred solution of N-Boc protected cis-4-hydroxycyclohexylamine (1 mmol, prepared as described in WO 2005/019222) in toluene (10 mL) and THF (1 mL) at 0° C. was added triphenylphosphine (1.5 mmol), diisopropylazodicarboxylate (1.7 mmol) and phenol (2 mmol). The mixture was allowed to stir at room temperature for 4 h and then concentrated under reduced pressure, taken up in DCM and washed with aqueous Na2CO3. The organic phase was dried, filtered and concentrated to give a crude product which was purified by flash chromatography to give the desired N-Boc protected trans-4-phenoxycyclohexylamine which was used without further purification.

Step 2

(4-Phenoxy-cyclohexyl)-carbamic acid tert-butyl ester (1 mmol) is dissolved in 5 mL of dichloromethane and 5 mL of trifluoroacetic acid is added. The mixture is stirred for 2 h, concentrated in vacuo and stripped twice from dichloromethane to afford the TFA salt of trans-4-phenoxy-cyclohexylamine as a white solid.

Step 3

To a mixture of trans-4-phenoxycyclohexylamine (1 mmol) in 6 ml of THF and 6 ml of MeOH was added cyclohexanone (2 mmol), NaOAc (2 mmol) and 3 g of 3 Å molecular sieves. The mixture is stirred for 10 min after which 1N sodiumcyanoborohydride in tetrahydrofuran (2.4 mmol) is added. The reaction is stirred 1 day at room temperature then filtered through celite washing through with 30 mL of dichloromethane. The organic phase is washed with 10 ml of water, 10 mL of brine, dried (MgSO4), filtered and concentrated in vacuo to give crude cyclohexyl-(trans-4-phenoxy-cyclohexyl)amine which was used in the next step without further purification.

Step 4 (Coupling and Hydrolysis).

The title compound was prepared in a similar manner as {2-[3-cyclopentyl-3-(trans-4-methoxy-cyclohexyl)-ureido]-thiazol-5-ylsulfanyl}-acetic acid using cyclohexyl-(trans-4-phenoxy-cyclohexyl)-amine and amino-thiazol-5-ylsulfanyl)-acetic acid ethyl ester.

HPLC-MS method 2: m/z=490 (M+H).

$^1$H-NMR (DMSO-$d_6$) δ 7.40 (s, 1H), 7.28 (t, 2H), 6.95 (d, 2H), 6.90 (t, 1H), 4.34-4.28 (m, 1H), 3.51 (br s, 2H), 3.48 (s, 2H), 2.25-1.07 (m, 18H).

Example 158

(2-{3-Cyclohexyl-3-[trans-4-(pyridin-2-yloxy)-cyclohexyl]-ureido}-thiazol-5-ylsulfanyl)-acetic acid

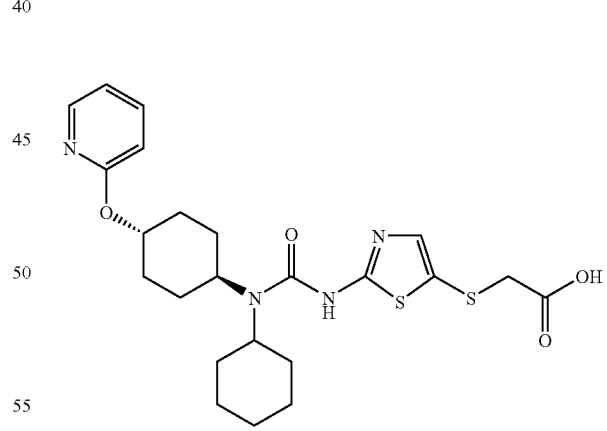

Prepared in a similar manner {2-[3-cyclohexyl-3-(trans-4-phenoxy-cyclohexyl)-ureido]-thiazol-5-ylsulfanyl}-acetic acid via cyclohexyl-[trans-4-(pyridin-2-yloxy)-cyclohexyl]-amine and (2-amino-thiazol-5-ylsulfanyl)-acetic acid ethyl ester to give the title compound.

HPLC-MS method 2: m/z=491 (M+H).

$^1$H-NMR (DMSO-$d_6$) δ 12.2 (br s, 1H), 8.15 (dd, 1H), 7.69 (dt, 1H), 7.41 (s, 1H), 6.95 (dt, 1H), 6.76 (d, 1H), 5.00-4.92 (m, 1H), 3.55 (br s, 2H), 3.48 (s, 2H), 2.28-1.05 (m, 18H).

Example 159

3-(2-{3-Cyclohexyl-3-[trans-4-(pyridin-2-yloxy)-cyclohexyl]-ureido}-thiazol-5-ylsulfanyl)-propionic acid

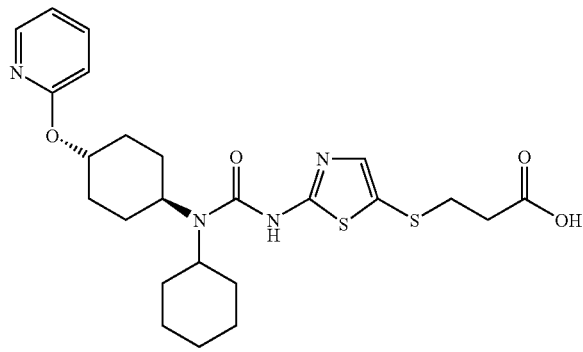

Prepared in a similar manner {2-[3-cyclohexyl-3-(trans-4-phenoxy-cyclohexyl)-ureido]-thiazol-5-ylsulfanyl}-acetic acid via cyclohexyl-[trans-4-(pyridin-2-yloxy)-cyclohexyl]-amine and 3-(2-amino-thiazol-5-ylsulfanyl)-propionic acid ethyl ester to give the title compound.

HPLC-MS: m/z=505 (M+H).

$^1$H-NMR (DMSO-d$_6$) δ 11.9 (br s, 1H), 8.15 (dd, 1H), 7.69 (dt, 1H), 7.39 (s, 1H), 6.94 (dd, 1H), 6.77 (d, 1H), 5.01-4.93 (m, 1H), 3.58 (br s, 2H), 2.85 (t, 2H), 2.50 (t, 2H), 2.28-1.05 (m, 18H).

Example 160

(2-{3-Cyclohexyl-3-[trans-4-(2,2,2-trifluoro-ethoxy)-cyclohexyl]-ureido}-thiazol-5-ylsulfanyl)-acetic acid

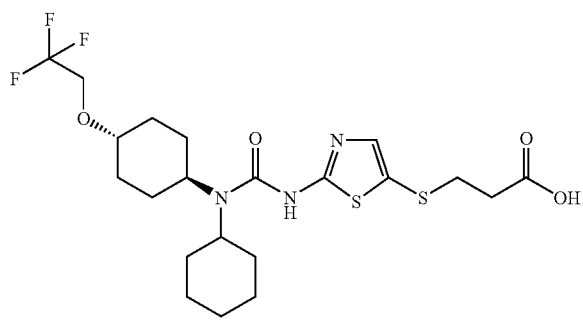

Prepared in a similar manner {2-[3-cyclohexyl-3-(trans-4-phenoxy-cyclohexyl)-ureido]-thiazol-5-ylsulfanyl}-acetic acid via cyclohexyl-[trans-4-(2,2,2-trifluoro-ethoxy)-cyclohexyl]-amine and (2-amino-thiazol-5-ylsulfanyl)-acetic acid ethyl ester to give the title compound.

$^1$H-NMR (CDCl$_3$) δ 7.25 (s, 1H), 3.84 (q, 2H), 3.54-3.22 (m, 3H), 3.33 (s, 2H), 2.40-1.10 (m, 18H).

Example 161

2-[3-Cyclohexyl-3-(trans-4-methyl-cyclohexyl)-ureido]-thiazole-5-sulfonic acid methyl-amide

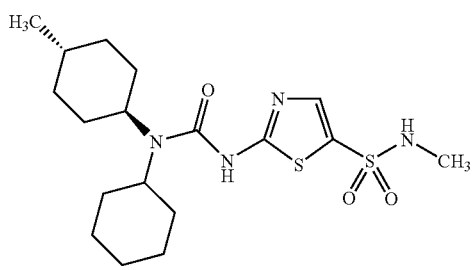

Step 1.

Methylamine (2M in THF, 40 mmol) was added to a suspension of 2-acetylamino-thiazole-5-sulfonyl chloride (10 mmol) (prepared as described in *J. Am. Chem. Soc* 69, 2063, 1947) in THF (10 mL) at −20° C. The mixture was stirred at room temperature over night and evaporated to dryness. The crude methylsulfonamide was suspended in EtOH (15 mL) and added 4N HCl in dioxane (15 mL) and heated for 4 h at 80° C. and then cooled to room temperature and evaporated to dryness to give crude 2-amino-thiazole-5-sulfonic acid methylamide.

Step 2.

An equimolar mixture of 1,1-carbonyldiimidazole, 2-amino-thiazole-5-sulfonic acid methylamide and DMAP (5 mol %) in THF was heated for 2 h at 50-60° C. and then cooled to room temperature. Then cyclohexyl-(trans-4-methyl-cyclohexyl)-amine (1 equivalent; General procedure E) was added and the reaction was stirred overnight at room temperature. The reaction mixture was quenched with water. The organic phase was isolated and the aqueous phase was extracted with CH$_2$Cl$_2$, and the combined organic phases were dried and concentrated in vacuo. The crude product was dissolved in MeCN and purified (HPLC method 1) to give the title compound.

HPLC-MS: m/z=415 (M+H).

$^1$H NMR (CDCl$_3$) δ 7.80 (s, 1H), 5.46 (br q, 1H), 3.40 (br s, 2H), 2.74 (d, 3H), 1.99-1.62 (m, 11H), 1.45-1.01 (m, 8H), 0.90 (d, 3H).

Example 162

2-{2-[3-Cyclohexyl-3-(trans-4-methyl-cyclohexyl)-ureido]-thiazole-5-sulfonylamino}-N,N-diethyl-acetamide

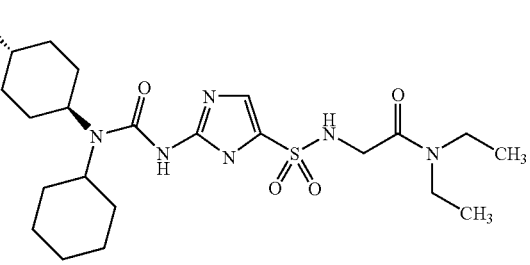

The title compound was prepared in a similar manner to 2-({2-[3-cyclohexyl-3-(trans-4-methyl-cyclohexyl)-ureido]- thiazole-5-sulfonyl}-methyl-amino)-N,N-diethyl-acetamide using {2-[3-cyclohexyl-3-(trans-4-methyl-cyclohexyl)-ureido]-thiazole-5-sulfonylamino}-acetic acid and diethylamine.

HPLC-MS: m/z=514 (M+H).

$^1$H NMR (CDCl$_3$) δ 7.81 (s, 1H), 5.93 (br t, 1H), 3.86 (d, 2H), 3.47-3.33 (m, 4H), 3.21 (q, 2H), 1.98-1.65 (m, 13H), 1.47-1.01 (m, 12H), 0.93 (d, 3H).

Example 163

2-{2-[3-Cyclohexyl-3-(trans-4-methyl-cyclohexyl)-ureido]-thiazole-5-sulfonylamino}-N-methyl-acetamide

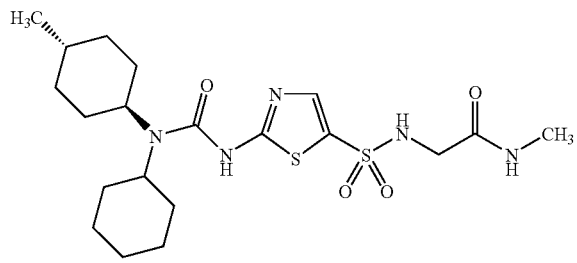

The title compound was prepared in a similar manner to 2-({2-[3-cyclohexyl-3-(trans-4-methyl-cyclohexyl)-ureido]-thiazole-5-sulfonyl}-methyl-amino)-N,N-diethyl-acetamide using {2-[3-cyclohexyl-3-(trans-4-methyl-cyclohexyl)-ureido]-thiazole-5-sulfonylamino}-acetic acid and methylamine.

HPLC-MS: m/z=472 (M+H).

$^1$H NMR (CDCl$_3$) δ 7.80 (s, 1H), 6.50 (br q, 1H), 6.28 (br s, 1H), 3.66 (br s, 2H), 3.42 (br s, 2H), 2.84 (d, 3H), 1.99-1.65 (m, 13H), 1.47-1.00 (m, 6H), 0.91 (d, 3H).

Example 164

2-{2-[3-Cyclohexyl-3-(trans-4-methyl-cyclohexyl)-ureido]-thiazole-5-sulfonylamino}-N-isopropyl-acetamide

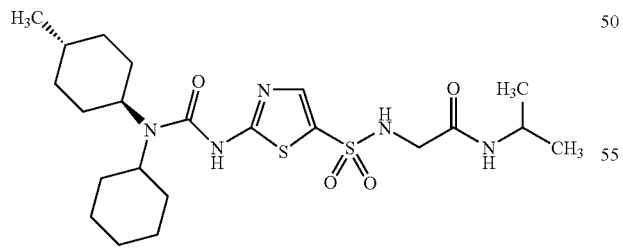

The title compound was prepared in a similar manner to 2-({2-[3-cyclohexyl-3-(trans-4-methyl-cyclohexyl)-ureido]-thiazole-5-sulfonyl}-methyl-amino)-N,N-diethyl-acetamide using {2-[3-cyclohexyl-3-(trans-4-methyl-cyclohexyl)-ureido]-thiazole-5-sulfonylamino}-acetic acid and isopropylamine.

HPLC-MS: m/z=500 (M+H).

$^1$H NMR (CDCl$_3$) δ 7.80 (s, 1H), 6.68 (br s, 1H), 6.25 (br s, 1H), 4.05 (octet, 1H), 3.64 (br s, 2H), 3.42 (br s, 2H), 1.99-1.64 (m, 13H), 1.47-1.00 (m, 6H), 1.14 (d, 6H), 0.92 (d, 3H).

Example 165

2-[3-Cyclohexyl-3-(trans-4-methyl-cyclohexyl)-ureido]-thiazole-5-sulfonic acid (2-morpholin-4-yl-2-oxo-ethyl)-amide

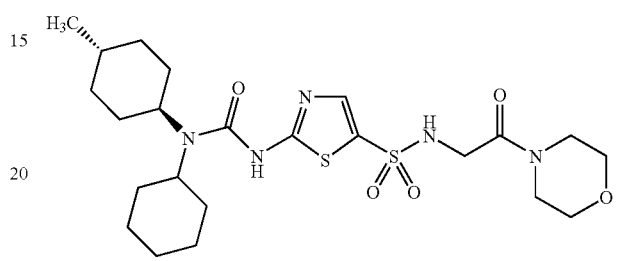

The title compound was prepared in a similar manner to 2-({2-[3-cyclohexyl-3-(trans-4-methyl-cyclohexyl)-ureido]-thiazole-5-sulfonyl}-methyl-amino)-N,N-diethyl-acetamide using {2-[3-cyclohexyl-3-(trans-4-methyl-cyclohexyl)-ureido]-thiazole-5-sulfonylamino}-acetic acid and morpholine.

HPLC-MS: m/z=528 (M+H).

$^1$H NMR (CDCl$_3$) δ 7.92 (s, 1H), 6.04 (br s, 1H), 3.89 (br s, 2H), 3.73-3.32 (m, 10H), 1.98-1.65 (m, 13H), 1.45-1.01 (m, 6H), 0.92 (d, 3H).

Example 166

2-{2-[3-Cyclohexyl-3-(trans-4-ethoxy-cyclohexyl)-ureido]-thiazol-5-ylsulfanyl}-2-methyl-propionic acid

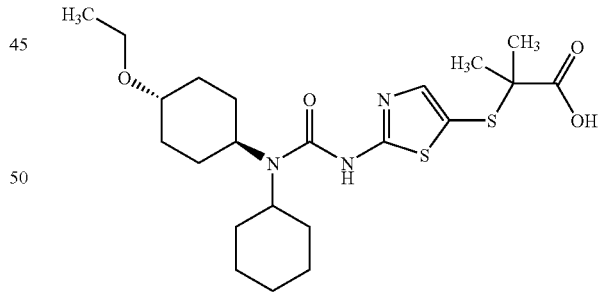

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-ethoxoxy-cyclohexyl]-amine was prepare using (trans-4-hydroxy-cyclohexyl)-isoindole-1,3-dione, 1-iodoethane and cyclohexanone.

Step 2: 2-{2-[3-Cyclohexyl-3-(4-ethoxy-cyclohexyl)-ureido]-thiazol-5-ylsulfanyl}-2-methyl-propionic acid was prepared using cyclohexyl-[trans-4-ethoxy-cyclohexyl]-amine and 2-(2-amino-thiazol-5-ylsulfanyl)-2-methyl-propionic acid ethyl ester.

¹H NMR (DMSO-d₆) δ 7.39 (s, 1H), 3.42 (q, 2H), 3.20 (m, 1H), 3.70-3.20 (m, 2H), 1.40 (s, 6H), 1.09 (t, 3H), 2.20-1.20 (m, 18H)
HPLC-MS: m/z 470 (M+H).

Example 167

2-{2-[3-Cycloheptyl-3-(trans-4-ethoxy-cyclohexyl)-ureido]-thiazol-5-ylsulfanyl}-2-methyl-propionic acid

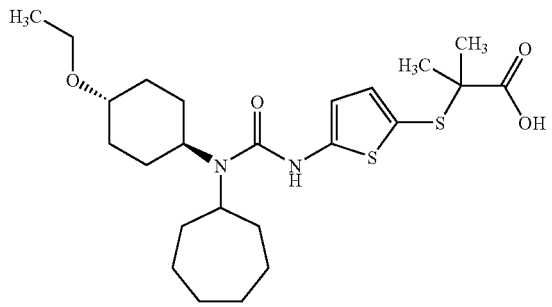

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-ethoxoxy-cyclohexyl]-amine was prepare using (trans-4-hydroxy-cyclohexyl)-isoindole-1,3-dione, 1-iodoethane and cycloheptanone.

Step 2: 2-{2-[3-Cycloheptyl-3-(trans-4-ethoxy-cyclohexyl)-ureido]-thiazol-5-ylsulfanyl}-2-methyl-propionic acid was prepared using cycloheptyl-[trans-4-ethoxoxy-cyclohexyl]-amine and 2-(2-amino-thiazol-5-ylsulfanyl)-2-methyl-propionic acid ethyl ester.

¹H NMR (DMSO-d₆) δ 7.39 (s, 1H), 3.43 (q, 2H), 3.30-3.15 (m, 3H), 2.20-1.15 (m, 20H), 1.39 (s, 6H), 1.09 (t, 3H)
HPLC-MS: m/z 484 (M+H).

Example 168

2-{2-[3-Cyclohexyl-3-(trans-4-methoxy-cyclohexyl)-ureido]-thiazol-5-ylsulfanyl}-2-methyl-propionic acid

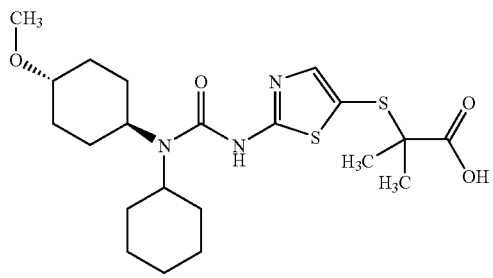

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cyclohexyl-[trans-4-methoxoxy-cyclohexyl]-amine was prepare using (trans-4-hydroxy-cyclohexyl)-isoindole-1,3-dione, 1-iodomethane and cyclohexanone.

Step 2: 2-{2-[3-Cyclohexyl-3-(trans-4-methoxy-cyclohexyl)-ureido]-thiazol-5-ylsulfanyl}-2-methyl-propionic acid was prepared using cyclohexyl-[trans-4-methoxy-cyclohexyl]-amine and 2-(2-amino-thiazol-5-ylsulfanyl)-2-methyl-propionic acid ethyl ester.

¹H NMR (DMSO-d₆) δ 7.39 (s, 1H), 3.70-3.30 (m, 2H), 3.21 (s, 3H); 3.15-3.03 (m, 1H), 2.20-1.05 (m, 18H); 1.40 (s, 6H)
HPLC-MS: m/z 456 (M+H).

Example 169

2-{2-[3-Cycloheptyl-3-(trans-4-methoxy-cyclohexyl)-ureido]-thiazol-5-ylsulfanyl}-2-methyl-propionic acid

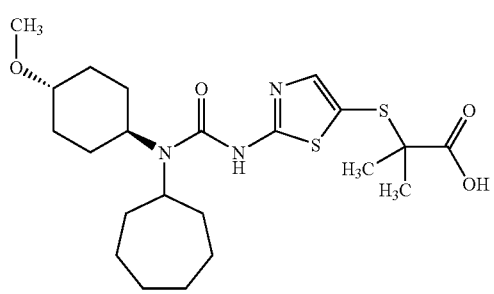

Prepared according to the procedure for the synthesis of {2-[3-cyclopentyl-3-(trans-4-methoxy-cyclohexyl)-ureido]-thiazol-5-ylsulfanyl}-acetic acid.

Step 1: Cycloheptyl-[trans-4-methoxoxy-cyclohexyl]-amine was prepare using (trans-4-hydroxy-cyclohexyl)-isoindole-1,3-dione, 1-iodomethane and cycloheptanone.

Step 2: 2-{2-[3-Cycloheptyl-3-(trans-4-methoxy-cyclohexyl)-ureido]-thiazol-5-ylsulfanyl}-2-methyl-propionic acid was prepared using cycloheptyl-[trans-4-methoxy-cyclohexyl]-amine and 2-(2-amino-thiazol-5-ylsulfanyl)-2-methyl-propionic acid ethyl ester.

¹H NMR (DMSO-d₆) δ 7.39 (s, 1H), 3.23 (s, 3H), 3.20-3.04 (m, 3H), 2.20-1.05 (m, 20H), 1.40 (s, 6H)
HPLC-MS: m/z 470 (M+H).

Example 170

5-[3-Cyclohexyl-3-(trans-4-methyl-cyclohexyl)-ureido]-[1,3,4]thiadiazole-2-sulfonic acid methylamide

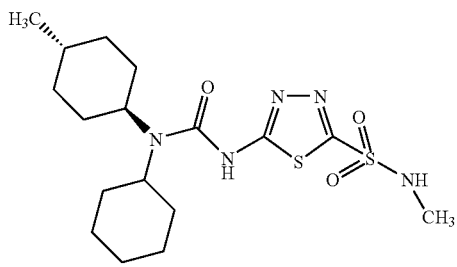

Step 1.

Methylamine (2M in THF, 40 mmol) was added to a suspension of 5-acetylamino-1,3,4-thiadiazole-2-sulfonyl chloride (10 mmol) (prepared as described in *Bioorg. Med. Chem.* 5, 515, 1997) in THF (10 mL) at −20° C. The mixture was stirred at room temperature over night and evaporated to dryness. The crude methylsulfonamide was suspended in EtOH (15 mL) and added 4N HCl in dioxane (15 mL) and heated for 4 h at 80° C. and then cooled to room temperature and evaporated to dryness to give crude 5-amino-1,3,4-thiadiazole-2-sulfonic acid methylamide.

Step 2.

An mixture of 1,1-carbonyldiimidazole (2 equiv), 5-amino-1,3,4-thiadiazole-2-sulfonic acid methylamide, cyclohexyl-(trans-4-methyl-cyclohexyl)-amine (1 equivalent) and DMAP (5 mol %) in THF-toluene (1:1) was heated for 16 h at 40° C. and then cooled to room temperature. The reaction mixture was concentrated in vacuo and the crude product was dissolved in MeCN and purified (HPLC method 1) to give the title compound.

HPLC-MS: m/z=417 (M+H).

$^1$H NMR (400 MHz, CDCl$_3$) δ 9.46 (br s, 1H), 6.81 (br s, 1H), 3.43 (br s, 2H), 2.83 (s, 3H), 1.50-2.38 (m, 13H), 1.22-1.48 (m, 3H), 0.94-1.22 (m, 3H), 0.84 (d, 3H)

Example 171

{5-[3-Cyclohexyl-3-(trans-4-methyl-cyclohexyl)-ureido]-[1,3,4]thiadiazole-2-sulfonylamino}-acetic acid

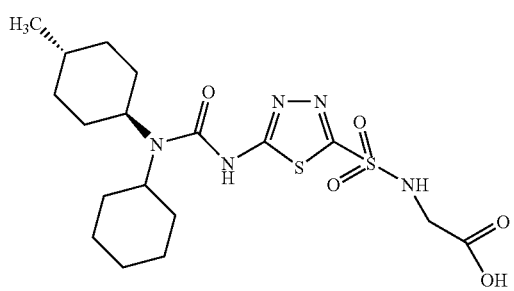

Prepared in a similar manner to [2-(3,3-dicyclohexyl-ureido)-thiazole-5-sulfonylamino]-acetic acid (Example 76) using 5-acetylamino-1,3,4-thiadiazole-2-sulfonyl chloride and then via cyclohexyl-(trans-4-methyl-cyclohexyl)-amine and (5-amino-1,3,4-thiadiazole-2-sulfonylamino)-acetic acid ethyl ester to give the title compound.

HPLC-MS: m/z=461 (M+H).

$^1$H NMR (400 MHz, CDCl$_3$) δ 3.93 (s, 2H), 3.48 (br s, 2H), 1.52-2.22 (m, 12H), 0.96-1.51 (m, 7H), 0.87 (d, 3H)

Example 172

({5-[3-Cyclohexyl-3-(trans-4-methyl-cyclohexyl)-ureido]-[1,3,4]thiadiazole-2-sulfonyl}-methyl-amino)-acetic acid

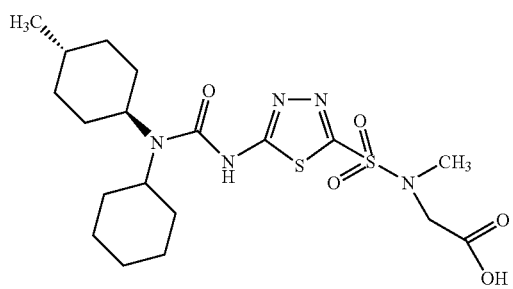

Prepared in a similar manner to {5-[3-cyclohexyl-3-(trans-4-methyl-cyclohexyl)-ureido]-[1,3,4]thiadiazole-2-sulfonylamino}-acetic acid via cyclohexyl-(trans-4-methyl-cyclohexyl)-amine and [(5-amino-1,3,4-thiadiazole-2-sulfonyl)-methyl-amino]-acetic acid ethyl ester to give the title compound.

HPLC-MS: m/z=475 (M+H).

$^1$H NMR (400 MHz, CDCl$_3$) δ 10.84 (br s, 1H), 4.26 (s, 2H), 3.52 (br s, 2H), 3.16 (s, 3H), 1.50-1.88 (m, 12H), 0.95-1.50 (m, 7H), 0.91 (d, 3H)

Example 173

2-[3-Cyclohexyl-3-(trans-4-methyl-cyclohexyl)-ureido]-4-methyl-thiazole-5-sulfonic acid methylamide

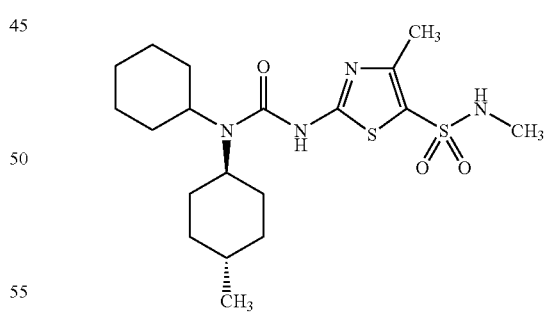

The title compound was prepared in a similar manner to 2-[3-cyclohexyl-3-(trans-4-methyl-cyclohexyl)-ureido]-thiazole-5-sulfonic acid methylamide using 2-acetylamino-4-methyl-thiazole-5-sulfonyl chloride as the sulfonyl chloride.

HPLC-MS: m/z=429 (M+H).

$^1$H NMR (400 MHz, CDCl$_3$) δ 8.16 (br s, 1H), 3.39 (br s, 2H), 2.74 (d, 3H), 2.52 (s, 3H), 0.96-2.00 (m, 19H), 0.91 (d, 3H)

Example 174

{2-[3-Cyclohexyl-3-(trans-4-methyl-cyclohexyl)-ureido]-4-methyl-thiazole-5-sulfonylamino}-acetic acid

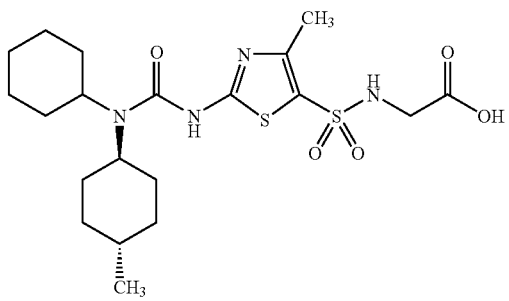

Prepared in a similar manner to [2-(3,3-dicyclohexyl-ureido)-thiazole-5-sulfonylamino]-acetic acid (Example 76) using 2-acetylamino-4-methyl-thiazole-5-sulfonyl chloride as the sulfonyl chloride and then via cyclohexyl-(trans-4-methyl-cyclohexyl)-amine and (2-amino-4-methyl-thiazole-5-sulfonylamino)-acetic acid ethyl ester to give the title compound.

HPLC-MS: m/z=473 (M+H).

1H NMR (400 MHz, DMSO-$d_6$) δ 8.15 (t, 1H), 3.63 (d, 2H), 2.38 (s, 3H), 0.92-2.12 (m, 19H), 0.87 (d, 3H), two protons not observed.

Example 175

({2-[3-Cyclohexyl-3-(trans-4-methyl-cyclohexyl)-ureido]-4-methyl-thiazole-5-sulfonyl}-methyl-amino)-acetic acid

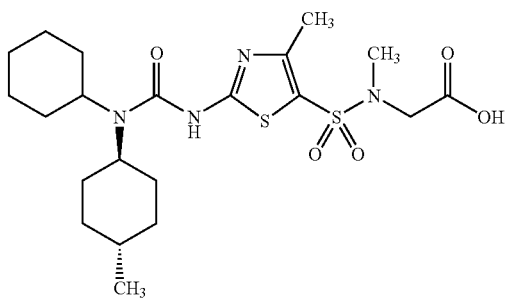

Prepared in a similar manner to [2-(3,3-dicyclohexyl-ureido)-thiazole-5-sulfonylamino]-acetic acid (Example 76) using 2-acetylamino-4-methyl-thiazole-5-sulfonyl chloride as the sulfonyl chloride and then via cyclohexyl-(trans-4-methyl-cyclohexyl)-amine and [(2-amino-4-methyl-thiazole-5-sulfonyl)-methyl-amino]-acetic acid methyl ester to give the title compound.

HPLC-MS: m/z=487 (M+H).

$^1$H NMR (400 MHz, DMSO-$d_6$) δ 12.78 (br s, 1H), 11.40 (br s, 1H), 3.90 (s, 2H), 2.84 (s, 3H), 2.41 (s, 3H), 0.95-2.21 (m, 19H), 0.87 (d, 3H), two protons not observed.

Example 176

1-Cyclohexyl-1-(trans-4-methyl-cyclohexyl)-3-[5-(piperidine-1-sulfonyl)-[1,3,4]thiadiazol-2-yl]-urea

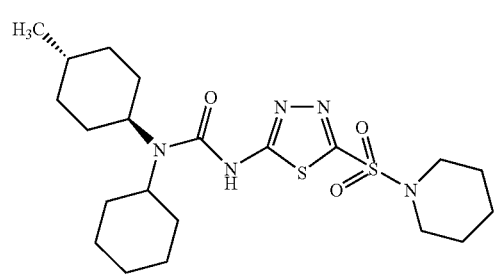

Prepared in a similar manner to 5-[3-cyclohexyl-3-(trans-4-methyl-cyclohexyl)-ureido]-[1,3,4]thiadiazole-2-sulfonic acid methylamide via cyclohexyl-(trans-4-methyl-cyclohexyl)-amine and 5-(piperidine-1-sulfonyl)-1,3,4-thiadiazol-2-ylamine to give the title compound.

HPLC-MS: m/z=470 (M+H).

$^1$H NMR (400 MHz, CD$_3$OD) δ 3.49 (br s, 2H), 3.27 (t, 4H), 2.03 (br s, 4H), 1.71-1.88 (m, 4H), 1.49-1.71 (m, 11H), 1.29-1.49 (m, 3H), 0.99-1.28 (m, 3H), 0.92 (d, 3H)

Example 177

5-[3-Cyclohexyl-3-(trans-4-methyl-cyclohexyl)-ureido]-[1,3,4]thiadiazole-2-sulfonic acid (2-methoxy-ethyl)-amide

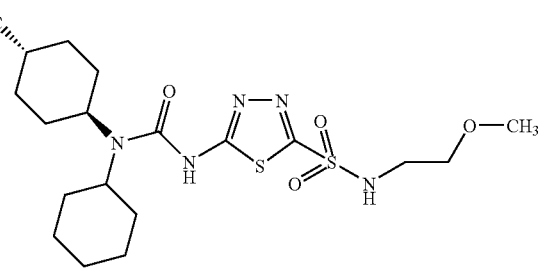

Prepared in a similar manner to 5-[3-cyclohexyl-3-(trans-4-methyl-cyclohexyl)-ureido]-[1,3,4]thiadiazole-2-sulfonic acid methylamide via cyclohexyl-(trans-4-methyl-cyclohexyl)-amine and 5-amino-1,3,4-thiadiazole-2-sulfonic acid (2-methoxy-ethyl)-amide to give the title compound.

HPLC-MS: m/z=460 (M+H).

$^1$H NMR (400 MHz, CD$_3$OD) δ 3.45 (t, 2H), 3.47 (br s, 2H), 3.29-3.33 (m, 5H), 2.00 (br s, 4H), 1.71-1.87 (m, 4H), 1.56-1.71 (m, 5H), 1.29-1.50 (m, 3H), 1.03-1.29 (m, 3H), 0.92 (d, 3H)

Example 178

5-[3-Cyclohexyl-3-(trans-4-methyl-cyclohexyl)-ureido]-[1,3,4]thiadiazole-2-sulfonic acid isopropylamide

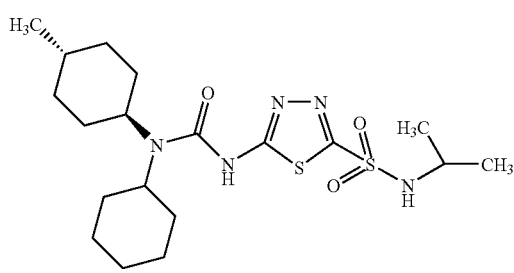

Prepared in a similar manner to 5-[3-cyclohexyl-3-(trans-4-methyl-cyclohexyl)-ureido]-[1,3,4]thiadiazole-2-sulfonic acid methylamide via cyclohexyl-(trans-4-methyl-cyclohexyl)-amine and 5-amino-1,3,4-thiadiazole-2-sulfonic acid isopropylamide to give the title compound.

HPLC-MS: m/z=444 (M+H).

$^1$H NMR (400 MHz, CD$_3$OD) δ 3.56-3.73 (m, 1H), 3.48 (br s, 2H), 2.01 (br s, 3H), 1.70-1.86 (m, 4H), 1.50-1.70 (m, 5H), 1.30-1.49 (m, 4H), 0.99-1.29 (m, 9H), 0.92 (d, 4H)

Example 179

5-[3-Cyclohexyl-3-(trans-4-methyl-cyclohexyl)-ureido]-[1,3,4]thiadiazole-2-sulfonic acid phenylamide

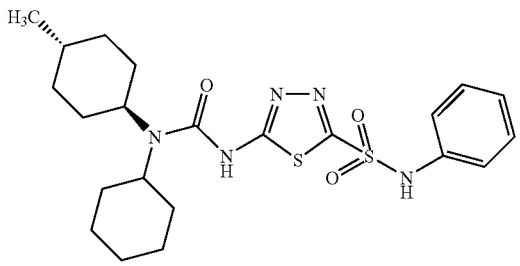

Prepared in a similar manner to 5-[3-cyclohexyl-3-(trans-4-methyl-cyclohexyl)-ureido]-[1,3,4]thiadiazole-2-sulfonic acid methylamide via cyclohexyl-(trans-4-methyl-cyclohexyl)-amine and 5-amino-1,3,4-thiadiazole-2-sulfonic acid phenylamide to give the title compound.

HPLC-MS: m/z=478 (M+H).

$^1$H NMR (400 MHz, CD$_3$OD) δ 7.18-7.35 (m, 4H), 7.13 (t, 1H), 3.45 (br s, 2H), 1.55-2.17 (m, 11H), 0.99-1.48 (m, 6H), 0.92 (d, 3H).

Example 180

1-Cyclohexyl-1-(trans-4-methyl-cyclohexyl)-3-[5-(piperidine-1-sulfonyl)-thiazol-2-yl]-urea

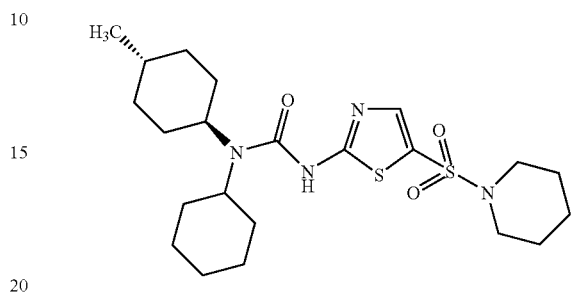

Prepared in a similar manner to 2-[3-cyclohexyl-3-(trans-4-methyl-cyclohexyl)-ureido]-thiazole-5-sulfonic acid methylamide via cyclohexyl-(trans-4-methyl-cyclohexyl)-amine and 5-(piperidine-1-sulfonyl)-thiazol-2-ylamine to give the title compound.

HPLC-MS: m/z=469 (M+H).

$^1$H NMR (400 MHz, benzene-d$_6$) δ 8.56 (br s, 1H), 7.75 (s, 1H), 3.41 (br s, 2H), 3.05 (t, 4H), 0.96-2.20 (m, 25H), 0.91 (d, 3H)

Example 181

2-[3-Cyclohexyl-3-(trans-4-methyl-cyclohexyl)-ureido]-thiazole-5-sulfonic acid isopropylamide

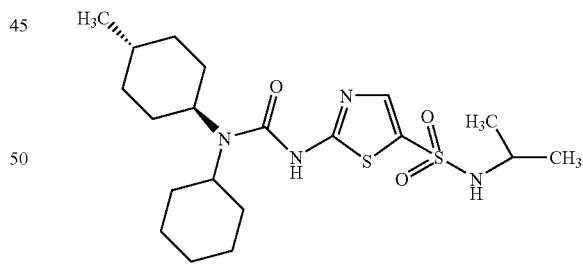

Prepared in a similar manner to 2-[3-cyclohexyl-3-(trans-4-methyl-cyclohexyl)-ureido]-thiazole-5-sulfonic acid methylamide via cyclohexyl-(trans-4-methyl-cyclohexyl)-amine and 2-amino-thiazole-5-sulfonic acid isopropylamide to give the title compound.

HPLC-MS: m/z=443 (M+H).

$^1$H NMR (300 MHz, CDCl$_3$) δ 8.68 (br s, 1H), 7.80 (s, 1H), 5.05 (d, 1H), 3.47-3.66 (m, 1H), 3.41 (br s, 2H), 1.52-2.14 (m, 13H), 0.96-1.52 (m, 12H), 0.90 (d, 3H),

Example 182

1-Cyclohexyl-3-[5-(cis-2,6-dimethyl-piperidine-1-sulfonyl)-thiazol-2-yl]-1-(trans-4-methyl-cyclohexyl)-urea

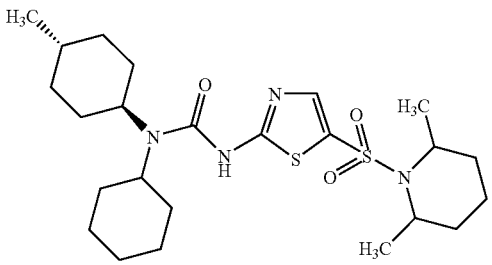

Prepared in a similar manner to 2-[3-cyclohexyl-3-(trans-4-methyl-cyclohexyl)-ureido]-thiazole-5-sulfonic acid methylamide via cyclohexyl-(trans-4-methyl-cyclohexyl)-amine and 5-(cis-2,6-dimethyl-piperidine-1-sulfonyl)-thiazol-2-ylamine to give the title compound.

HPLC-MS: m/z=497 (M+H).

$^1$H NMR (300 MHz, CDCl$_3$) δ 8.33 (br s, 1H), 7.75 (s, 1H), 4.11-4.29 (m, 2H), 3.43 (br s, 2H), 1.60-2.06 (m, 14H), 0.96-1.60 (m, 17H), 0.91 (d, 3H).

Example 183

2-[3-Cyclohexyl-3-(trans-4-methyl-cyclohexyl)-ureido]-thiazole-5-sulfonic acid tert-butylamide

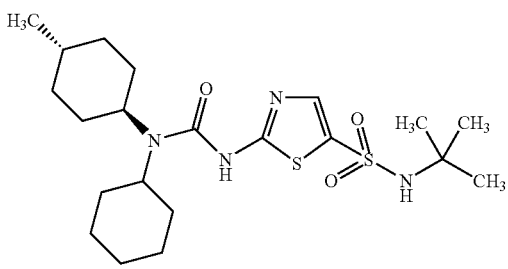

Prepared in a similar manner to 2-[3-cyclohexyl-3-(trans-4-methyl-cyclohexyl)-ureido]-thiazole-5-sulfonic acid methylamide via cyclohexyl-(trans-4-methyl-cyclohexyl)-amine and 2-amino-thiazole-5-sulfonic acid tert-butylamide to give the title compound.

HPLC-MS: m/z=457 (M+H).

$^1$H NMR (400 MHz, CDCl$_3$) δ 8.81 (br s, 1H), 7.77 (s, 1H), 5.51-5.75 (br s, 1H), 3.39 (br s, 2H), 0.95-2.15 (m, 27H), 0.89 (d, 3H).

The invention claimed is:

1. A compound of formula (I)

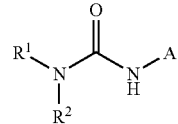

wherein R$^1$ is

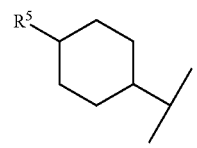

and R$^2$ is cyclohexyl; and
A is

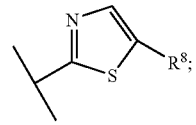

and

R$^5$ is selected from the group consisting of C$_{3-6}$-alkenyloxy, aryloxy-C$_{1-6}$-alkyl, C$_{3-8}$-cycloalkyl-C$_{1-6}$-alkyloxy-C$_{1-6}$-alkyl, aryl-C$_{1-6}$-alkyloxy-C$_{1-6}$-alkyl, heteroaryl-C$_{1-6}$-alkyloxy-C$_{1-6}$-alkyl, C$_{3-6}$-alkenylthio, arylthio-C$_{1-6}$-alkyl, C$_{3-8}$-cycloalkyl-C$_{1-6}$-alkylthio-C$_{1-6}$-alkyl, or heteroaryloxy-C$_{1-6}$-alkyl, each of which is optionally substituted with one or more substituents independently selected from R$^{12}$, and wherein each aryl is phenyl and heteroaryl is pyridyl; and R$^{12}$ is halogen, cyano, hydroxy, carboxy, —CF$_3$, C$_{1-6}$-alkyloxy, C$_{3-8}$-cycloalkyloxy, aryloxy, aryl-C$_{1-6}$-alkyloxy or C$_{1-6}$-alkyl; and R$^8$ is selected from halogen, carboxy, —CF$_3$, —S—CH$_3$, —S—CH$_2$CH$_3$, —S—CH$_2$CH$_2$CH$_3$, methyl, ethyl, propyl, isopropyl, butyl, isobutyl, tert-butyl, methoxy, ethoxy, —CH$_2$—C(O)—O—CH$_3$, —CH$_2$—C(O)—O—CH$_2$CH$_3$, —CH$_2$CH$_2$—C(O)—O—CH$_3$, —CH$_2$CH$_2$—C(O)—O—CH$_2$CH$_3$, —CH$_2$—O—C(O)—CH$_3$, —CH$_2$—O—C(O)—CH$_2$CH$_3$, —CH$_2$CH$_2$—O—C(O)—CH$_3$, —CH$_2$CH$_2$—O—C(O)—CH$_2$CH$_3$, —C(O)—O—CH$_3$, —C(O)—O—CH$_2$CH$_3$, each of which is optionally substituted with one or more substituents independently selected from R$^{16}$; or heteroarylthio, wherein heteroaryl is pyridyl or imidazolyl, each optionally substituted on the heteroaryl part with one or more substituents independently selected from R$^{17}$, or pyrrolidinyl, piperidyl, piperazinyl, or morpholinyl, each of which is optionally substituted with one or more substituents independently selected from R$^{16}$; or —S(O)$_2$—NR$^{19}$R$^{20}$ or —S(O)$_2$—R$^{21}$ R$^{16}$ and R$^{17}$ are independently C$_{1-6}$-alkyl, halogen, nitro, cyano, hydroxy, carboxy, oxo, —CF$_3$, carboxy-C$_{1-6}$-alkyl, hydroxy-C$_{1-6}$-alkyl, —C$_{1-6}$-alkyl-C(O)—O—C$_{1-6}$-alkyl, —C$_{1-6}$-alkyl-C(O)—NR$^{19}$R$^{20}$, —C(O)—

O—$C_{1-6}$-alkyl, —C(O)—$C_{1-6}$-alkyl-C(O)—$C_{1-6}$-alkyl, —$NR^{19}R^{20}$, —$NHS(O)_2C_{1-6}$-alkyl, —$NHS(O)_2CF_3$, —$NHS(O)_2CH_2CF_3$, —$C(O)NR^{19}R^{20}$, —$S(O)_2C_{1-6}$-alkyl, —$S(O)_2CF_3$, —$S(O)_2CH_2CF_3$ or —$S(O)_2NR^{19}R^{20}$; and $R^{19}$ and independently represent hydrogen, methyl, ethyl, or propyl, $S(O)_2$—$CH_3$, or $R^{19}$ and $R^{20}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$; and $R^{21}$ is selected from carboxy-methyl, carboxy-ethyl, or carboxy-propyl; and $R^{24}$ is halogen, carboxy, $C_{1-6}$-alkyl, carboxy-$C_{1-6}$-alkyl, or —C(O)—O—$C_{1-6}$-alkyl; and as well as any salt hereof with a pharmaceutically acceptable acid or base, or any optical isomer or mixture of optical isomers, racemic mixture, or any tautomeric forms thereof.

2. A compound according to claim 1 wherein $R^5$ is selected from the group consisting of $C_{3-6}$-alkenyloxy, phenyloxy-$C_{1-6}$-alkyl, benzyloxy-$C_{1-6}$-alkyl, $C_{3-8}$-cycloalkyl-$C_{1-6}$-alkyloxy-$C_{1-6}$-alkyl.

3. A compound according to claim 2 wherein $R^5$ is selected from the group consisting of $C_{3-4}$-alkenyloxy, phenyloxy-methyl, benzyloxy-methyl, or cyclopropyl-methoxymethyl.

4. A compound according to claim 1 wherein $R^{12}$ is halogen, cyano, hydroxy, carboxy, —$CF_3$, methoxy, ethoxy, propoxy, cyclopropyloxy, cyclobutyloxy, cyclopentyloxy, cyclohexyloxy, cycloheptyloxy, phenoxy, benzyloxy, phenyl-ethyloxy, phenyl-propoxy, methyl, ethyl or propyl.

5. A compound according to claim 4 wherein $R^{12}$ is halogen, carboxy, ethoxy, propoxy, cyclopropyloxy, cyclobutyloxy, cyclopentyloxy, cyclohexyloxy, cycloheptyloxy, phenoxy, benzyloxy, phenyl-ethyloxy, phenyl-propoxy, methyl, ethyl or propyl.

6. A compound according to claim 1 wherein $R^8$ is selected from Cl, —S—$CH_3$, —S—$CH_2CH_3$, —S—$CH_2CH_2CH_3$, —S—$CH(CH_3)_2$, —S—$CH_2CH(CH_3)_2$, methyl, or ethyl, each of which is optionally substituted with one or more substituents independently selected from $R^{16}$; —$S(O)_2$—$NR^{19}R^{20}$ or —$S(O)_2$—$R^{21}$.

7. A compound according to claim 1 wherein $R^{16}$ and $R^{17}$ are independently $C_{1-6}$-alkyl, halogen, hydroxy, oxo, carboxy, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$NR^{19}R^{20}$, —$C(O)NR^{19}R^{20}$ or —$S(O)_2$—$C_{1-6}$-alkyl.

8. A compound according to claim 7 wherein $R^{16}$ and $R^{17}$ are independently methyl, ethyl, propyl, isopropyl, isobutyl, halogen, hydroxy, oxo, carboxy, —$CF_3$, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

9. A compound according to claim 8 wherein $R^{16}$ and $R^{17}$ are independently methyl, ethyl, propyl, isopropyl, isobutyl, halogen, oxo, carboxy, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

10. A compound according to claim 7 wherein $R^{16}$ and $R^{17}$ are independently $C_{1-6}$-alkyl, carboxy, —$NR^{19}R^{20}$, —C(O)—O—$C_{1-6}$-alkyl, —$S(O)_2CH_3$ or —$C(O)NR^{19}R^{20}$.

11. A compound according to claim 10 wherein $R^{16}$ or $R^{20}$ are carboxy.

* * * * *

UNITED STATES PATENT AND TRADEMARK OFFICE
CERTIFICATE OF CORRECTION

PATENT NO. : 7,582,769 B2  
APPLICATION NO. : 11/994728  
DATED : September 1, 2009  
INVENTOR(S) : Anthony Murray et al.

Page 1 of 1

It is certified that error appears in the above-identified patent and that said Letters Patent is hereby corrected as shown below:

Column 190, Claim 11, Line 35: delete "$R^{20}$" and insert --$R^{17}$--.

Signed and Sealed this

Fourth Day of September, 2012

David J. Kappos
*Director of the United States Patent and Trademark Office*